United States Patent
Hyun et al.

(10) Patent No.: US 11,629,142 B2
(45) Date of Patent: Apr. 18, 2023

(54) ORGANIC ELECTROLUMINESCENT 3,6-DISUBSTITUTED CARBAZOLE COMPOUNDS AND ORGANIC ELECTROLUMINESCENT DEVICE INCLUDING THE SAME

(71) Applicant: P&H TECH Co., Ltd, Gyeonggi-do (KR)

(72) Inventors: Seo-Yong Hyun, Gyeonggi-do (KR); Seok-Keun Yoon, Gyeonggi-do (KR)

(73) Assignee: P&H TECH CO., LTD., Gyeonggi-do (KR)

( * ) Notice: Subject to any disclaimer, the term of this patent is extended or adjusted under 35 U.S.C. 154(b) by 319 days.

(21) Appl. No.: 16/817,820

(22) Filed: Mar. 13, 2020

(65) Prior Publication Data
US 2020/0377492 A1 Dec. 3, 2020

(30) Foreign Application Priority Data
May 29, 2019 (KR) .................. 10-2019-0063298

(51) Int. Cl.
*C07D 413/14* (2006.01)
*C07D 417/14* (2006.01)
(Continued)

(52) U.S. Cl.
CPC ......... *C07D 413/14* (2013.01); *C07D 417/14* (2013.01); *H01L 51/0052* (2013.01);
(Continued)

(58) Field of Classification Search
CPC . C07D 413/14; C07D 417/14; H01L 51/0052; H01L 51/0067; H01L 51/0071; H01L 51/0072; H01L 51/0074
(Continued)

(56) References Cited

U.S. PATENT DOCUMENTS

2003/0129448 A1   7/2003   Lin et al.
2010/0060154 A1*  3/2010   Nomura ............... C07D 413/10
                                                   313/504
(Continued)

FOREIGN PATENT DOCUMENTS

CN   104650066 A   5/2015
CN   104650067 A   5/2015
(Continued)

OTHER PUBLICATIONS

Chen, H-F., et al.; "Carbazole and benzimidazole/oxadiazole hybrids as bipolar host materials for sky blue, green, and red PhOLEDs", Organic Electronics 13 (2012) 2671-2681.
(Continued)

*Primary Examiner* — Sheng-Bai Zhu
(74) *Attorney, Agent, or Firm* — Harness, Dickey & Pierce, P.L.C.

(57) ABSTRACT

Disclosed is a novel organic electroluminescent compound represented by Formula (I):

(Continued)

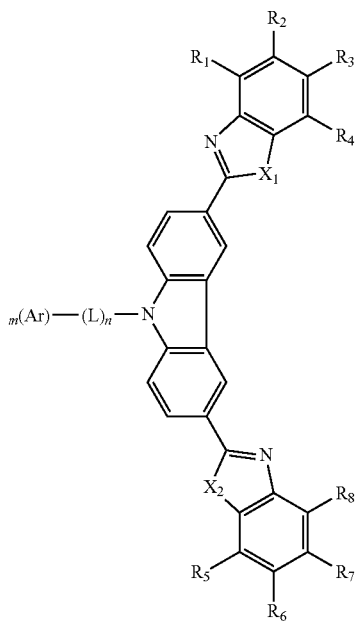

Formula (I)

The organic electroluminescent compound is employed as a material for at least one organic layer of an organic electroluminescent device such as a light emitting layer, a hole transport layer, an electron transport layer, an electron blocking layer, and/or a capping layer, achieving excellent luminescent properties (including high luminous efficiency and quantum efficiency) of the device. Also disclosed is an organic electroluminescent device including the organic electroluminescent compound.

11 Claims, 4 Drawing Sheets

(51) Int. Cl.
H01L 51/00 (2006.01)
H01L 51/50 (2006.01)
H01L 51/52 (2006.01)
(52) U.S. Cl.
CPC ...... *H01L 51/0067* (2013.01); *H01L 51/0071* (2013.01); *H01L 51/0072* (2013.01); *H01L 51/0074* (2013.01); *H01L 51/5016* (2013.01); *H01L 51/5253* (2013.01); *H01L 2251/5384* (2013.01)
(58) Field of Classification Search
USPC .......................................................... 428/690
See application file for complete search history.

(56) References Cited

U.S. PATENT DOCUMENTS

| 2012/0179089 | A1* | 7/2012 | Sisk | A61P 31/04 |
| | | | | 257/E51.026 |
| 2013/0048956 | A1* | 2/2013 | Balaganesan | C07D 487/16 |
| | | | | 257/E51.026 |
| 2017/0005276 | A1* | 1/2017 | Kim | C07D 491/048 |
| 2018/0040829 | A1* | 2/2018 | Lee | H01L 51/0071 |

FOREIGN PATENT DOCUMENTS

| CN | 104650855 A | 5/2015 |
| CN | 108218867 A | 6/2018 |
| KR | 10-2013-0118269 A | 10/2013 |
| KR | 10-2017-0094714 A | 8/2017 |
| KR | 10-2017-0116927 A | 10/2017 |

OTHER PUBLICATIONS

Gao, Z., et al.; "High-efficiency deep blue fluorescent emitters based on phenanthro[9,10-d]imidazole substituted carbazole and their applications in organic light emitting diodes", Organic Electronics 15 (2014) 2667-2676.
Office Action from corresponding Korean Patent Application No. 10-2019-0063298, dated Oct. 16, 2019.

* cited by examiner

ORGANIC ELECTROLUMINESCENT 3,6-DISUBSTITUTED CARBAZOLE COMPOUNDS AND ORGANIC ELECTROLUMINESCENT DEVICE INCLUDING THE SAME

CROSS-REFERENCE TO RELATED APPLICATION

This application claims priority to Korean Patent Application No. 10-2019-0063298, filed on May 29, 2019. The entire disclosure of the application identified in this paragraph is incorporated herein by reference.

FIELD

The present disclosure relates to an organic electroluminescent compound, and more particularly to an organic electroluminescent compound that is employed as a material for at least one organic layer of an organic electroluminescent device such as a light emitting layer, a hole transport layer, an electron transport layer, an electron blocking layer, and/or a capping layer. The present disclosure also relates to an organic electroluminescent device that employs the organic electroluminescent compound, achieving greatly improved luminescent properties such as high luminous efficiency and quantum efficiency.

BACKGROUND

Organic electroluminescent devices can be fabricated even on transparent substrates. In addition, organic electroluminescent devices can be driven at low voltages of 10 V or less with relatively low power consumption and have good color representation compared to plasma display panels and inorganic electroluminescent (EL) displays. Organic electroluminescence devices can display three colors: green, blue, and red. Due to these advantages, organic electroluminescence devices have been the subject of intense interest as next-generation display devices.

Stability and efficiency of materials for organic layers are prerequisites for the fabrication of organic electroluminescent devices with excellent characteristics described above. That is, organic electroluminescent devices should be supported by stable and efficient organic layer materials, for example, hole injecting materials, hole transport materials, light emitting materials, electron transport materials, and electron injecting materials, for their excellent characteristics described above. However, stable and efficient organic layer materials for organic electroluminescent devices remain at the early stage of development.

Thus, further improvements in terms of efficiency and life characteristics are required for good stability, high efficiency, long lifetime, and large size of organic electroluminescent devices. Particularly, there is a strong need to develop new materials for organic layers of organic electroluminescent devices.

In this connection, considerable research efforts have recently been made to improve the mobility of organic materials for constituent layers (particularly, hole transport layers) of organic electroluminescent devices.

There has been much research aimed at improving the characteristics of organic electroluminescent devices by changes in the performance of organic layer materials. In addition, a technique for improving the color purity and enhancing the luminous efficiency of a device by optimizing the optical thickness of layers between an anode and a cathode is considered as a crucial factor for improving the device performance. For example, the formation of a capping layer on an electrode achieves increased luminous efficiency and high color purity.

SUMMARY

The present disclosure intends to provide a novel organic electroluminescent compound that is employed as a material for at least one organic layer of an organic electroluminescent device, achieving excellent luminescent properties (including high luminous efficiency and quantum efficiency) of the device, and an organic electroluminescent device including the organic electroluminescent compound.

One aspect of the present disclosure provides an organic electroluminescent compound represented by Formula (I):

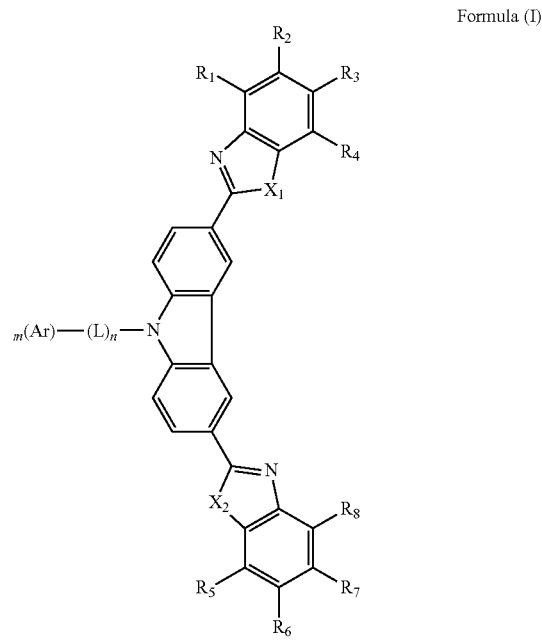

Formula (I)

Structural features of Formula (I) are described below and $X_1$, $X_2$, $R_1$ to $R_8$, L, and Ar in Formula (I) are as defined below.

The use of the organic electroluminescent compound according to the present invention as a material for at least one organic layer of an organic electroluminescent device such as a light emitting layer, a hole transport layer, an electron transport layer, an electron blocking layer and/or a capping layer ensures excellent luminescent properties of the device such as high luminous efficiency and quantum efficiency. Therefore, the organic electroluminescent compound of the present invention is suitable for use in a variety of display devices.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION

Figure 1:
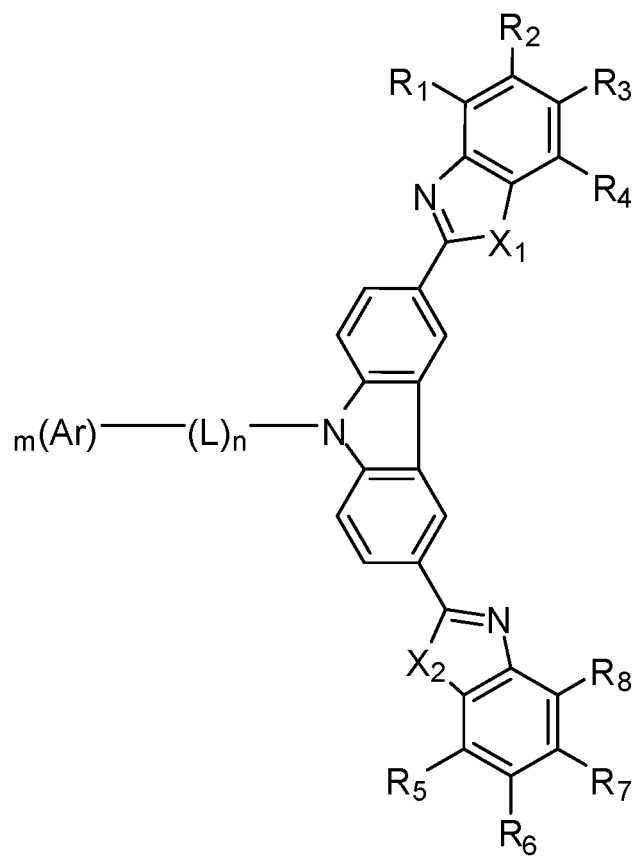
FIG. 1 shows the structural formula of an organic electroluminescent compound according to the present invention.
Figure 2:
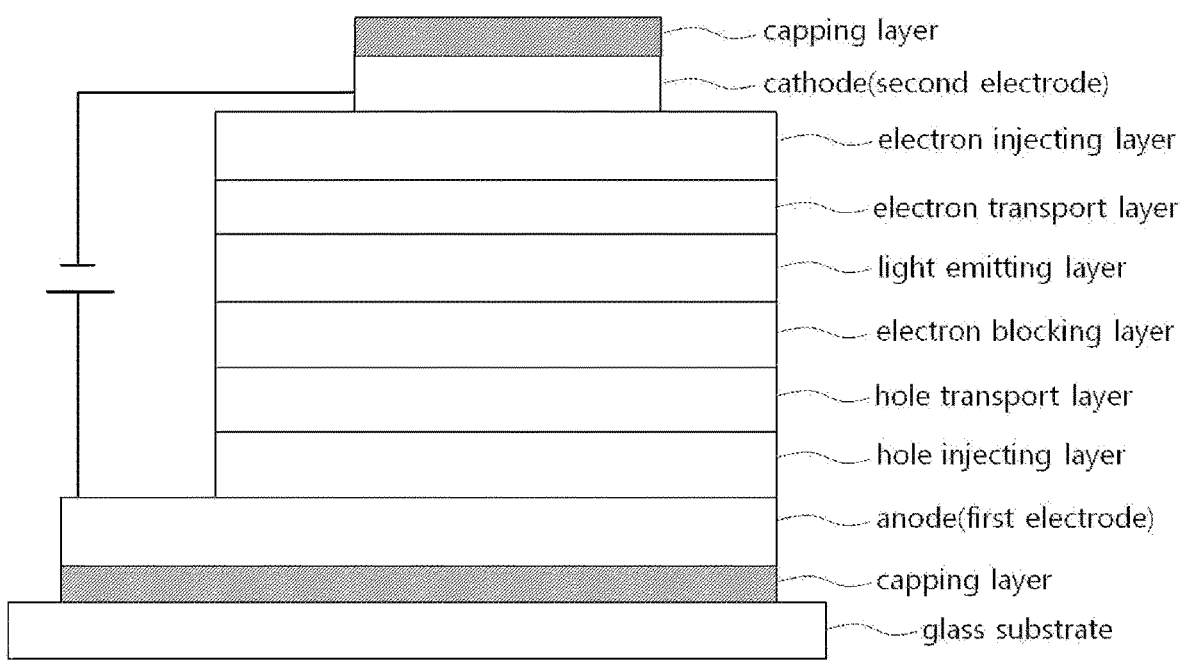
FIGS. 2, 3, and 4 illustrate embodiments of a device comprising a capping layer.
Figure 3:
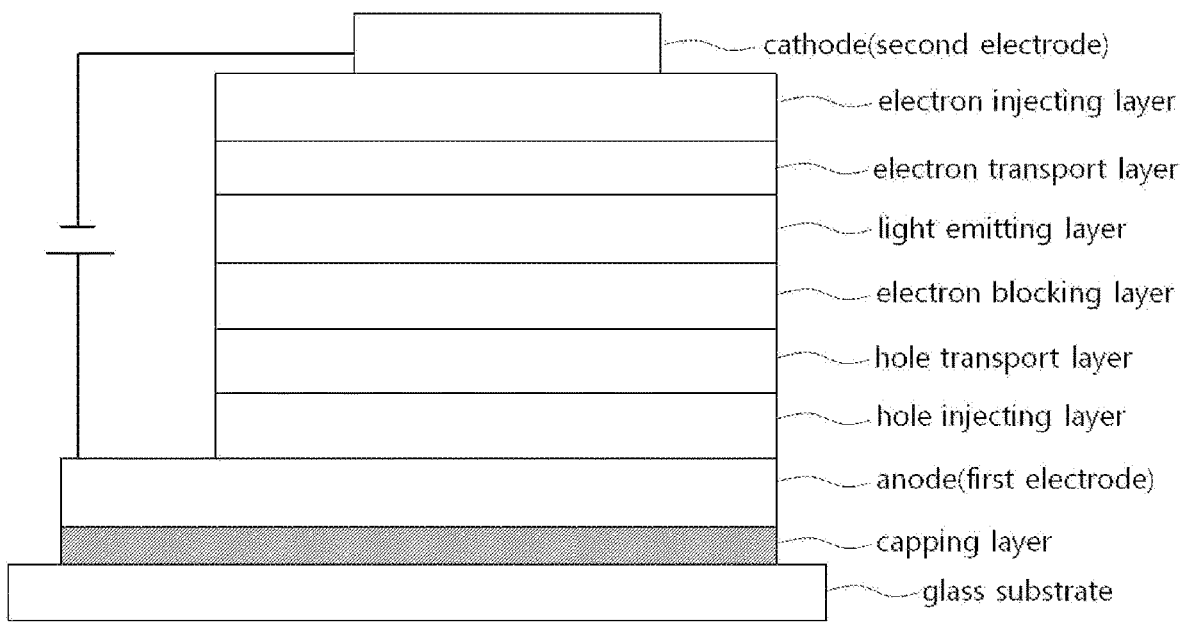
Figure 4:
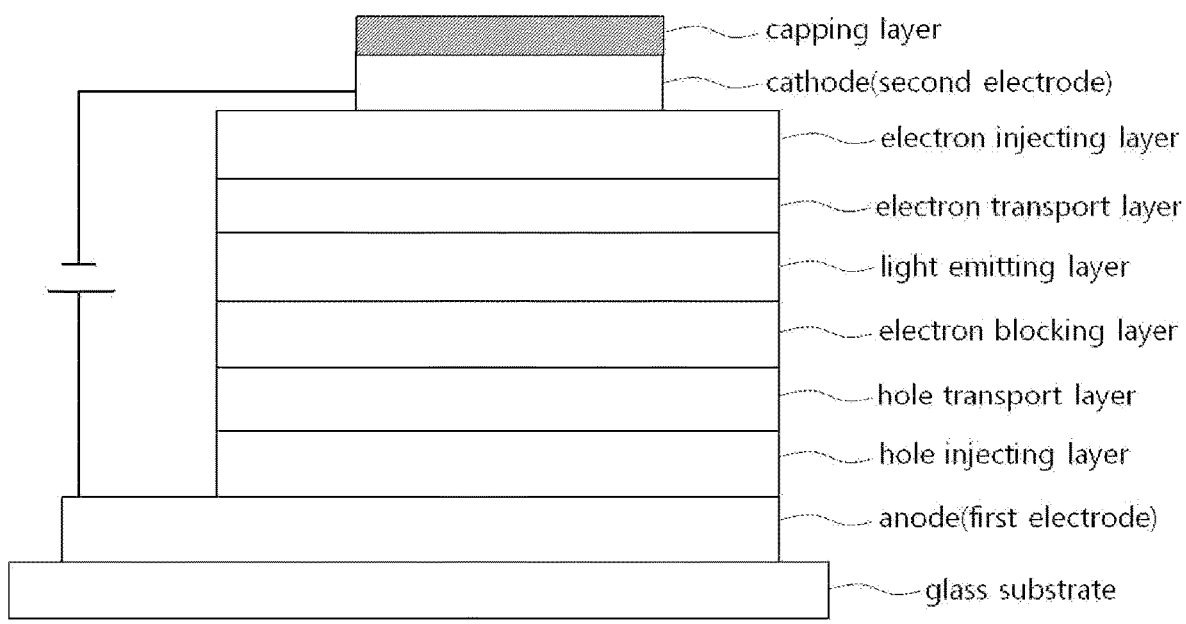

The present invention will now be described in more detail.

The present disclosure provides an organic electroluminescent compound with excellent luminescent properties such as high luminous efficiency and quantum efficiency, represented by Formula (I):

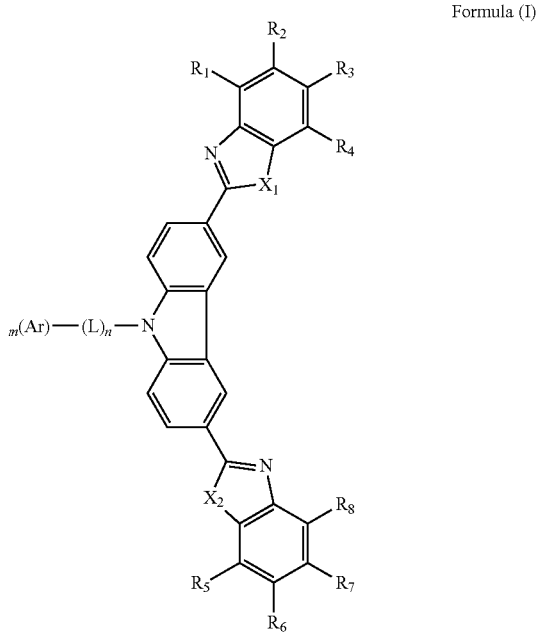

Formula (I)

wherein $X_1$ and $X_2$ are each independently O or S;

$R_1$, $R_2$, $R_3$, $R_4$, $R_5$, $R_6$, $R_7$, and $R_8$ are each independently selected from —H, deuterium, halo, cyano, alkyl, aryl, heteroaryl, cycloalkyl, and heterocyclyl, wherein $R_1$, $R_2$, $R_3$, $R_4$, $R_5$, $R_6$, $R_7$, and $R_8$ are optionally substituted with one or more substituents selected from the group consisting of deuterium, halo, cyano, nitro, hydroxyl, silyl, alkyl, cycloalkyl, alkoxy, alkenyl, aryl, and heterocyclyl, and wherein $R_1$, $R_2$, $R_3$, $R_4$, $R_5$, $R_6$, $R_7$, and $R_8$ are optionally bonded to each other or joined to one or more adjacent substituents to form a monocyclic or polycyclic group optionally containing one or more heteroatoms selected from N, S, and O;

L is a bond, arylene, or heteroarylene;

n is 0, 1, 2, or 3,

Ar is aryl, heteroaryl, fluorenyl, cycloalkyl, or heterocyclyl, and m is 1, 2, or 3.

In another embodiment, the compound of the present disclosure is a compound of Formula (I), wherein $X_1$ and $X_2$ are each independently O or S, $R_1$ to $R_8$ are each independently selected from hydrogen, deuterium, substituted or unsubstituted $C_1$-$C_{10}$ alkyl groups, substituted or unsubstituted $C_6$-$C_{30}$ aryl groups, substituted or unsubstituted $C_3$-$C_{30}$ heteroaryl groups, substituted or unsubstituted $C_6$-$C_{30}$ aryl groups fused with one or more substituted or unsubstituted $C_3$-$C_{20}$ cycloalkyl groups, and substituted or unsubstituted $C_3$-$C_{30}$ heteroaryl groups fused with one or more substituted or unsubstituted $C_3$-$C_{20}$ cycloalkyl groups, $R_1$ to $R_8$ are each independently selected from hydrogen, deuterium, halogen groups, a cyano group, substituted or unsubstituted $C_1$-$C_{10}$ alkyl groups, substituted or unsubstituted $C_6$-$C_{30}$ aryl groups, substituted or unsubstituted $C_3$-$C_{30}$ heteroaryl groups, substituted or unsubstituted $C_6$-$C_{30}$ aryl groups fused with one or more substituted or unsubstituted $C_3$-$C_{20}$ cycloalkyl groups, and substituted or unsubstituted $C_3$-$C_{30}$ heteroaryl groups fused with one or more substituted or unsubstituted $C_3$-$C_{20}$ cycloalkyl groups, with the proviso that $R_1$ to $R_8$ are optionally bonded to each other or joined to one or more adjacent substituents to form at least one alicyclic or aromatic monocyclic or polycyclic ring whose carbon atoms are optionally substituted with one or more heteroatoms selected from nitrogen (N), sulfur (S), and oxygen (O) atoms, L is a single bond or is selected from substituted or unsubstituted $C_6$-$C_{30}$ arylene groups and substituted or unsubstituted $C_3$-$C_{30}$ heteroarylene groups, n is an integer from 0 to 3, Ar is selected from substituted or unsubstituted $C_6$-$C_{30}$ aryl groups, substituted or unsubstituted $C_3$-$C_{30}$ heteroaryl groups, substituted or unsubstituted fluorenyl groups, substituted or unsubstituted $C_6$-$C_{30}$ aryl groups fused with one or more substituted or unsubstituted $C_3$-$C_{20}$ cycloalkyl groups, and substituted or unsubstituted $C_3$-$C_{30}$ heteroaryl groups fused with one or more substituted or unsubstituted $C_3$-$C_{20}$ cycloalkyl groups, and m is an integer from 1 to 3.

The term "substituted" in the definition of $R_1$ to $R_8$, L, and Ar indicates substitution with one or more substituents selected from the group consisting of hydrogen, deuterium, halogen groups, a cyano group, a nitro group, a hydroxyl group, silyl groups, alkyl groups, cycloalkyl groups, alkoxy groups, alkenyl groups, aryl groups, heterocyclic groups, and combinations thereof. The term "unsubstituted" in the same definition indicates having no substituent.

Specifically, the substituted arylene groups may be, for example, phenyl, biphenyl, naphthalene, fluorenyl, pyrenyl, phenanthrenyl, perylene, tetracenyl, and anthracenyl groups substituted with one or more other substituents.

The substituted heteroarylene groups are pyridyl, thiophenyl, triazine, quinoline, phenanthroline, imidazole, thiazole, oxazole, carbazole groups, and their condensed heterocyclic groups, for example, benzquinoline, benzimidazole, benzoxazole, benzothiazole, benzocarbazole, dibenzothiophenyl, and dibenzofuran groups, that are substituted with one or more other substituents.

The above substituents are specifically exemplified below without limitation.

The alkyl groups may be straight or branched. The number of carbon atoms in the alkyl groups is not particularly limited but is preferably from 1 to 20. Specific examples of the alkyl groups include, but are not limited to, methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, and 5-methylhexyl groups.

The alkoxy groups may be straight or branched. The number of carbon atoms in the alkoxy groups is not particularly limited but is preferably from 1 to 20 as long as steric hindrance is avoided. Specific examples of the alkoxy groups include, but are not limited to, methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, and p-methylbenzyloxy groups.

The aryl groups may be monocyclic or polycyclic. The number of carbon atoms in the aryl groups is not particularly limited but is preferably from 6 to 30. Examples of the monocyclic aryl groups include phenyl, biphenyl, terphenyl, and stilbene groups but the scope of the present invention is not limited thereto. Examples of the polycyclic aryl groups include naphthyl, anthracenyl, phenanthrenyl, pyrenyl, perylenyl, tetracenyl, chrysenyl, fluorenyl, acenaphathcenyl, triphenylene, and fluoranthrene groups but the scope of the present invention is not limited thereto.

The heteroaryl groups refer to heterocyclic groups containing one or more heteroatoms selected from O, N, and S. The number of carbon atoms in the heteroaryl groups is preferably from 2 to 30. Specific examples of the heteroaryl groups include, but are not limited to, thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phthalazinyl, pyridopyrimidinyl, pyridopyrazinyl, pyrazino-pyrazinyl, isoquinoline, indole, carbazole, benzoxazole, benzimidazole, benzothiazole, benzocarbazole, benzothiophene, dibenzothiophene, benzofuranyl, dibenzofuranyl, phenanthroline, thiazolyl, isoxazolyl, oxadiazolyl, thiadiazolyl, benzothiazolyl, phenothiazinyl, phenoxazine, and phenothiazine groups.

As used herein, the term "cycloalkyl" is a hydrocarbyl group containing at least one saturated or partially unsaturated ring structure, and attached via a ring carbon. In various embodiments, it refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl.

As used herein, the term "heterocyclyl" includes the heteroaryls defined below and refers to a saturated or partially unsaturated monocyclic, bicyclic or tricyclic group of 2 to 14 ring-carbon atoms and, in addition to ring-carbon atoms, 1 to 4 heteroatoms selected from P, N, O and S.

Specific examples of the silyl groups include, but are not limited to, trimethylsilyl, triethylsilyl, t-butyldimethylsilyl, vinyldimethylsilyl, propyldimethylsilyl, triphenylsilyl, diphenylsilyl, and phenylsilyl groups.

Specific examples of the halogen groups include fluorine (F), chlorine (Cl), and bromine (Br).

The fluorenyl groups refer to structures in which two cyclic organic compounds are linked through one atom, and examples thereof include

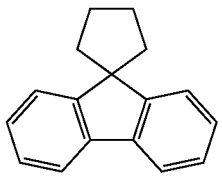 and 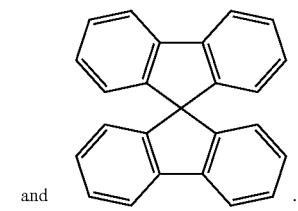.

The fluorenyl groups include open structures in which one of the two cyclic organic compounds linked through one atom is cleaved. Examples of the open structures of the fluorenyl groups include

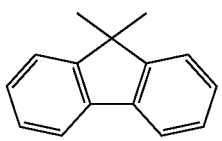 and 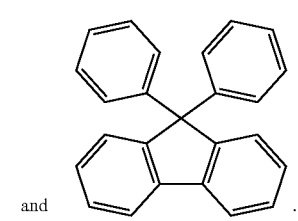.

The organic electroluminescent compound of Formula I according to the present invention can be used to form various organic layers of an organic electroluminescent device due to its structural features. More specifically, the organic electroluminescent compound of Formula I can be used as a material for a light emitting layer or a capping layer of an organic electroluminescent device.

In some embodiments, the organic electroluminescent compound of Formula (I) is selected from, but is not limited to:

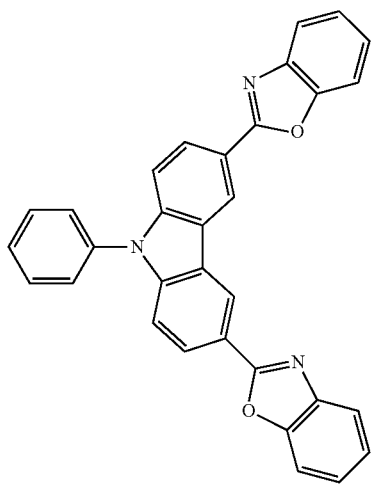

1

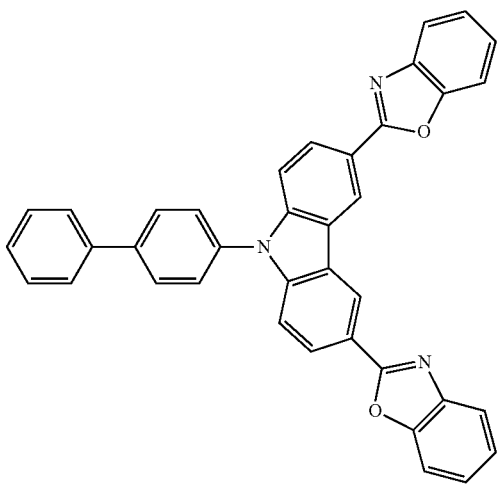

2

-continued
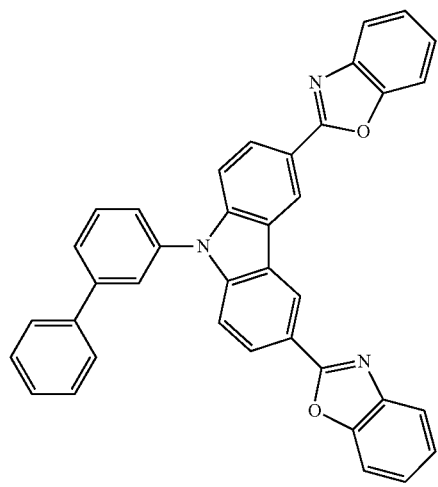
3
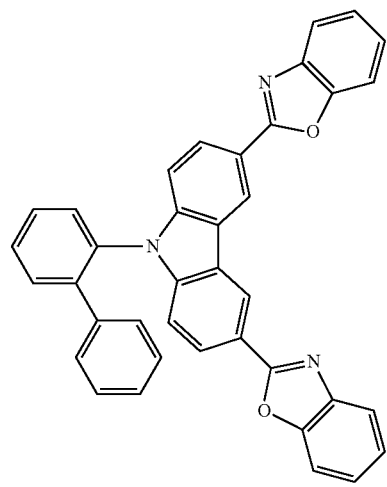
4
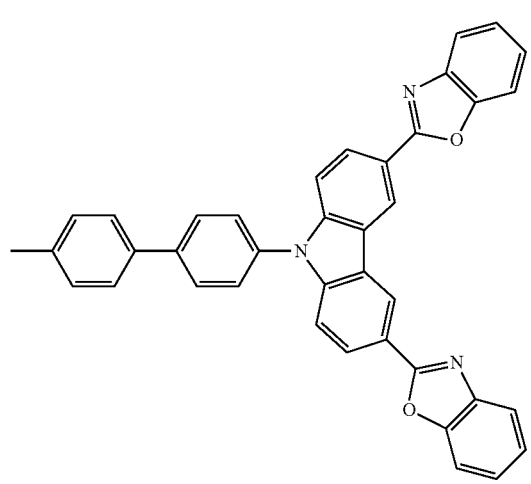
5
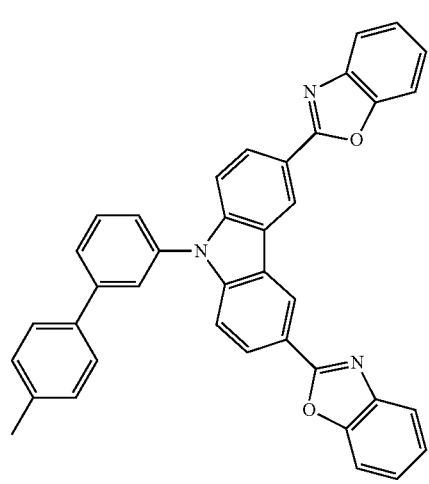
6
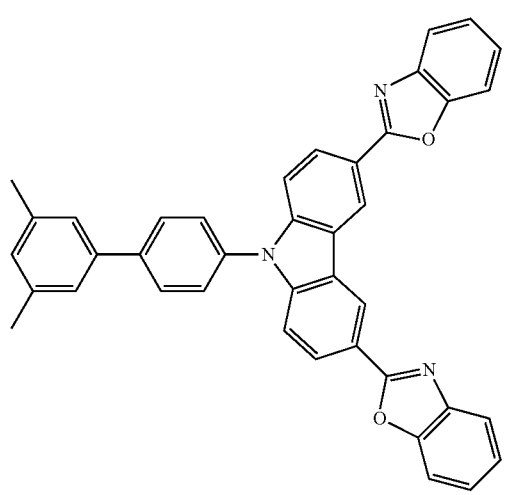
7
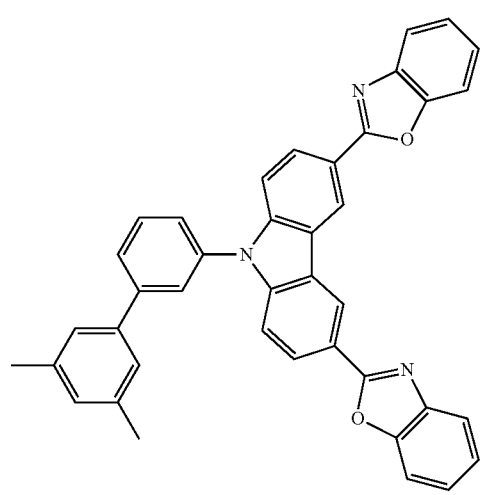
8

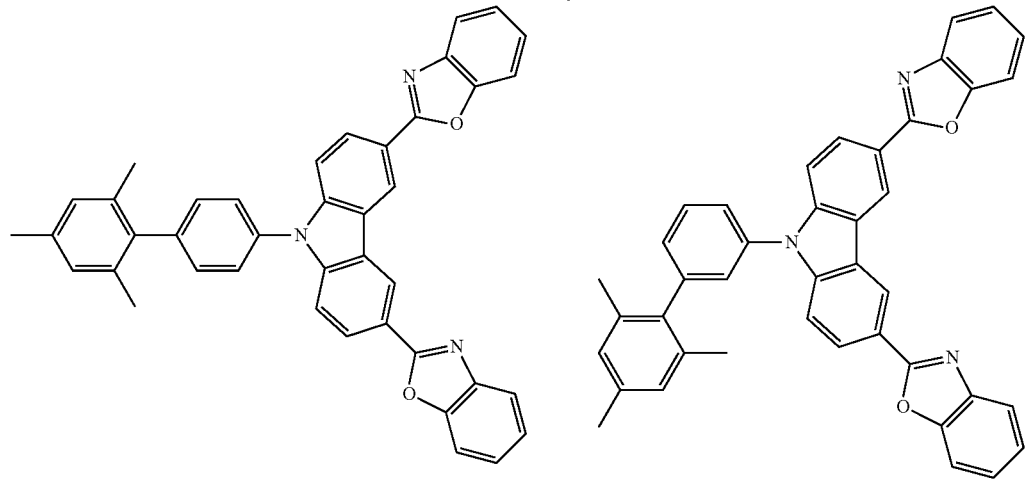
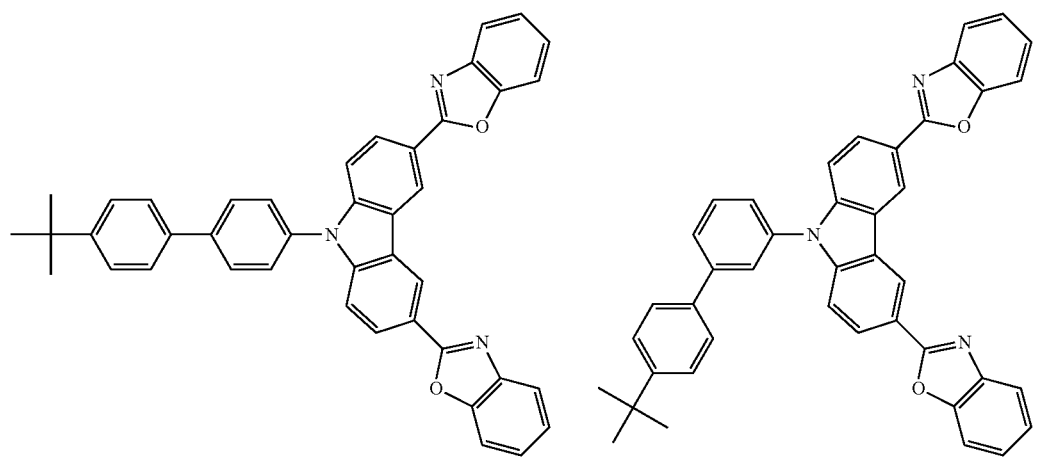
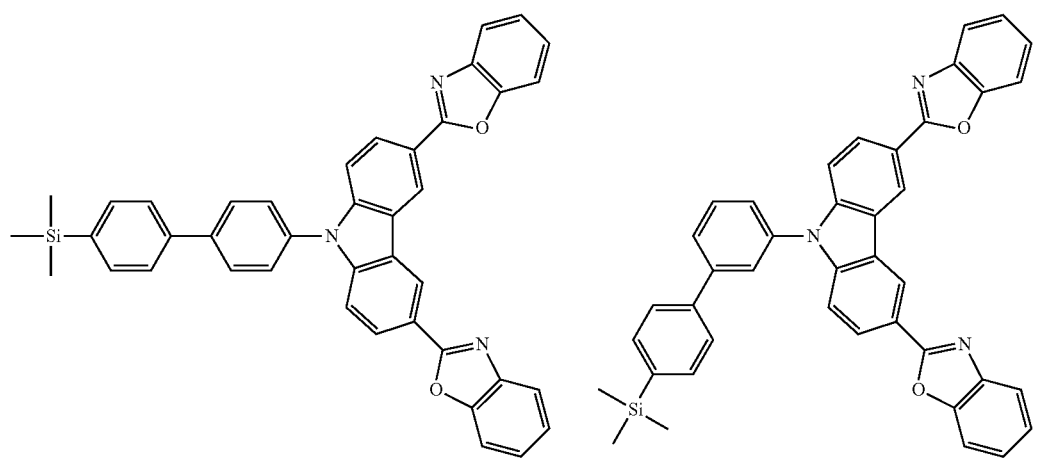

-continued
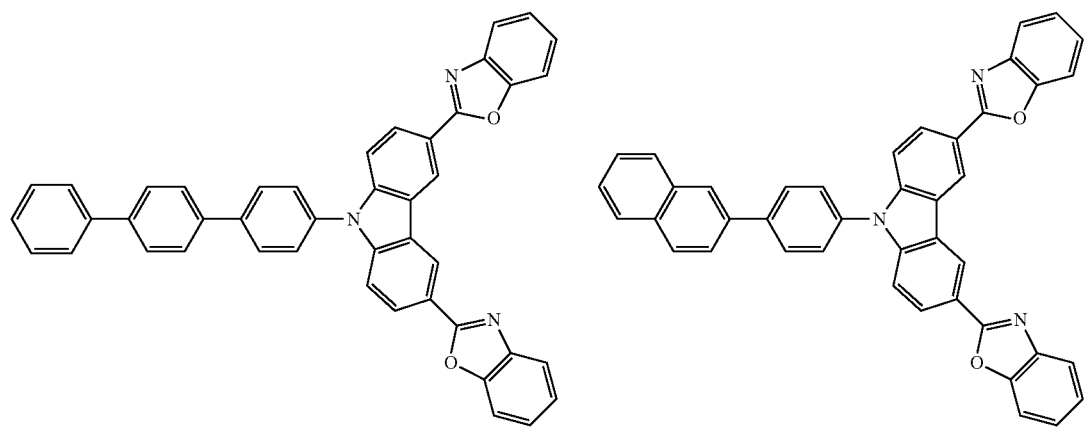
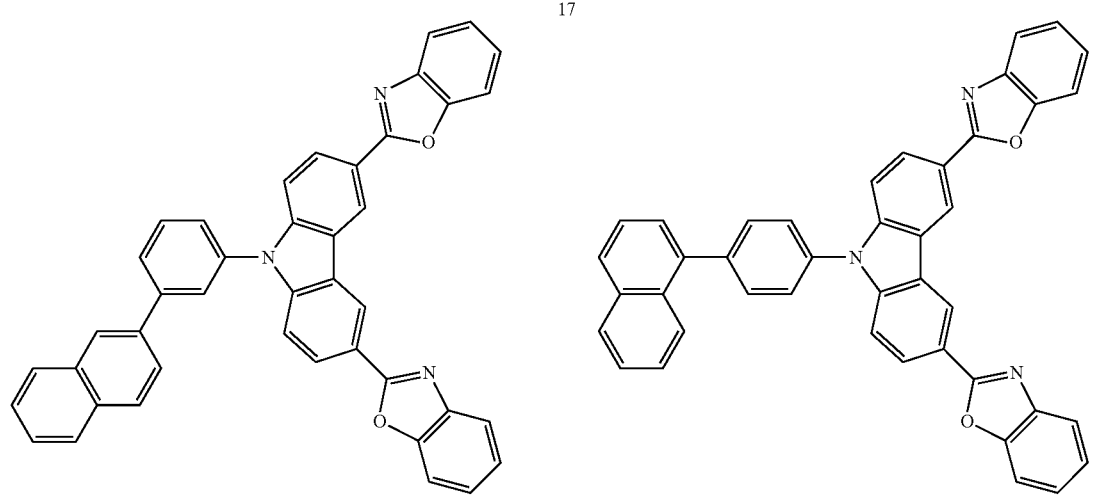
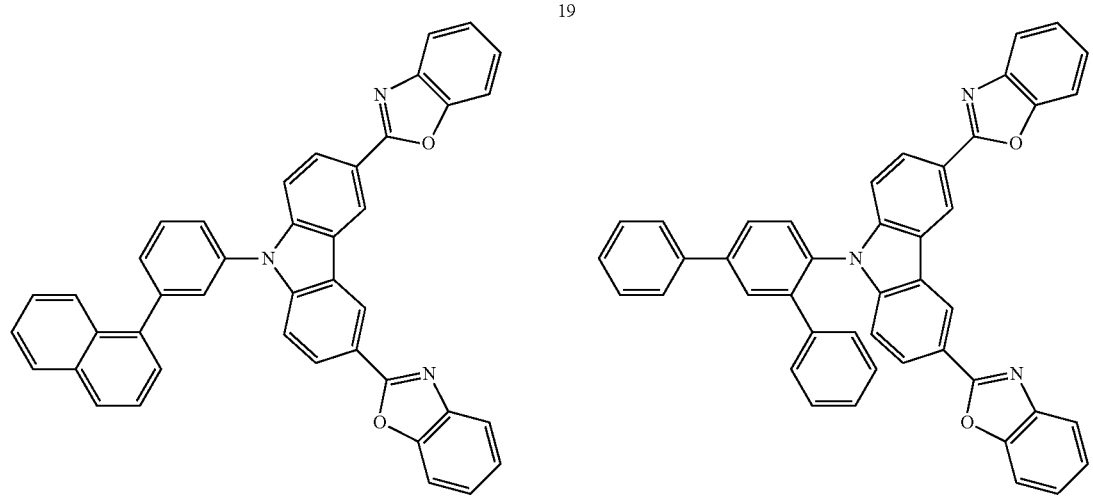

-continued
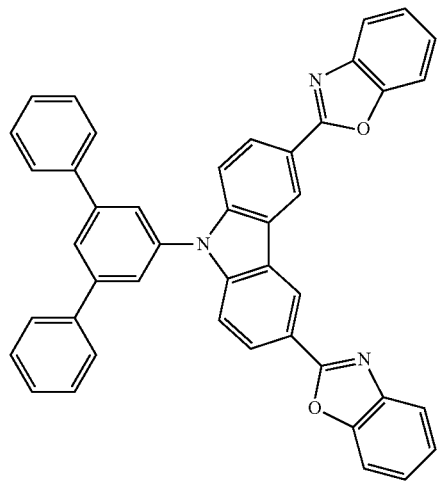
21
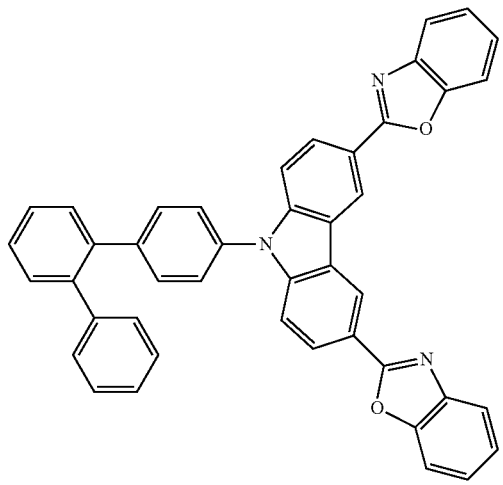
22
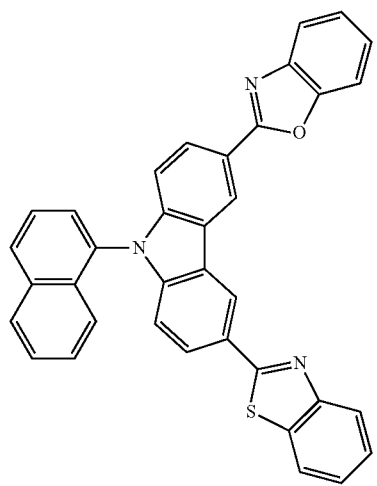
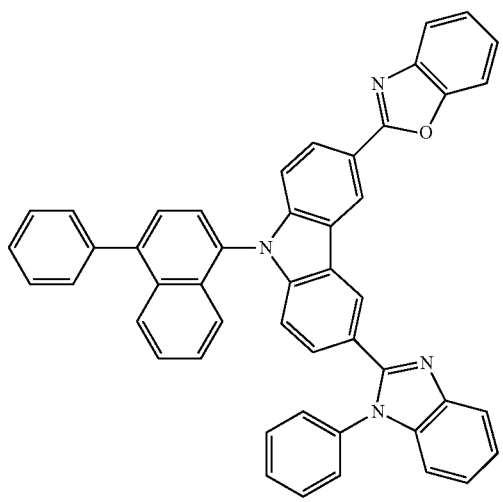
24
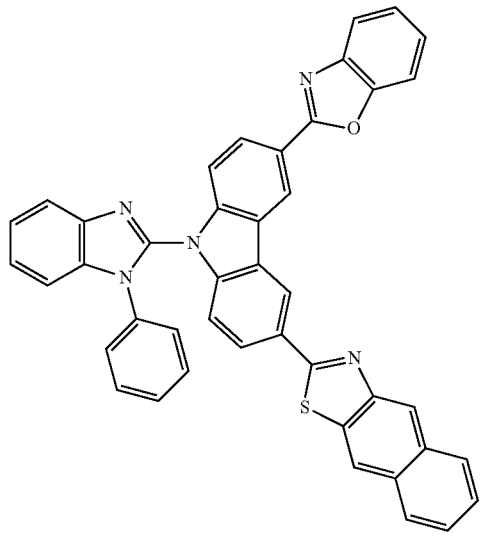
25
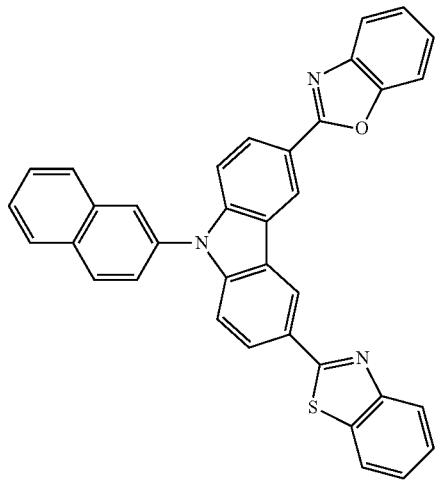
26

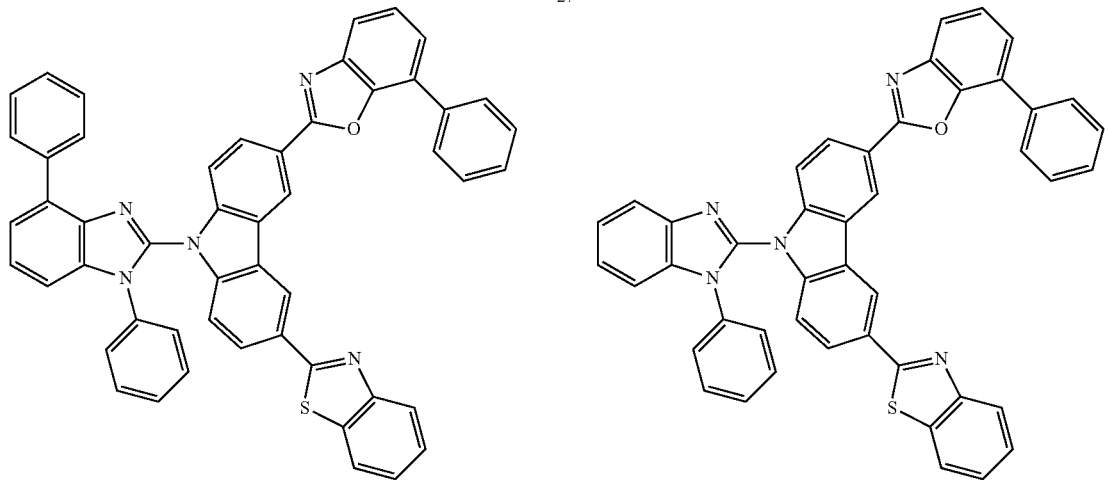
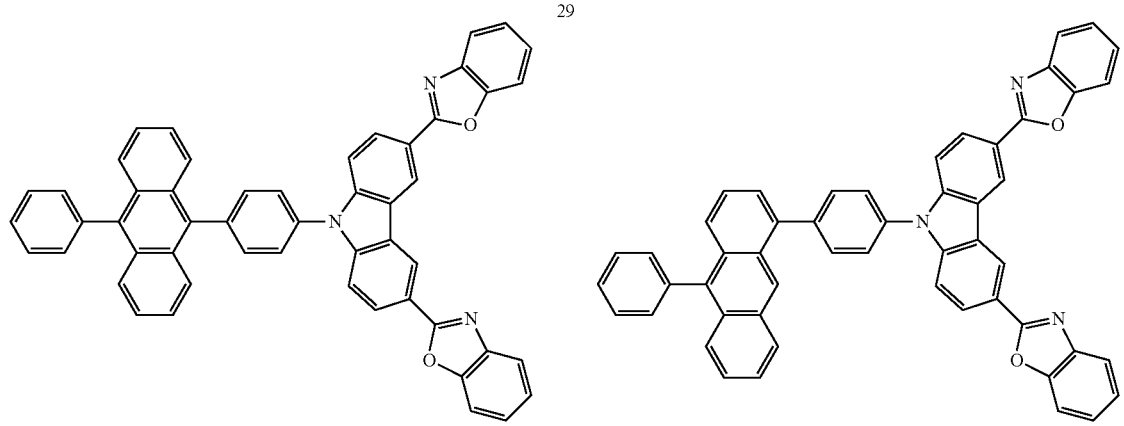
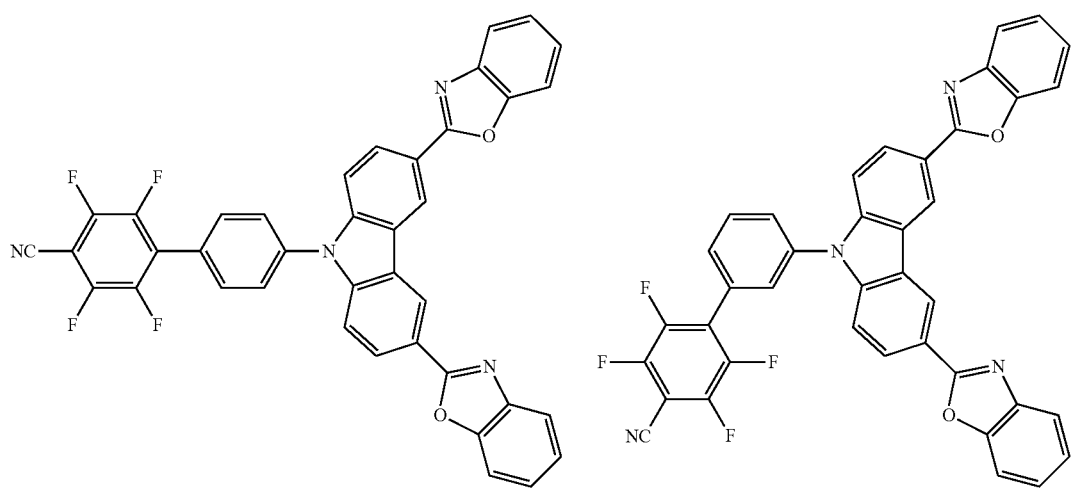

-continued
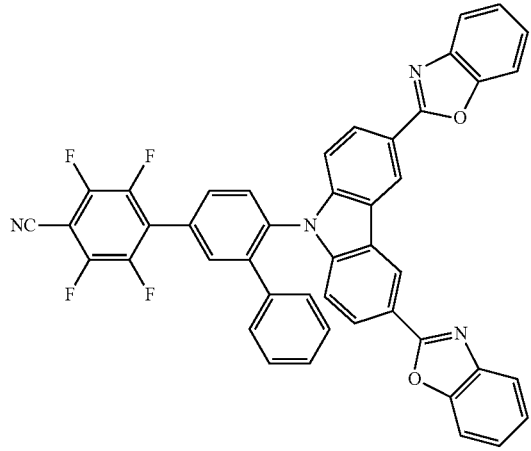
33
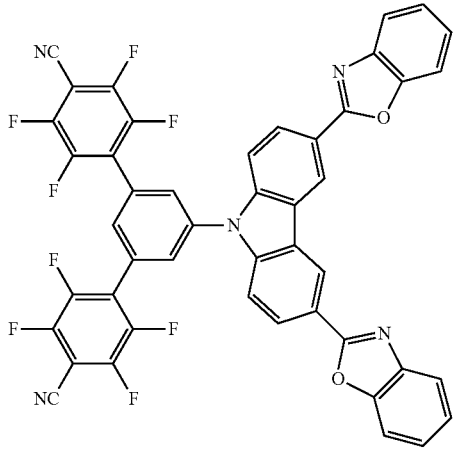
34
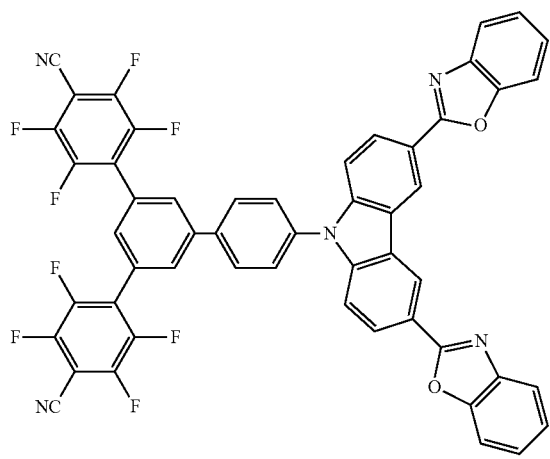
35
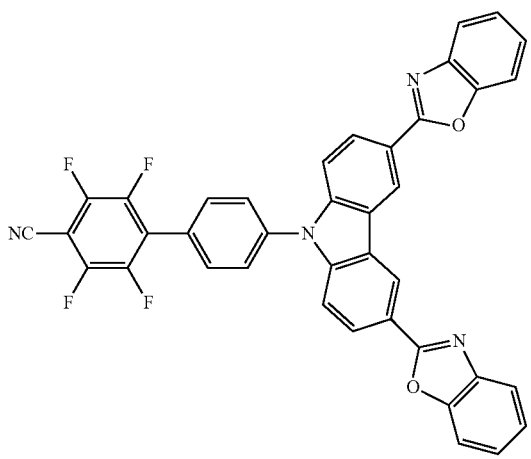
36
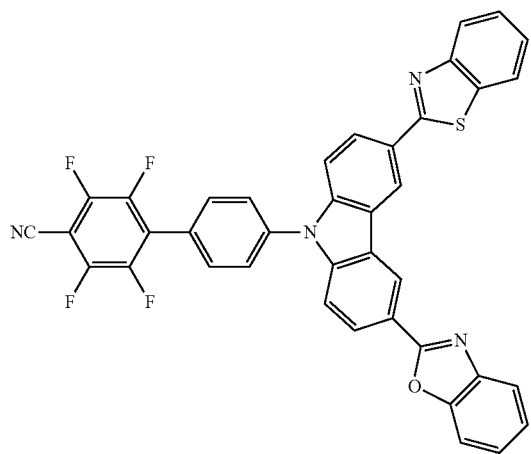
37
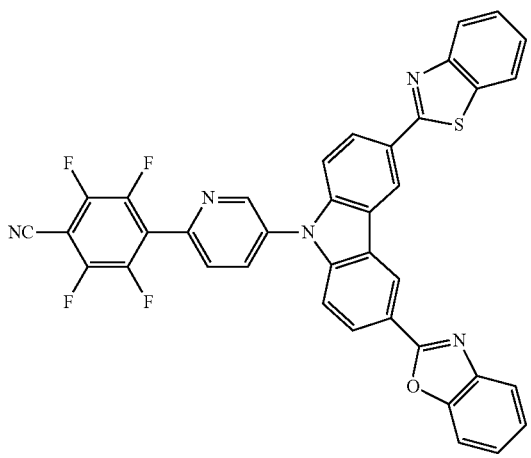
38

-continued
39
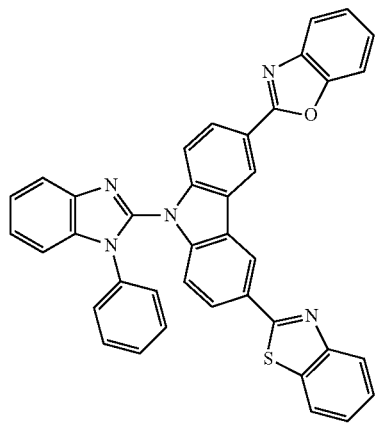
40
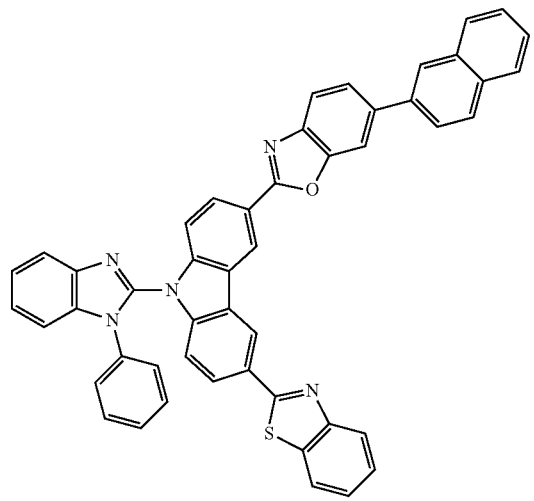
41
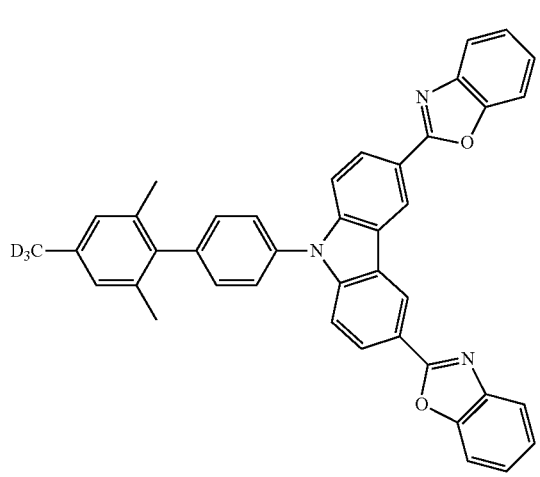
42
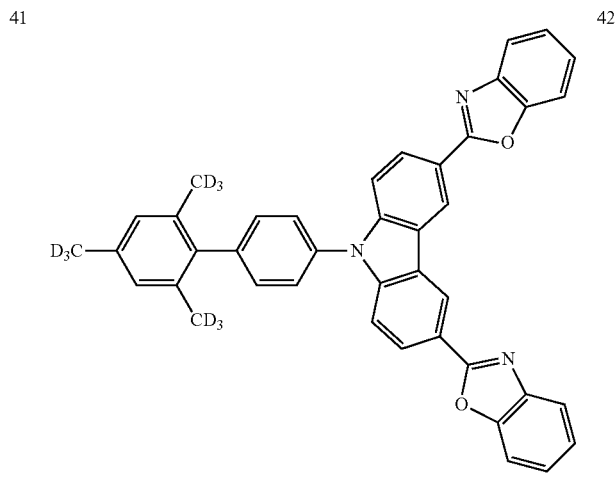
43
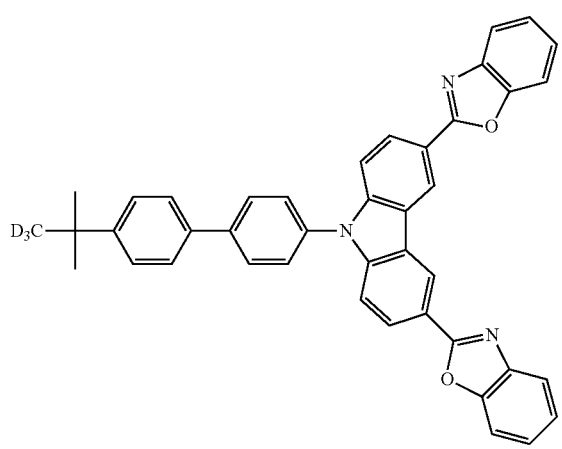
44
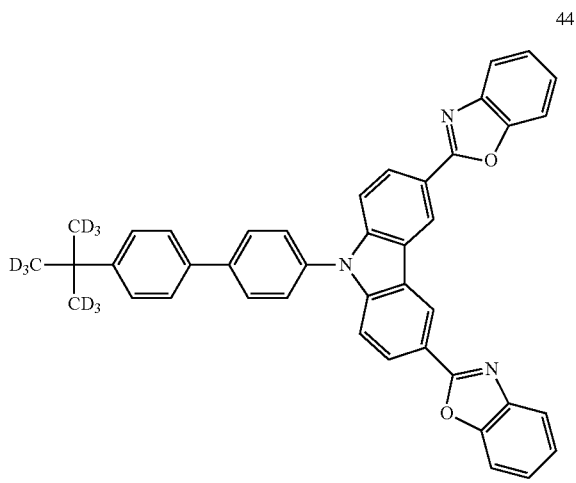

-continued
45
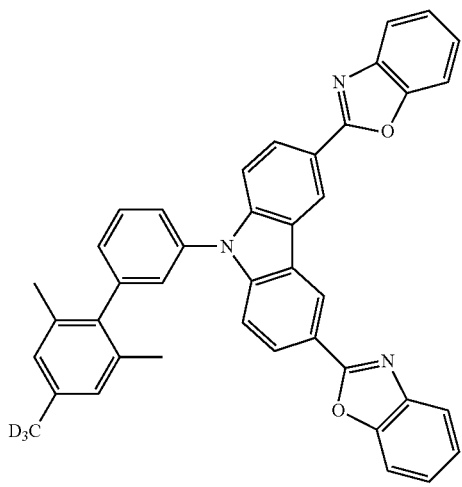
46
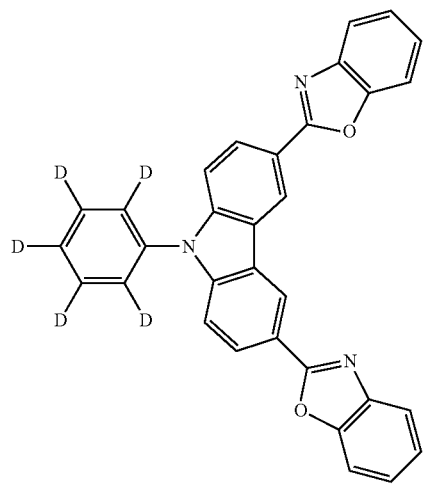
47
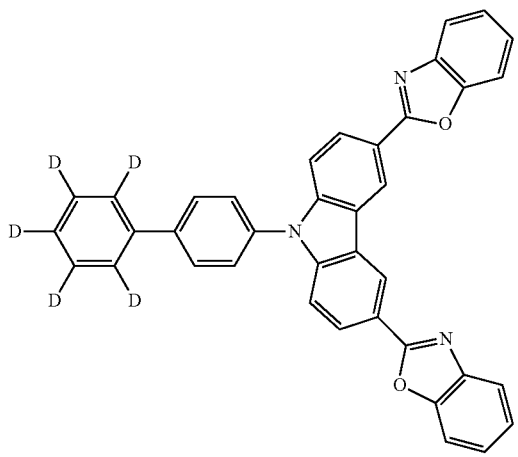
48
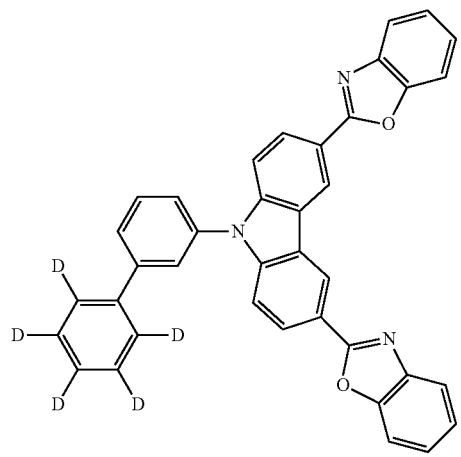
49
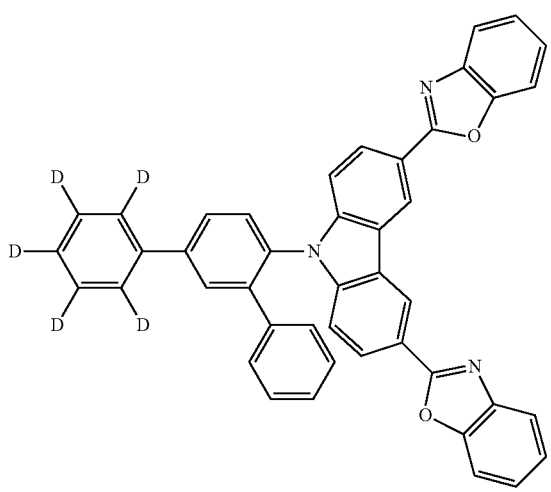
50
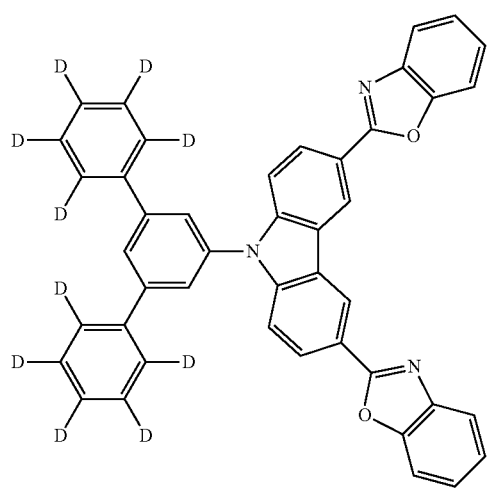

-continued
51
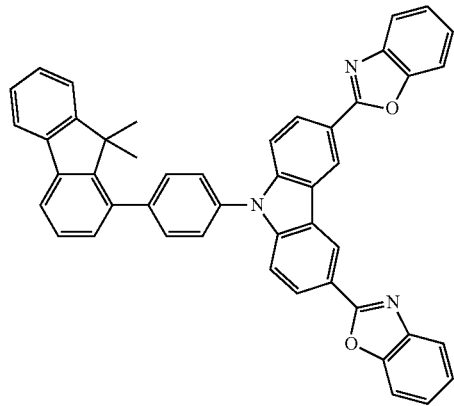
52
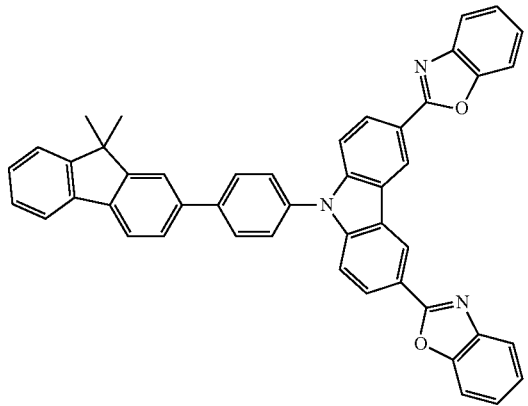
53
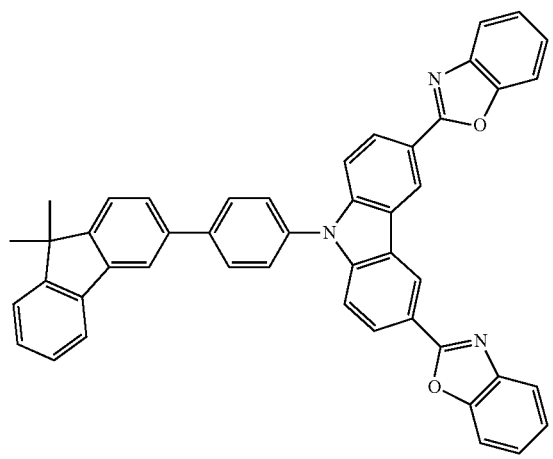
54
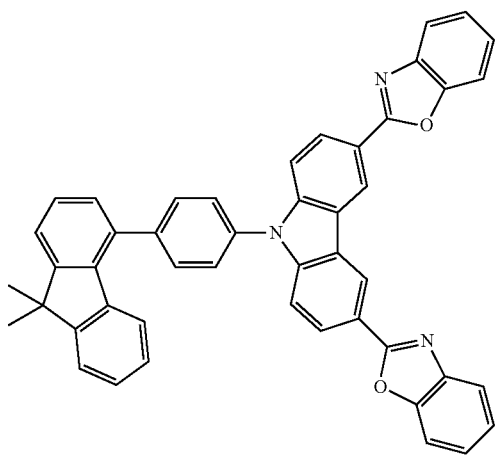
55
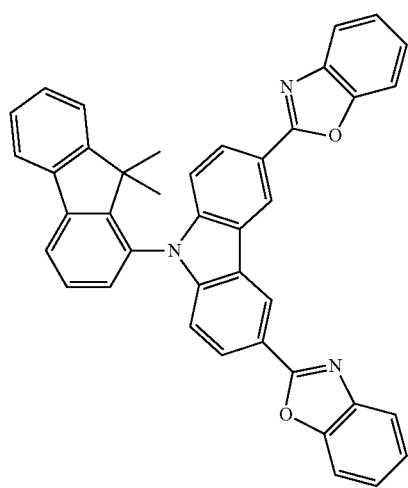
56
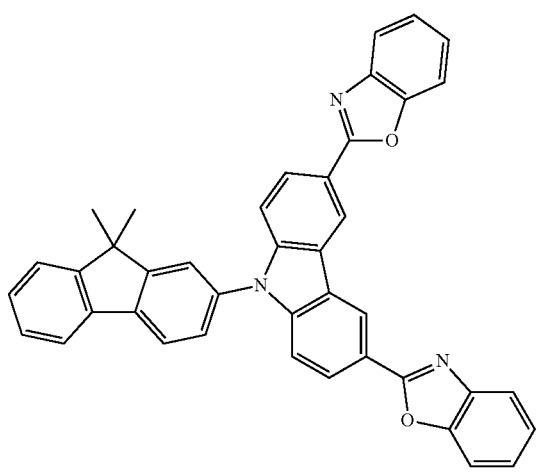

-continued
57
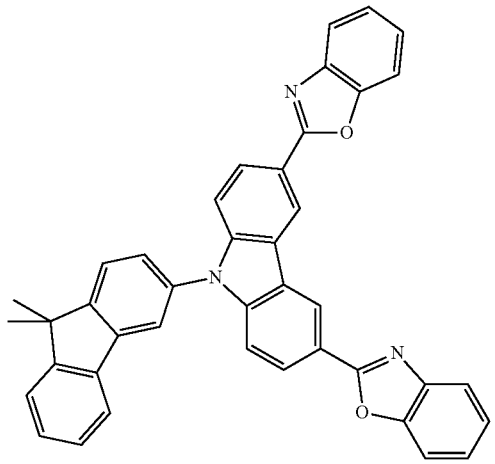
58
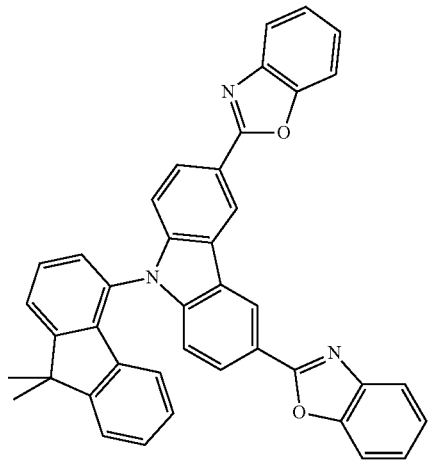
59
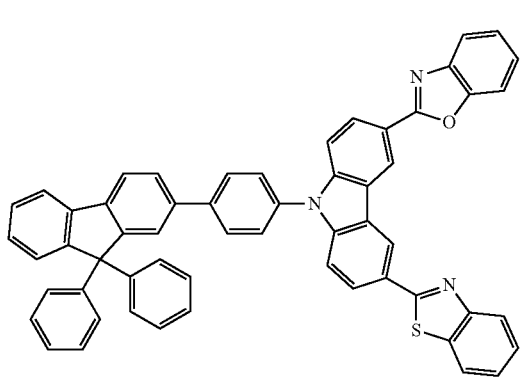
60
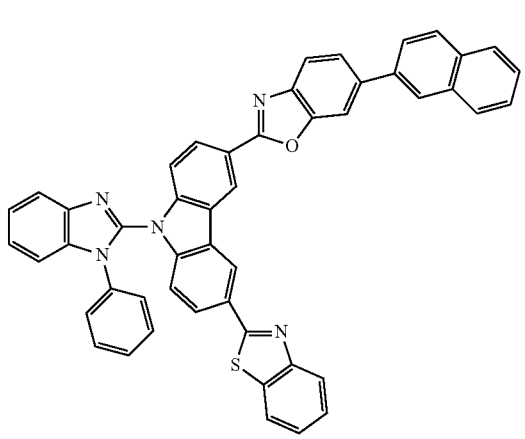
61
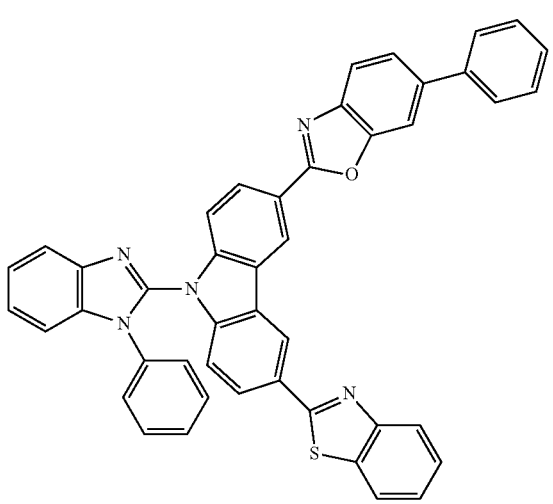
62
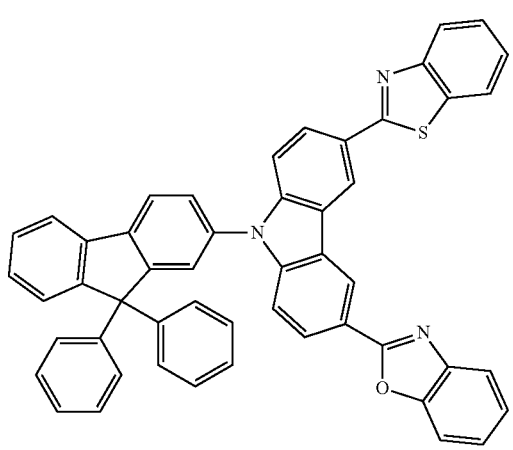

-continued
63 64
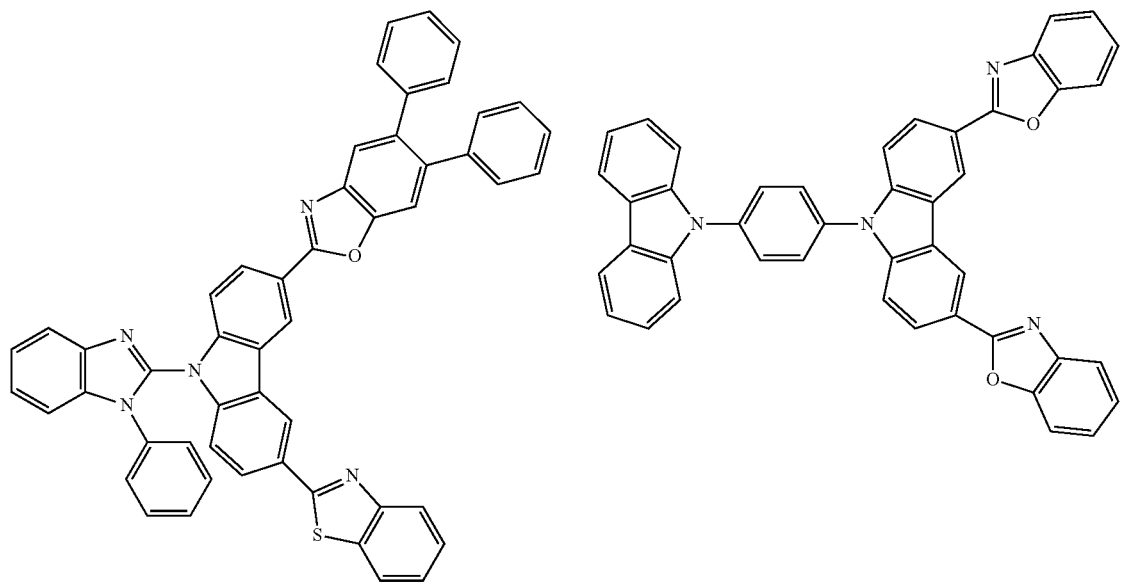
65 66
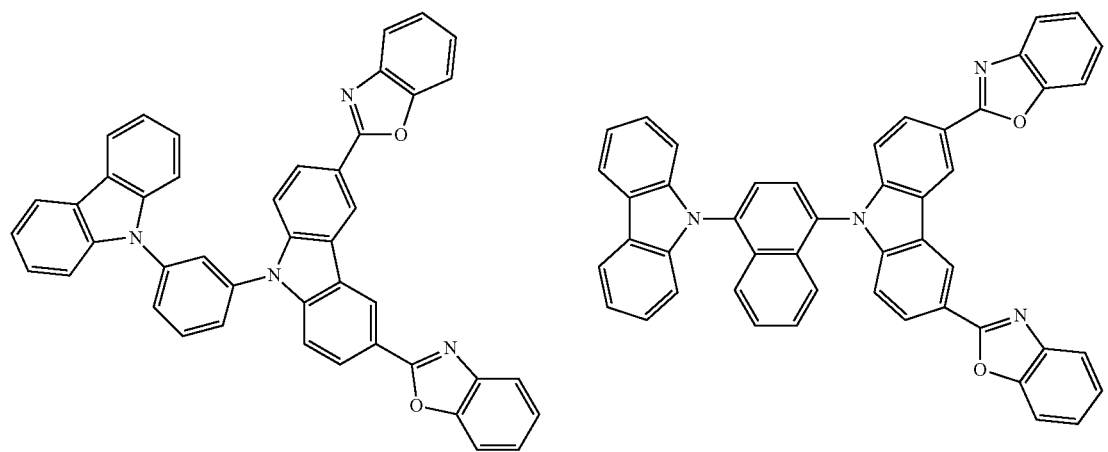
67 68
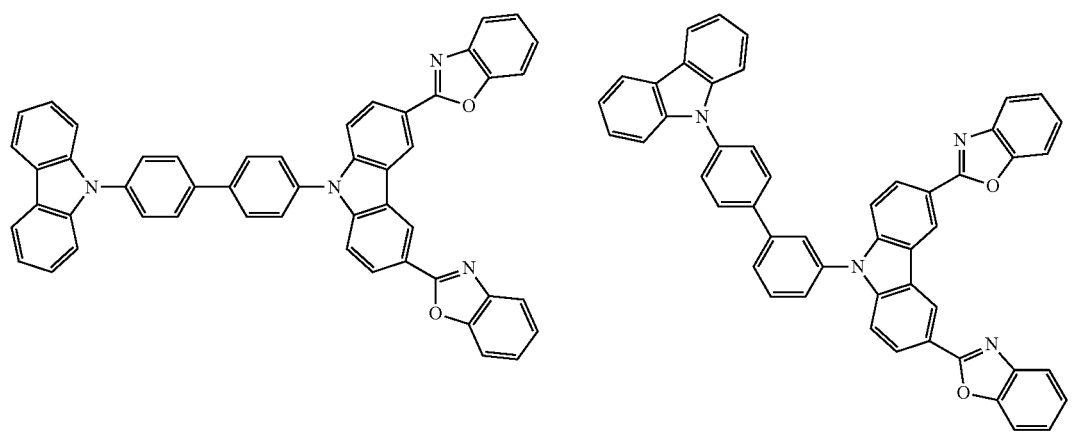

-continued
69
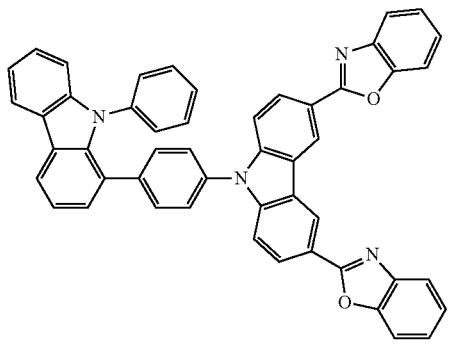
70
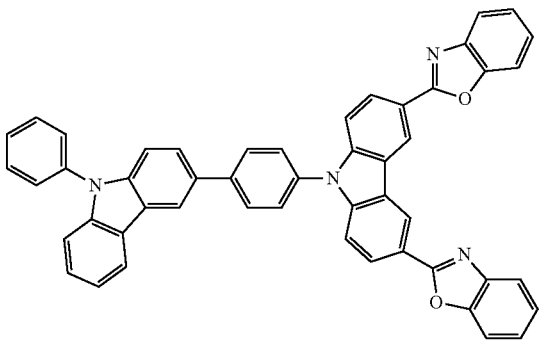
71
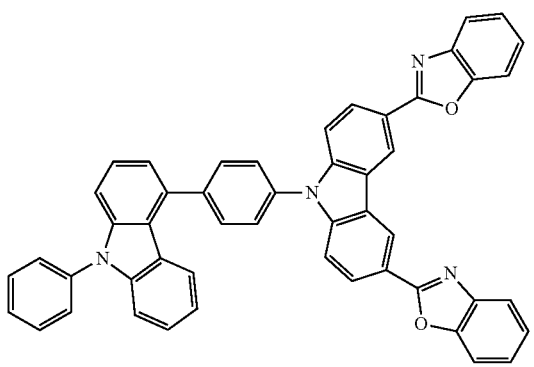
72
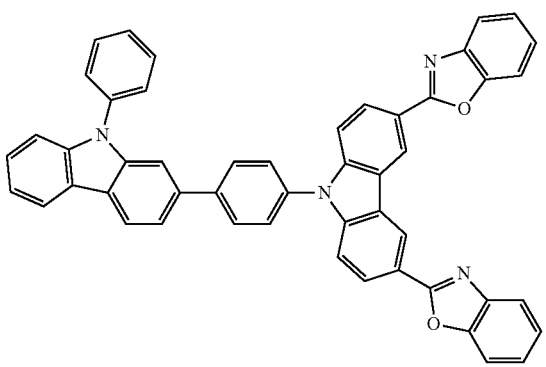
73
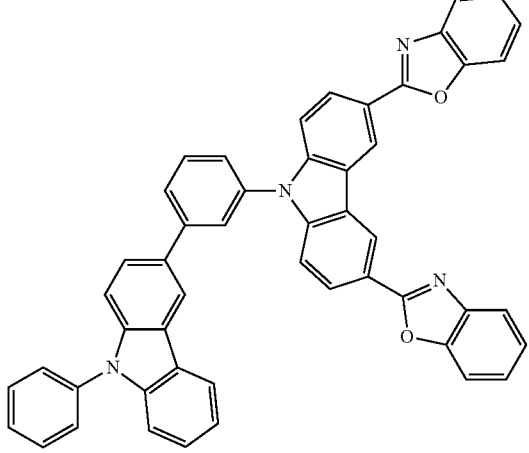
74
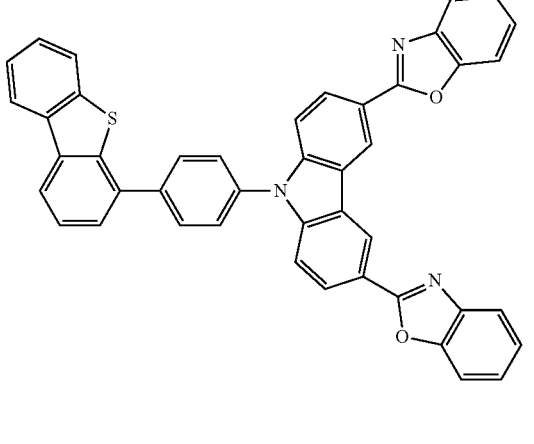
75
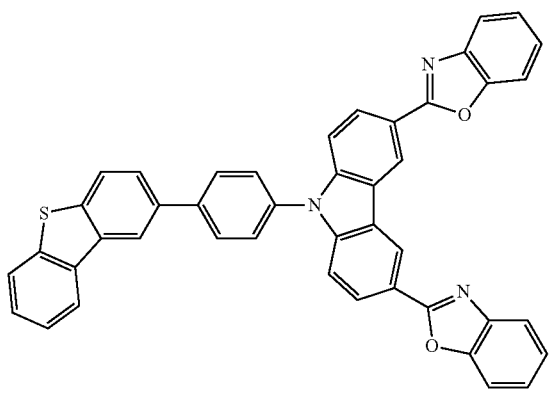
76
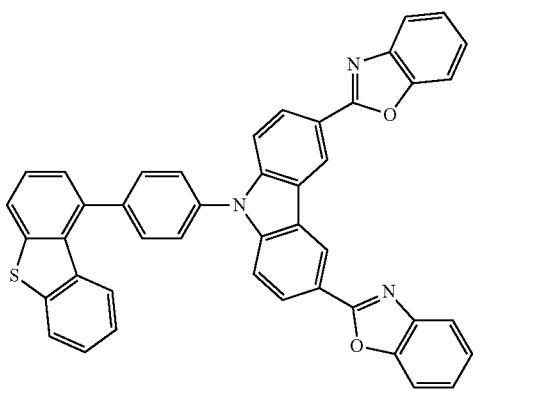

-continued
77
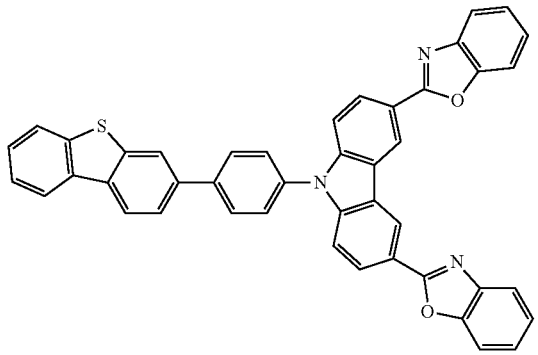
78
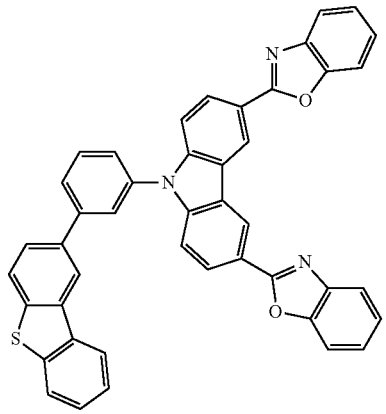
79
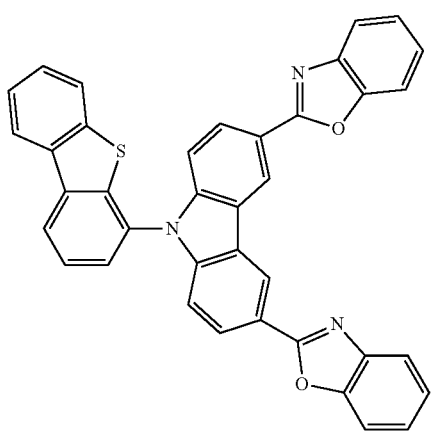
80
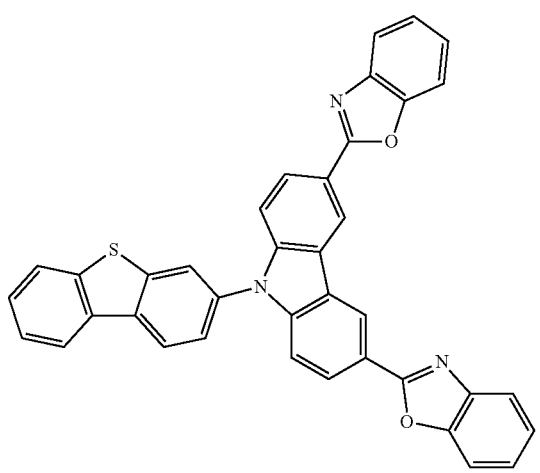
81
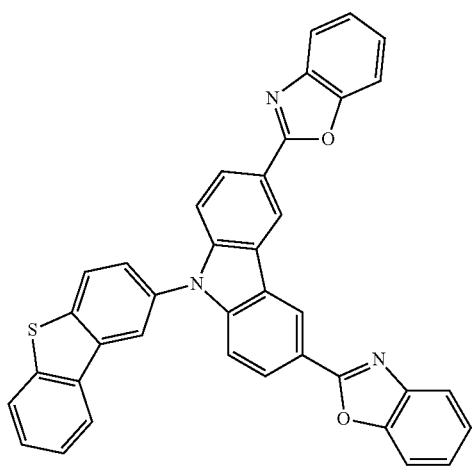
82
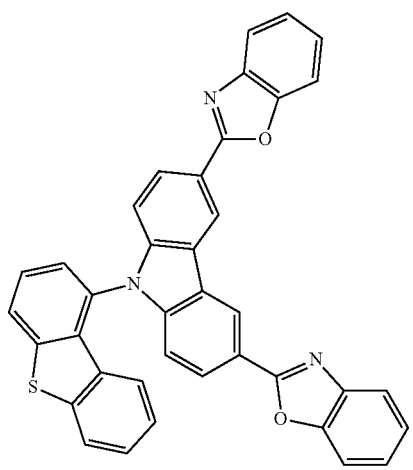

-continued
83
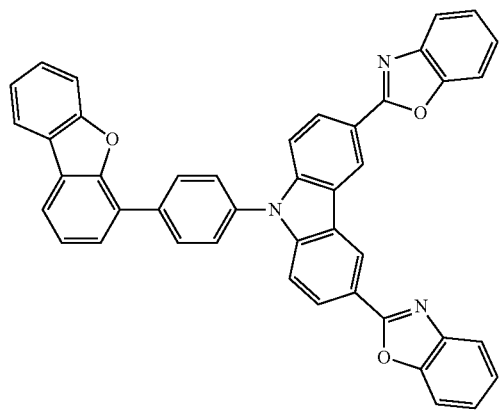
84
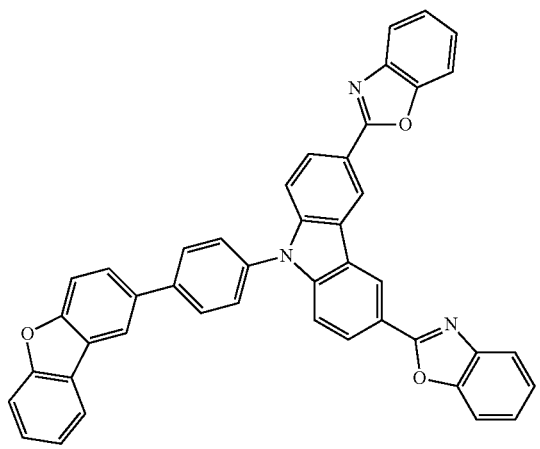
85
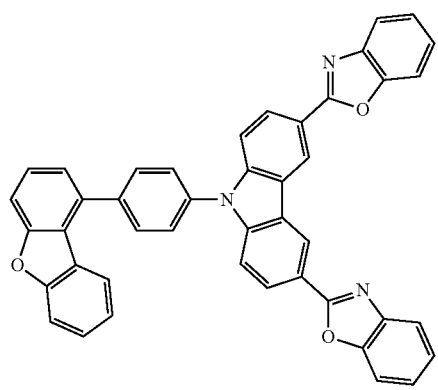
86
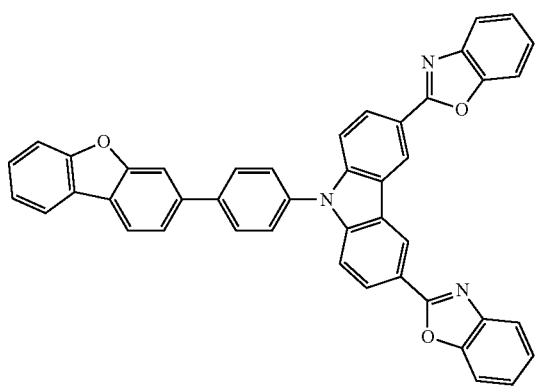
87
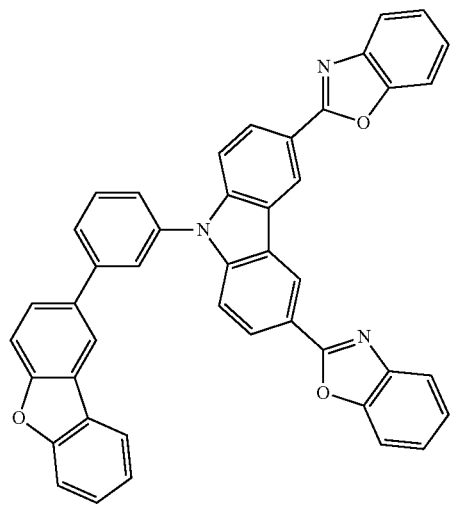
88
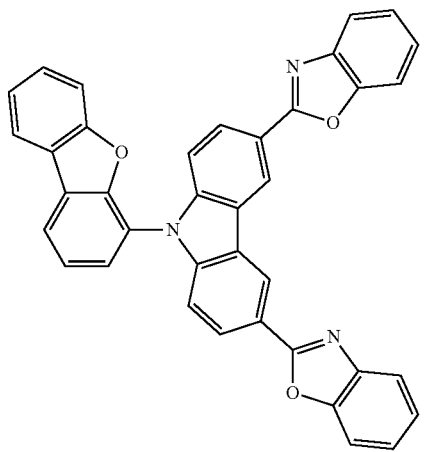

-continued
89
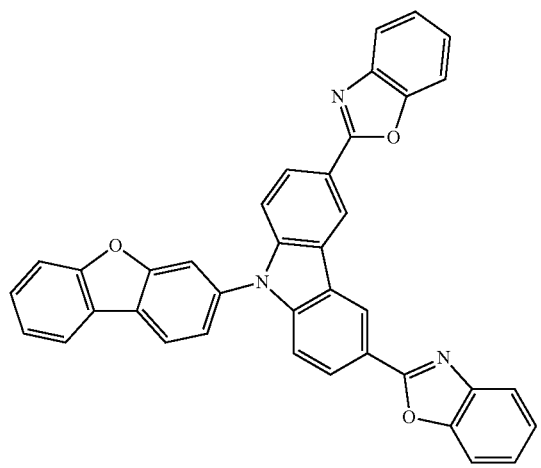
90
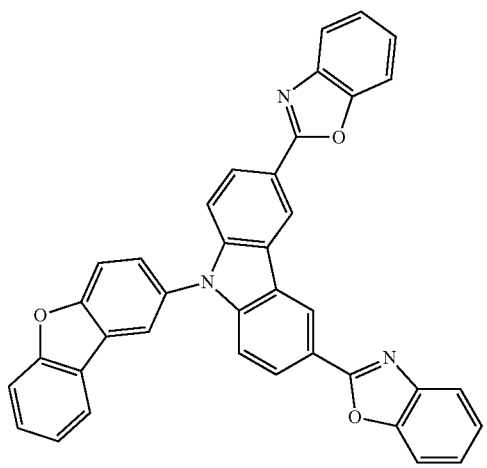
91
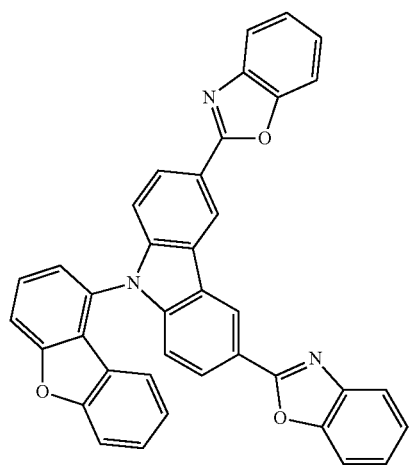
92
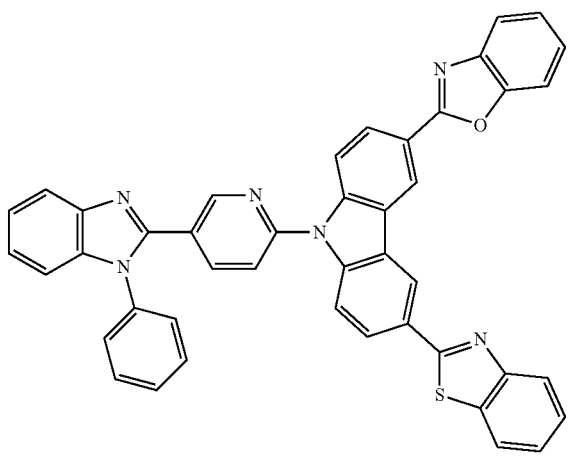
93
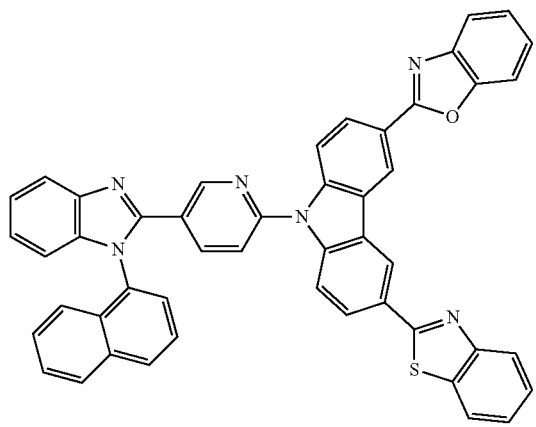
94
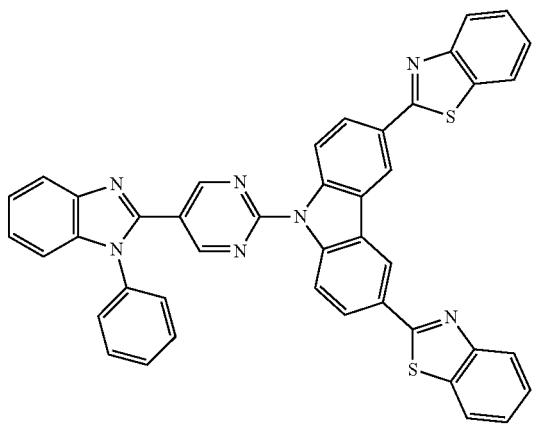

-continued
95
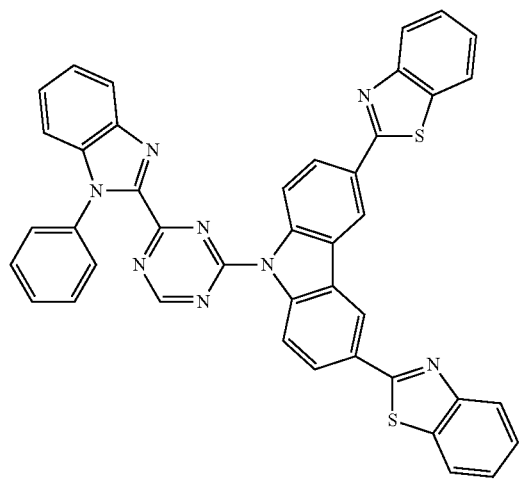
96
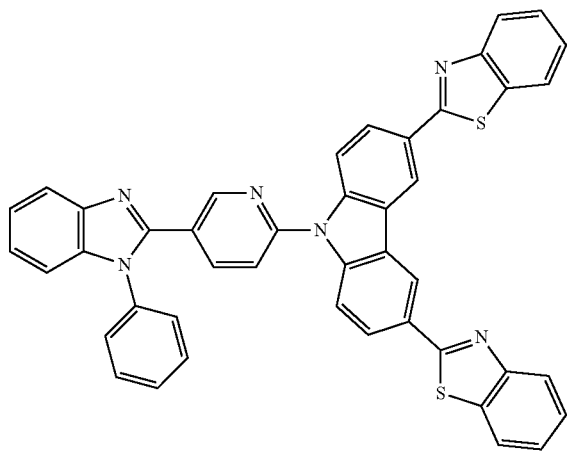
97
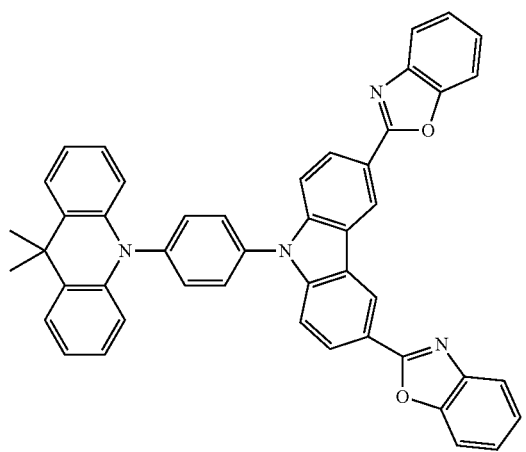
98
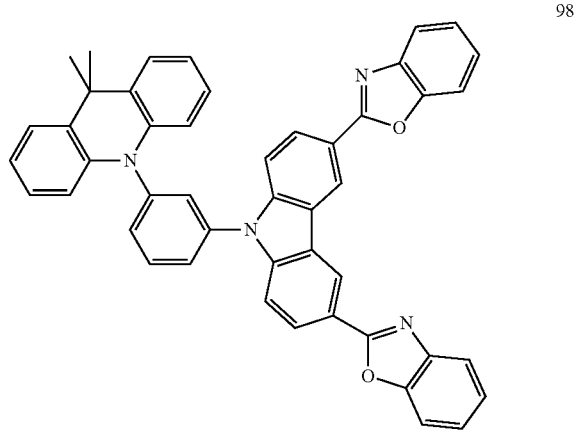
99
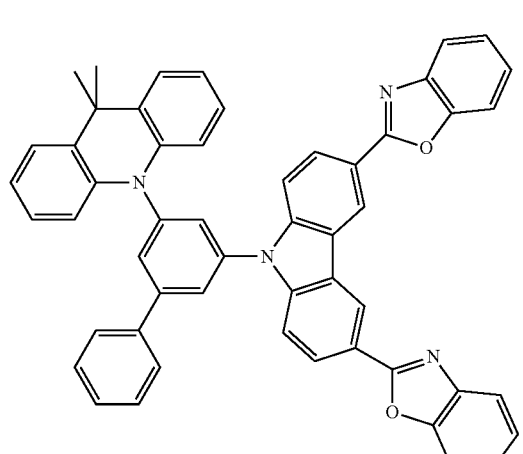
100
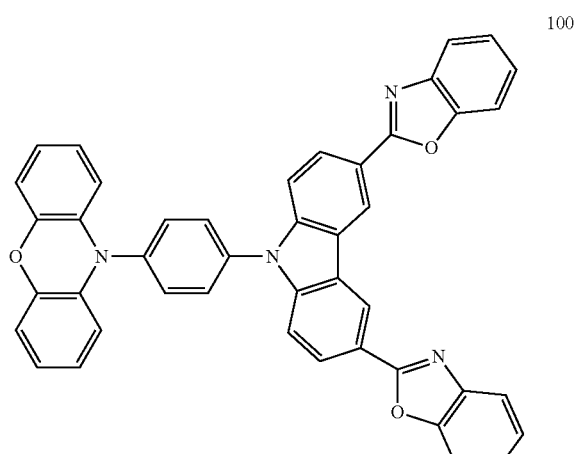

-continued
101
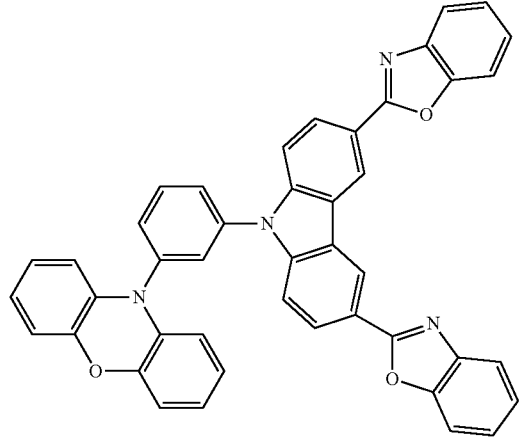
102
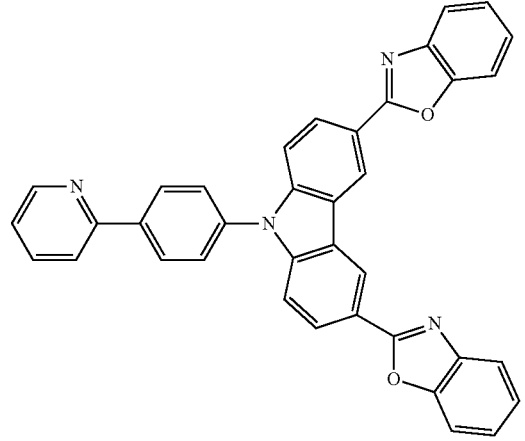
103
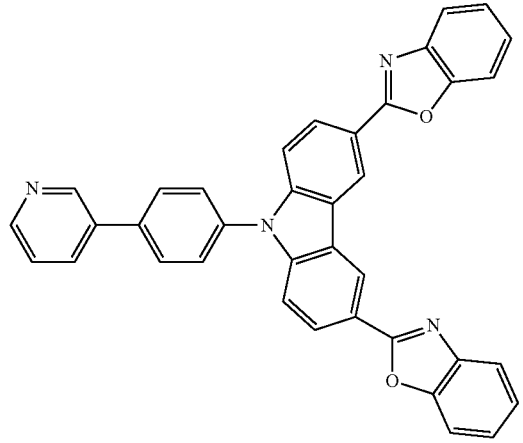
104
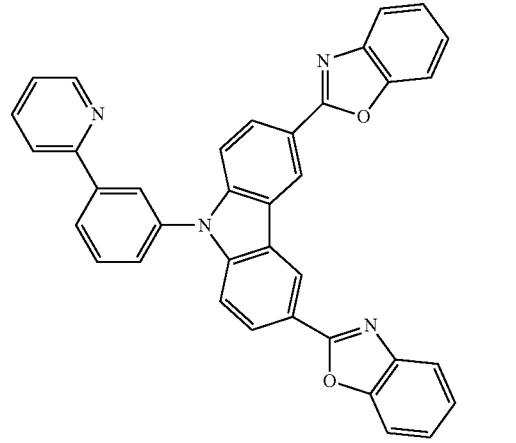
105
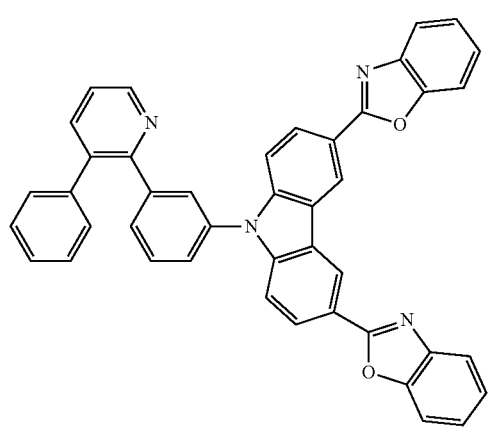
106
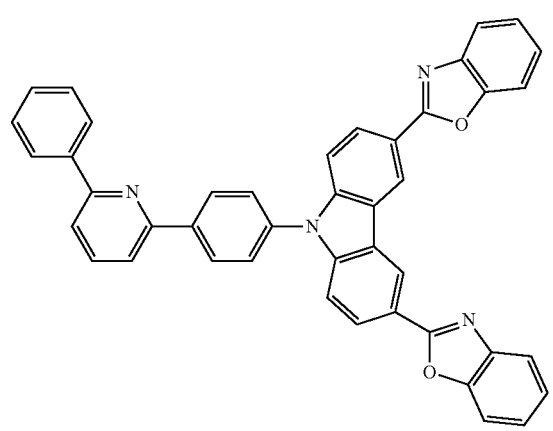

-continued
107
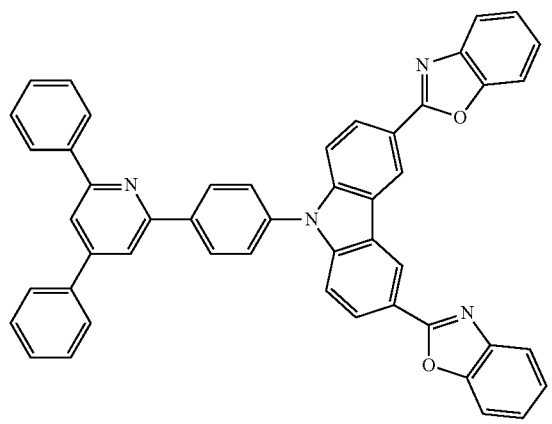
108
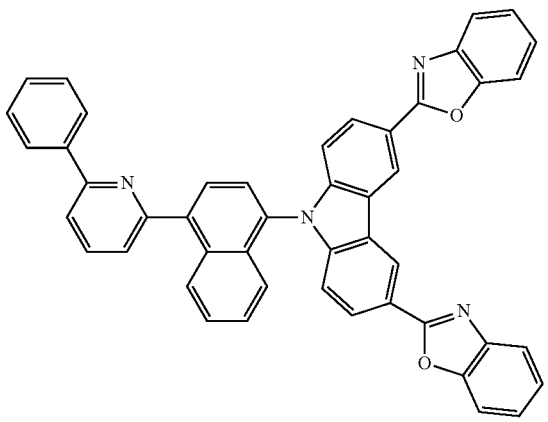
109
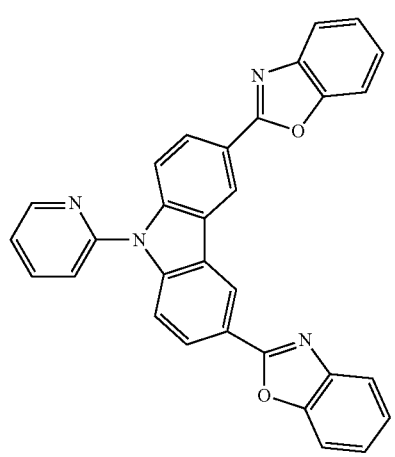
110
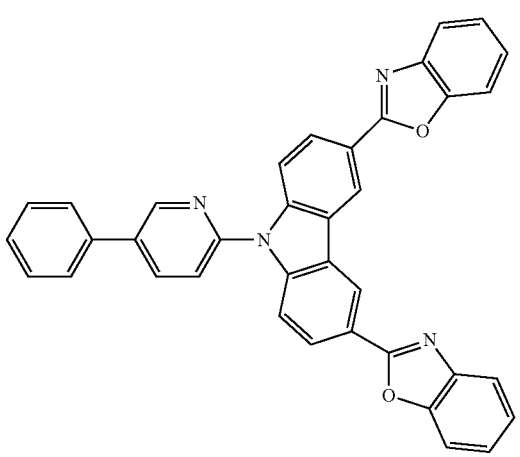
111
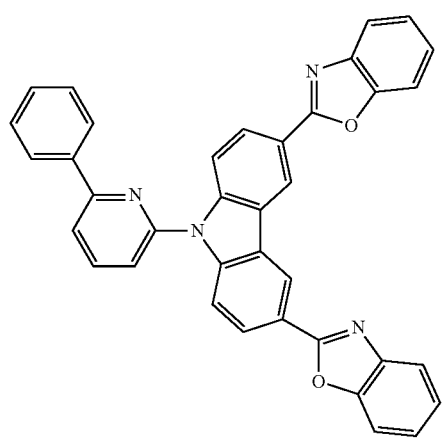
112
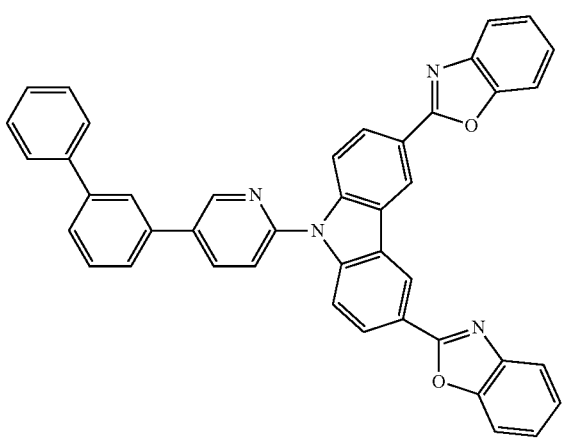

-continued
113
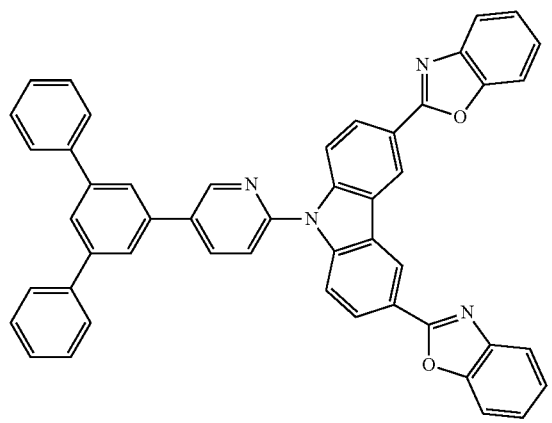
114
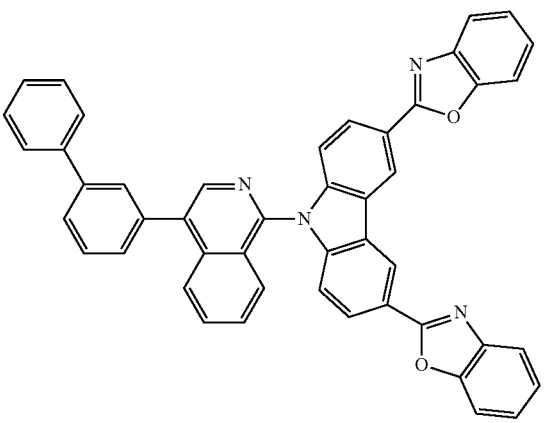
115
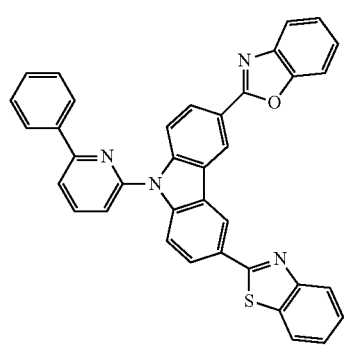
116
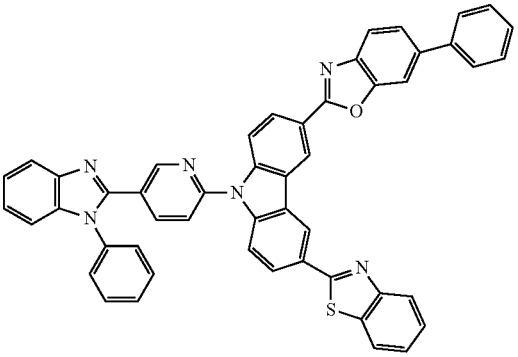
117
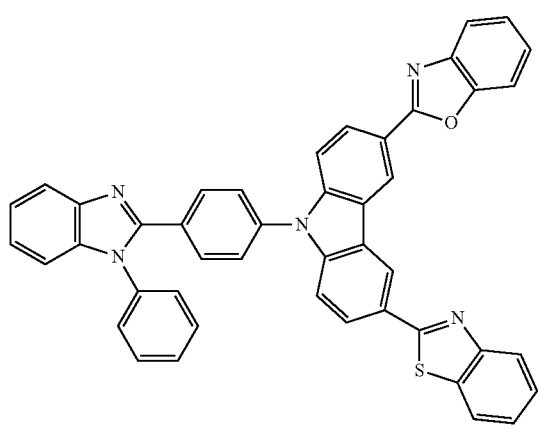
118
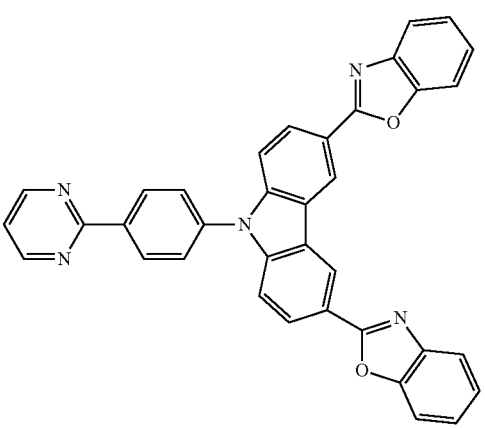
119
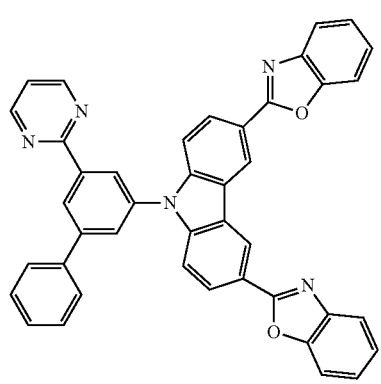
120
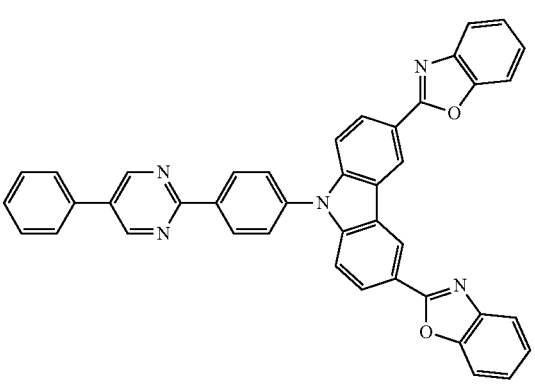

-continued
121 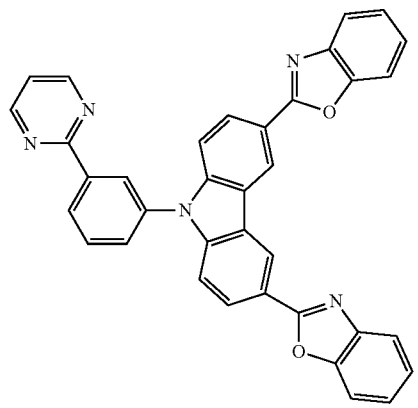
122 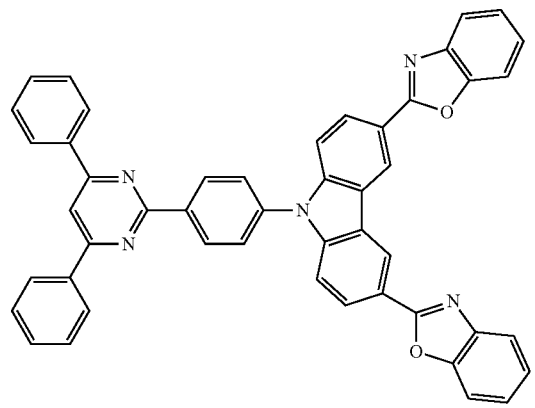
123 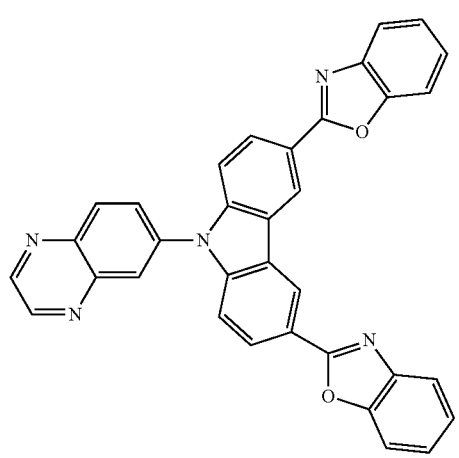
124 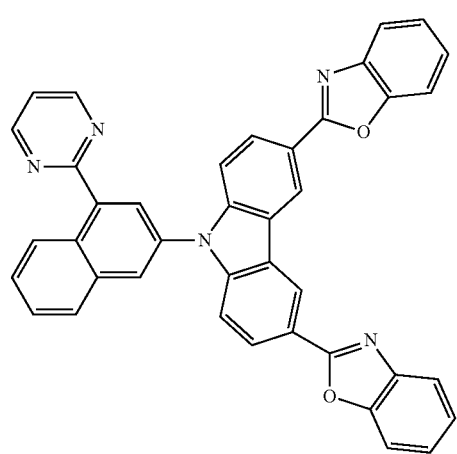
125 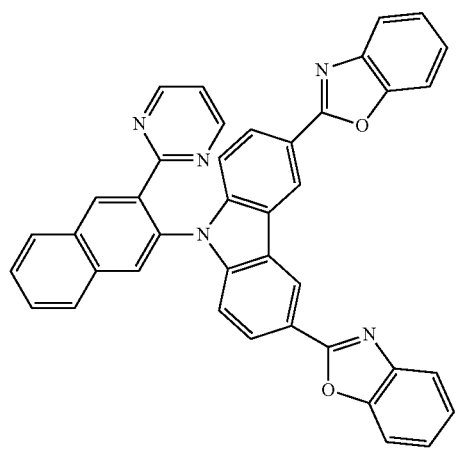
126 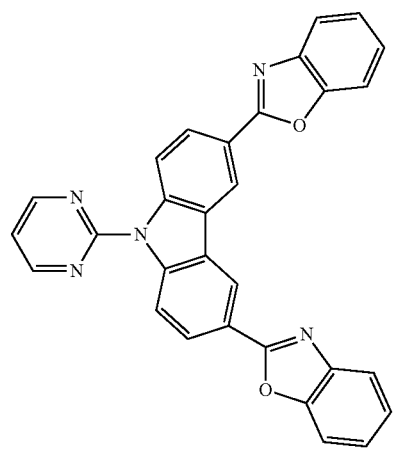

-continued
127 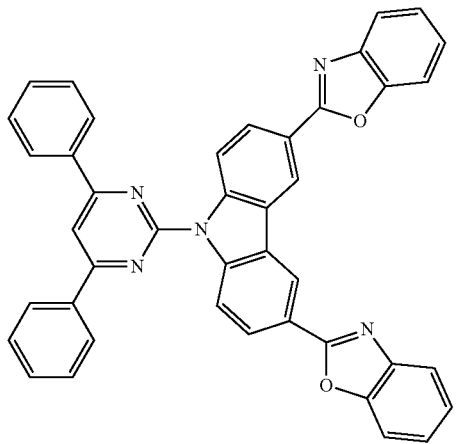
128 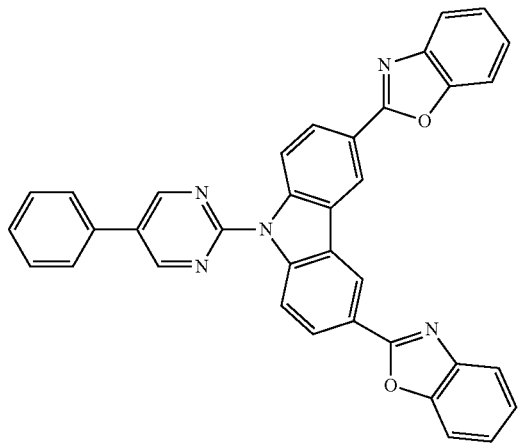
129 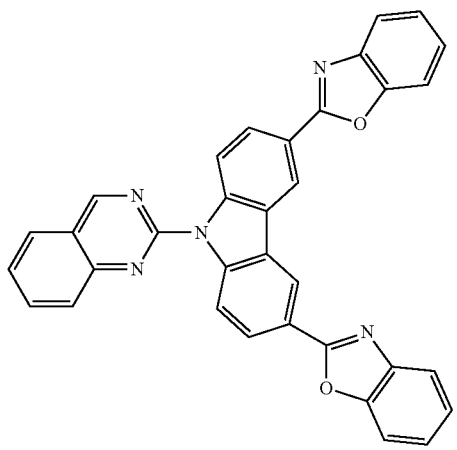
130 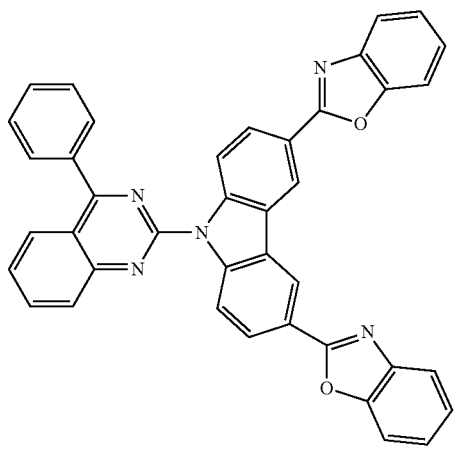
131 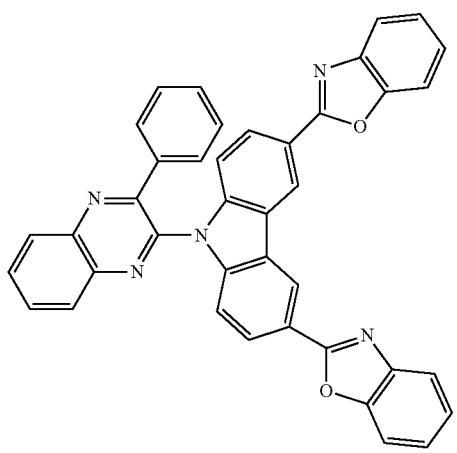
132 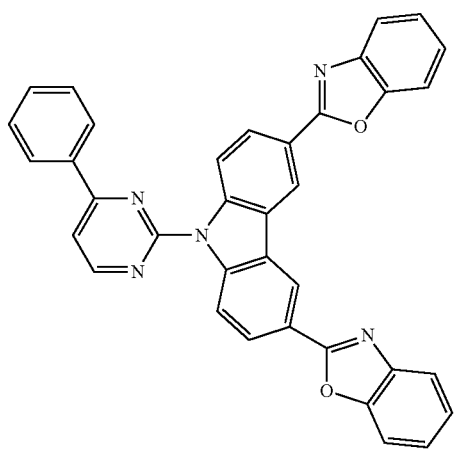

-continued
133
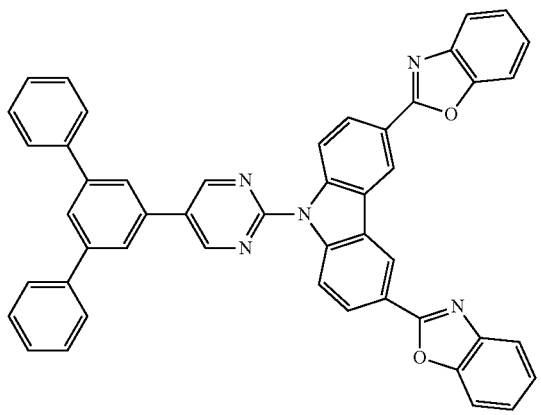
134
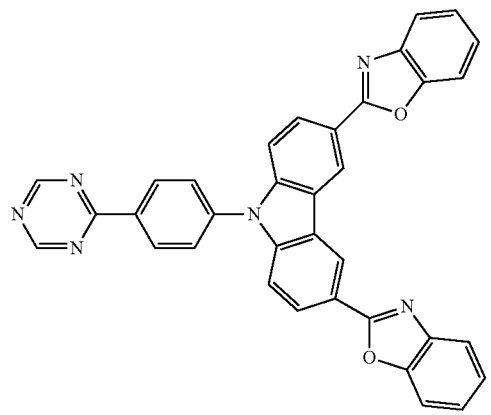
135
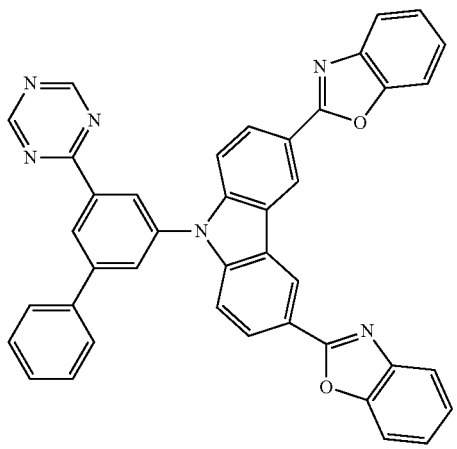
136
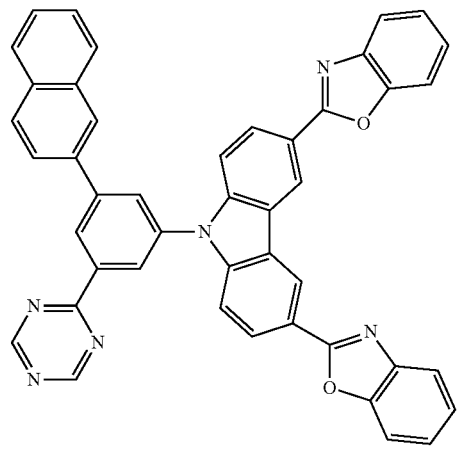
137
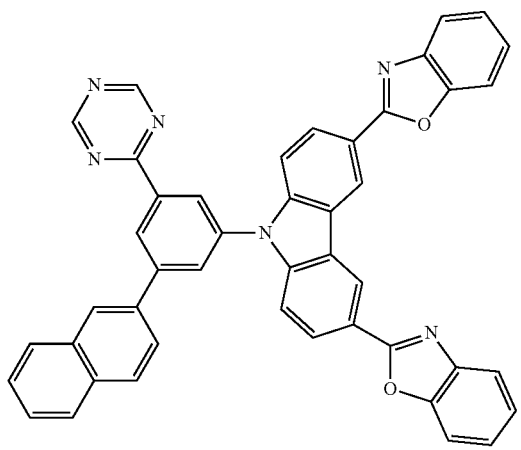
138
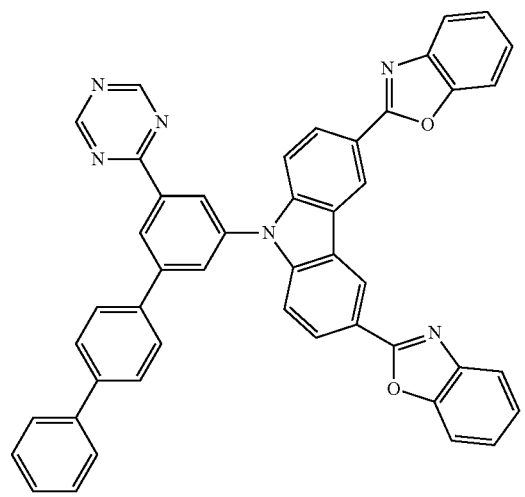

139
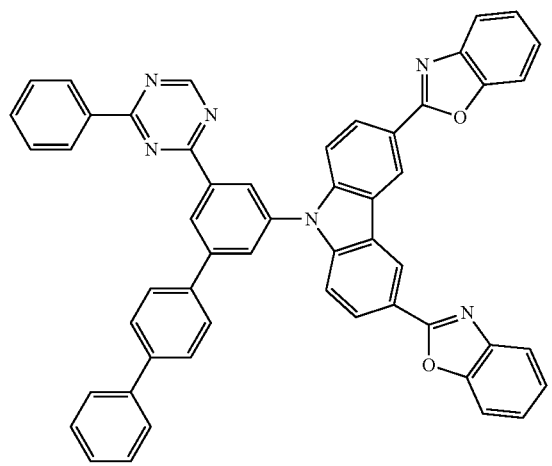
140
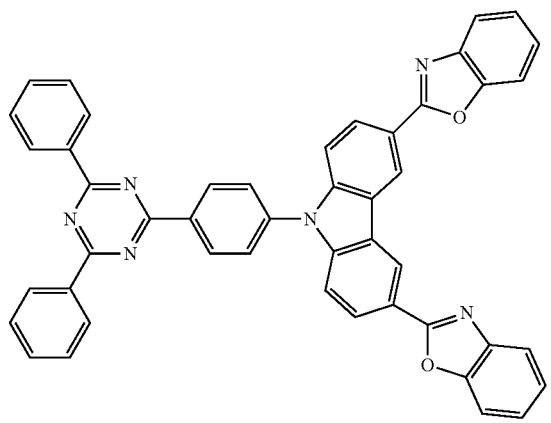
141
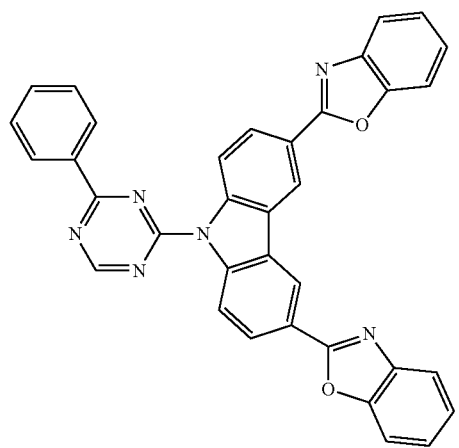
142
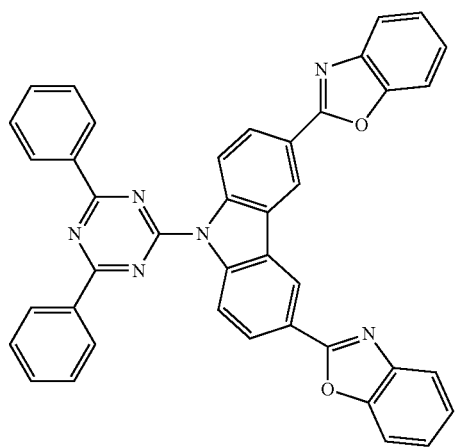
143
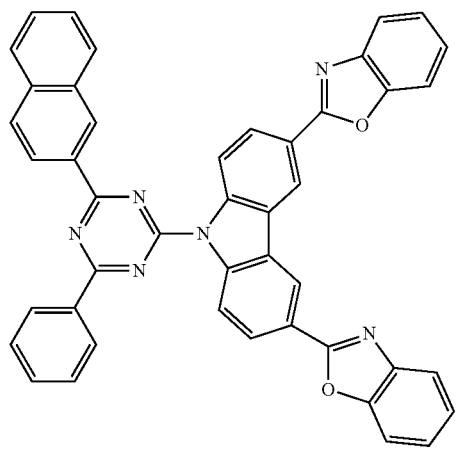
144
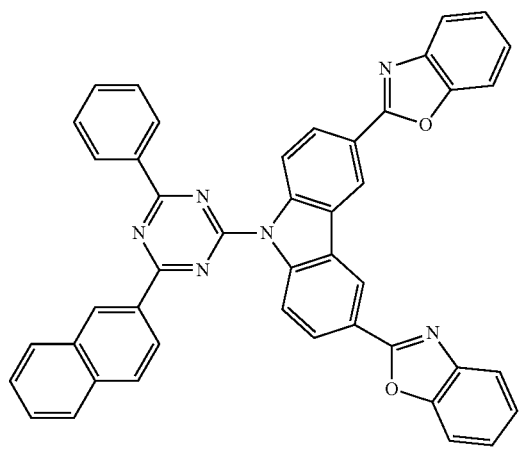

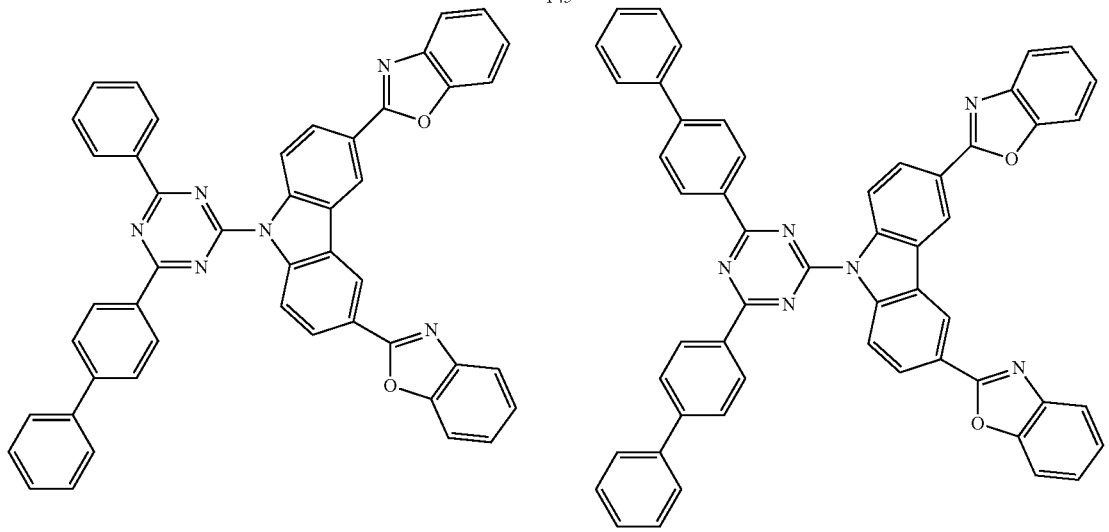
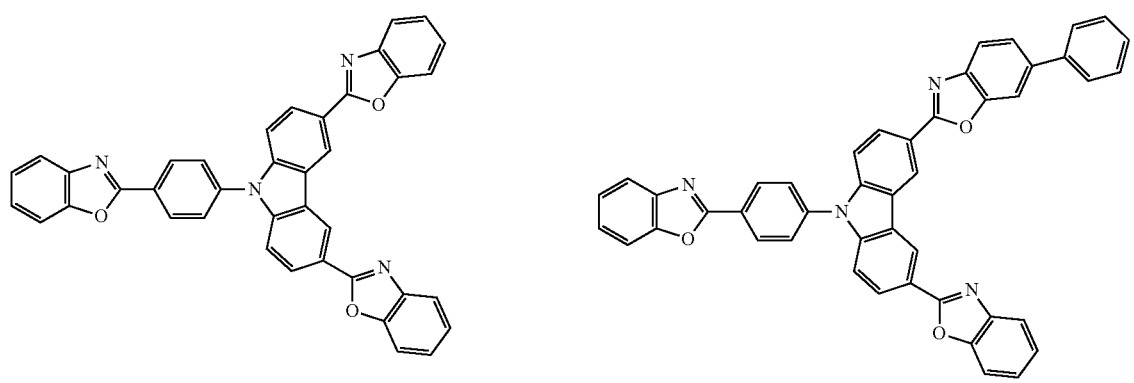
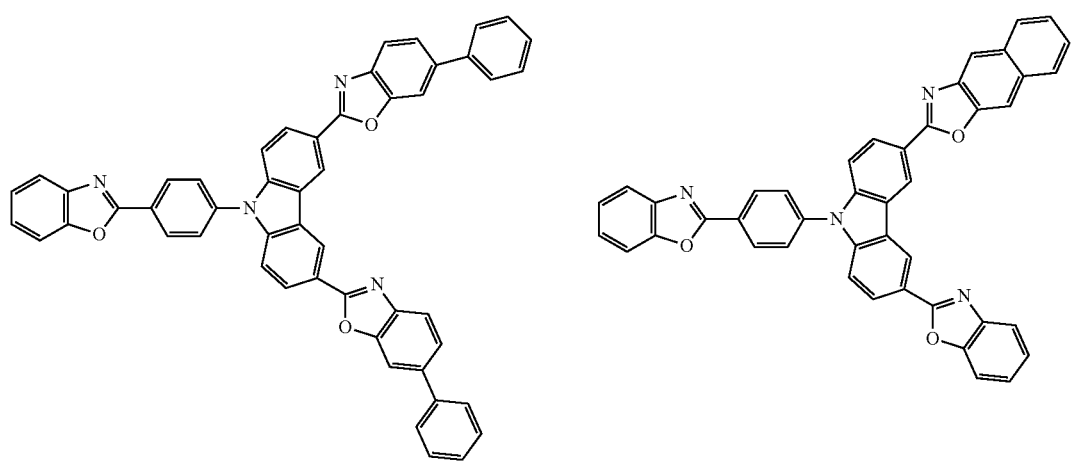

-continued
151
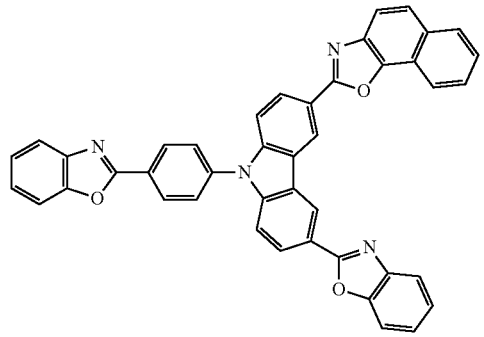
152
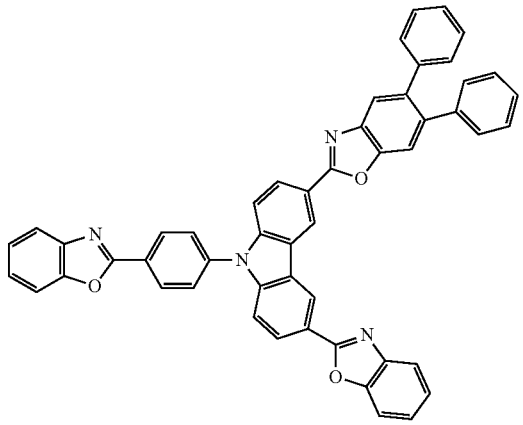
153
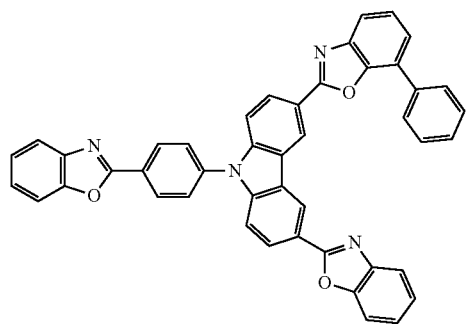
154
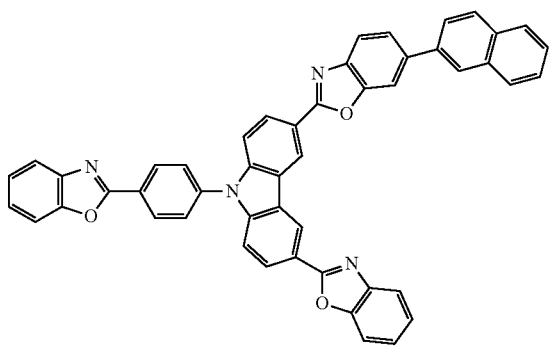
155
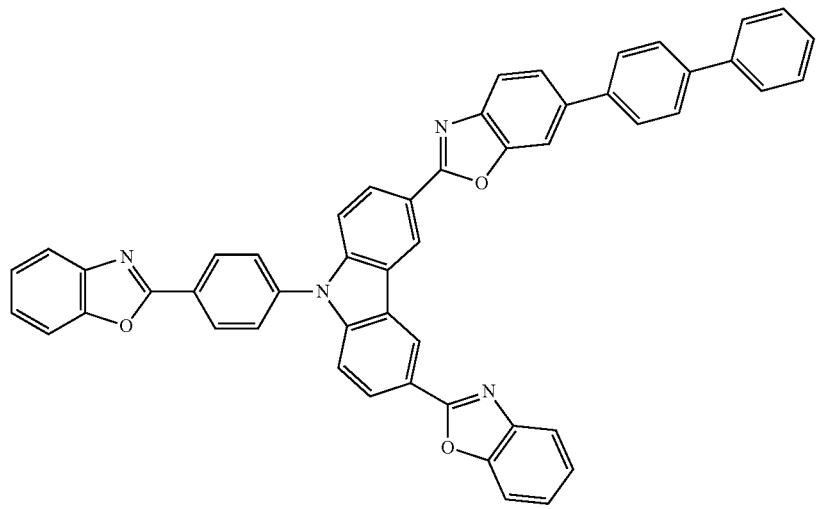

-continued
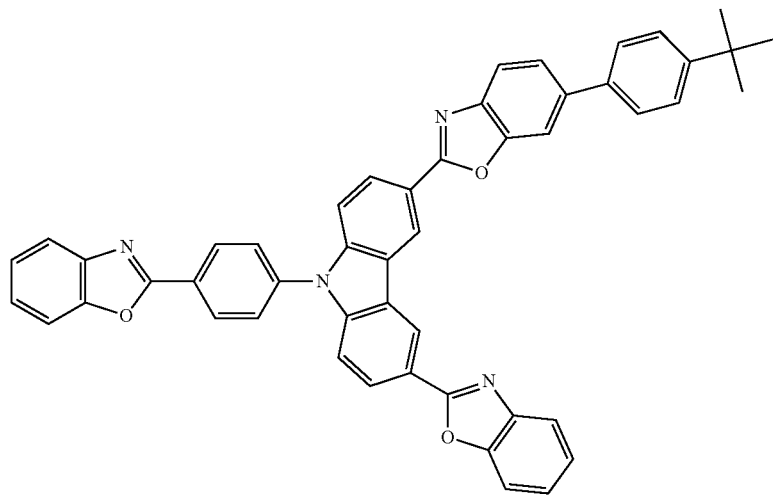
156
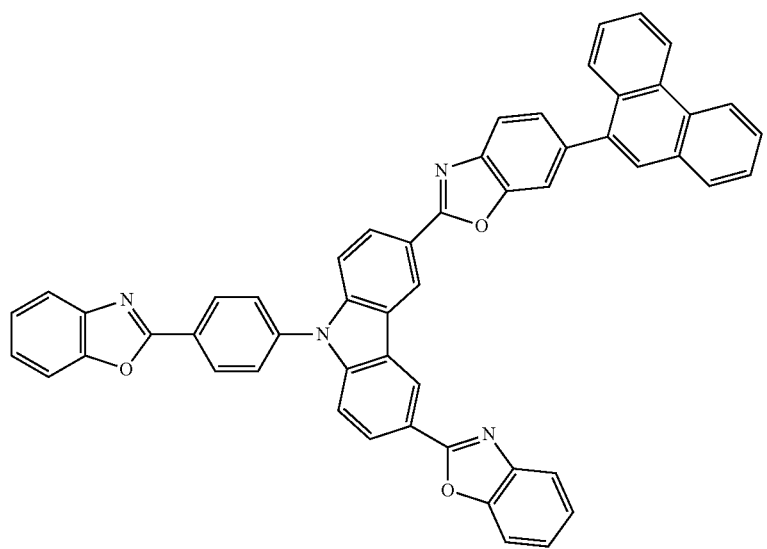
157
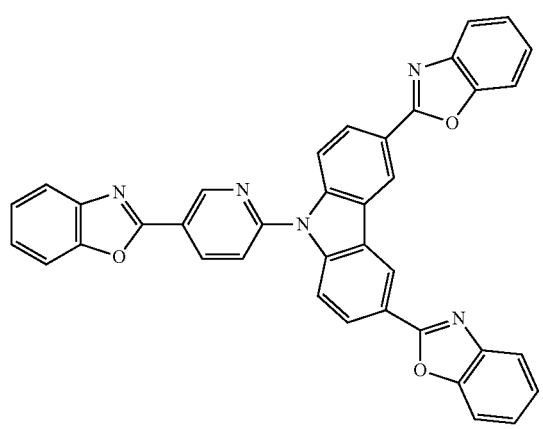
158
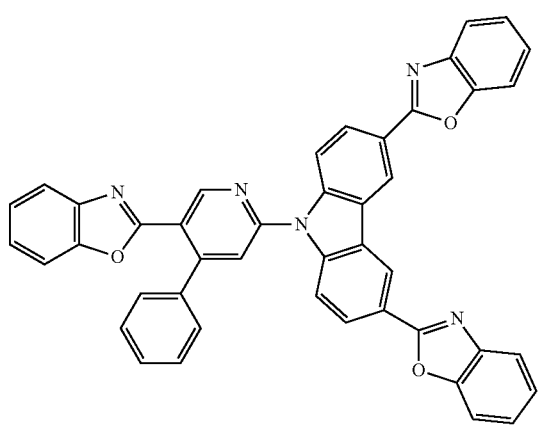
159

160 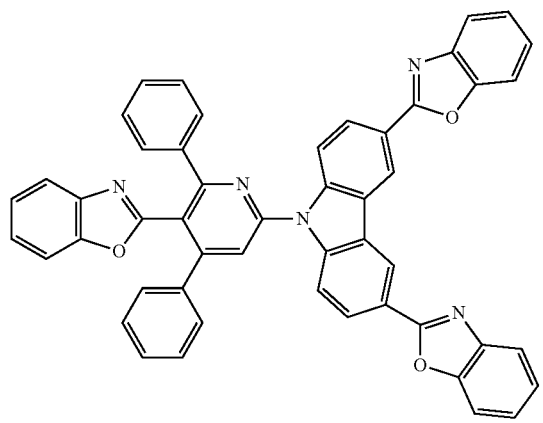
161 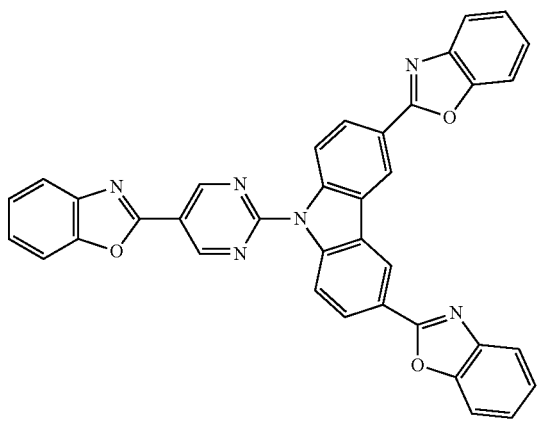
162 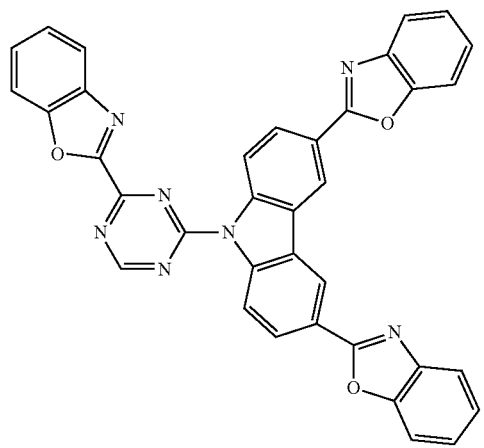
163 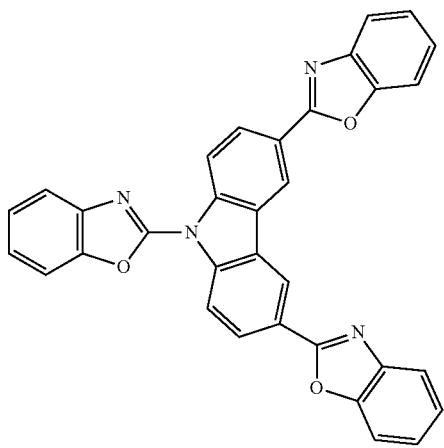
164 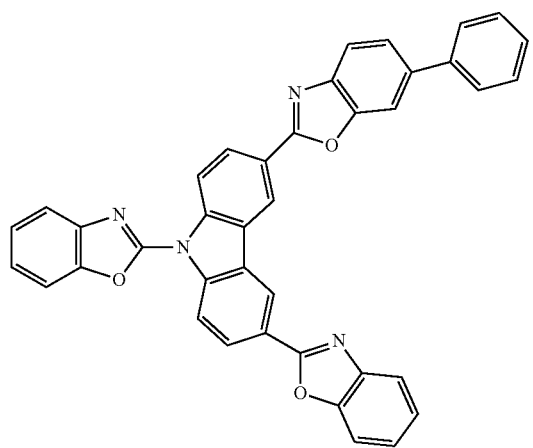
165 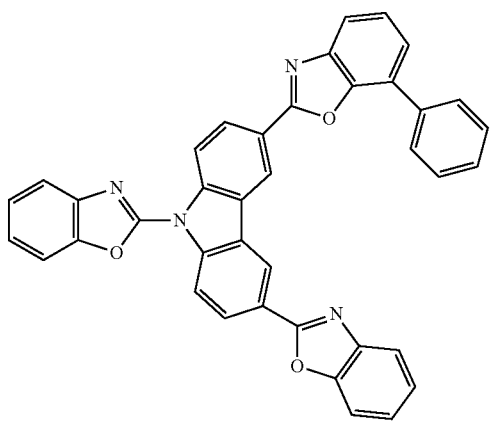

-continued
166
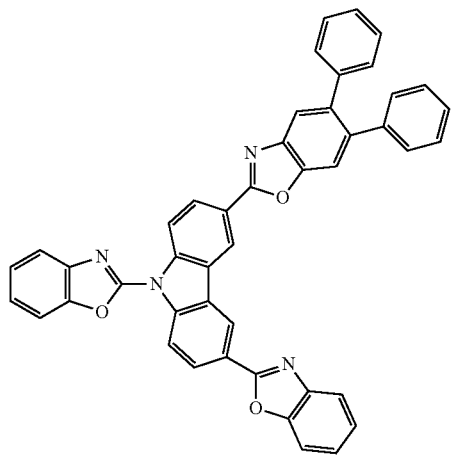
167
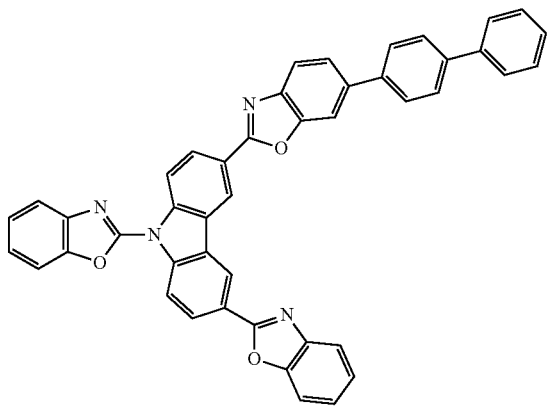
168
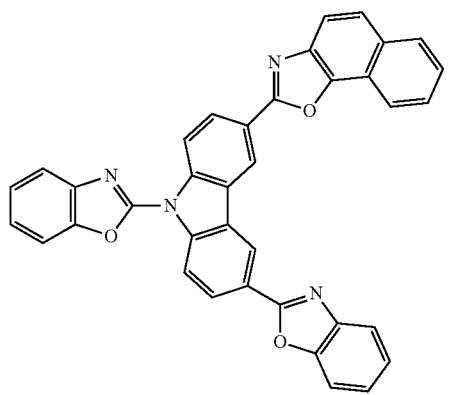
169
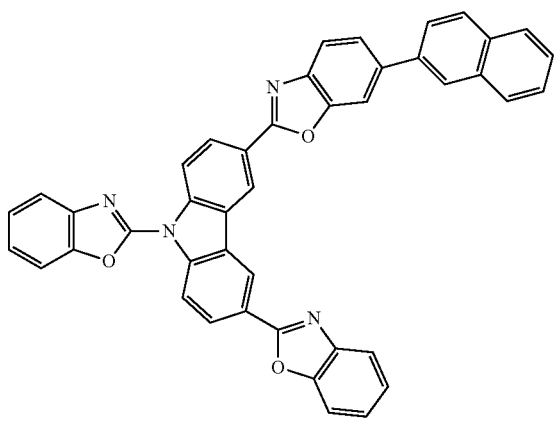
170
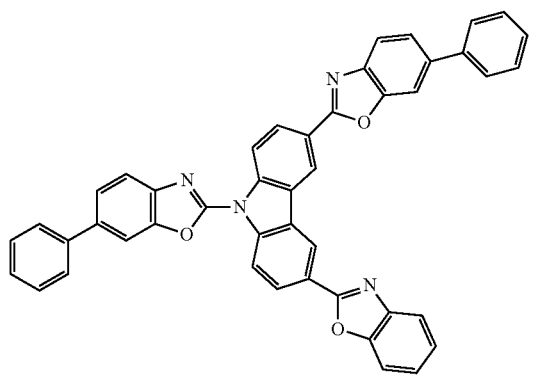
171
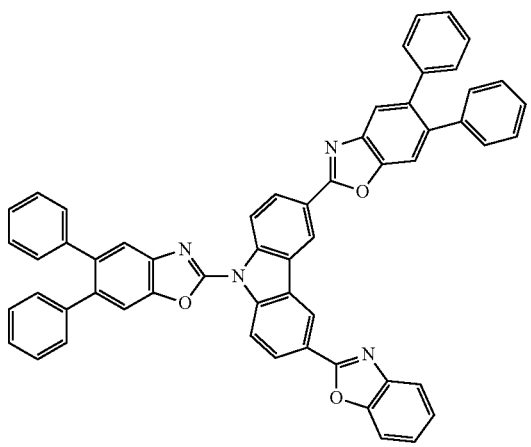

172
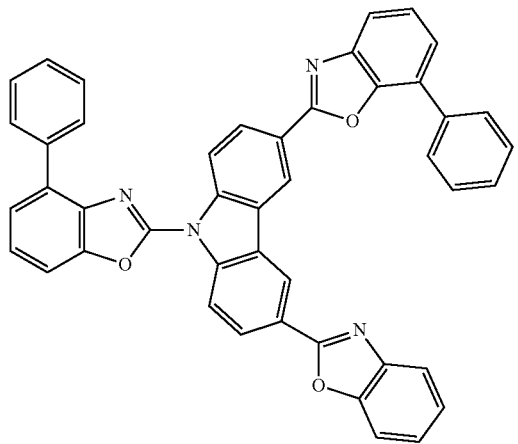
173
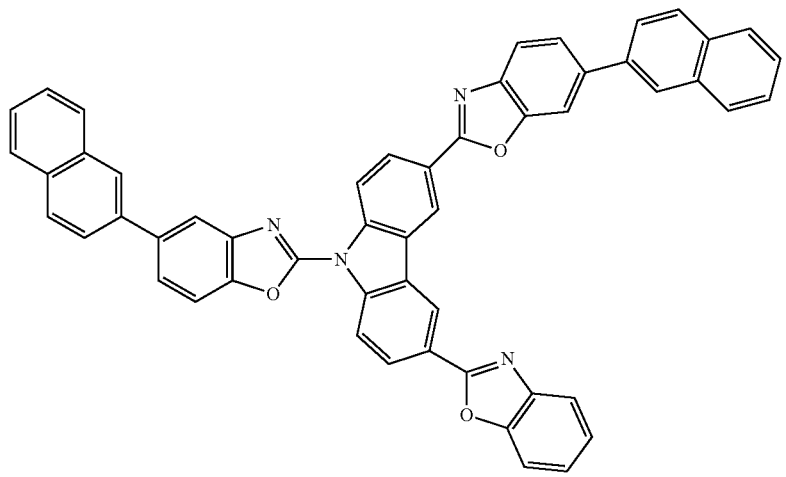
174
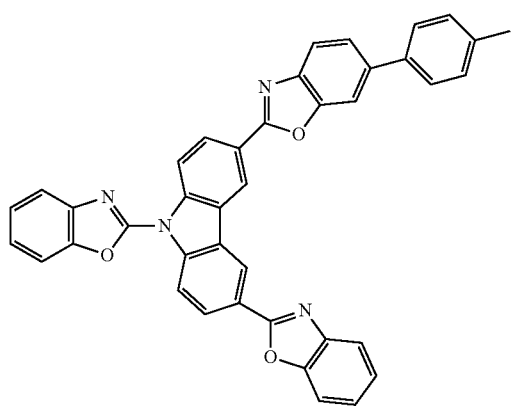
175
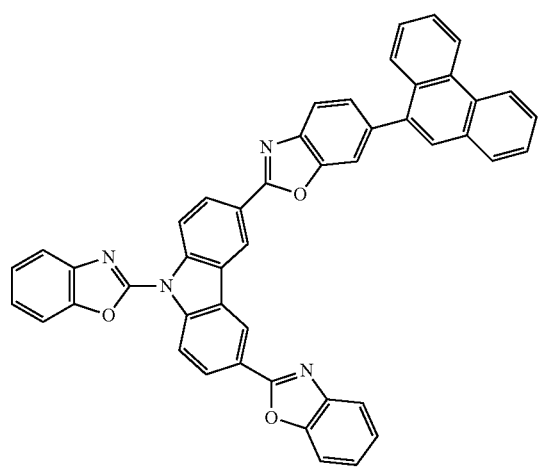

-continued
176
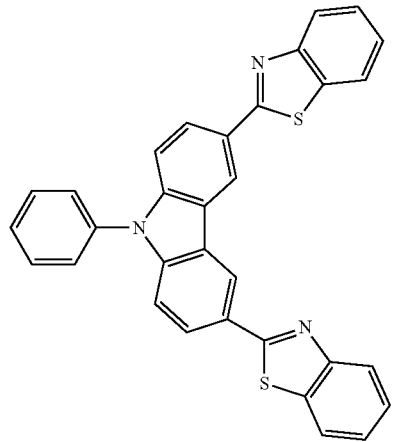
177
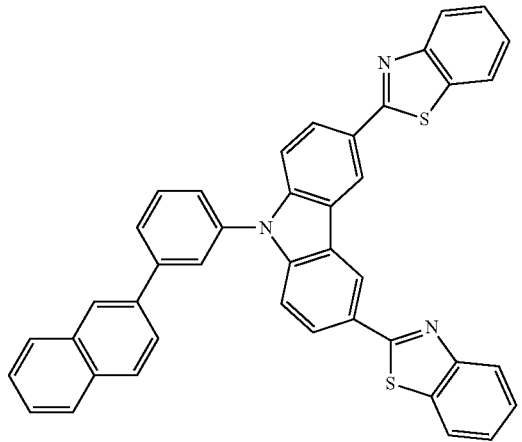
178
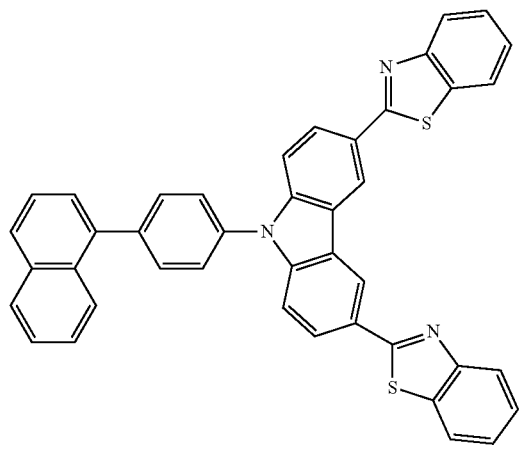
179
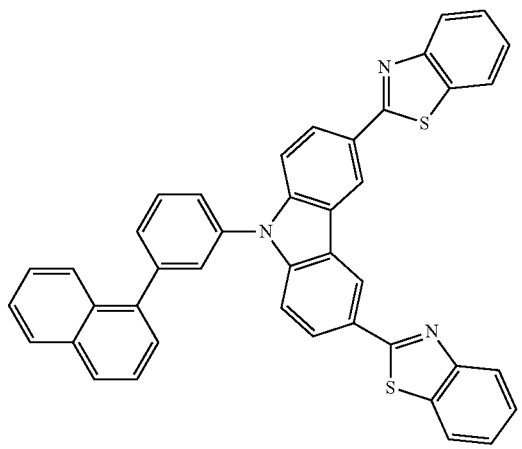
180
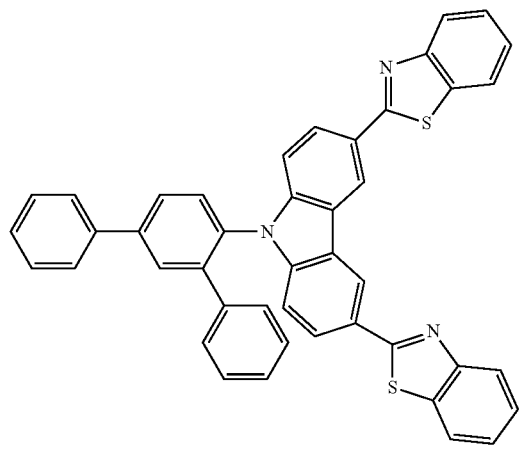
181
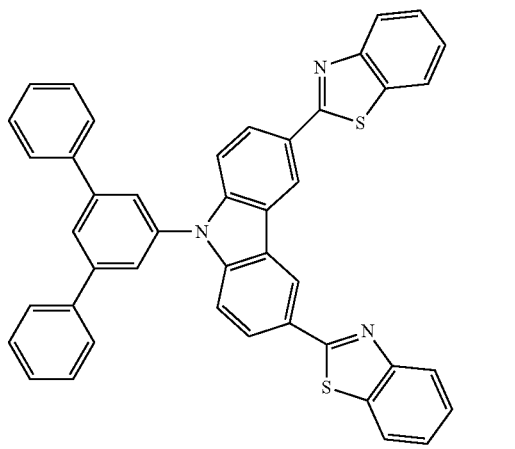

-continued
182
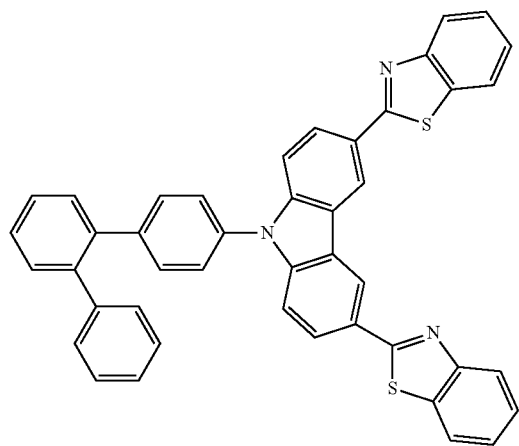
183
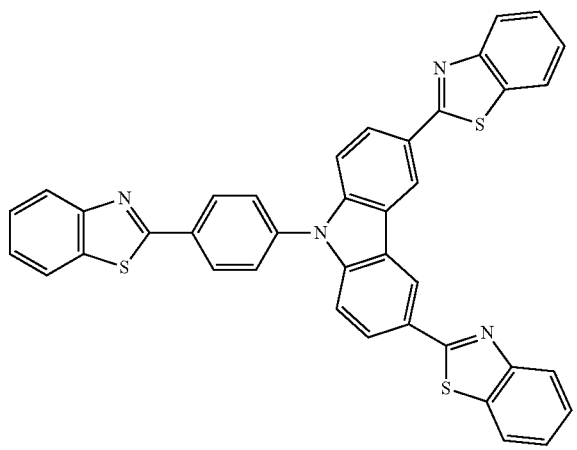
184
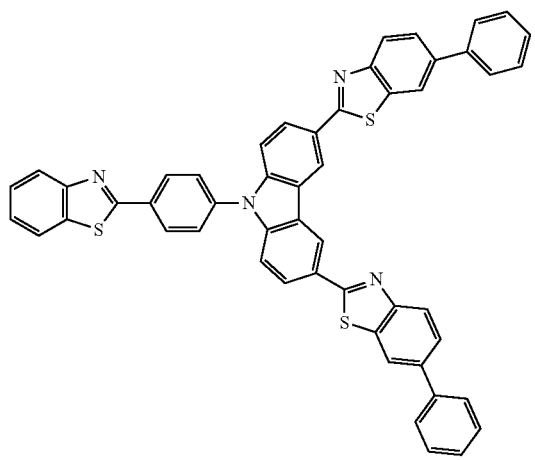
185
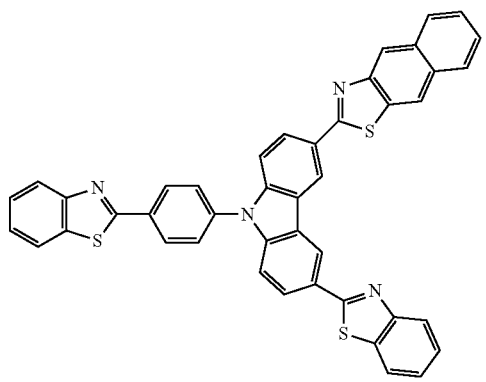
186
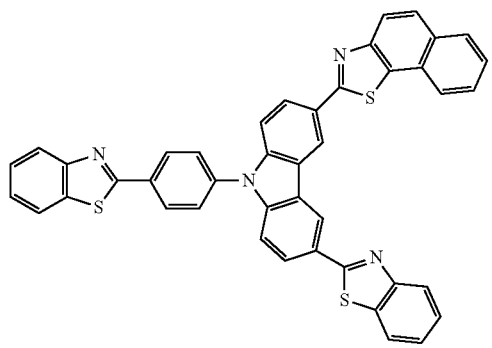
187
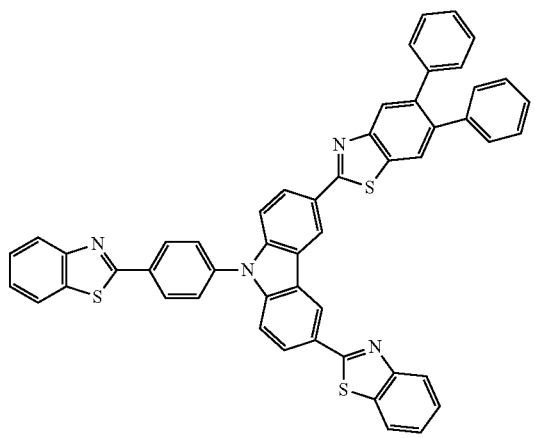

188
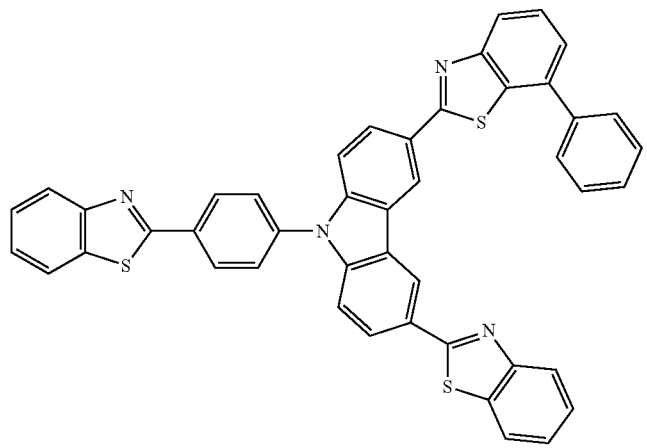
189
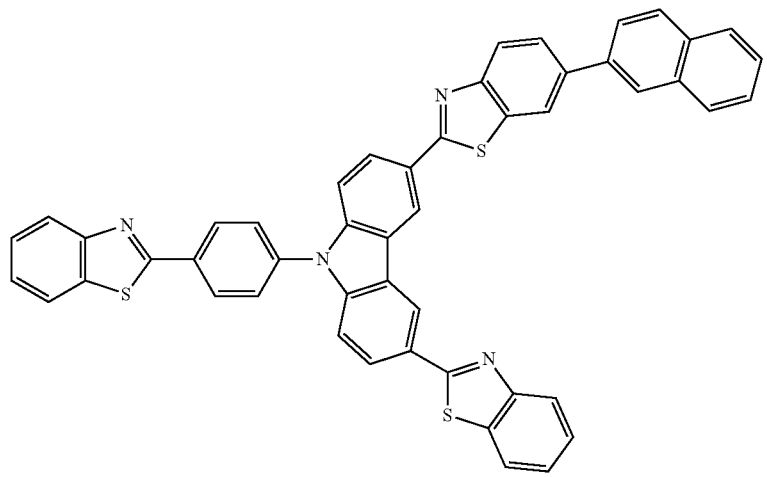
190
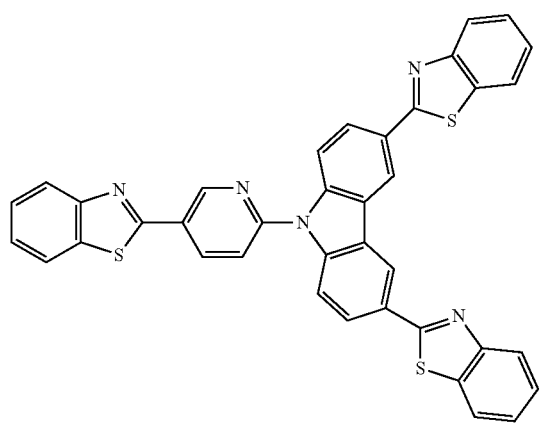
191
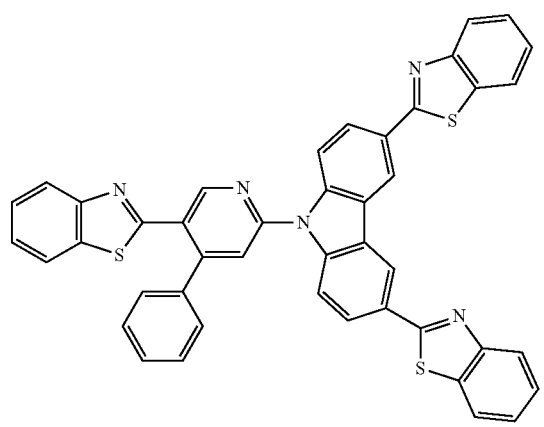

-continued
192
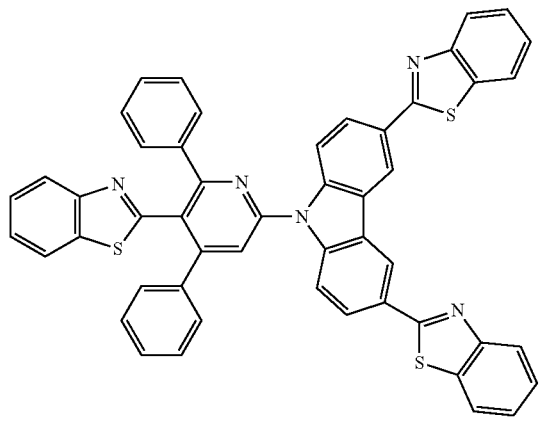
193
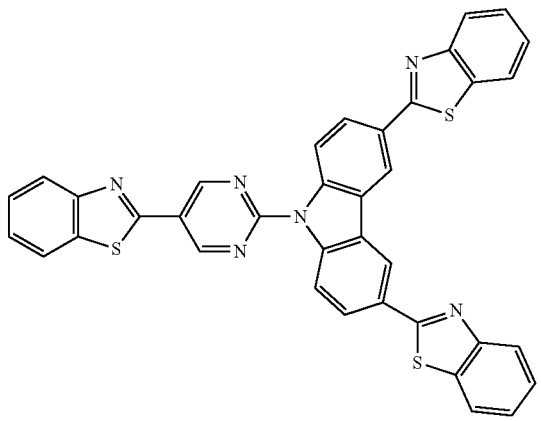
194
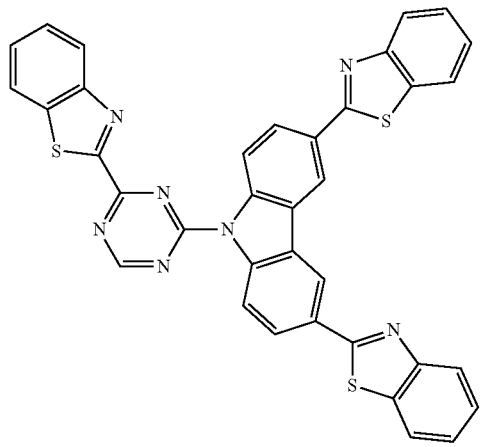
195
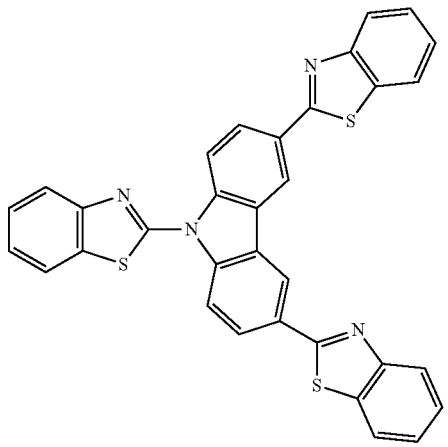
196
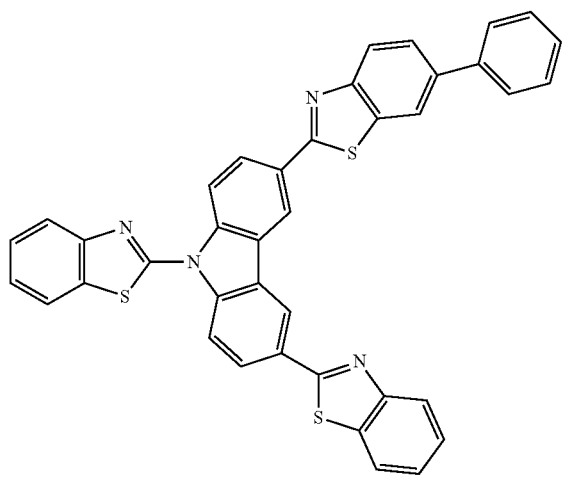
197
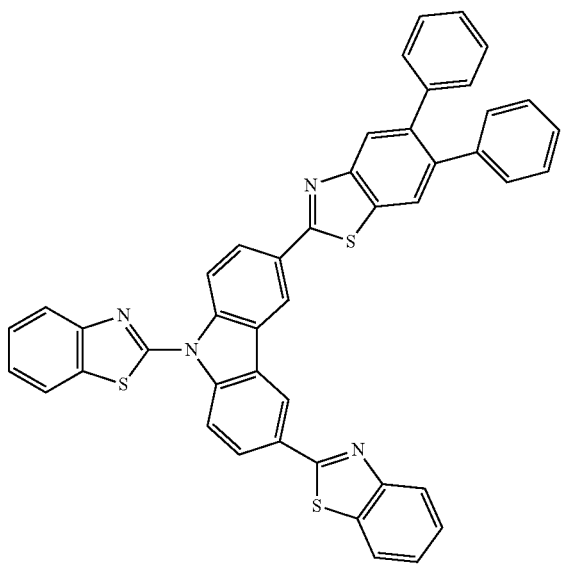

-continued
198
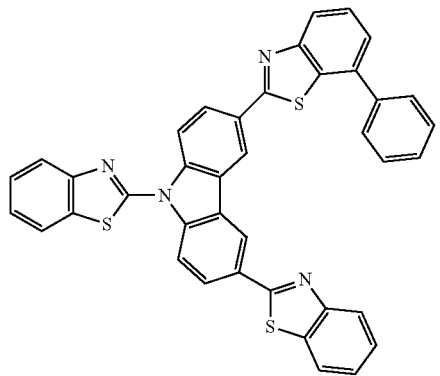
199
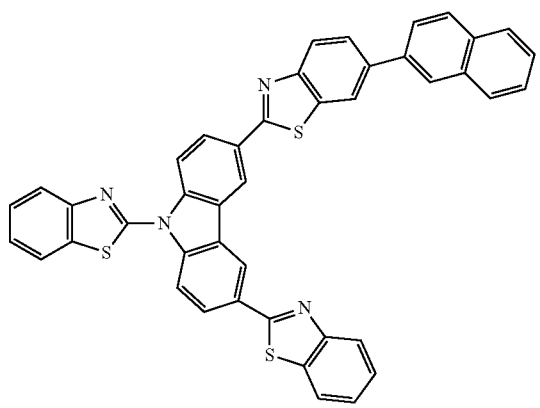
200
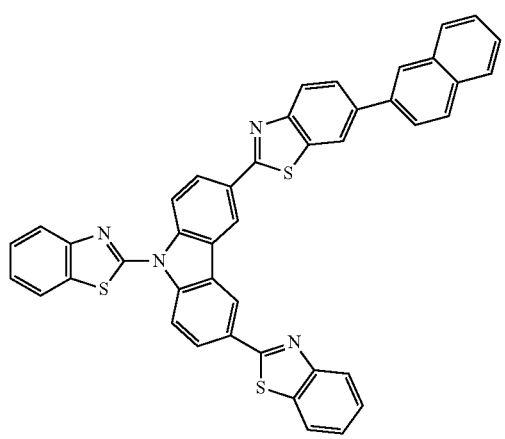
201
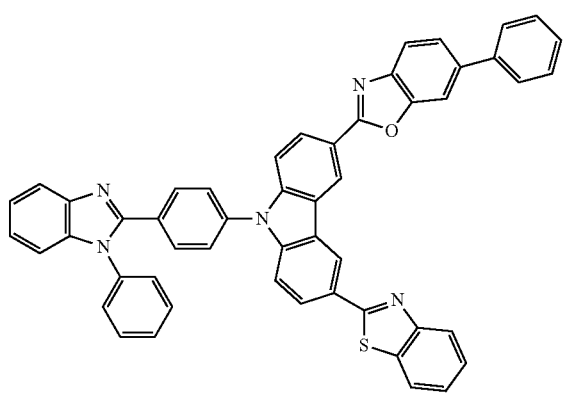
202
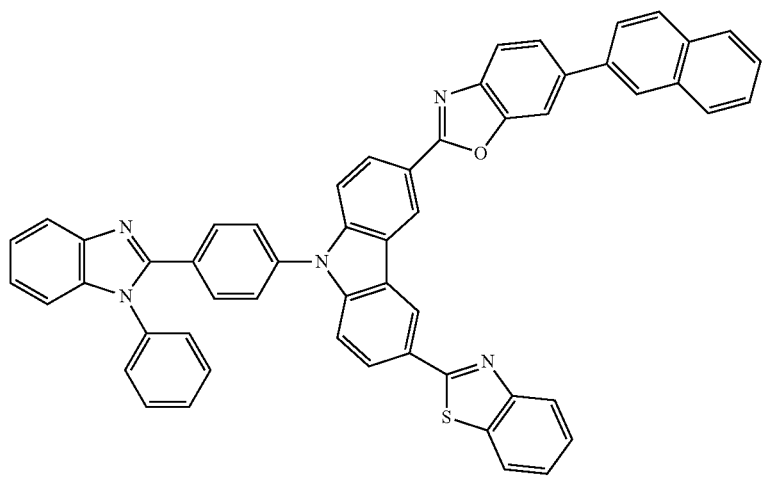

-continued
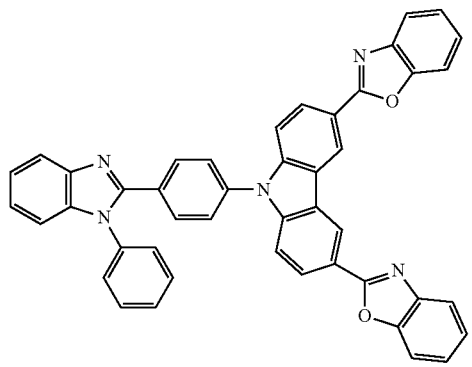
203
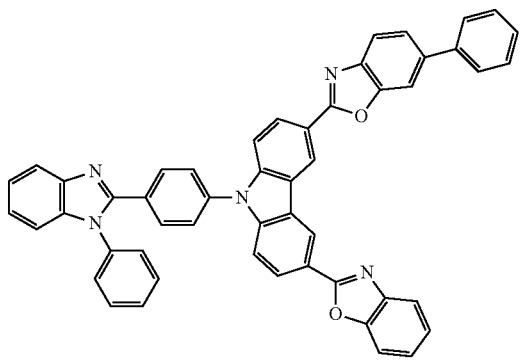
204
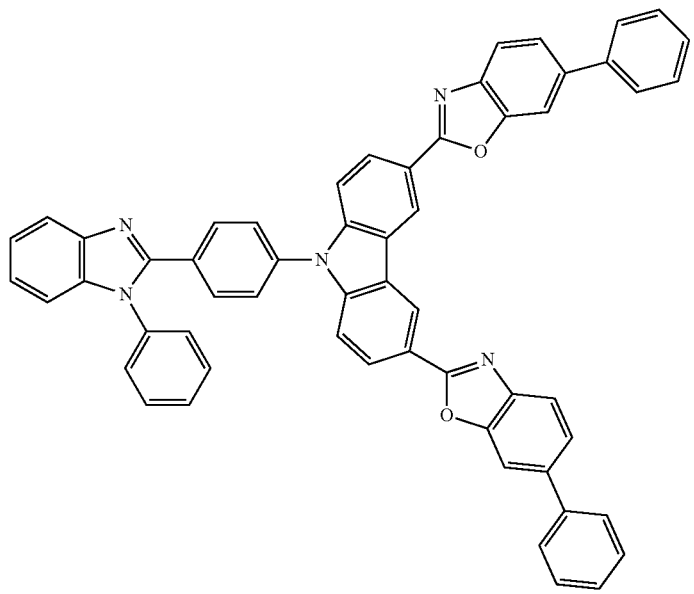
205
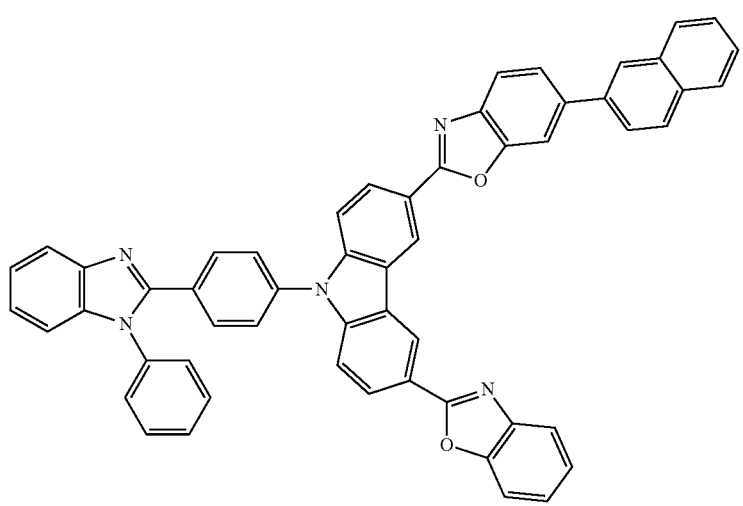
206

207
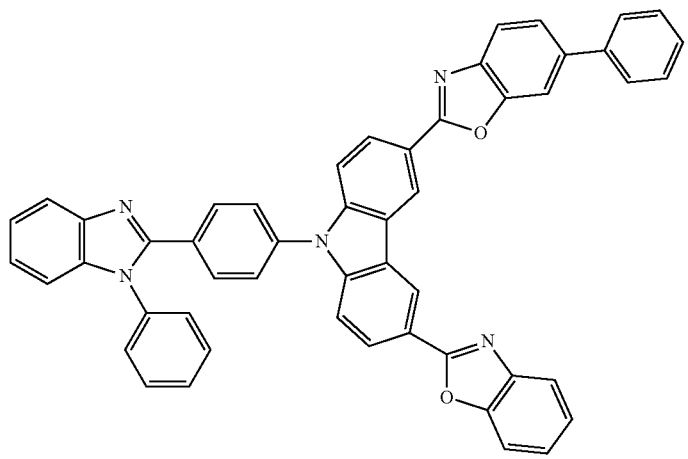
208 209
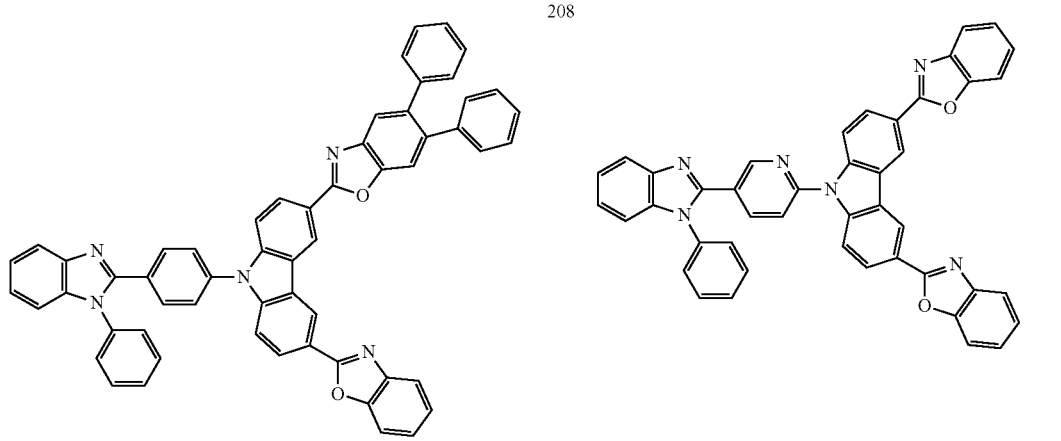
210 211
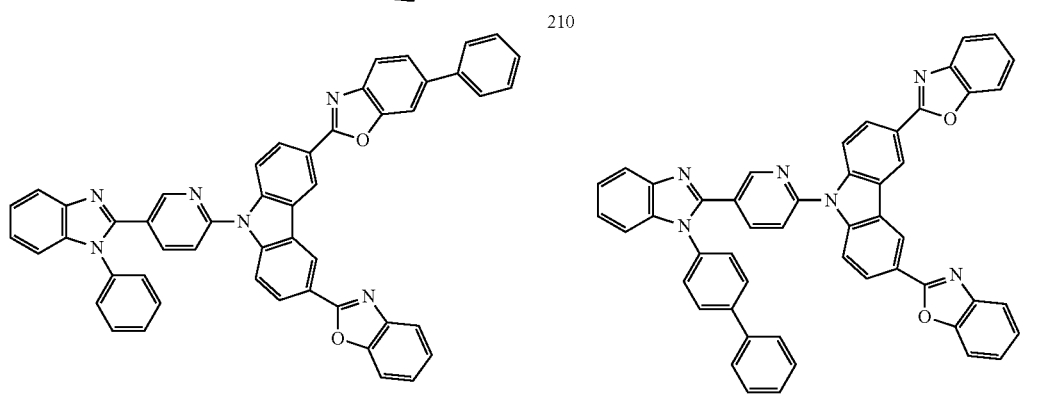
212 213
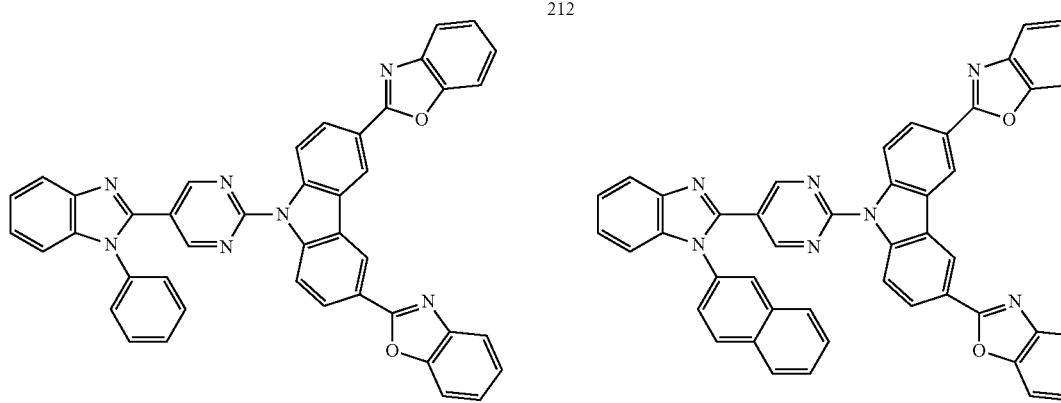

-continued
214
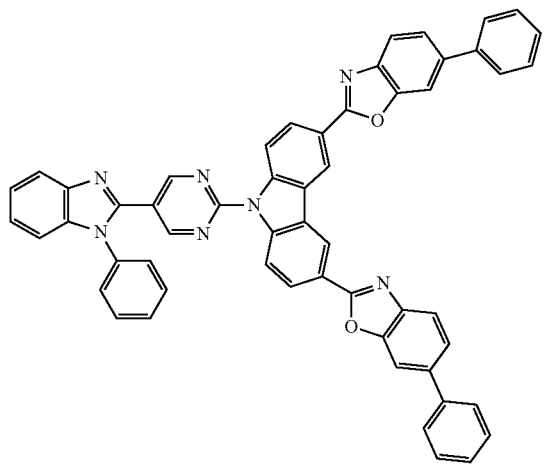
215
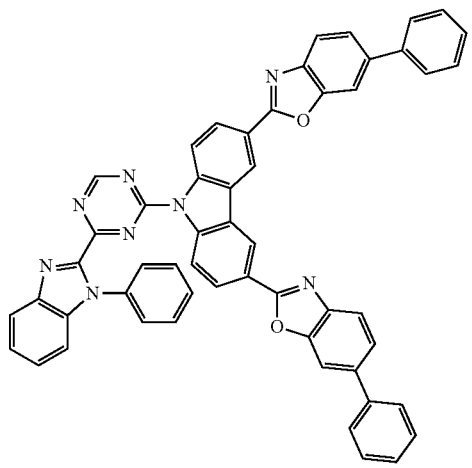
216
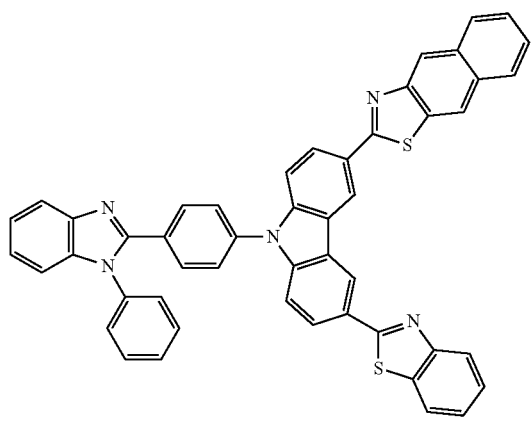
217
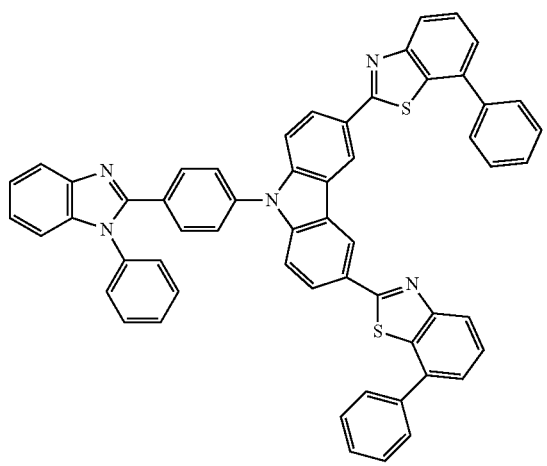
218
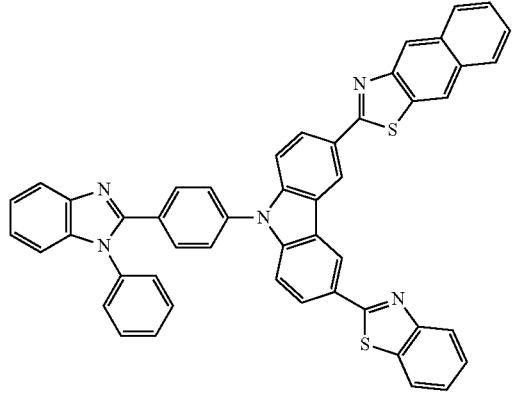
219
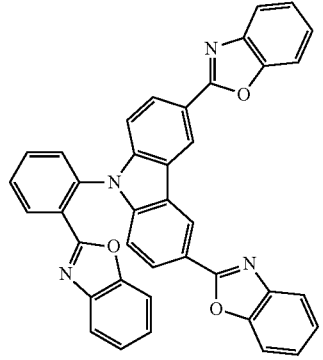

220
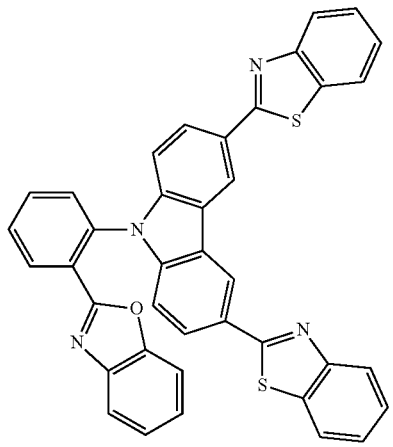

221
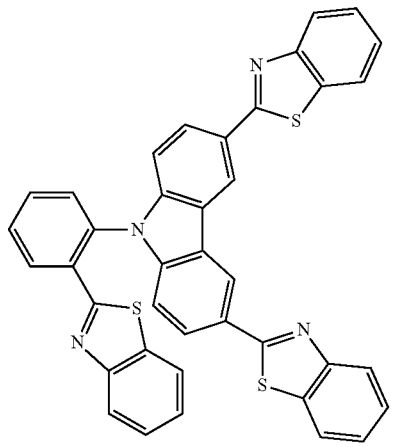

222
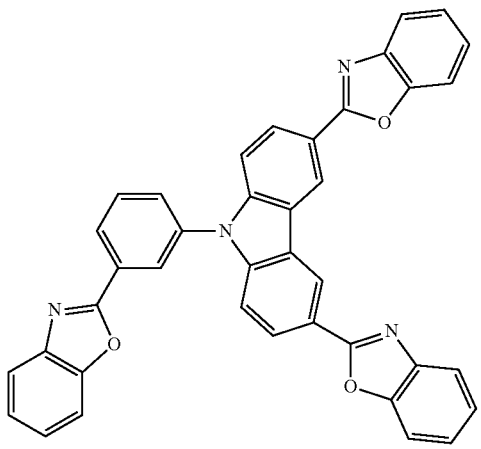

223
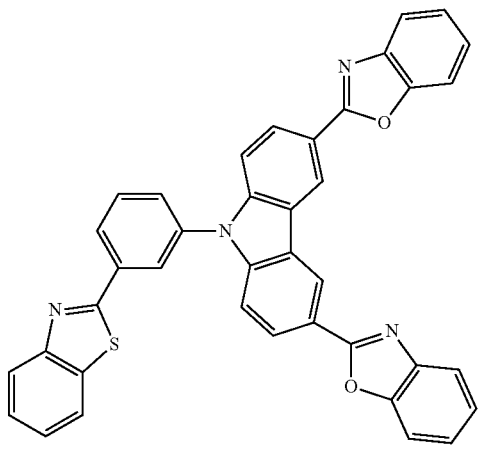

The organic electroluminescent compound of the present invention exhibits inherent characteristics due to its characteristic skeleton and has various characteristics due to the inherent characteristics of the moieties introduced into the skeleton. As a result, the organic electroluminescent compound of the present invention can be employed as a material for various organic layers of an organic electroluminescent device such as a light emitting layer, a capping layer, a hole transport layer, an electron transport layer and/or an electron blocking layer, achieving further improved luminescent properties (including high luminous efficiency) of the device.

The compound of the present invention can be applied to an organic electroluminescent device by a suitable method known in the art.

An organic electroluminescent device according to one embodiment of the present invention may include a first electrode, a second electrode, and at least one organic layer arranged therebetween. The organic electroluminescent device may be fabricated by a general method using suitable materials known in the art, except that the organic electroluminescent compound of the present invention is used to form the organic layer.

The organic layer of the organic electroluminescent device may have a monolayer structure. Alternatively, the organic layer may be provided in plurality. In this case, the organic layers have a multilayer laminate structure. For example, the structure of the organic layers may include a hole injecting layer, a hole transport layer, a light emitting layer, an electron transport layer, an electron injecting layer, an electron blocking layer, a hole blocking layer, and a capping layer, but is not limited thereto. The number of the organic layers is not limited and may be increased or decreased.

According to one embodiment, the organic electroluminescent device may include a substrate, a first electrode (anode), one or more organic layers, a second electrode (cathode), and a capping layer formed under the first electrode (bottom emission type) or on the second electrode (top emission type).

When the organic electroluminescent device is of a top emission type, light from the light emitting layer is emitted to the cathode and passes through the capping layer (CPL) formed using the compound of the present invention having a relatively high refractive index. The wavelength of the light is amplified in the capping layer, resulting in an increase in luminous efficiency. Also when the organic electroluminescent device is of a bottom emission type, the compound of the present invention can be employed in the capping layer to improve the luminous efficiency of the organic electroluminescent device based on the same principle.

Preferred structures of the organic layers of the organic electroluminescent device according to the present invention will be explained in more detail in the Examples section that follows.

The organic electroluminescent device of the present invention can be fabricated by depositing a metal, an electrically conductively metal oxide or an alloy thereof on a substrate by a physical vapor deposition (PVD) process such as sputtering or e-beam evaporation to form an anode, forming organic layers including a hole injecting layer, a hole transport layer, a light emitting layer, and an electron transport layer, and depositing a cathode material thereon.

Alternatively, the organic electroluminescent device may be fabricated by depositing a cathode material, organic layer materials, and an anode material in this order on a substrate. The organic layers may have a multilayer structure including a hole injecting layer, a hole transport layer, a light emitting layer, and an electron transport layer but is not limited to this structure. Alternatively, the organic electroluminescent device may include only one organic layer. The organic layers can be formed by a solvent process using various polymer materials rather than by a deposition process. The solvent process may be, for example, spin coating, dip coating, doctor blading, screen printing, inkjet printing or thermal transfer. In this case, the number of the organic layers may be decreased.

Preferably, the anode material has a high work function for easy injection of holes into the organic layers. Specific examples of anode materials suitable for use in the present invention include, but are not limited to: metals such as vanadium, chromium, copper, zinc, and gold and alloys thereof; metal oxides such as zinc oxide, indium oxide, indium thin oxide (ITO), and indium zinc oxide (IZO); combinations of metals and oxides such as ZnO:Al and $SnO_2$:Sb; and electrically conductive polymers such as poly(3-methylthiophene), poly[3,4-(ethylene-1,2-dioxy)thiophene] (PEDT), polypyrrole, and polyaniline.

Preferably, the cathode material has a low work function for easy injection of electrons into the organic layers. Specific examples of suitable cathode materials include, but are not limited to: metals such as magnesium, calcium, sodium, potassium, titanium, indium, yttrium, lithium, gadolinium, aluminum, silver, tin, and lead and alloys thereof; and multilayer structure materials such as LiF/Al and $LiO_2$/Al.

The hole injecting material is preferably a material that can receive holes injected from the anode at low voltage. The highest occupied molecular orbital (HOMO) of the hole injecting material is preferably between the work function of the anode material and the HOMO of the adjacent organic layer material. Specific examples of suitable hole injecting materials include, but are not limited to, metal porphyrin, oligothiophene, arylamine-based organic materials, hexanitrile hexaazatriphenylene, quinacridone-based organic materials, perylene-based organic materials, anthraquinone, polyaniline, and polythiophene-based conductive polymers.

The hole transport material is a material that can receive holes transported from the anode or the hole injecting layer and can transfer the holes to the light emitting layer. A material with high hole mobility is suitable as the hole transport material. Specific examples of suitable hole transport materials include arylamine-based organic materials, conductive polymers, and block copolymers consisting of conjugated and non-conjugated segments. The use of the organic electroluminescent compound according to the present invention ensures further improved low-voltage driving characteristics, high luminous efficiency, and excellent life characteristics of the device.

The light emitting material is a material that can receive and recombine holes from the hole transport layer and electrons from the electron transport layer to emit light in the visible range. A material with high quantum efficiency for fluorescence and phosphorescence is preferred as the light emitting material. Specific examples of suitable light emitting materials include, but are not limited to, 8-hydroxyquinoline aluminum complex ($Alq_3$), carbazole-based compounds, dimerized styryl compounds, BAlq, 10-hydroxybenzoquinoline-metal compounds, benzoxazole-based compounds, benzthiazole-based compounds, and benzimidazole-based compounds, poly(p-phenylenevinylene) (PPV)-based polymers, spiro compounds, polyfluorene, and rubrene.

The electron transport material is a material that can receive electrons injected from the cathode and can transfer the electrons to the light emitting layer. A material with high electron mobility is suitable as the electron transport material. Specific examples of suitable electron transport materials include, but are not limited to, 8-hydroxyquinoline Al complex ($Alq_3$), $Alq_3$ complexes, organic radical compounds, hydroxyflavone-metal complexes.

The organic electroluminescent device of the present invention may be of a top emission, bottom emission or dual emission type according to the materials used.

The organic electroluminescent compound of the present invention can perform its function even in organic electronic devices, including organic solar cells, organic photoconductors, and organic transistors, based on a similar principle to that applied to the organic electroluminescent device.

The present invention will be explained in more detail with reference to the following examples. However, these examples are provided for illustrative purposes and do not serve to limit the scope of the invention. It will be obvious to those skilled in the art that various modifications and changes are possible without departing from the scope and spirit of the invention.

Synthesis Example 1: Synthesis of Compound 1

(1) Preparative Example 1: Synthesis of Compound 1

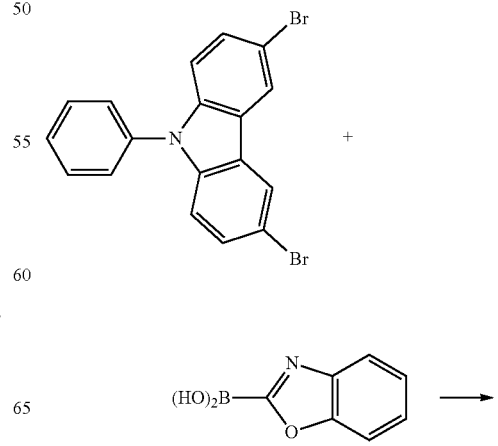

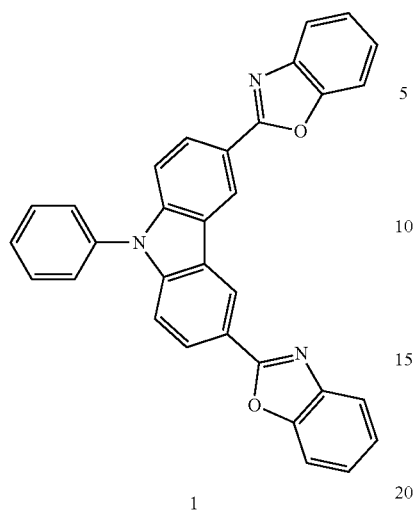

1

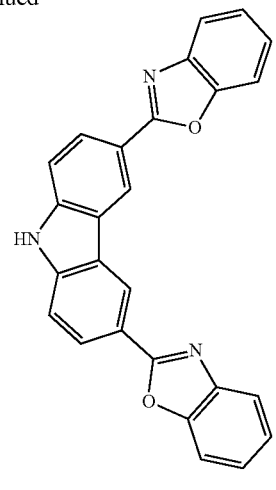

53-1

Toluene (100 mL), H₂O (30 mL), and ethanol (30 mL) were added to 3,6-dibromo-9-phenyl-9H-carbazole (10 g, 0.025 mol, Sigma-Aldrich), benzo[d]oxazol-2-ylboronic acid (8.97 g, 0.055 mol, mascot), potassium carbonate (13.78 g, 0.100 mol, Sigma-Aldrich), and Pd(PPh₃)₄ (1.73 g, 0.001 mol, Sigma-Aldrich). The mixture was refluxed with stirring at 95° C. for 6 h. After completion of the reaction, the reaction mixture was extracted and purified by column chromatography to afford 11.0 g (yield 92.3%) of Compound 1.

H-NMR (200 MHz, CDCl₃): δ ppm, 1H (8.18/d, 8.00/d, 7.87/d, 7.69/d, 7.45/m), 2H (7.77/s, 7.58/m, 7.50/d), 4H (7.74/m 7.39/d)

LC/MS: m/z=477[(M+1)⁺]

Synthesis Example 2: Synthesis of Compound 53

(1) Preparative Example 1: Synthesis of Intermediate 53-1

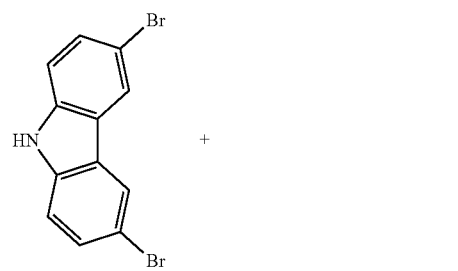

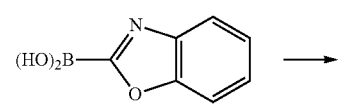

THF (100 mL), H₂O (30 mL), and ethanol (30 mL) were added to 3,6-dibromo-9H-carbazole (10 g, 0.035 mol, TCI), benzo[d]oxazol-2-ylboronic acid (30.43 g, 0.077 mol, mascot), potassium carbonate (17.01 g, 0.123 mol, Sigma-Aldrich), and Pd(PPh₃)₄ (2.13 g, 0.002 mol, Sigma-Aldrich) as a catalyst. The mixture was refluxed with stirring at 80° C. for 6 h. After completion of the reaction, the reaction mixture was extracted and purified by column chromatography to afford 7.1 g (yield 57.5%) of Intermediate 53-1.

(2) Preparative Example 2: Synthesis of Intermediate 53-2

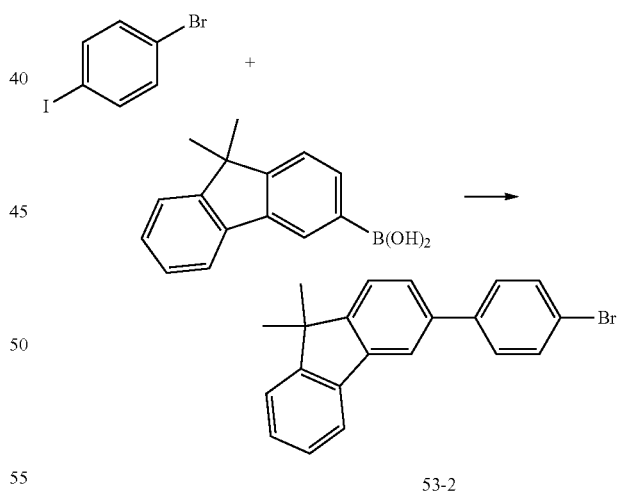

Toluene (100 mL), H₂O (30 mL), and ethanol (30 mL) were added to 1-bromo-4-iodobenzene (10 g, 0.035 mol, Sigma-Aldrich), (9,9-dimethyl-9H-fluoren-3-yl)boronic acid (8.42 g, 0.035 mol, mascot), potassium carbonate (9.77 g, 0.071 mol, Sigma-Aldrich), and Pd(PPh₃)₄ (1.23 g, 0.001 mol, Sigma-Aldrich). The mixture was refluxed with stirring at 95° C. for 6 h. After completion of the reaction, the reaction mixture was extracted and purified by column chromatography to afford 8.5 g (yield 68.9%) of Intermediate 53-2.

(3) Preparative Example 3: Synthesis of Compound 53

Synthesis Example 3: Synthesis of Compound 64

(1) Preparative Example 1: Synthesis of Compound 64

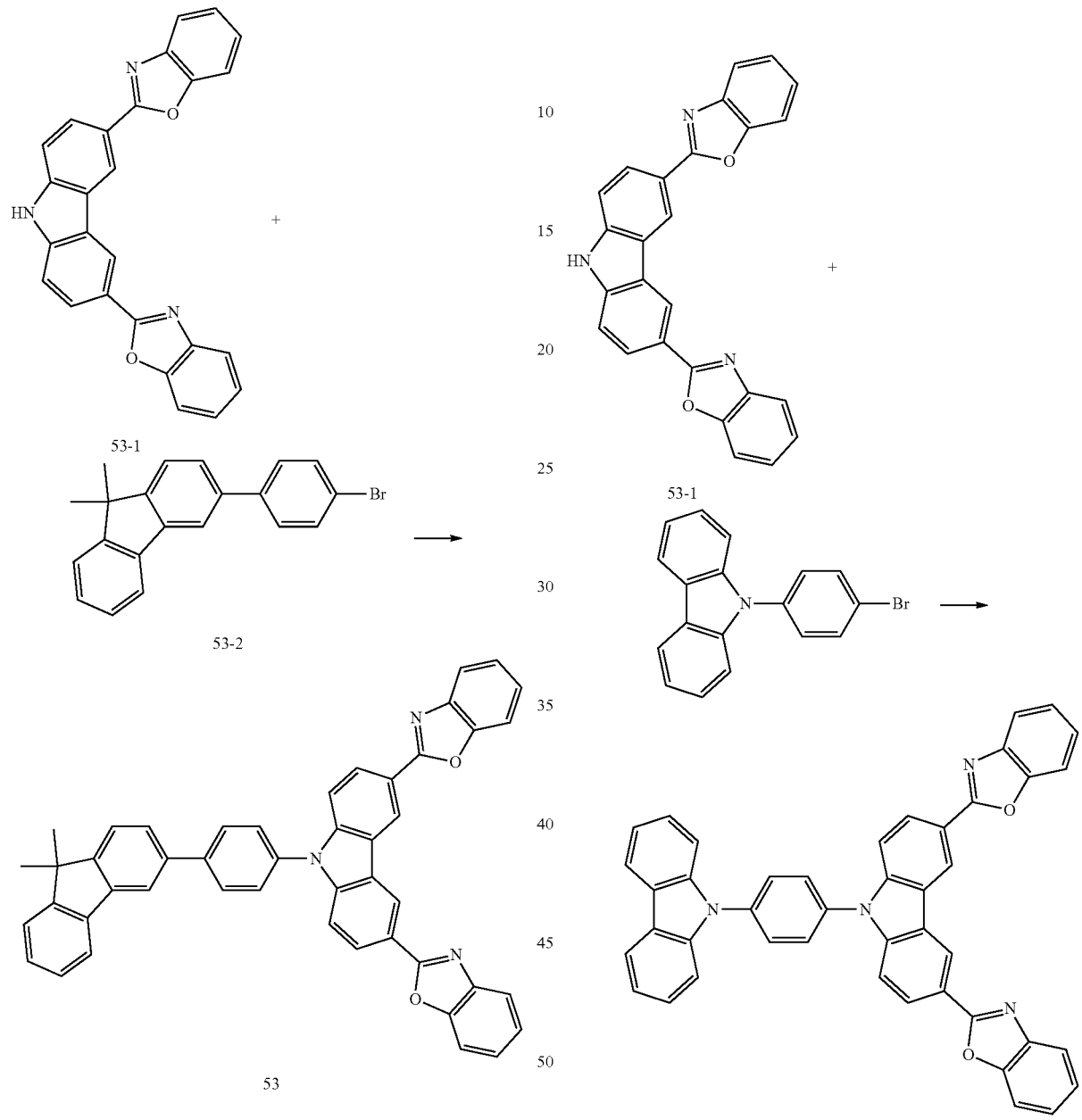

DMF (100 mL) was added to Intermediate 53-1 (10 g, 0.025 mol), Intermediate 53-2 (10.4 g, 0.030 mol), potassium carbonate (6.89 g, 0.050 mol, Sigma-Aldrich), dibenzo-18-crown-6 (0.9 g, 0.003 mol, Sigma-Aldrich), and Cu (3.17 g, 0.050 mol, Sigma-Aldrich). The mixture was refluxed with stirring at 150° C. for 6 h. After completion of the reaction, the reaction mixture was extracted and purified by column chromatography to afford 14.3 g (yield 85.7%) of Compound 53.

H-NMR (200 MHz, CDCl$_3$): δ ppm, 1H (8.18/d, 8.06/s, 8.00/d, 7.69/d, 7.61/d, 7.55/d, 7.53/d, 7.38/m, 7.28/m, 1.72/m), 2H (7.87/d, 7.79/d, 7.77/s, 7.68/d), 4H (7.74/m, 7.39/d)

LC/MS: m/z=669[(M+1)$^+$]

DMF (100 mL) was added to Intermediate 53-1 (10 g, 0.025 mol), 9-(4-bromophenyl)-9H-carbazole (9.6 g, 0.030 mol, TCI), potassium carbonate (6.89 g, 0.050 mol, Sigma-Aldrich), dibenzo-18-crown-6 (0.9 g, 0.003 mol, Sigma-Aldrich), and Cu (3.170 g, 0.050 mol, Sigma-Aldrich). The mixture was refluxed with stirring at 150° C. for 7 h. After completion of the reaction, the reaction mixture was extracted and purified by column chromatography to afford 11.3 g (yield 70.6%) of Compound 64.

H-NMR (200 MHz, CDCl$_3$): δ ppm, 1H (8.55/d, 8.18/d, 8.12/d, 8.00/d, 7.94/d, 7.87/d, 7.69/d, 7.63, d, 7.50/m, 7.33/m, 7.29/m, 7.25/m), 2H (7.77/s), 4H (7.74/m, 7.62/d, 7.39/d)

LC/MS: m/z=642[(M+1)⁺]

Synthesis Example 4: Synthesis of Compound 75

(1) Preparative Example 1: Synthesis of Intermediate 75-1

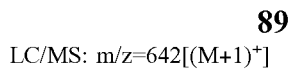

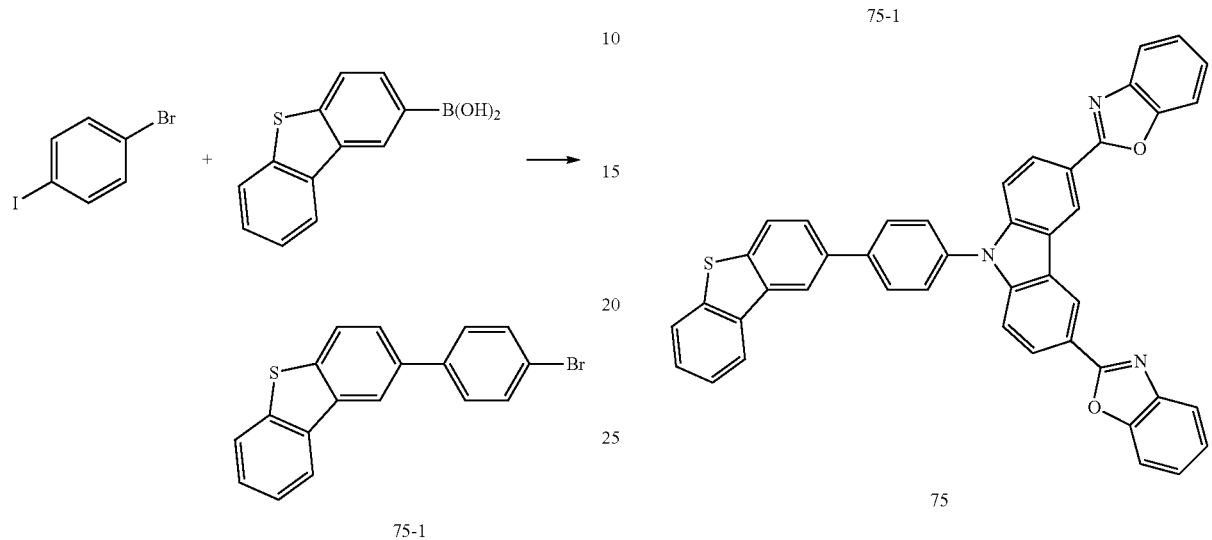

75-1

Toluene (100 mL), ethanol (30 mL), and H₂O (30 mL) were added to 1-bromo-4-iodobenzene (10 g, 0.035 mol), dibenzo[b,d]thiophen-2-ylboronic acid (8.06 g, 0.035 mol, mascot), potassium carbonate (9.77 g, 0.071 mol, Sigma-Aldrich), and Pd(PPh₃)₄ (1.23 g, 0.001 mol, Sigma-Aldrich) as a catalyst. The mixture was refluxed with stirring at 90° C. for 6 h. After completion of the reaction, the reaction mixture was extracted and purified by column chromatography to afford 7.6 g (yield 63.4%) of Intermediate 75-1.

(1) Preparative Example 2: Synthesis of Compound 75

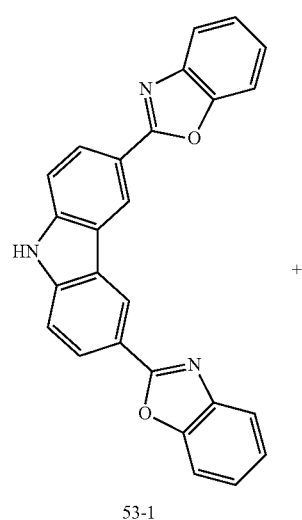

53-1

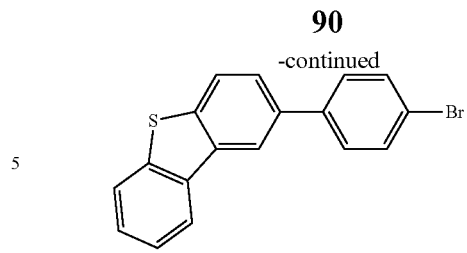

75-1

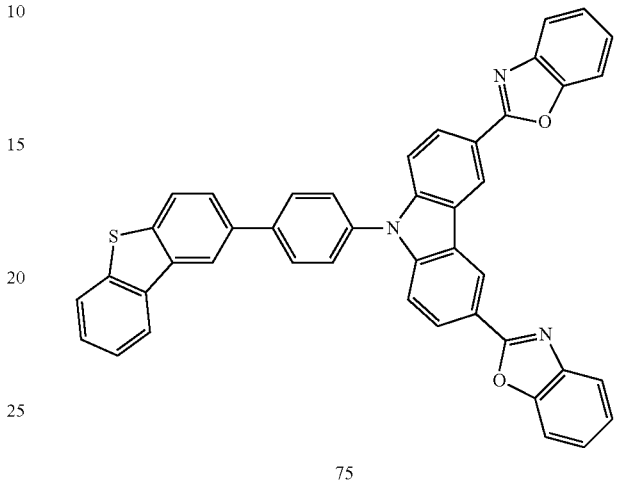

75

DMF (100 mL) was added to Intermediate 53-1 (10 g, 0.030 mol), Intermediate 75-1 (14.2 g, 0.035 mol), potassium carbonate (8.15 g, 0.060 mol, Sigma-Aldrich), dibenzo-18-crown-6 (1.06 g, 0.003 mol, Sigma-Aldrich), and Cu (3.75 g, 0.060 mol, Sigma-Aldrich). The mixture was refluxed with stirring at 150° C. for 7 h. After completion of the reaction, the reaction mixture was extracted and purified by column chromatography to afford 11.9 g (yield 72.4%) of Compound 75.

H-NMR (200 MHz, CDCl₃): δ ppm, 1H (8.45/d, 8.18/d, 7.98/d, 7.87/d, 7.86/d, 7.69/d, 7.52/m, 7.50/m), 2H (7.79/d, 7.77/s, 7.68/d), 3H (8.00/d), 4H (7.74/m, 7.39/d)

LC/MS: m/z=659[(M+1)⁺]

Synthesis Example 5: Synthesis of Compound 97

(1) Preparative Example 1: Synthesis of Compound 97

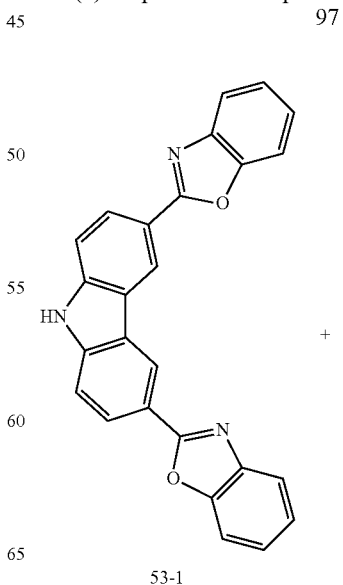

53-1

91
-continued

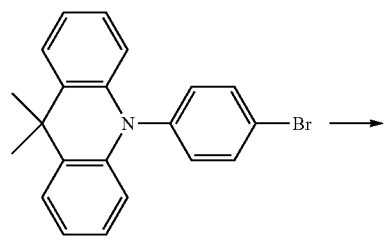

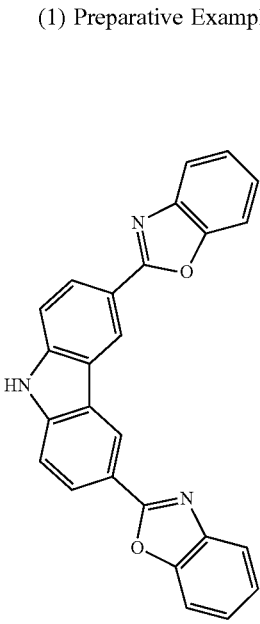

97

DMF (100 mL) was added to Intermediate 53-1 (10 g, 0.025 mol), 10-(4-bromophenyl)-9,9-dimethyl-9,10-dihydroacridine (10.9 g, 0.030 mol, mascot), potassium carbonate (6.89 g, 0.050 mol, Sigma-Aldrich), dibenzo-18-crown-6 (0.90 g, 0.003 mol, Sigma-Aldrich), and Cu (3.17 g, 0.050 mol, Sigma-Aldrich). The mixture refluxed with stirring at 160° C. for 9 h. After completion of the reaction, the reaction mixture was extracted and purified by column chromatography to afford 12.1 g (yield 70.9%) of Compound 97.

H-NMR (200 MHz, CDCl$_3$): δ ppm, 1H (8.18/d, 8.00/d, 7.87/d, 7.69/d), 2H (7.77/s, 7.37/d, 7.05/d, 7.02/m, 6.73/m, 6.63/d, 6.55/d, 1.72/m) 4H (7.74/m, 7.39/d)

LC/MS: m/z=684[(M+1)$^+$]

92

Synthesis Example 6: Synthesis of Compound 102

(1) Preparative Example 1: Synthesis of Compound 102

53-1

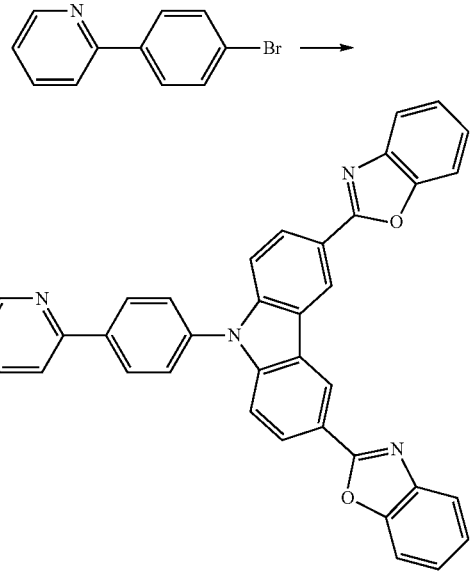

102

DMF (100 mL) was added to Intermediate 53-1 (10 g, 0.025 mol), 2-(4-bromophenyl)pyridine (7.0 g, 0.030 mol, TCl), potassium carbonate (6.89 g, 0.050 mol, Sigma-Aldrich), dibenzo-18-crown-6 (0.9 g, 0.003 mol, Sigma-Aldrich), and Cu (3.17 g, 0.050 mol, Sigma-Aldrich). The mixture was refluxed with stirring at 160° C. for 8 h. After completion of the reaction, the reaction mixture was extracted and purified by column chromatography to afford 10.3 g (yield 74.6%) of Compound 102.

H-NMR (200 MHz, CDCl$_3$): δ ppm, 1H (8.50/d, 8.18/d, 8.00/d, 7.87/d, 7.69/d, 7.51/m, 7.26/d, 7.00/m), 2H (8.30/d, 7.77/s, 7.71/d) 4H (7.74/m, 7.39/d)

LC/MS: m/z=554[(M+1)$^+$]

Synthesis Example 7: Synthesis of Compound 140

(1) Preparative Example 1: Synthesis of Compound 140

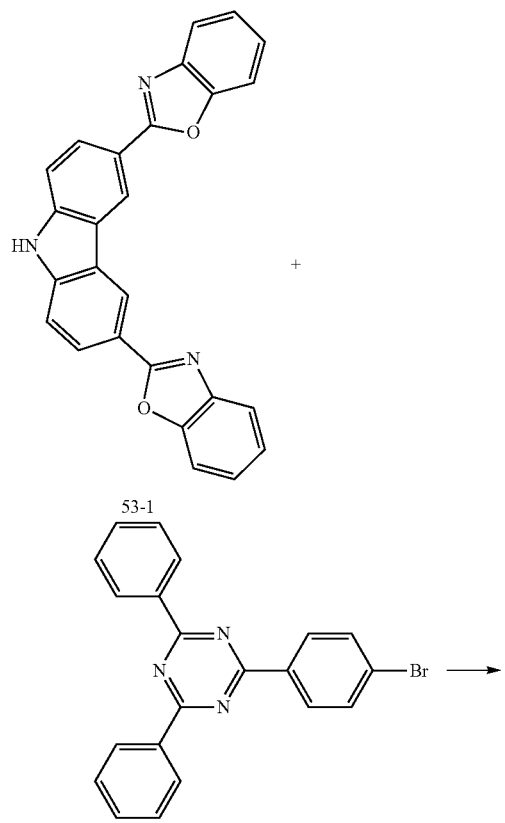

DMF (100 mL) was added to Intermediate 53-1 (10 g, 0.025 mol), 2-(4-bromophenyl)-4,6-diphenyl-1,3,5-triazine (11.6 g, 0.030 mol, TCl), potassium carbonate (6.89 g, 0.050 mol, Sigma-Aldrich), dibenzo-18-crown-6 (0.9 g, 0.003 mol, Sigma-Aldrich), and Cu (3.17 g, 0.050 mol, Sigma-Aldrich). The mixture was refluxed with stirring at 150° C. for 8 h. After completion of the reaction, the reaction mixture was extracted and purified by column chromatography to afford 14.6 g (yield 82.7%) of Compound 140.

H-NMR (200 MHz, CDCl$_3$): δ ppm, 1H (8.18/d, 8.00/d, 7.87/d, 7.69, d), 2H (7.79/d, 7.77/s, 7.68/d, 7.41/m) 4H (8.28/d, 7.74/m, 7.51/m, 7.39/d)

LC/MS: m/z=708[(M+1)$^+$]

Synthesis Example 8: Synthesis of Compound 147

(1) Preparative Example 1: Synthesis of Intermediate 147-1

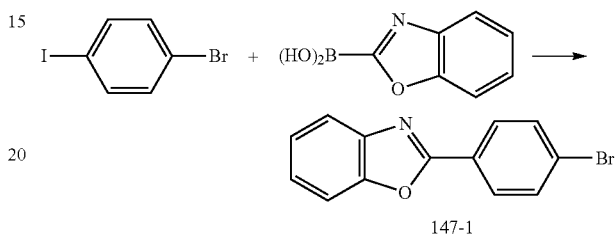

THF (100 Ml), ethanol (25 Ml), and H$_2$O (25 Ml) were added to 1-bromo-4-iodobenzene (10 g, 0.035 mol, Sigma-Aldrich), benzo[d]oxazol-2-ylboronic acid (6.91 g, 0.042 mol, mascot), potassium carbonate (9.77 g, 0.071 mol, Sigma-Aldrich), and Pd(PPh$_3$)$_4$ (1.23 g, 0.001 mol, Sigma-Aldrich) as a catalyst. The mixture was refluxed with stirring at 90° C. for 12 h. After completion of the reaction, the reaction mixture was extracted and purified by column chromatography to afford 5.5 g (yield 56.8%) of Intermediate 147-1.

(1) Preparative Example 2: Synthesis of Compound 147

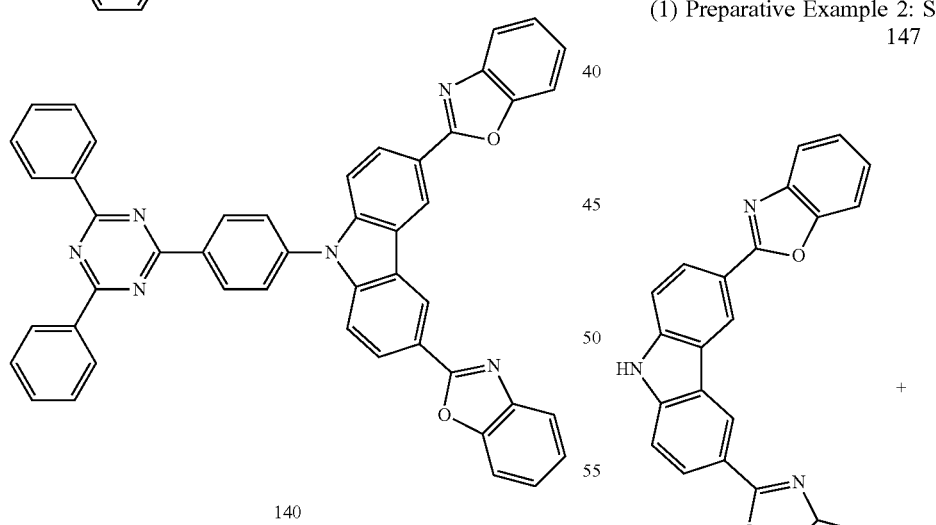

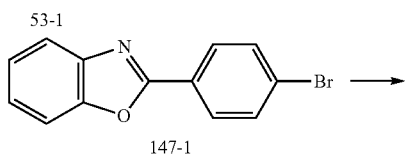

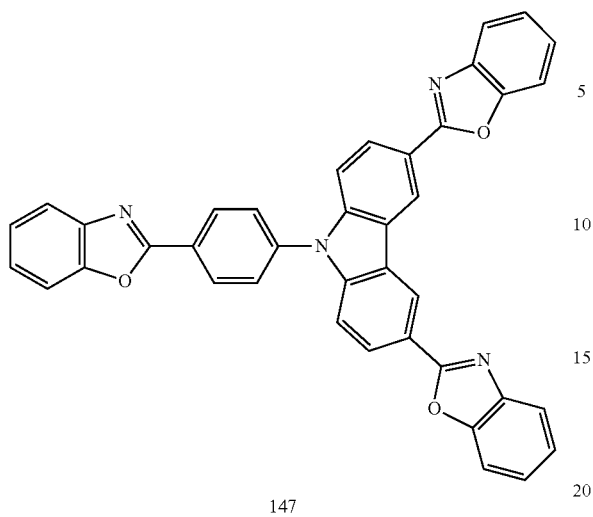

147

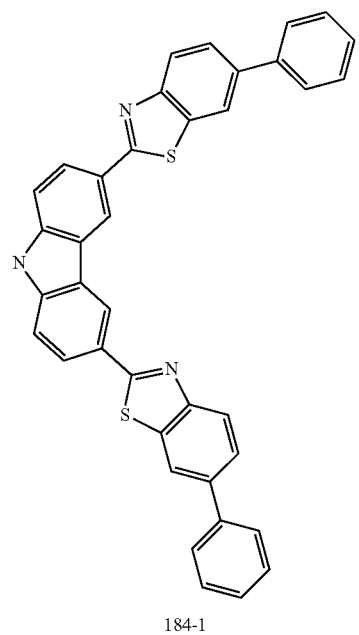

184-1

DMF (100 mL) was added to Intermediate 53-1 (10 g, 0.025 mol), Intermediate 147-1 (8.2 g, 0.044 mol), potassium carbonate (6.89 g, 0.050 mol, Sigma-Aldrich), dibenzo-18-crown-6 (0.90 g, 0.003 mol, Sigma-Aldrich), and Cu (4.38 g, 0.069 mol, Sigma-Aldrich). The mixture was refluxed with stirring at 150° C. for 7 h. After completion of the reaction, the reaction mixture was extracted and purified by column chromatography to afford 9.7 g (yield 65.5%) of Compound 147.

H-NMR (200 MHz, CDCl$_3$): δ ppm, 1H (8.18/d, 8.00/d, 7.87/d, 7.69/d), 2H (7.79/d, 7.68/d), 6H (7.74/m, 7.39/d)

LC/MS: m/z=594[(M+1)$^+$]

Synthesis Example 9: Synthesis of Compound 184

(1) Preparative Example 1: Synthesis of Intermediate 184-1

THF (100 mL), ethanol (25 mL), and H$_2$O (25 mL) were added to 3,6-dibromo-9H-carbazole (10 g, 0.031 mol, Sigma-Aldrich), 6-phenylbenzo[d]thiazol-2-ylboronic acid (17.3 g, 0.068 mol, mascot), potassium carbonate (17.01 g, 0.123 mol, Sigma-Aldrich), and Pd(PPh$_3$)$_4$ (1.78 g, 0.001 mol, Sigma-Aldrich) as a catalyst. The mixture was refluxed with stirring at 90° C. for 11 h. After completion of the reaction, the reaction mixture was extracted and purified by column chromatography to afford 11.4 g (yield 63.3%) of Intermediate 184-1.

(2) Preparative Example 2: Synthesis of Intermediate 184-2

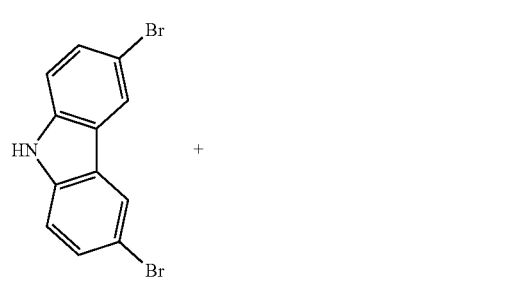

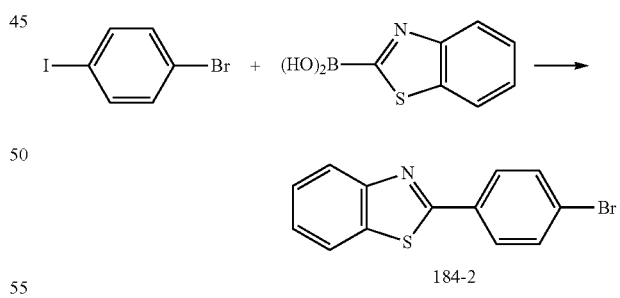

184-2

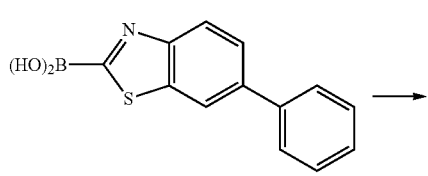

THF (100 mL), ethanol (25 mL), and H$_2$O (25 mL) were added to 1-bromo-4-iodobenzene (10 g, 0.035 mol, Sigma-Aldrich), benzo[d]thiazol-2-ylboronic acid (7.59 g, 0.042 mol, mascot), potassium carbonate (9.77 g, 0.071 mol, Sigma-Aldrich), and Pd(PPh$_3$)$_4$ (1.23 g, 0.001 mol, Sigma-Aldrich) as a catalyst. The mixture was refluxed with stirring at 90° C. for 12 h. After completion of the reaction, the reaction mixture was extracted and purified by column chromatography to afford 6.1 g (yield 59.5%) of Intermediate 184-2.

(3) Preparative Example 3: Synthesis of Compound 184

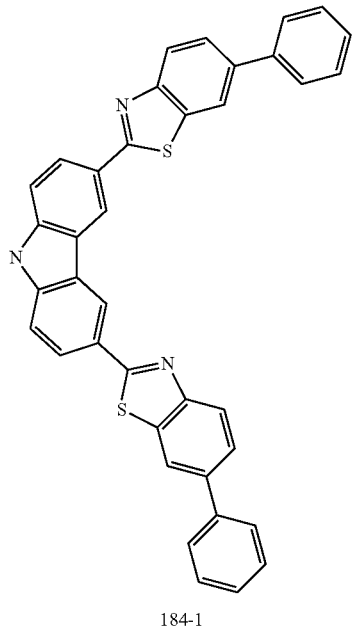

184-1

+

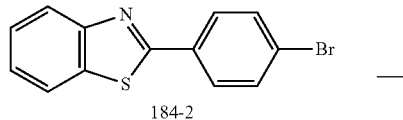

184-2

→

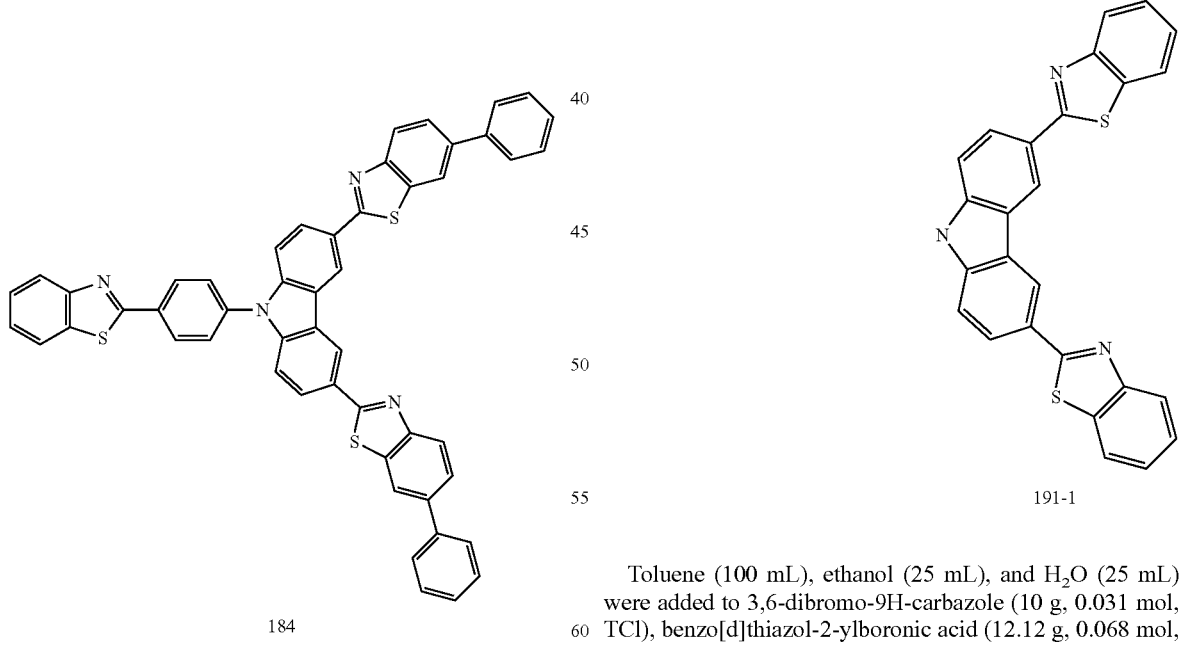

184

DMF (100 mL) was added to Intermediate 184-1 (10 g, 0.017 mol), Intermediate 184-2 (5.9 g, 0.021 mol), potassium carbonate (4.72 g, 0.034 mol, Sigma-Aldrich), dibenzo-18-crown-6 (0.62 g, 0.002 mol, Sigma-Aldrich), and Cu (2.17 g, 0.034 mol, Sigma-Aldrich). The mixture was refluxed with stirring at 150° C. for 7 h. After completion of the reaction, the reaction mixture was extracted and purified by column chromatography to afford 9.4 g (yield 69.3%) of Compound 184.

H-NMR (200 MHz, CDCl$_3$): δ ppm, 1H (8.01/d, 8.00/d, 7.87/d, 7.69/d), 2H (8.34/s, 8.18/d, 7.81/d, 7.79/d, 7.68/d, 7.53/m, 7.41/m) 4H (7.77/s, 7.52/d, 7.51/m)

LC/MS: m/z=794[(M+1)$^+$]

Synthesis Example 10: Synthesis of Compound 191

(1) Preparative Example 1: Synthesis of Intermediate 191-1

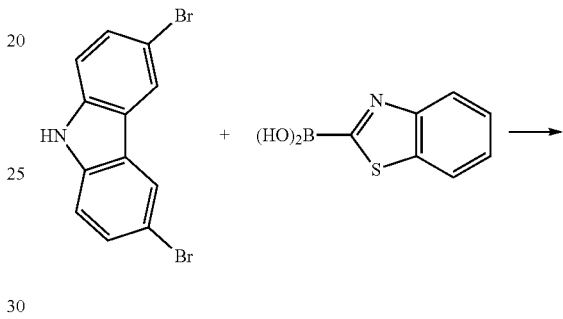

→

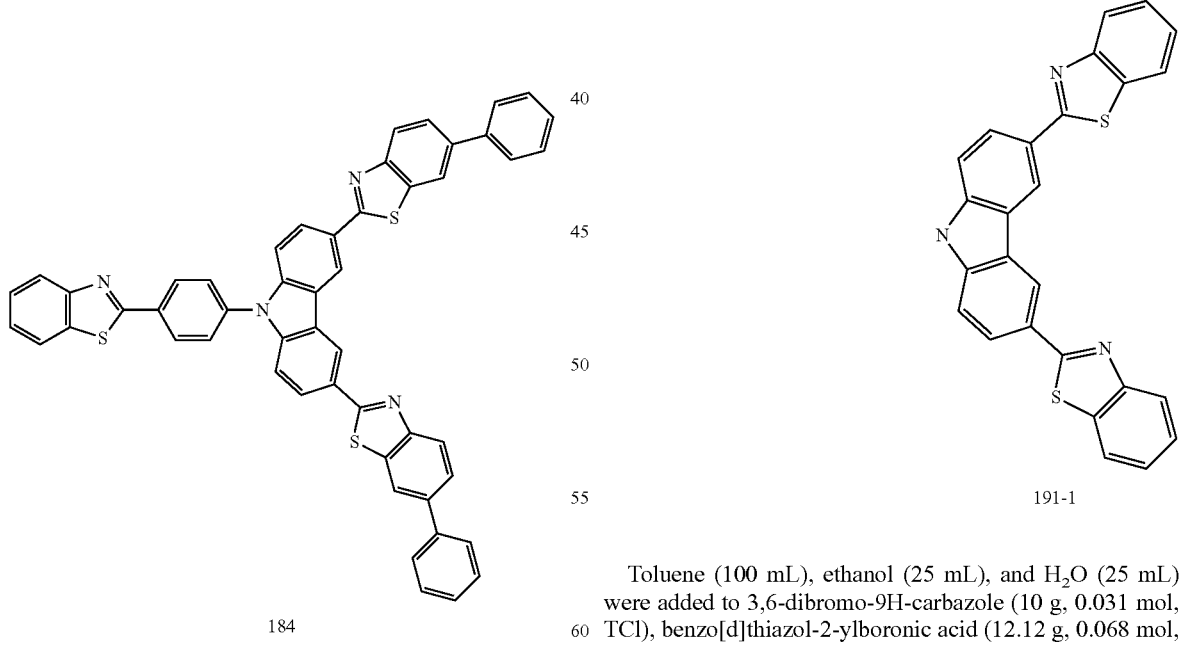

191-1

Toluene (100 mL), ethanol (25 mL), and H$_2$O (25 mL) were added to 3,6-dibromo-9H-carbazole (10 g, 0.031 mol, TCI), benzo[d]thiazol-2-ylboronic acid (12.12 g, 0.068 mol, Sigma-Aldrich), potassium carbonate (12.76 g, 0.092 mol, Sigma-Aldrich), and Pd(PPh$_3$)$_4$ (1.07 g, 0.001 mol, Sigma-Aldrich) as a catalyst. The mixture was refluxed with stirring at 100° C. for 5 h. After completion of the reaction, the reaction mixture was extracted and purified by column chromatography to afford 7.4 g (yield 55.5%) of Intermediate 191-1.

(2) Preparative Example 2: Synthesis of Intermediate 191-2

(3) Preparative Example 3: Synthesis of Compound 191

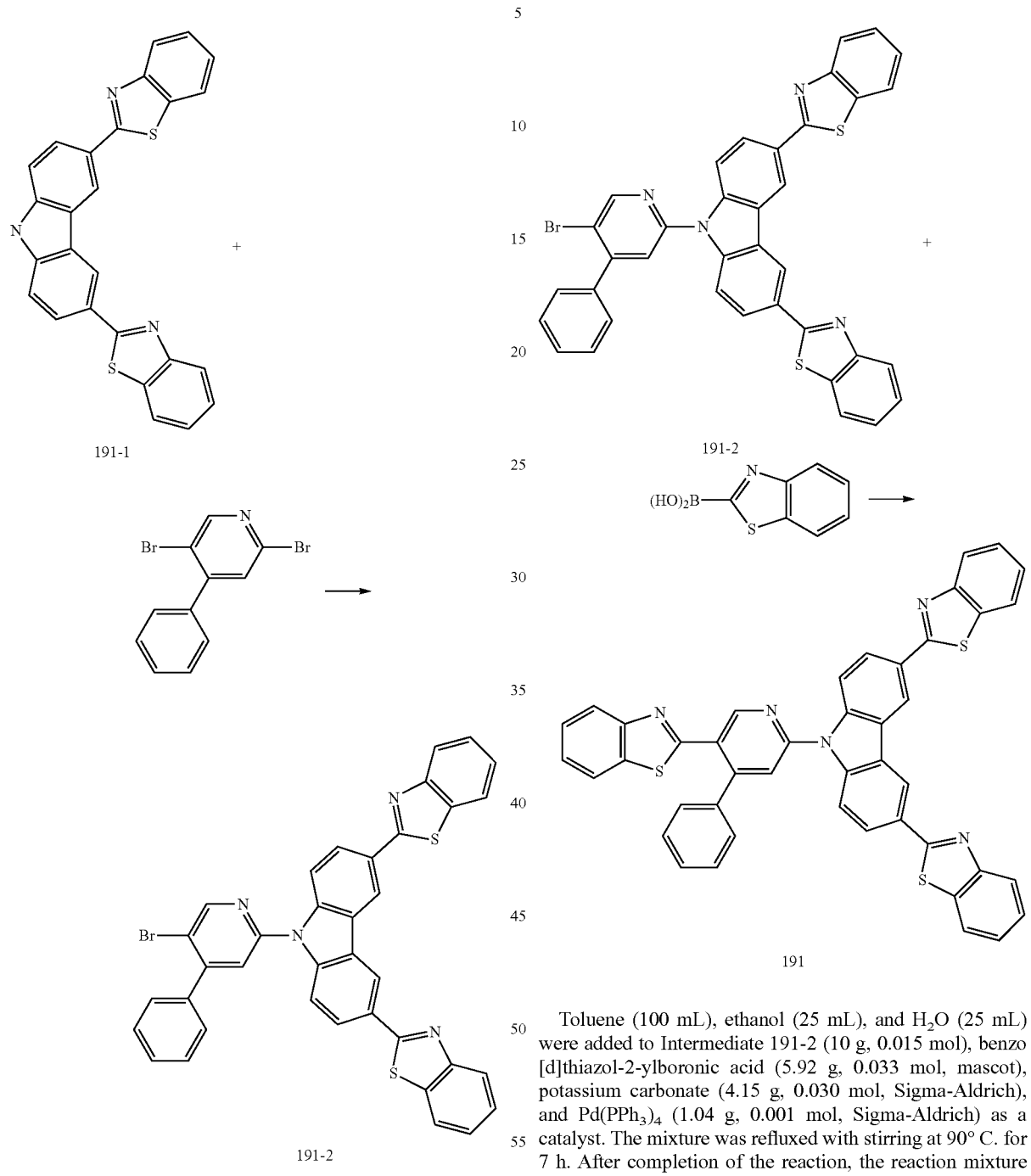

DMF (100 mL) was added to Intermediate 191-1 (10 g, 0.023 mol), 2,5-dibromo-4-phenylpyridine (8.7 g, 0.028 mol, mascot), potassium carbonate (6.38 g, 0.046 mol, Sigma-Aldrich), dibenzo-18-crown-6 (0.83 g, 0.002 mol, Sigma-Aldrich), and Cu (2.93 g, 0.046 mol, Sigma-Aldrich). The mixture was refluxed with stirring at 160° C. for 7 h. After completion of the reaction, the reaction mixture was extracted and purified by column chromatography to afford 7.4 g (yield 48.2%) of Intermediate 191-2.

Toluene (100 mL), ethanol (25 mL), and $H_2O$ (25 mL) were added to Intermediate 191-2 (10 g, 0.015 mol), benzo[d]thiazol-2-ylboronic acid (5.92 g, 0.033 mol, mascot), potassium carbonate (4.15 g, 0.030 mol, Sigma-Aldrich), and $Pd(PPh_3)_4$ (1.04 g, 0.001 mol, Sigma-Aldrich) as a catalyst. The mixture was refluxed with stirring at 90° C. for 7 h. After completion of the reaction, the reaction mixture was extracted and purified by column chromatography to afford 5.7 g (yield 52.7%) of Compound 191.

H-NMR (200 MHz, $CDCl_3$): δ ppm, 1H (8.90/s, 8.00/d, 7.87/d, 7.70/s, 7.69/d, 7.41/m), 2H (7.79/d, 7.77/s, 7.51/m), 3H (8.01/d), 4H (8.18/d), 6H (7.53/m)

LC/MS: m/z=719[(M+1)$^+$]

Device Examples (HOST)

An ITO transparent electrode having dimensions of 25 mm×25 mm×0.7 mm was attached to a glass substrate, patterned to have a light emitting area of 2 mm×2 mm, followed by cleaning. After the substrate was mounted in a vacuum chamber, the base pressure was adjusted to ≥1×10$^{-6}$ torr. Thereafter, organic materials and metals were deposited on the ITO substrate to fabricate a device having the following structure:

ITO/hole injecting layer (HAT-CN, 5 nm)/hole transport layer (α-NPB, 100 nm)/light emitting layer (20 nm)/electron transport layer (201:Liq, 30 nm)/LiF (1 nm)/Al (100 nm)

Examples 1-7

Green organic electroluminescent devices were fabricated using the corresponding host compounds 2 shown in Table 1 for light emitting layers. The luminescent properties (including current efficiencies) of the devices were measured.

Specifically, HAT-CN was used to form a 5 nm thick hole injecting layer on an ITO transparent electrode. Thereafter, a hole transport layer was formed using α-NPB. A 20 nm thick light emitting layer was formed using a 1:1 mixture of GH1 as a host compound 1 and the corresponding host compound 2 shown in Table 1. Ir(ppy)$_3$ was used as a dopant compound. A 30 nm thick electron transport layer was formed using the compound of Formula 201 doped with Liq (50%). Subsequently, a 1 nm thick LiF layer and a 100 nm thick aluminum layer were sequentially formed, completing the fabrication of an organic electroluminescent device.

Comparative Example 1

An organic electroluminescent device was fabricated in the same manner as in Examples 1-7, except that a light emitting layer was formed using GH2 as a host material 2 instead of the inventive compounds.

Experimental Example 1: Luminescent Properties of the Devices Fabricated in Examples 1-7

The driving voltages, current efficiencies, and color coordinates of the organic electroluminescent devices fabricated in Examples 1-7 and Comparative Example 1 were measured at 10,000 nits using a source meter (Model 237, Keithley) and a spectroradiometer (PR-650, Photo Research). The results are shown in Table 1.

TABLE 1

| Example No. | Host 2 | V | cd/A | CIEx | CIEy |
|---|---|---|---|---|---|
| 1 | Formula 1 | 4.3 | 81.3 | 0.332 | 0.633 |
| 2 | Formula 53 | 4.5 | 84.8 | 0.323 | 0.622 |
| 3 | Formula 64 | 4.4 | 82.9 | 0.333 | 0.623 |
| 4 | Formula 75 | 4.1 | 81.1 | 0.312 | 0.622 |
| 5 | Formula 97 | 4.4 | 82.3 | 0.331 | 0.632 |
| 6 | Formula 102 | 4.3 | 81.8 | 0.323 | 0.633 |
| 7 | Formula 140 | 4.5 | 85.1 | 0.332 | 0.602 |
| Comparative Example 1 | GH2 | 5.2 | 63.0 | 0.330 | 0.630 |

As can be seen from the results in Table 1, the devices of Examples 1-7, each of which employed the inventive compound as a host compound 2 for the light emitting layer, were driven at lower voltages and had higher current efficiencies than the device of Comparative Example 1.

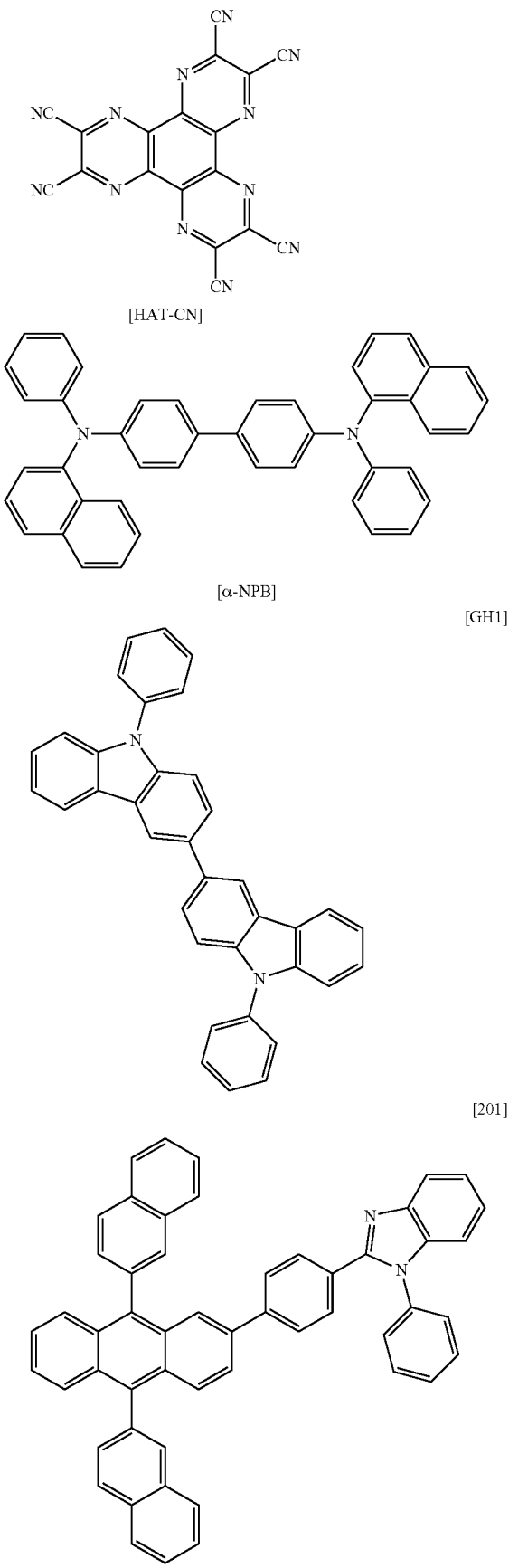

-continued

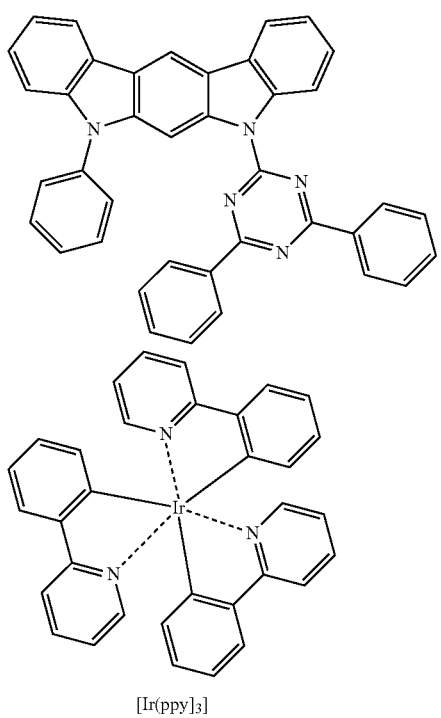

[GH2]

[Ir(ppy)₃]

Device Examples (Capping Layer)

An Ag-containing ITO transparent electrode having dimensions of 25 mm×25 mm×0.7 mm was attached to a glass substrate, patterned to have a light emitting area of 2 mm×2 mm, followed by cleaning. After the substrate was mounted in a vacuum chamber, the base pressure was adjusted to $1\times10^{-6}$ torr. Thereafter, organic materials and metals were deposited on the Ag-containing ITO glass substrate to fabricate a device having the following structure:

Ag:ITO/hole injecting layer (HAT-CN, 5 nm)/hole transport layer (α-NPB, 100 nm)/electron blocking layer (TCTA, 10 nm)/light emitting layer (20 nm)/electron transport layer (201:Liq, 30 nm)/LiF (1 nm)/Mg:Ag (15 nm)/capping layer (70 nm)

Examples 8-12

Blue organic electroluminescent devices were fabricated using the corresponding inventive compounds shown in Table 2 as materials for capping layers. The organic electroluminescent devices were measured for luminescent properties, including luminescent efficiencies.

Specifically, an Ag-containing ITO transparent electrode was disposed on a glass substrate and HAT-CN was used to form a 5 nm thick hole injecting layer on the ITO transparent electrode. Thereafter, a 100 nm thick hole transport layer was formed using α-NPB. A 10 nm thick electron blocking layer was formed using TCTA. A 20 nm thick light emitting layer was formed using BH1 as a host compound and BD1 as a dopant compound. A 30 nm thick electron transport layer was formed using the compound of Formula 201 doped with Liq (50%). A 1 nm thick LiF layer was formed. Subsequently, a 15 nm thick Mg:Ag (1:9) layer was formed. A 70 nm thick capping layer was formed using the corresponding inventive compound shown in Table 2, completing the fabrication of an organic electroluminescent device.

Comparative Example 2

An organic electroluminescent device was fabricated in the same manner as in Examples 8-12, except that the capping layer was not used.

Comparative Example 3

An organic electroluminescent device was fabricated in the same manner as in Examples 8-12, except that a capping layer was formed using Alq₃ instead of the inventive compounds.

Experimental Example 2: Luminescent Properties of the Devices Fabricated in Examples 8-12

The driving voltages, current efficiencies, and color coordinates of the organic electroluminescent devices fabricated in Examples 8-12 and Comparative Examples 2 and 3 were measured at 1,000 nits using a source meter (Model 237, Keithley) and a spectroradiometer (PR-650, Photo Research). The results are shown in Table 2.

TABLE 2

| Example No. | Capping layer | V | cd/A | CIEx | CIEy |
|---|---|---|---|---|---|
| 8 | Formula 147 | 3.8 | 8.4 | 0.143 | 0.045 |
| 9 | Formula 184 | 3.6 | 8.8 | 0.144 | 0.050 |
| 10 | Formula 191 | 3.7 | 8.9 | 0.142 | 0.048 |
| 11 | Formula 219 | 3.7 | 8.6 | 0.143 | 0.043 |
| 12 | Formula 222 | 3.8 | 8.5 | 0.142 | 0.046 |
| Comparative Example 2 | not used | 4.2 | 7.0 | 0.145 | 0.140 |
| Comparative Example 3 | Alq₃ | 4.0 | 7.8 | 0.145 | 0.057 |

As can be seen from the results in Table 2, the devices of Examples 8-12, in which the inventive compounds were used to form the capping layers, were driven at lower voltages and had higher current efficiencies than the devices of Comparative Examples 2 and 3.

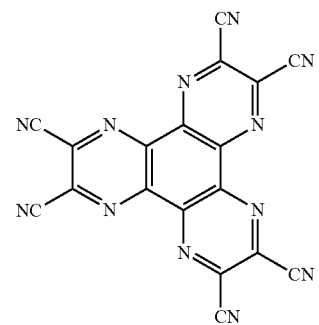

[HAT-CN]

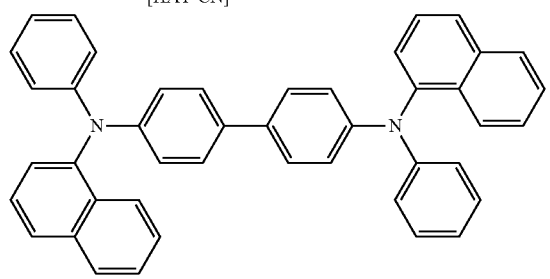

[α-NPB]

[BH1]

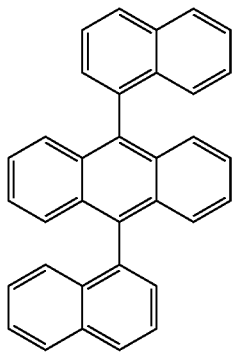

[BD1]

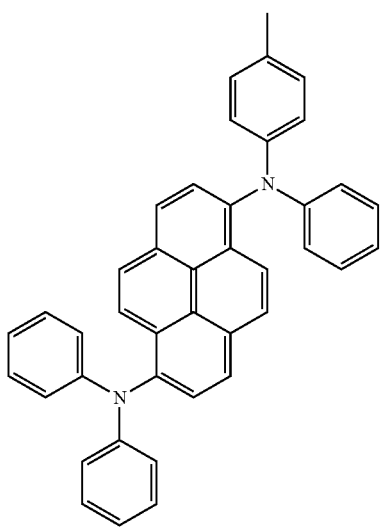

[201]

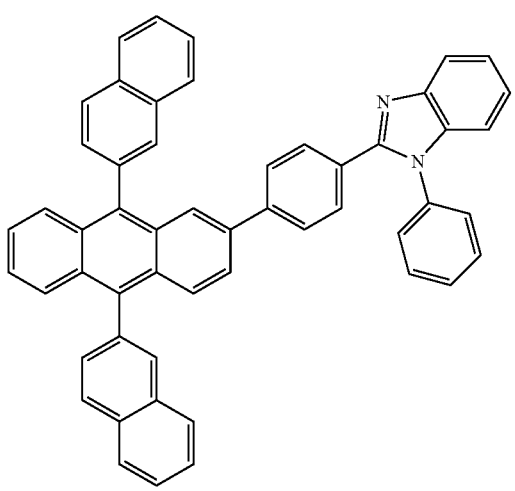

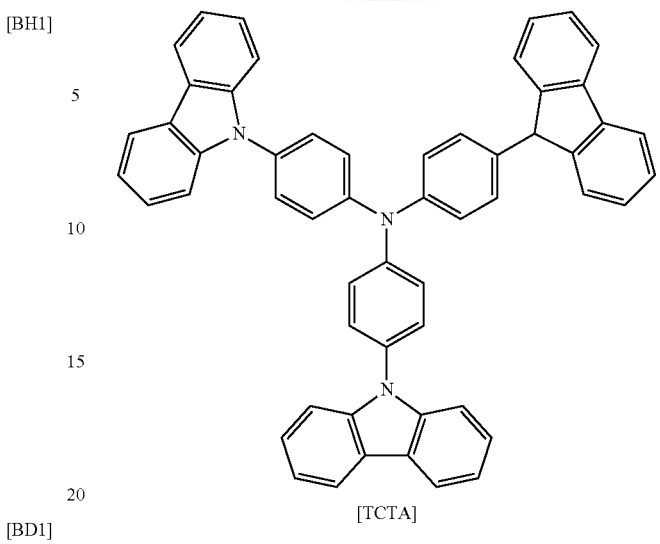

[TCTA]

What is claimed is:

1. A compound of Formula (I):

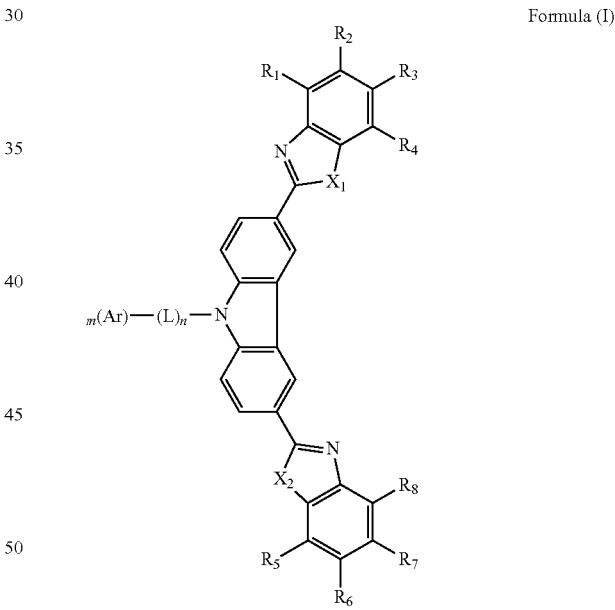

Formula (I)

wherein $X_1$ and $X_2$ are each independently O or S;

$R_1$, $R_2$, $R_3$, $R_4$, $R_5$, $R_6$, $R_7$, and $R_8$ are each independently selected from —H, deuterium, halo, cyano, alkyl, aryl, heteroaryl, cycloalkyl, and heterocyclyl, wherein $R_1$, $R_2$, $R_3$, $R_4$, $R_5$, $R_6$, $R_7$, and $R_8$ are optionally substituted with one or more substituents selected from the group consisting of deuterium, halo, cyano, nitro, hydroxyl, silyl, alkyl, cycloalkyl, alkoxy, alkenyl, aryl, and heterocyclyl, and wherein $R_1$, $R_2$, $R_3$, $R_4$, $R_5$, $R_6$, $R_7$, and $R_8$ are optionally bonded to each other or joined to one or more adjacent substituents to form a monocyclic or polycyclic group optionally containing one or more heteroatoms selected from N, S, and O;

L is a bond, arylene, or heteroarylene;

n is 0, 1, 2, or 3,

Ar is aryl, heteroaryl, fluorenyl, cycloalkyl, or heterocyclyl, and m is 1, 2, or 3.

2. The compound according to claim 1, wherein
wherein $R_1$, $R_2$, $R_3$, $R_4$, $R_5$, $R_6$, $R_7$, and $R_8$ are each independently selected from —H, deuterium, halo, cyano, $C_1$-$C_{10}$ alkyl, aryl, $C_3$-$C_{30}$ heteroaryl, $C_3$-$C_{20}$ cycloalkyl, and $C_3$-$C_{30}$ heterocyclyl, wherein $R_1$, $R_2$, $R_3$, $R_4$, $R_5$, $R_6$, $R_7$, and $R_8$ are optionally substituted with one or more substituents selected from the group consisting of deuterium, halo, cyano, nitro, hydroxyl, silyl, $C_1$-$C_{10}$ alkyl, $C_3$-$C_{20}$ cycloalkyl, $C_1$-$C_{10}$ alkoxy, $C_2$-$C_{10}$ alkenyl, aryl, and $C_3$-$C_{30}$ heterocyclyl, and wherein $R_1$, $R_2$, $R_3$, $R_4$, $R_5$, $R_6$, $R_7$, and $R_8$ are optionally bonded to each other or joined to one or more adjacent substituents to form a monocyclic or polycyclic group optionally containing one or more heteroatoms selected from N, S, and O.

3. The compound according to claim 1, wherein the compound of Formula (I) is selected from the group consisting of the following compounds:

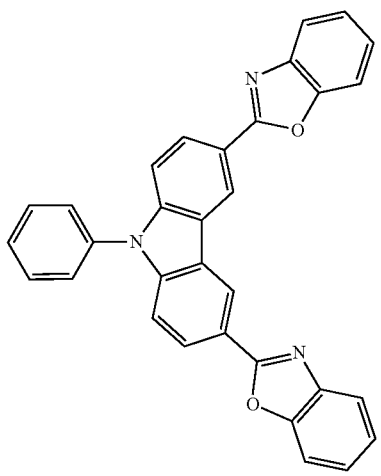
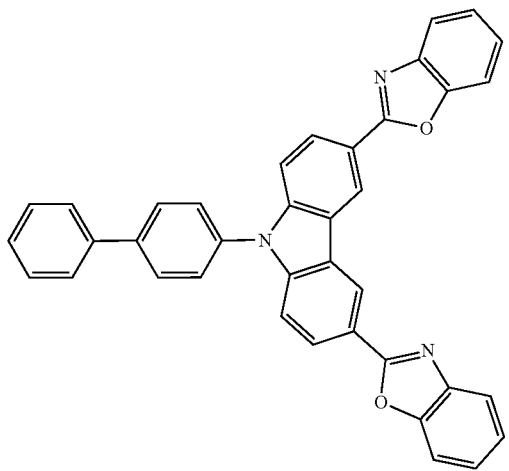
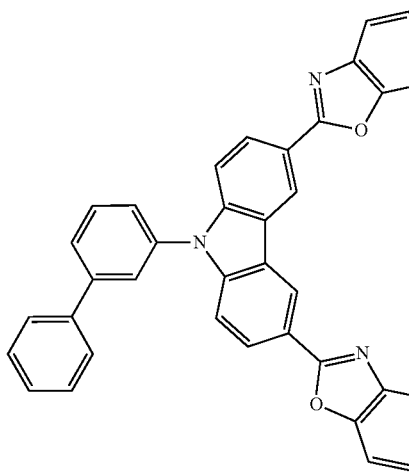
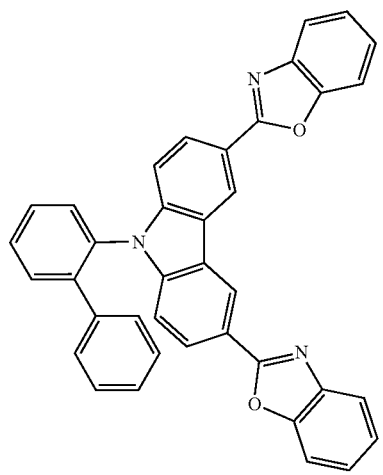

-continued
| 109 | 110 |
|---|---|
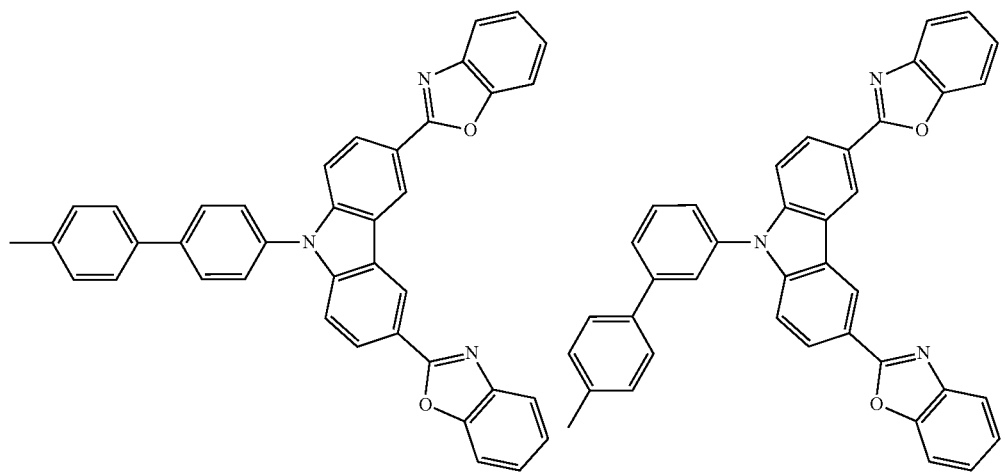
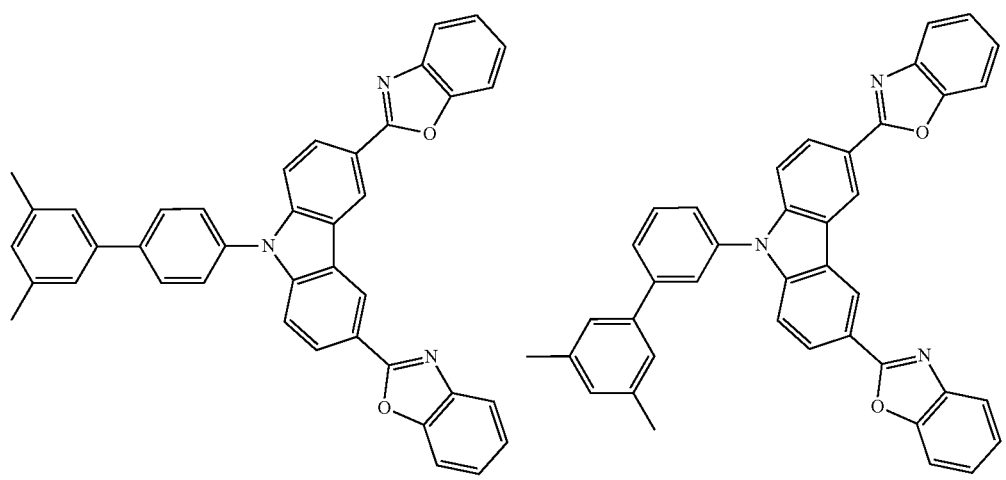
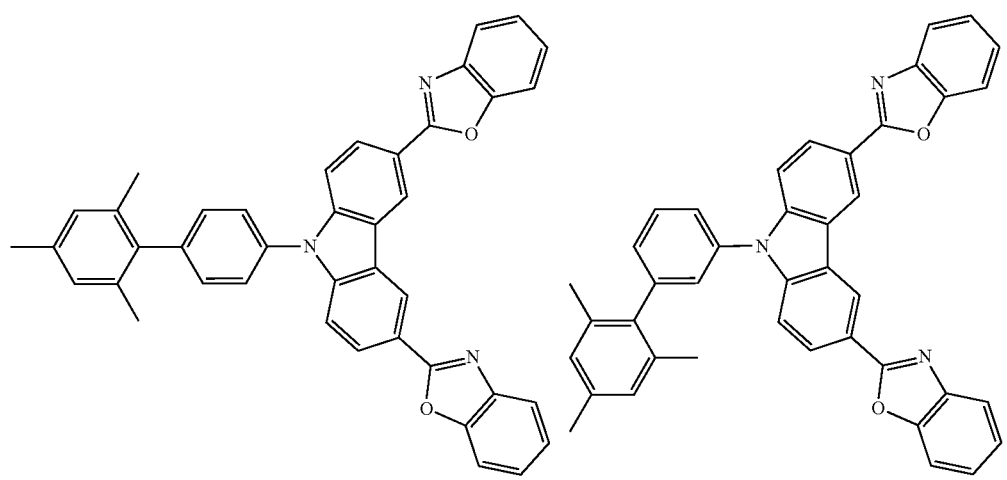

-continued
111
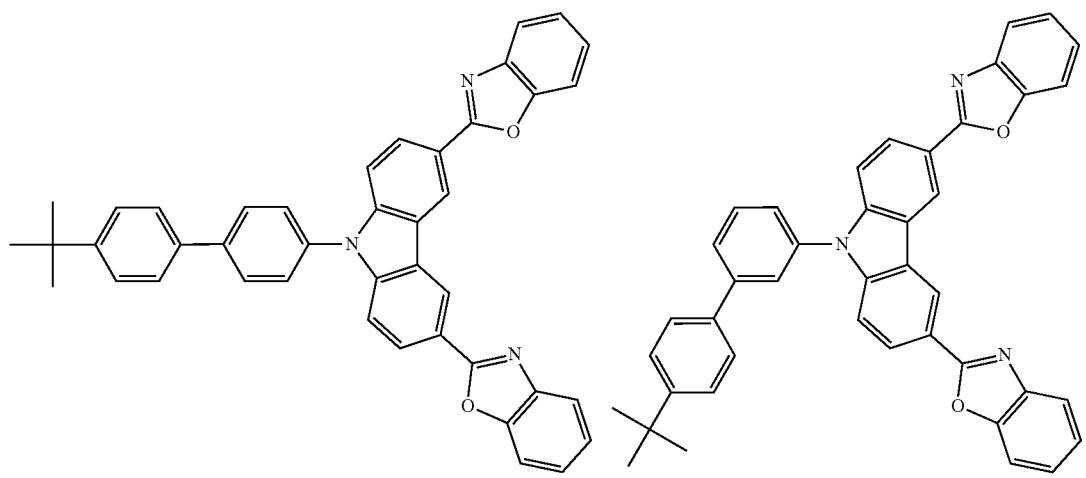
112
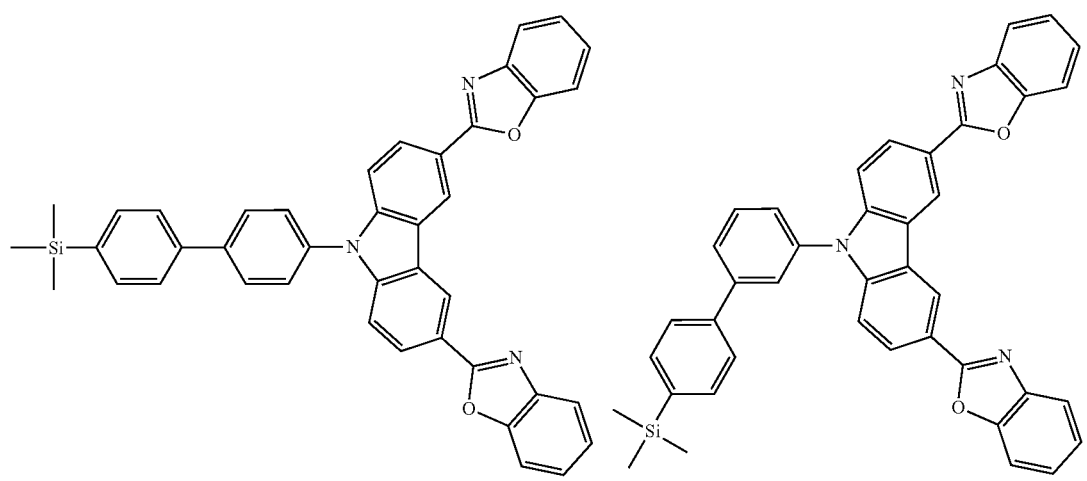
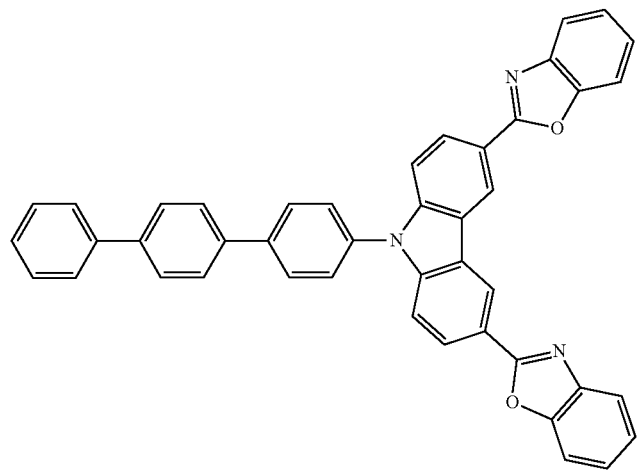

-continued
113
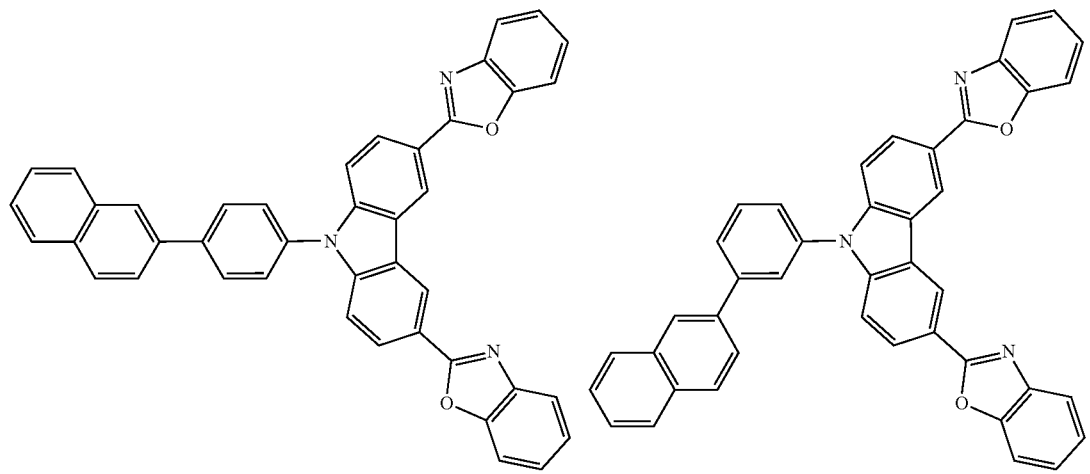
114
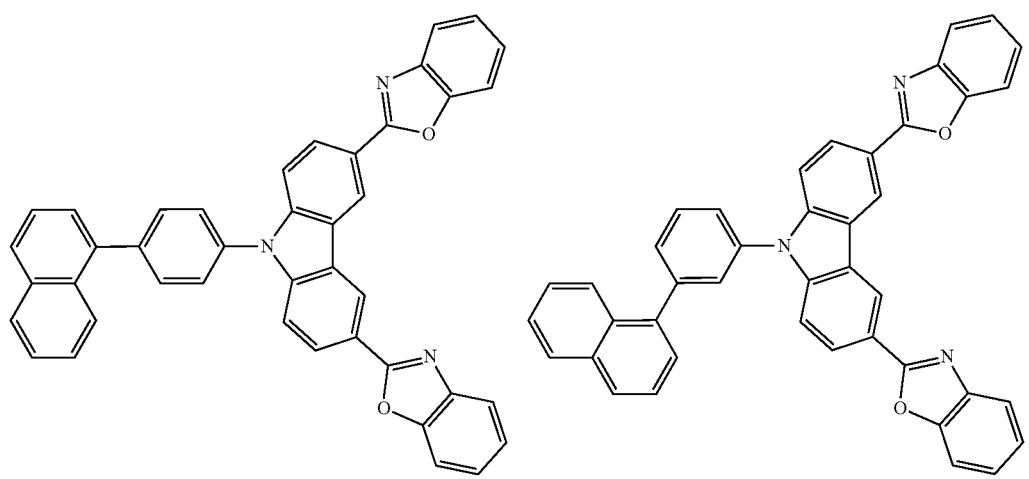
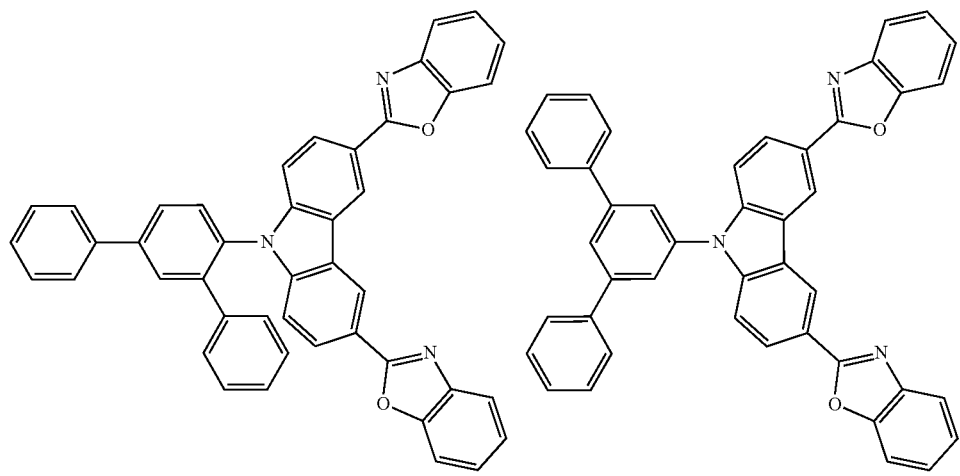

-continued
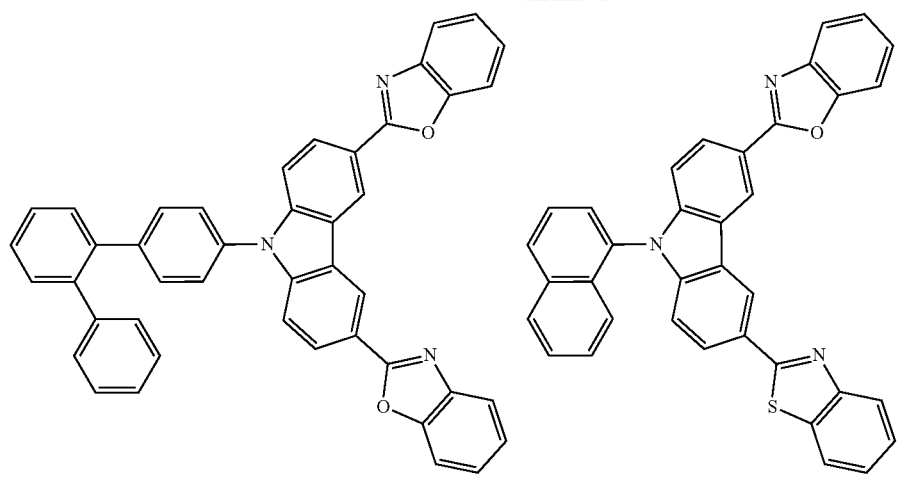
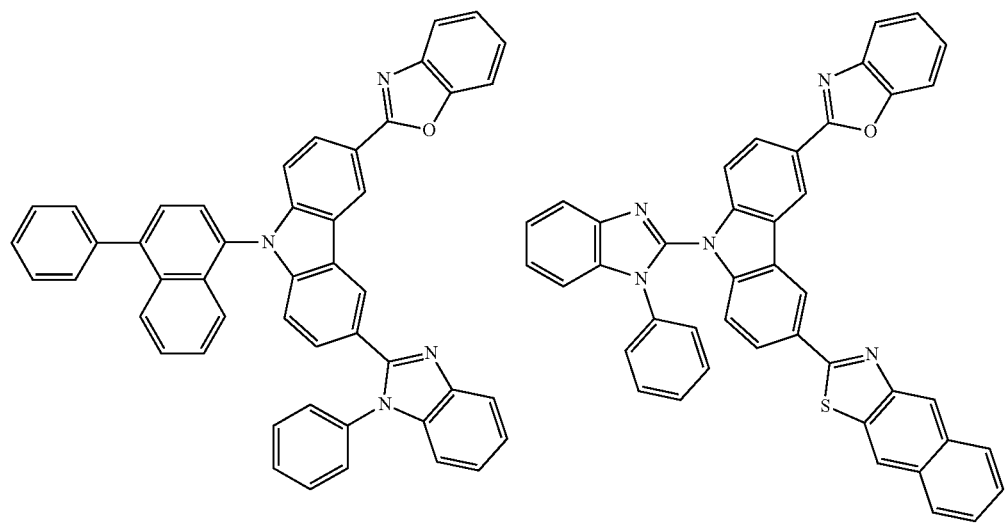
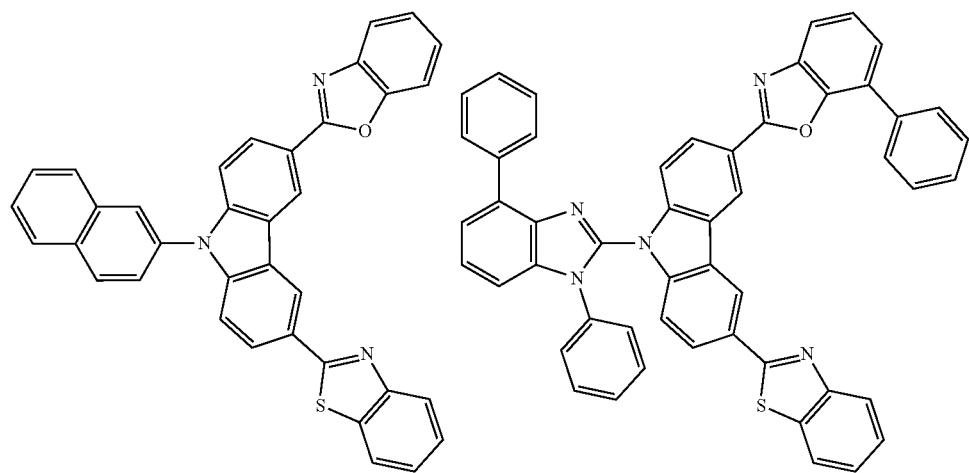

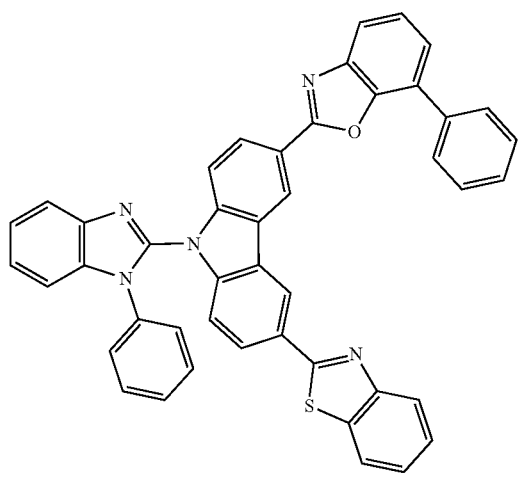
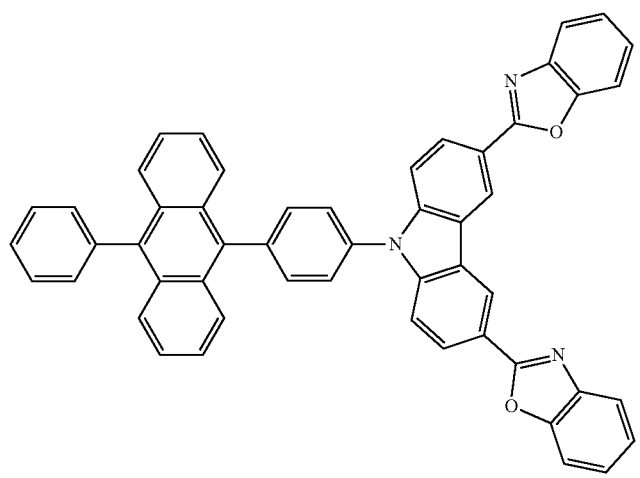
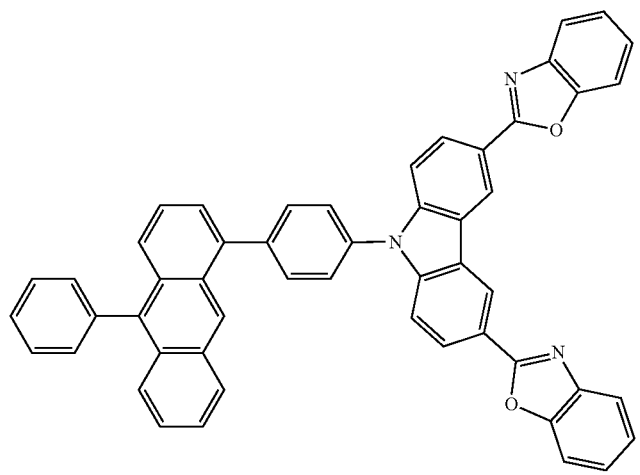

119                                    120
-continued
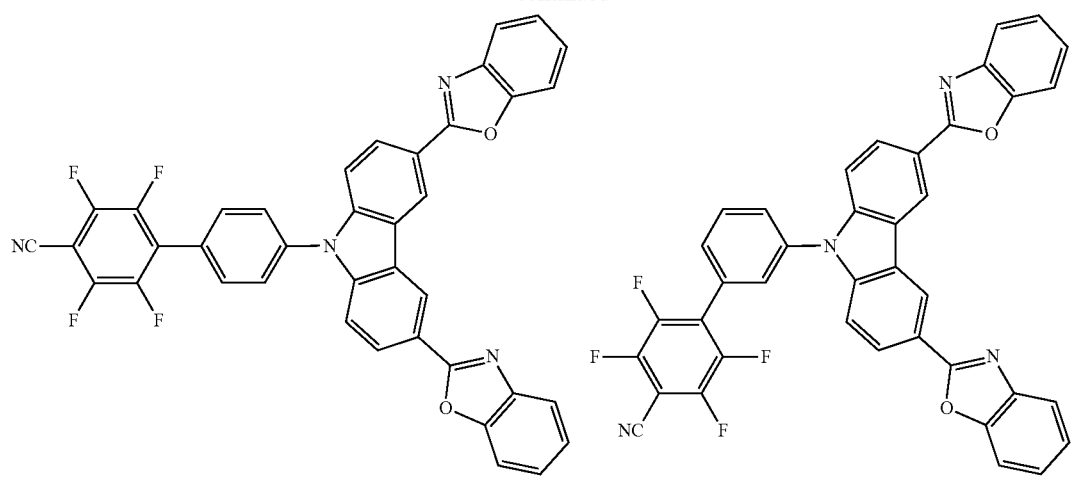
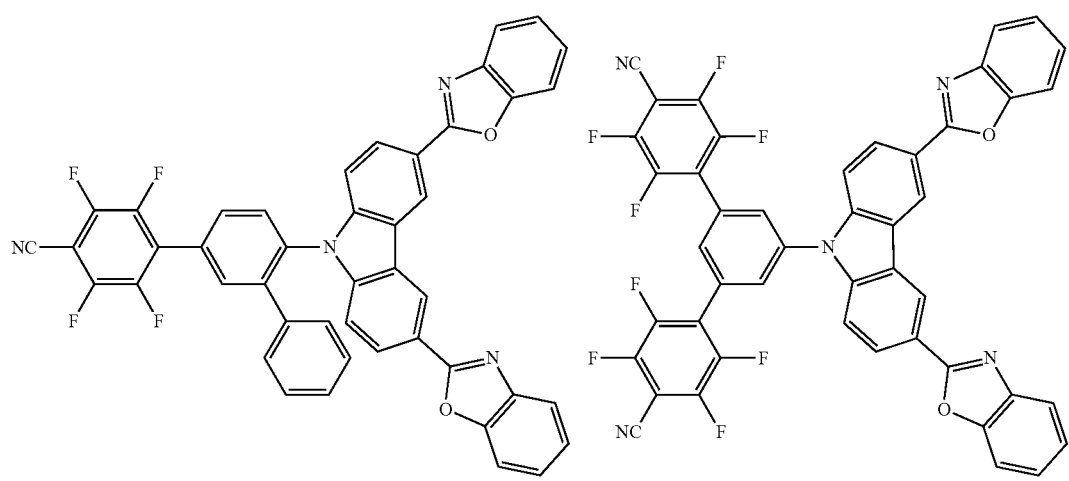
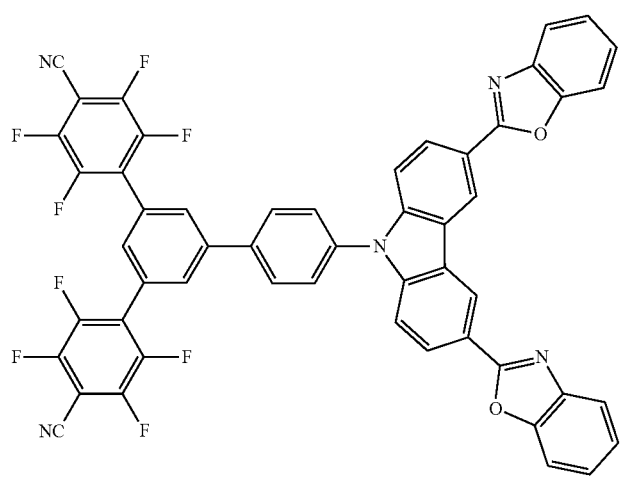

-continued
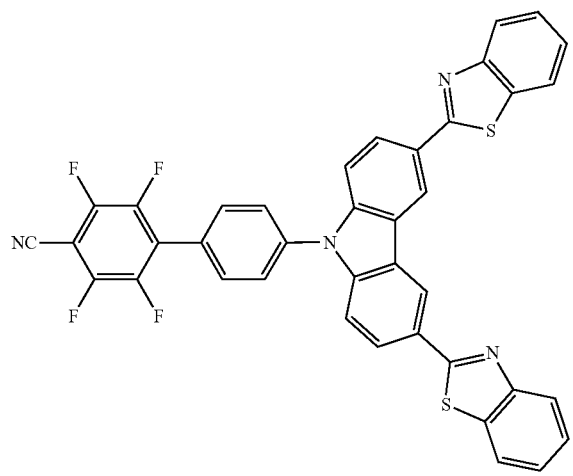
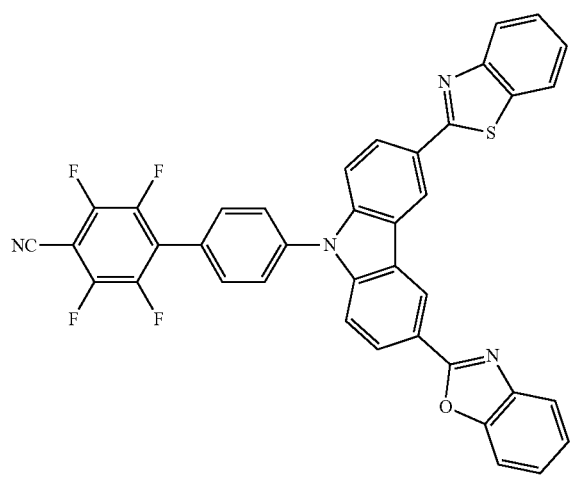
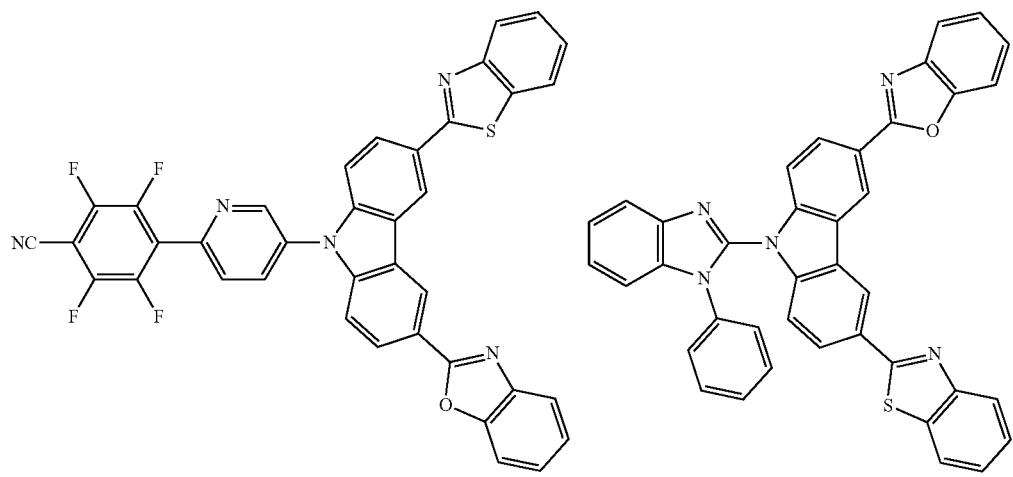

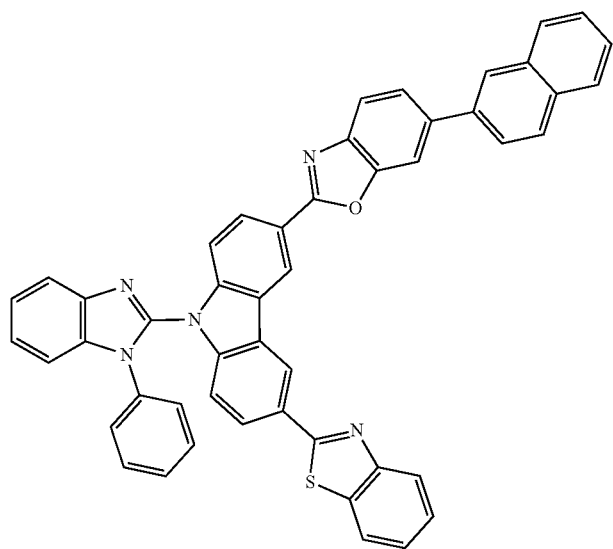
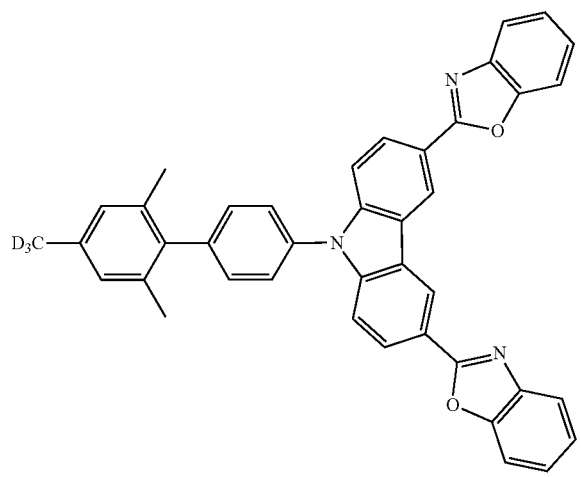
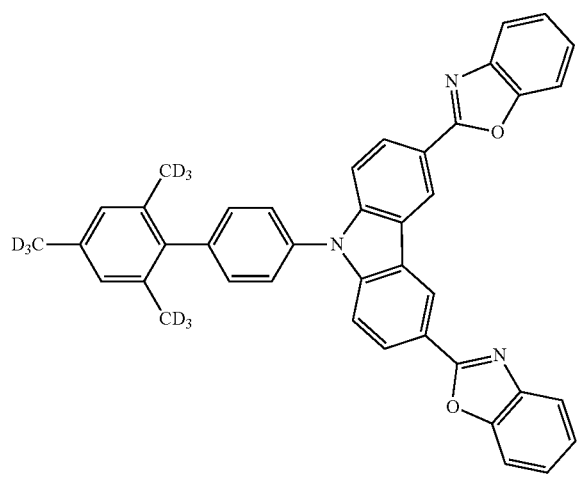

-continued
125
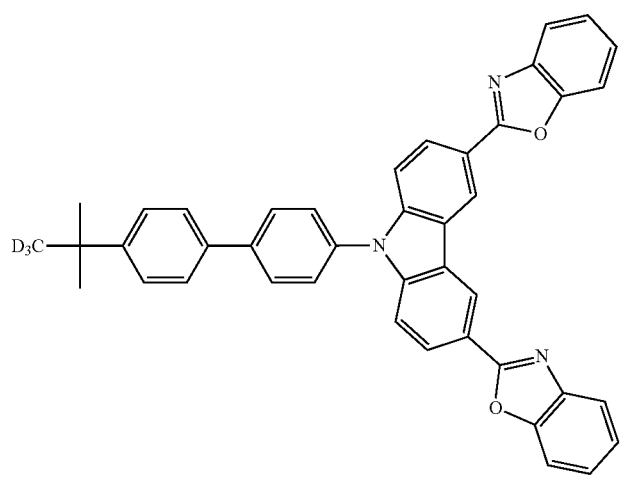
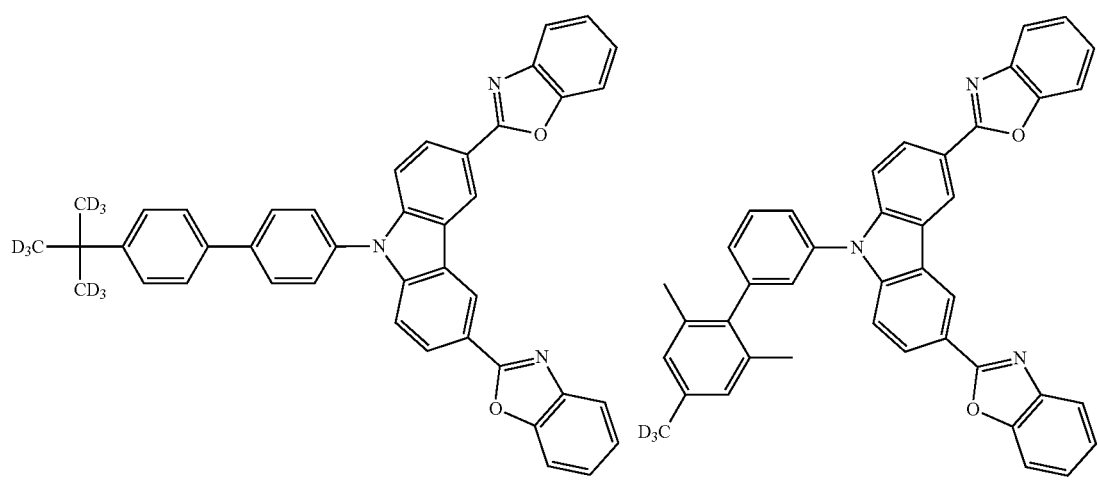
126
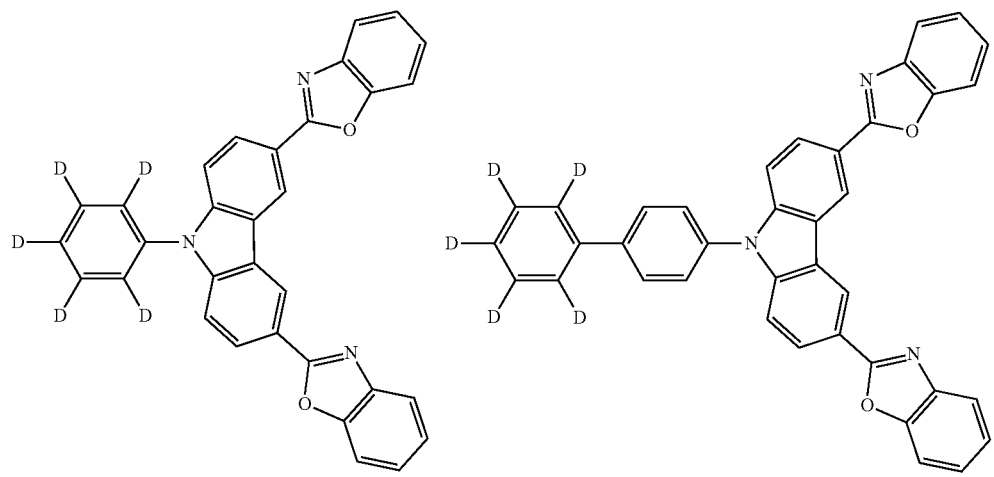

127 128
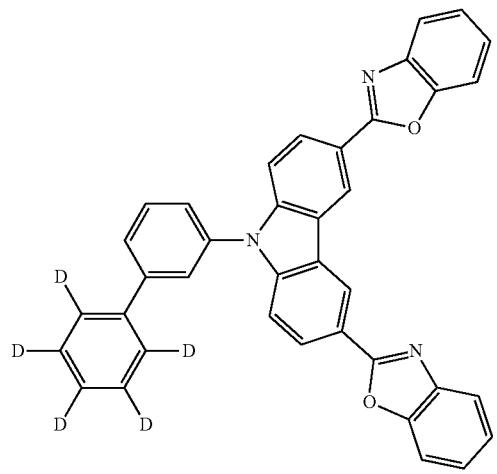
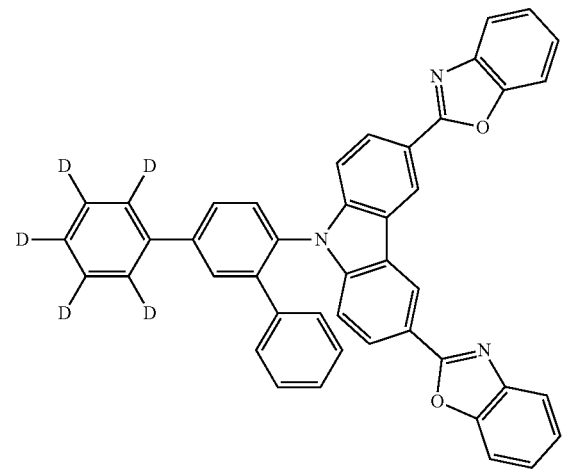
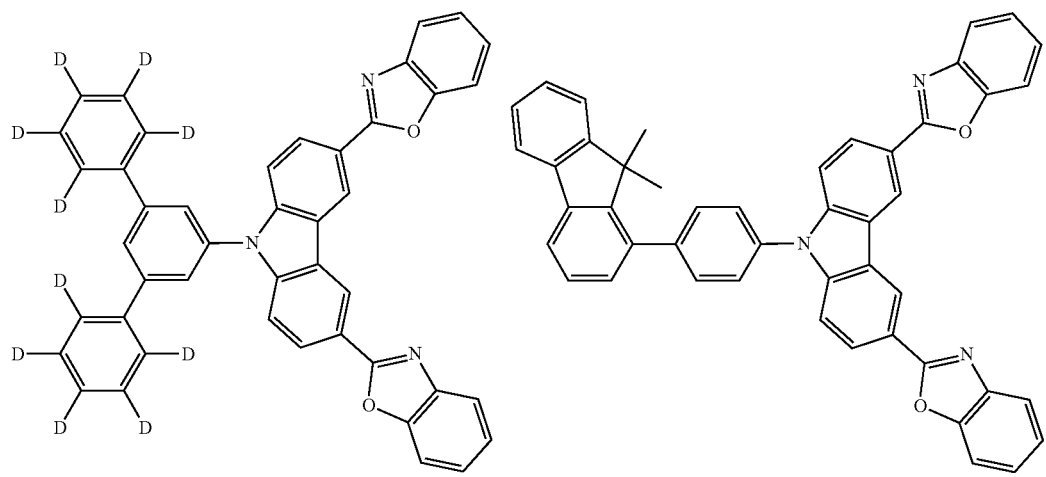
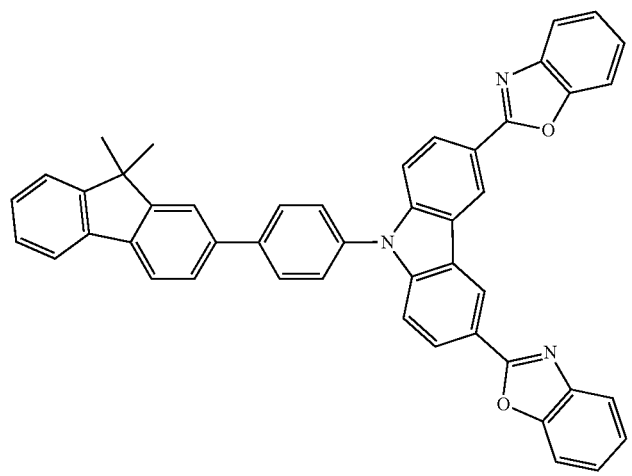

-continued
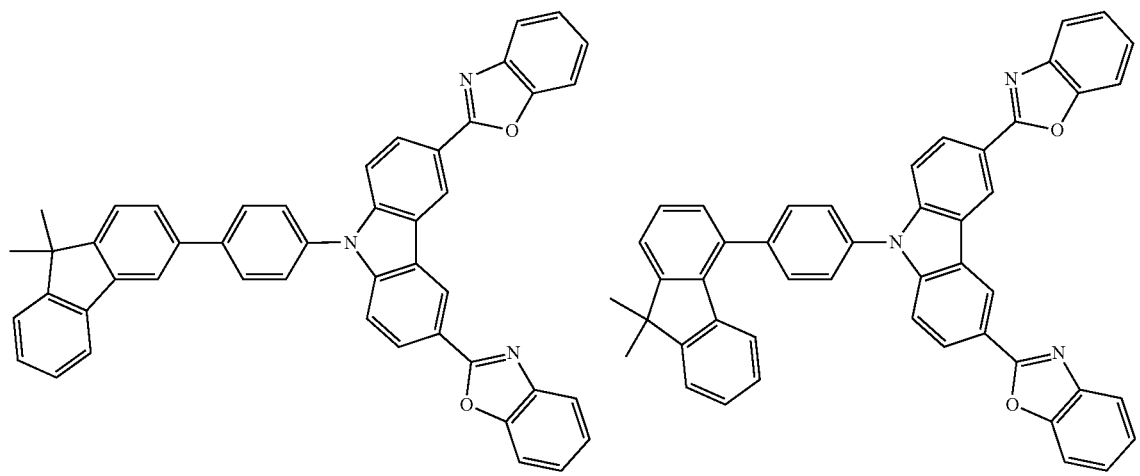
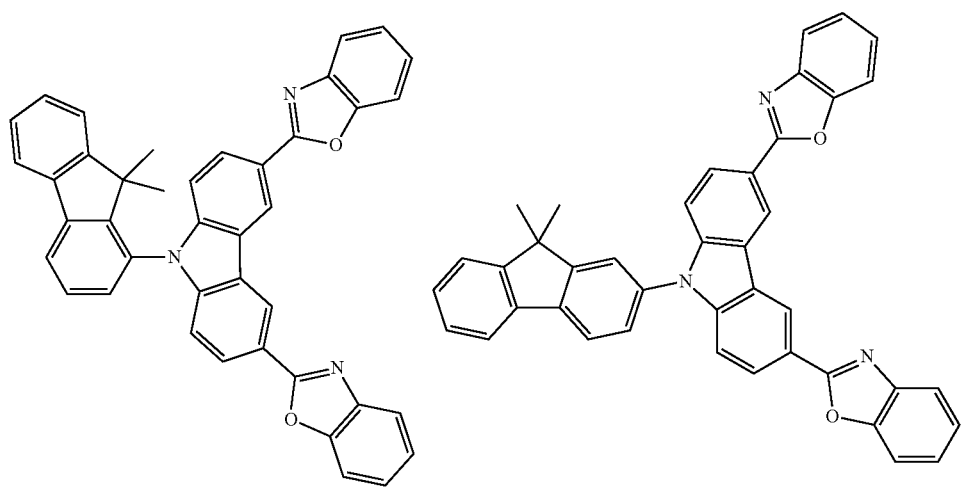
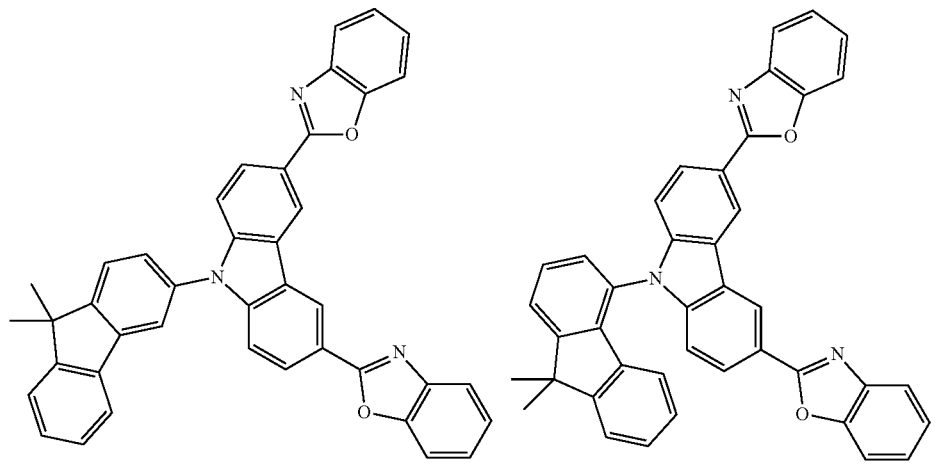

-continued
131
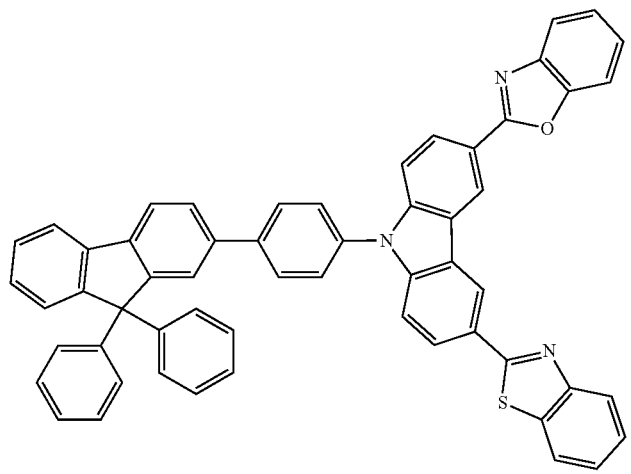
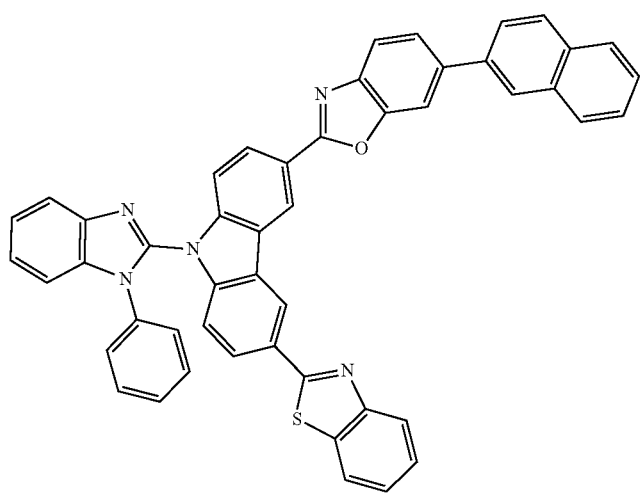
132
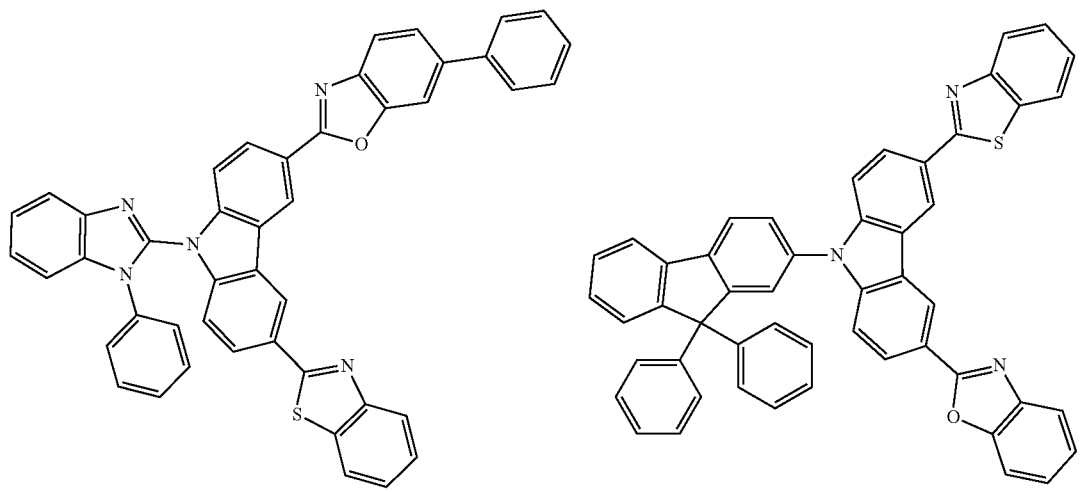

-continued
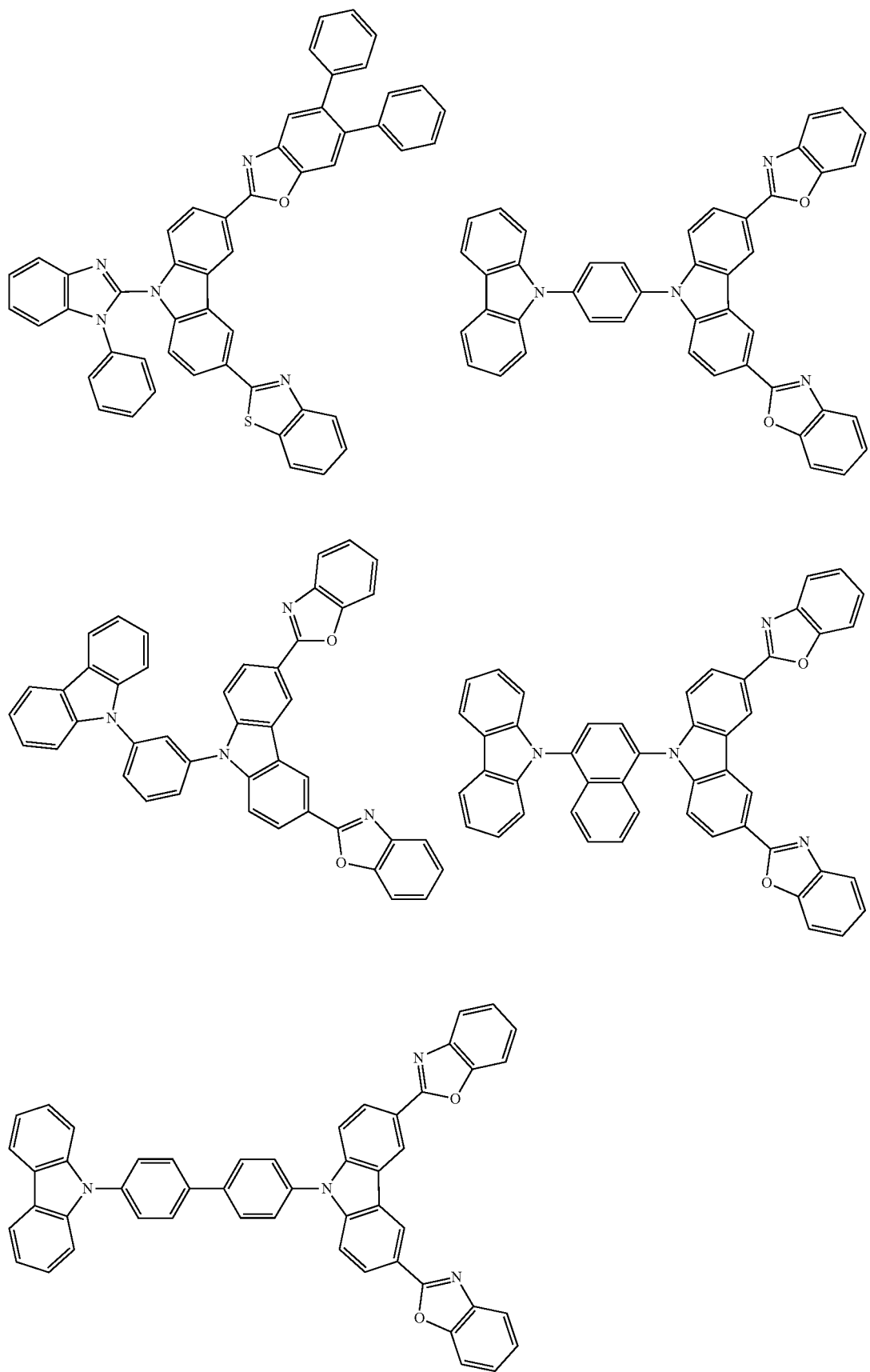

-continued
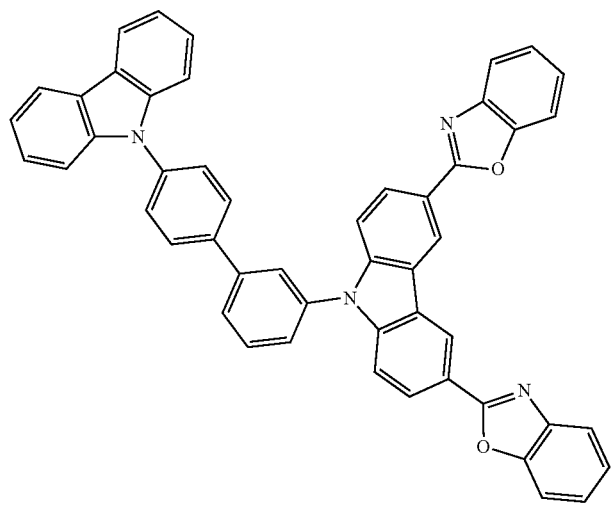
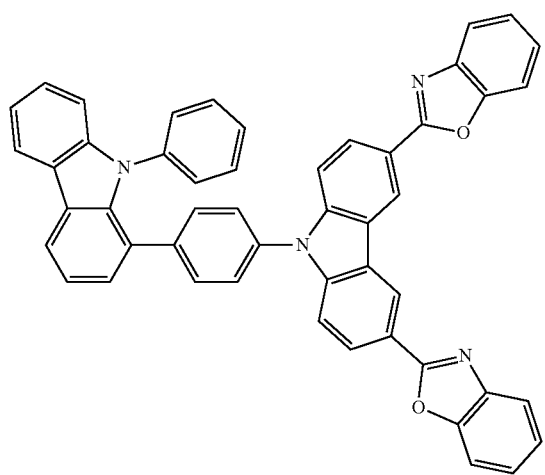
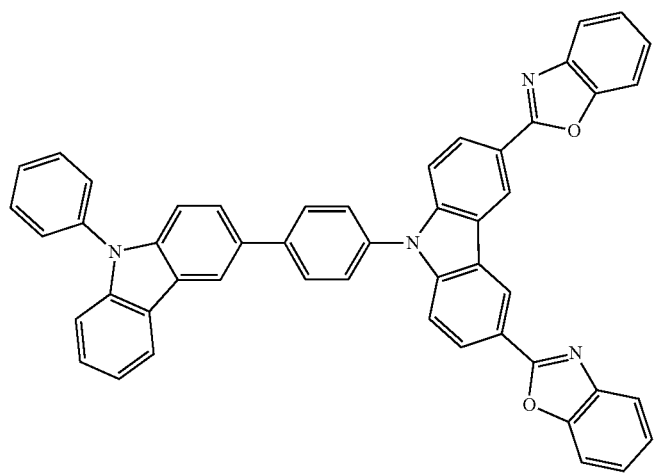

-continued
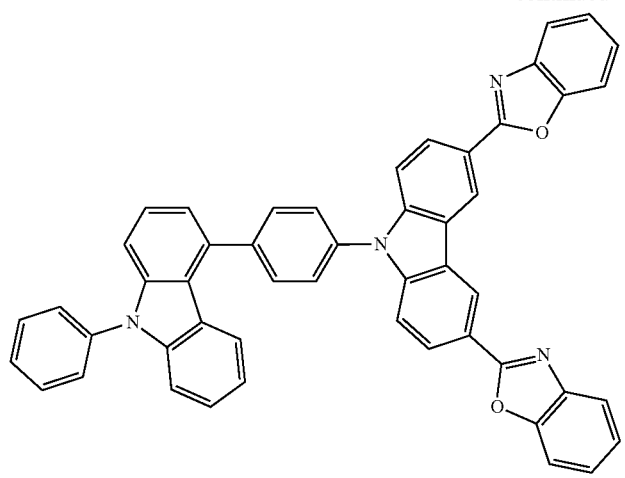
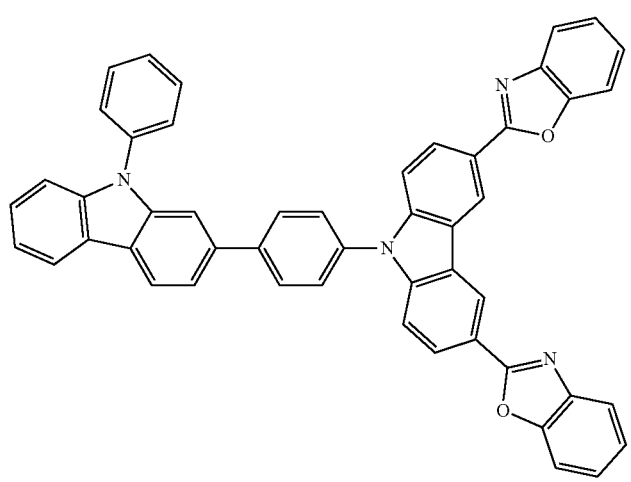
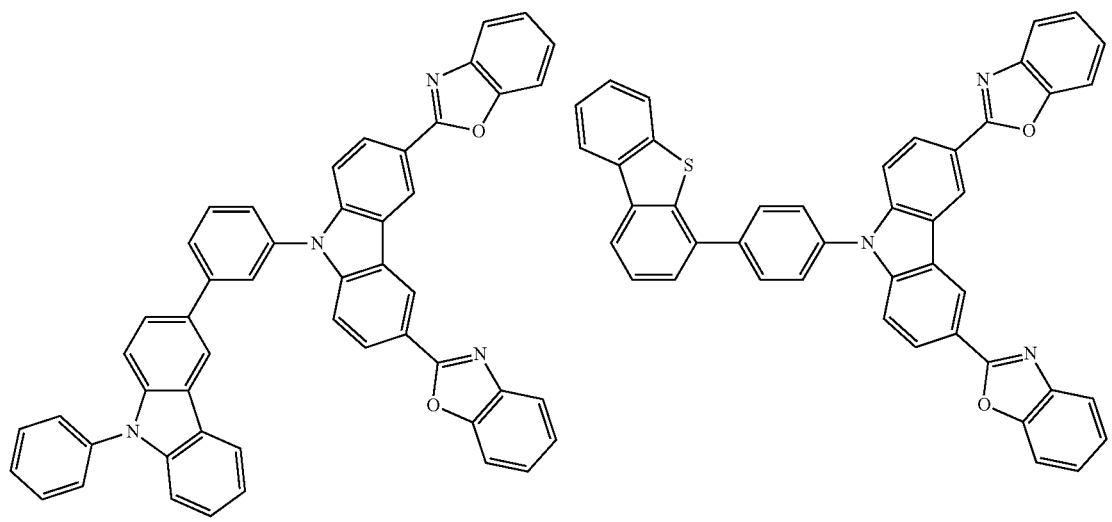

-continued
139
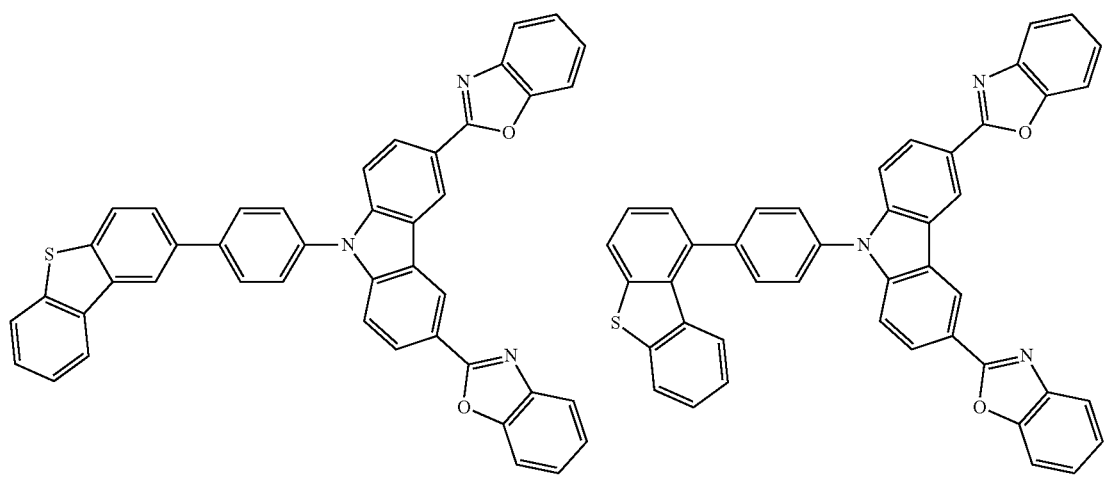
140
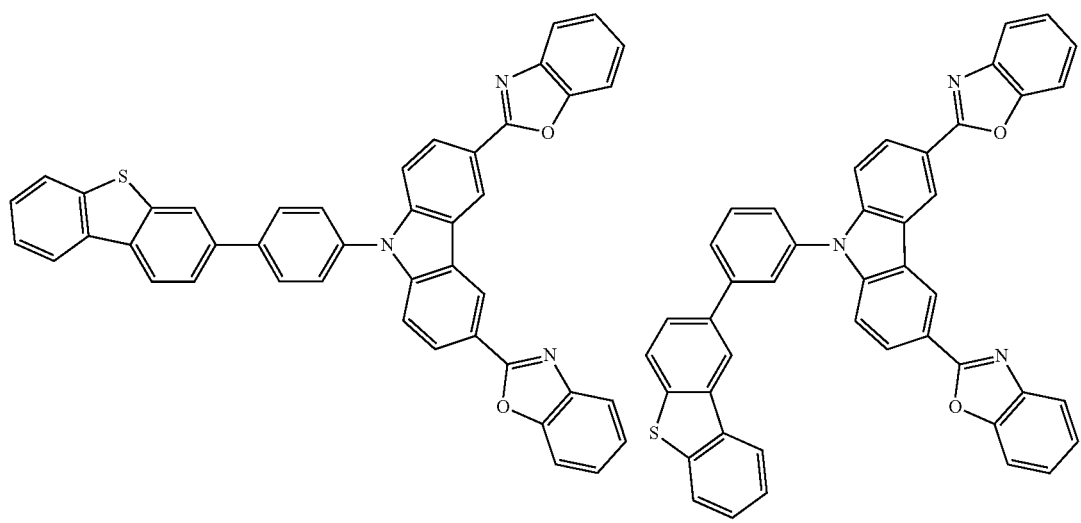
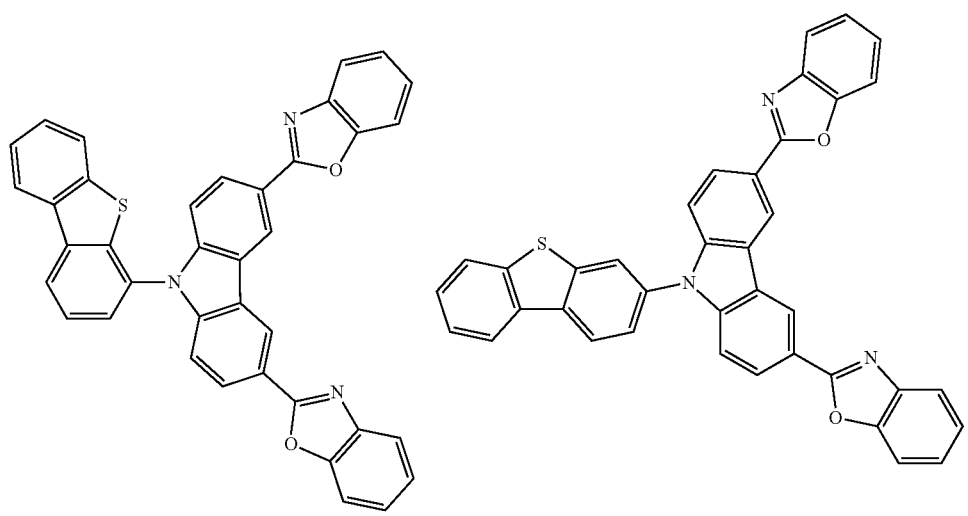

141
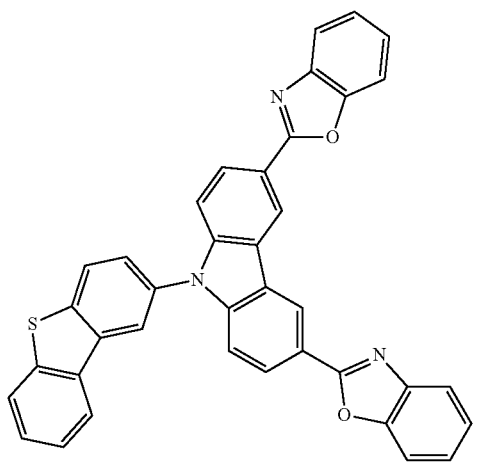
142
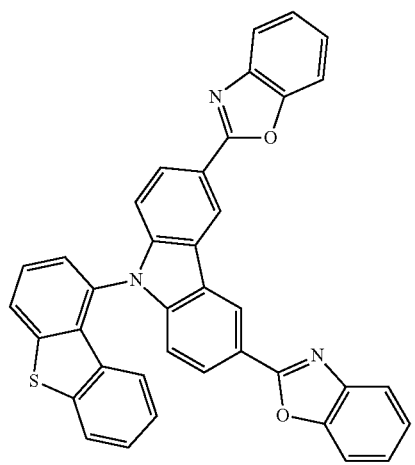
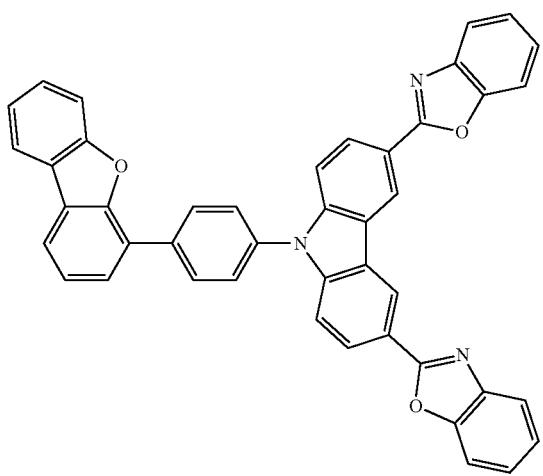
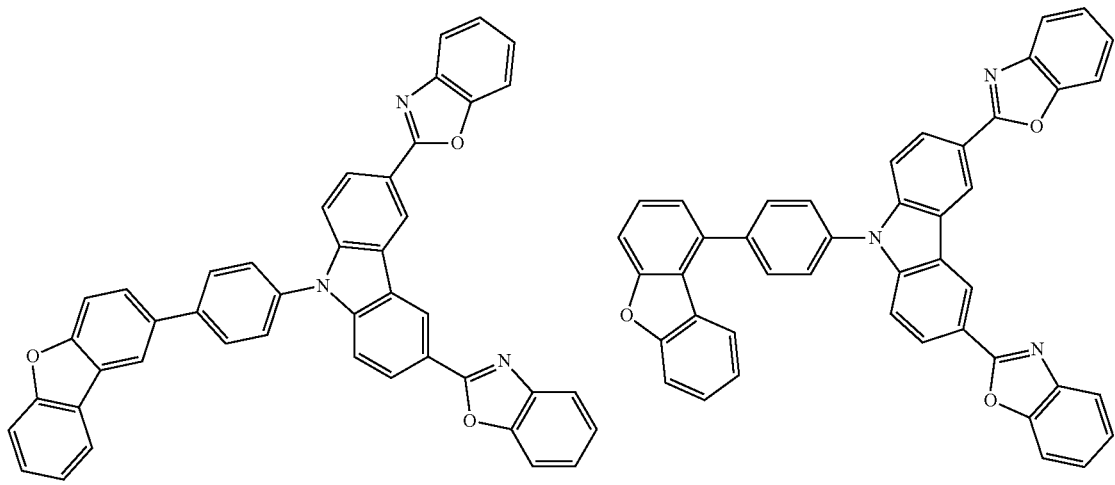

-continued
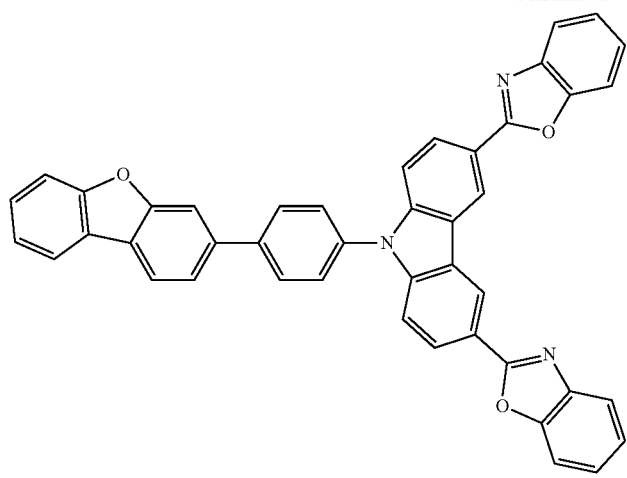
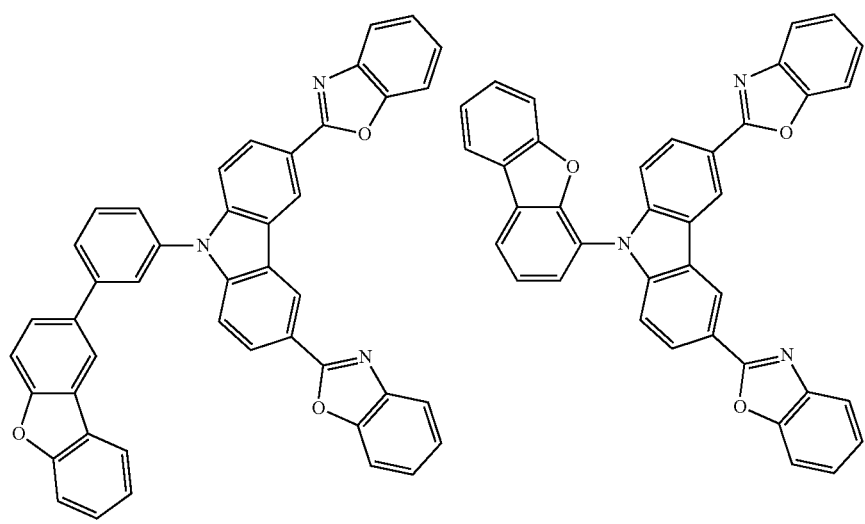
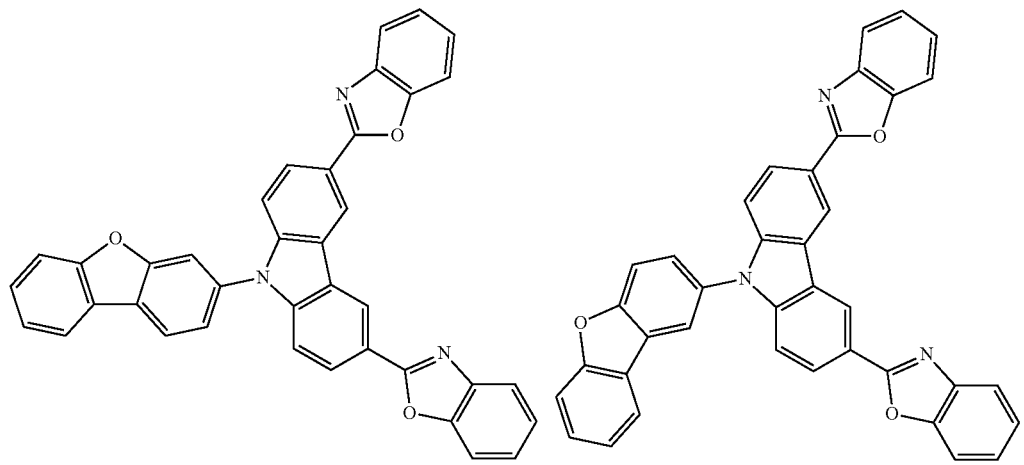

-continued
145
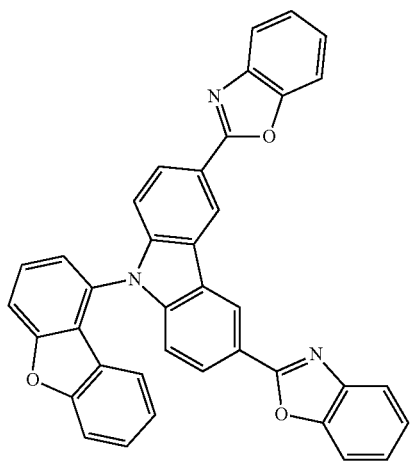
146
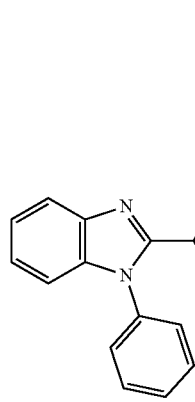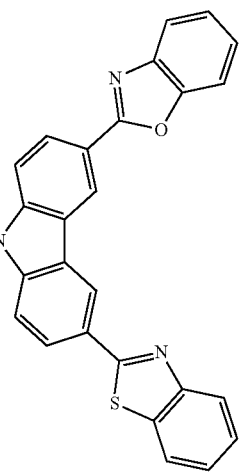
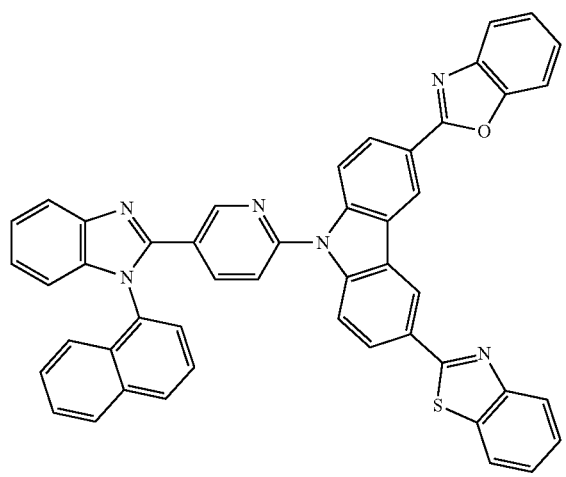
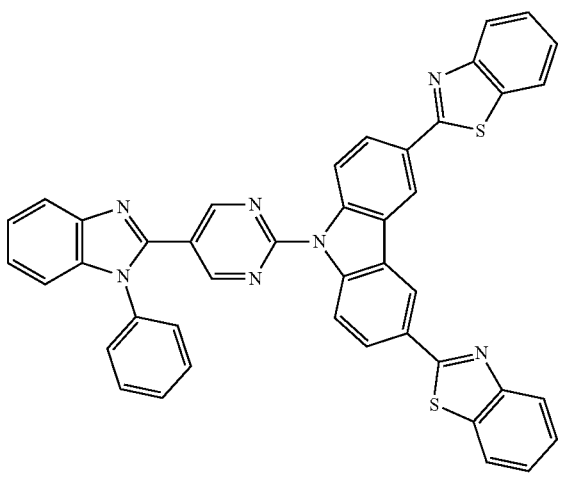
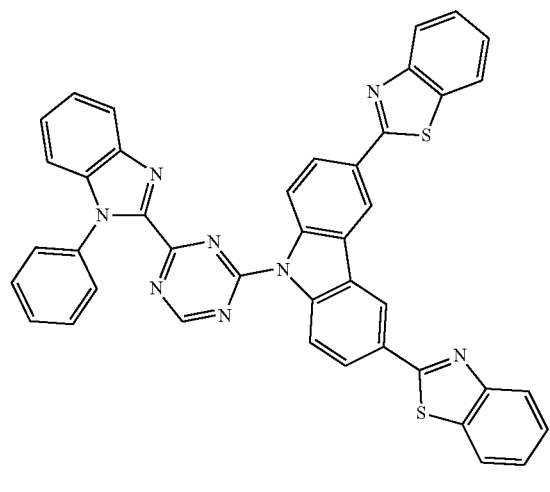
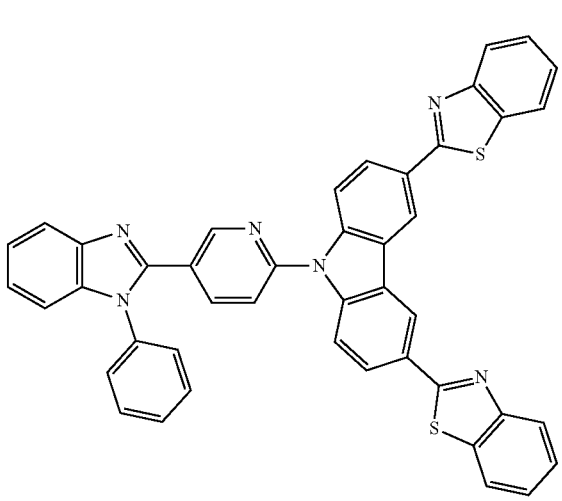 [SMILES: c1ccc(-n2c(-c3ccc(-n4c5ccc(-c6nc7ccccc7o6)cc5c5cc(-c6nc7ccccc7s6)ccc54)cc3)nc3ccccc32)cc1]

-continued
147
148
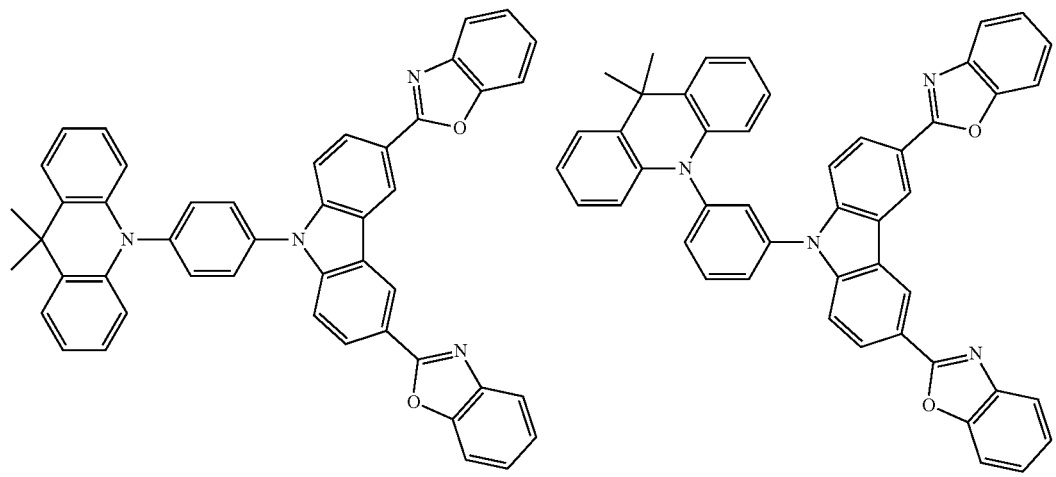
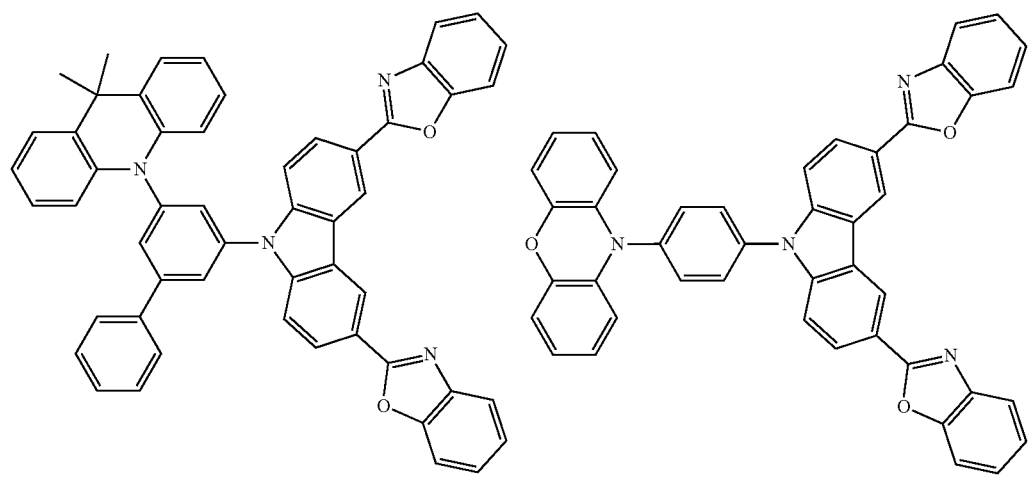
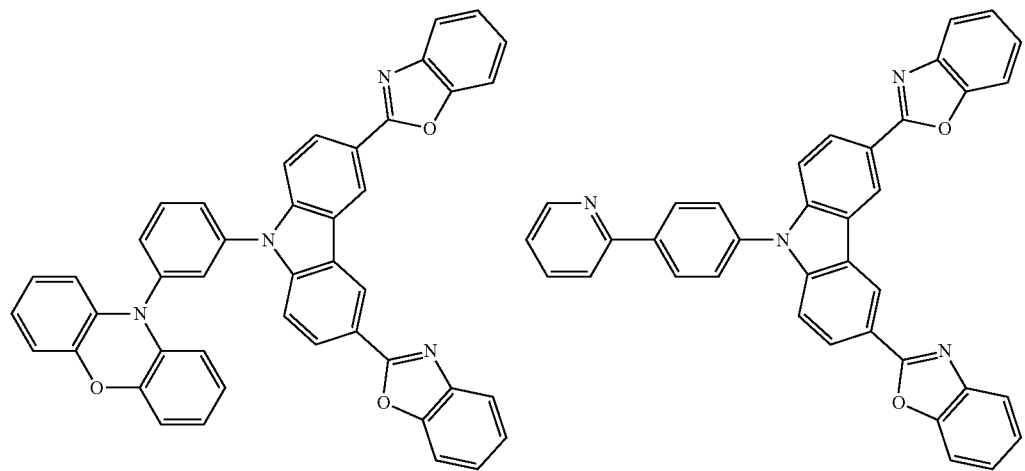

-continued
149 150
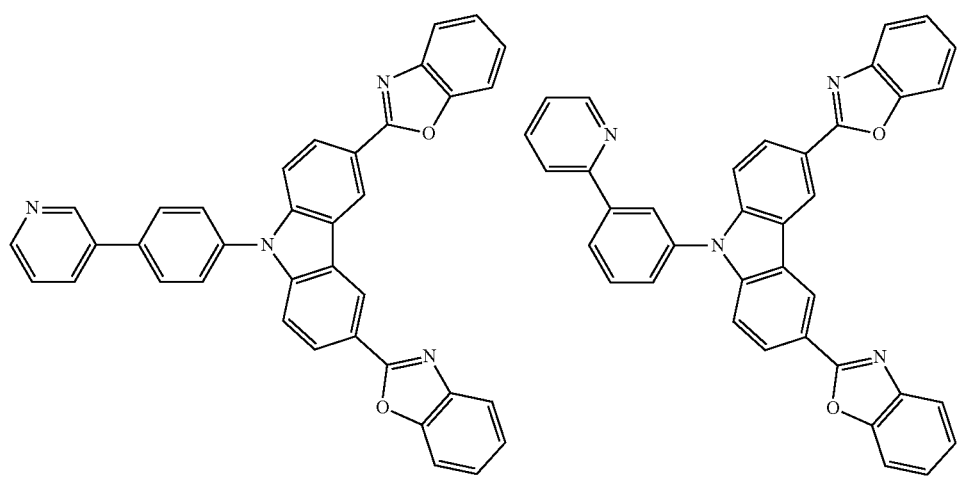
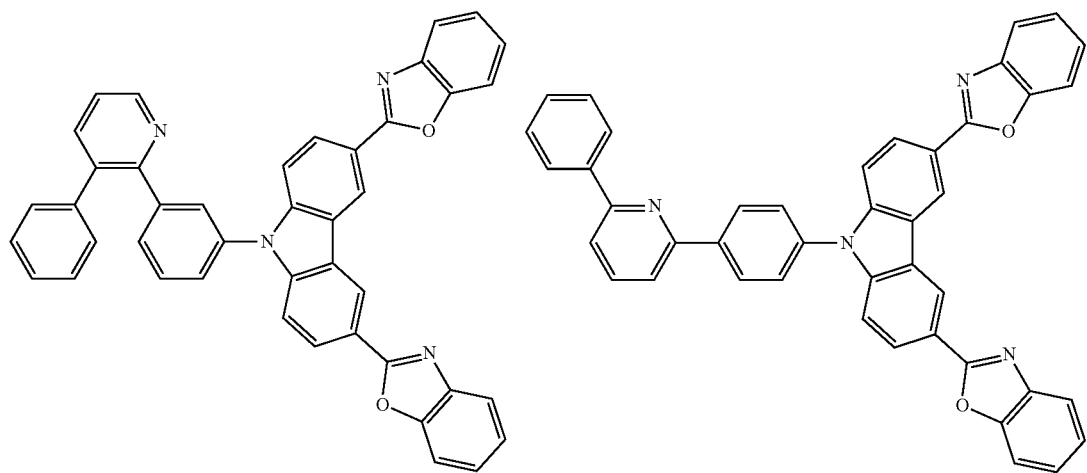
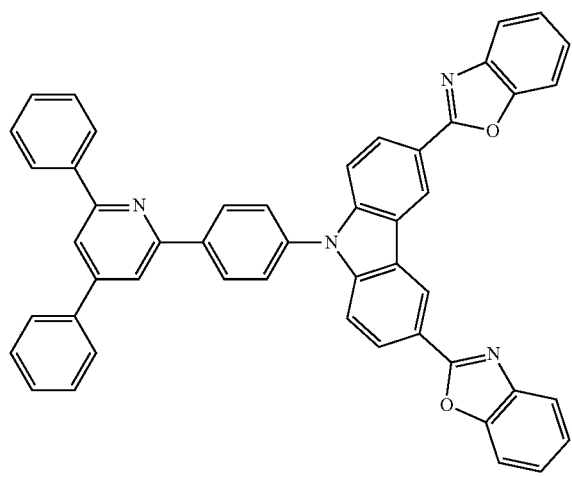

-continued
151
152
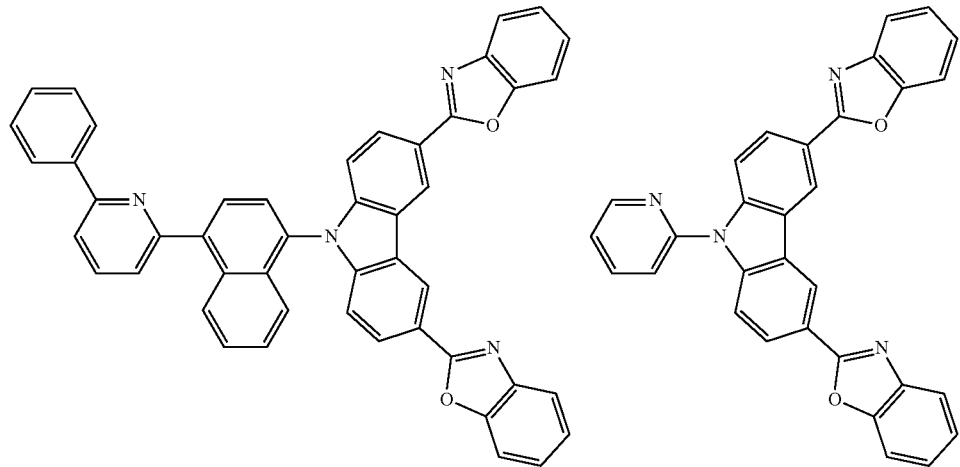
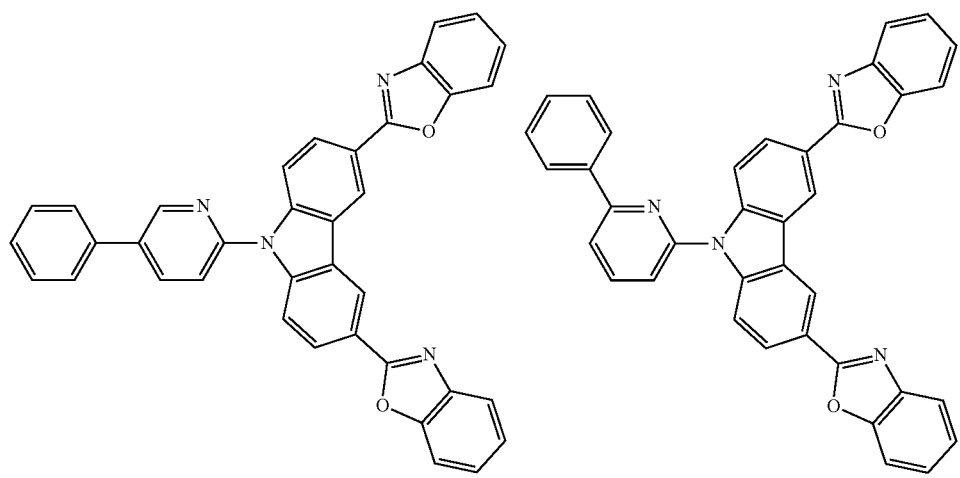
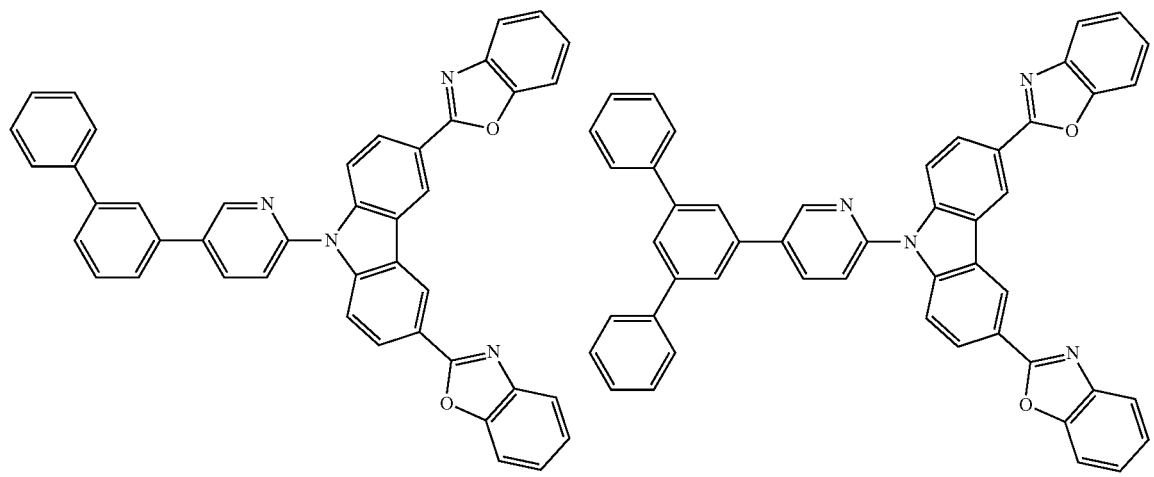

-continued
153      154
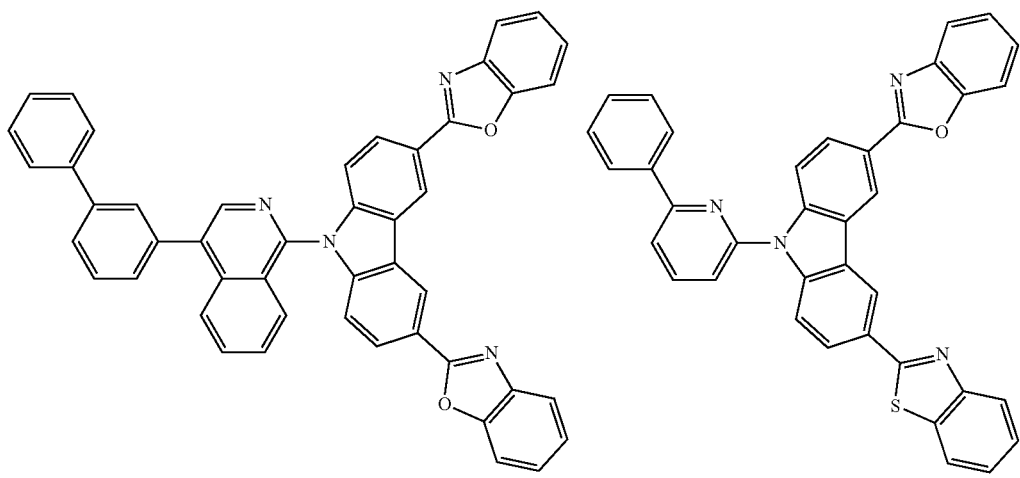
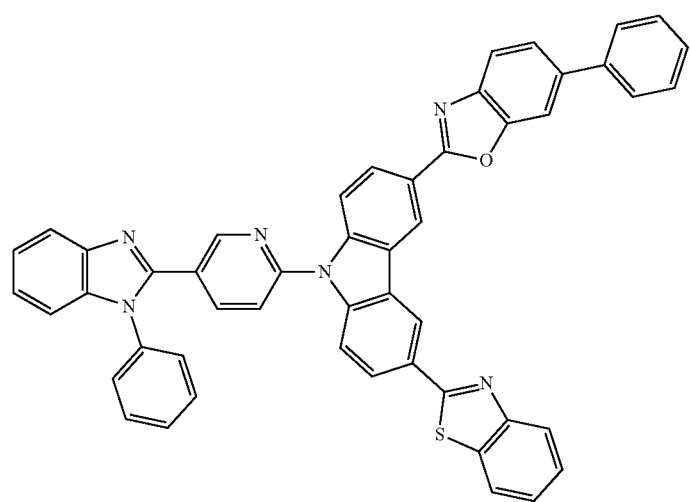
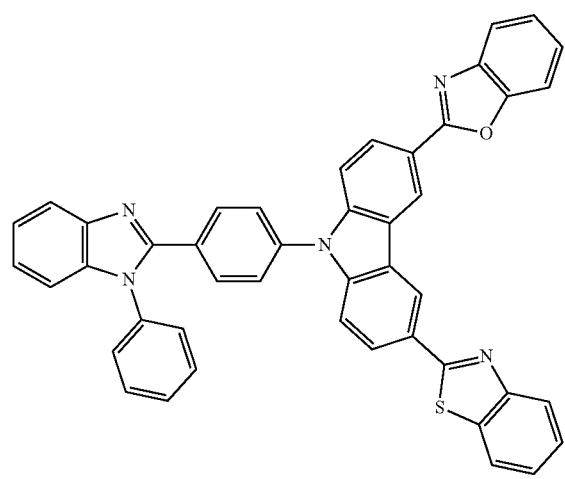

155 156
-continued
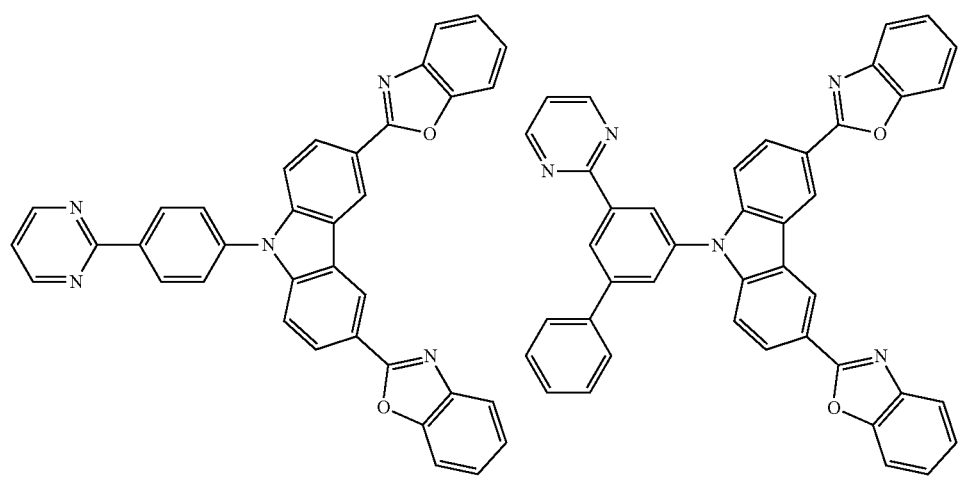
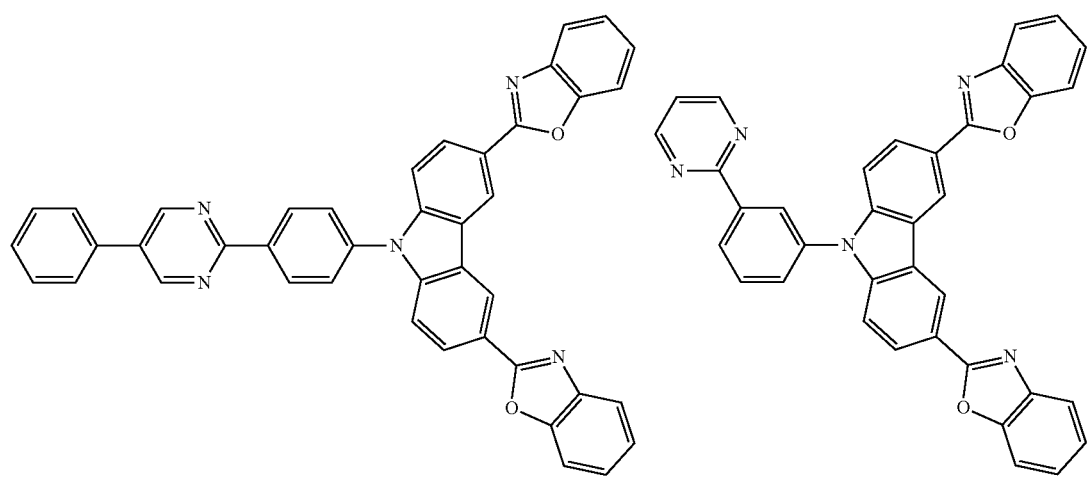
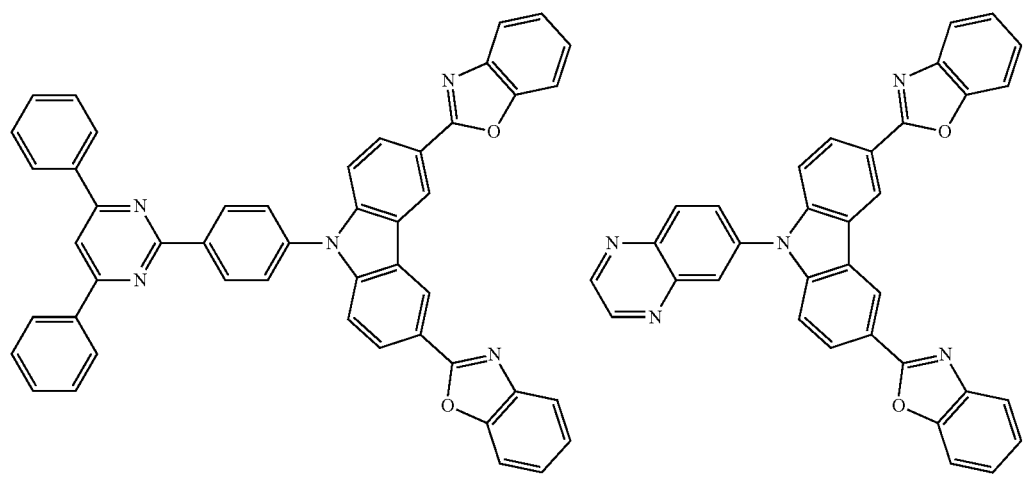

157
158
-continued
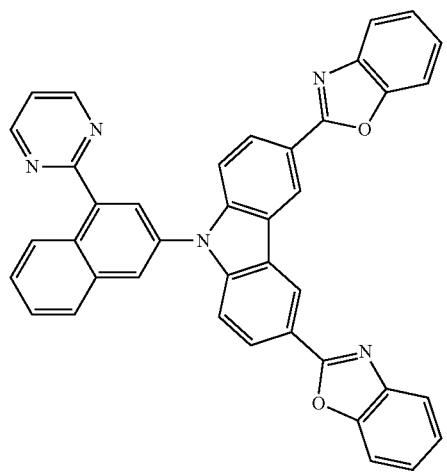
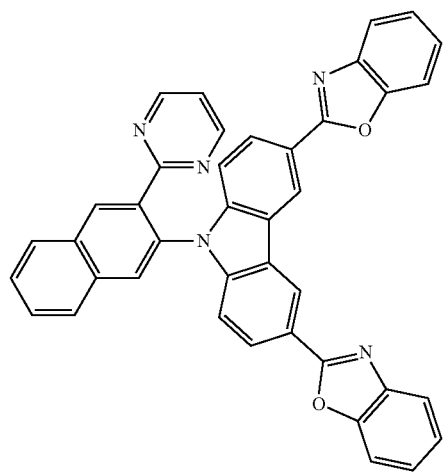
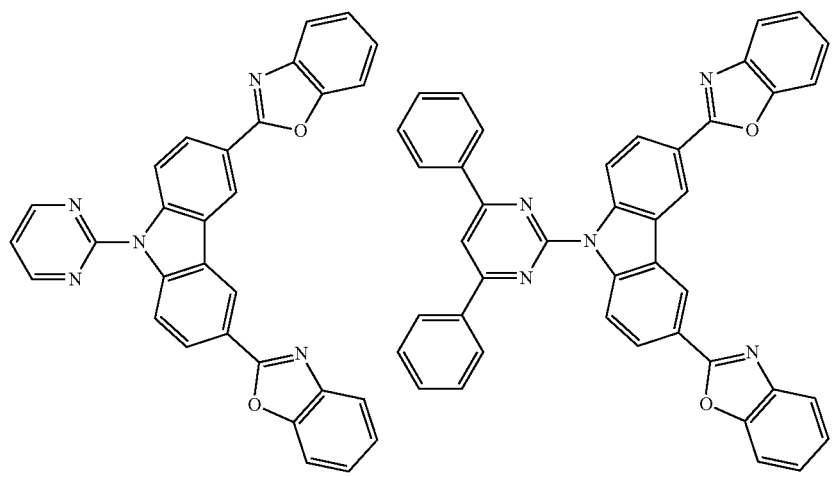
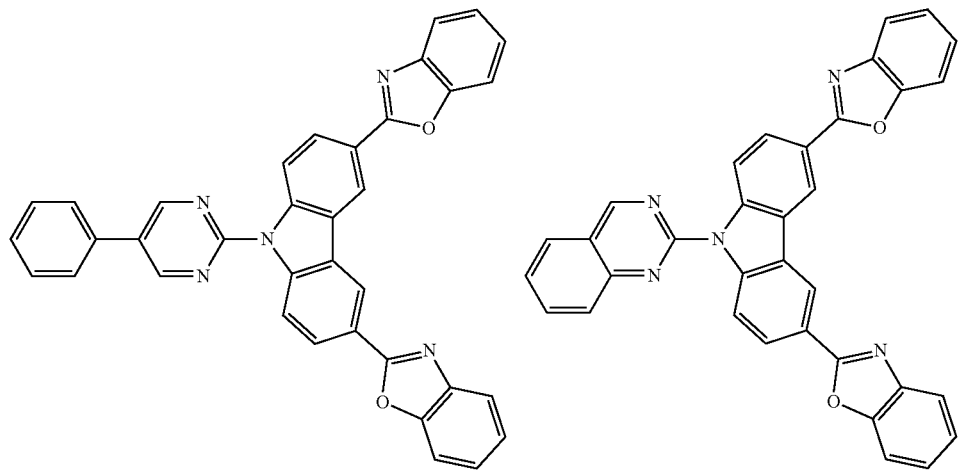

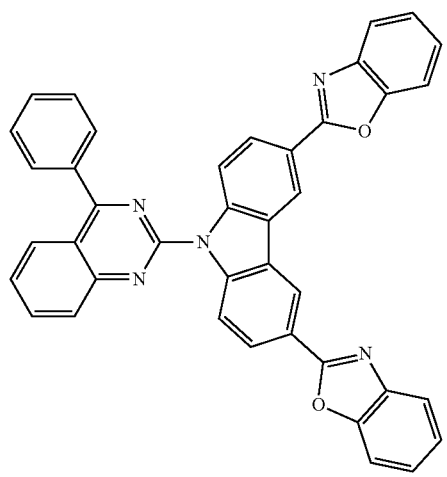
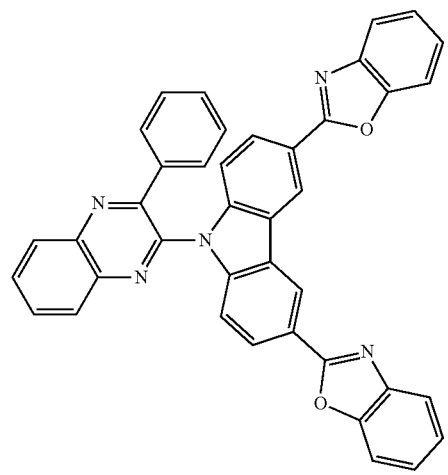
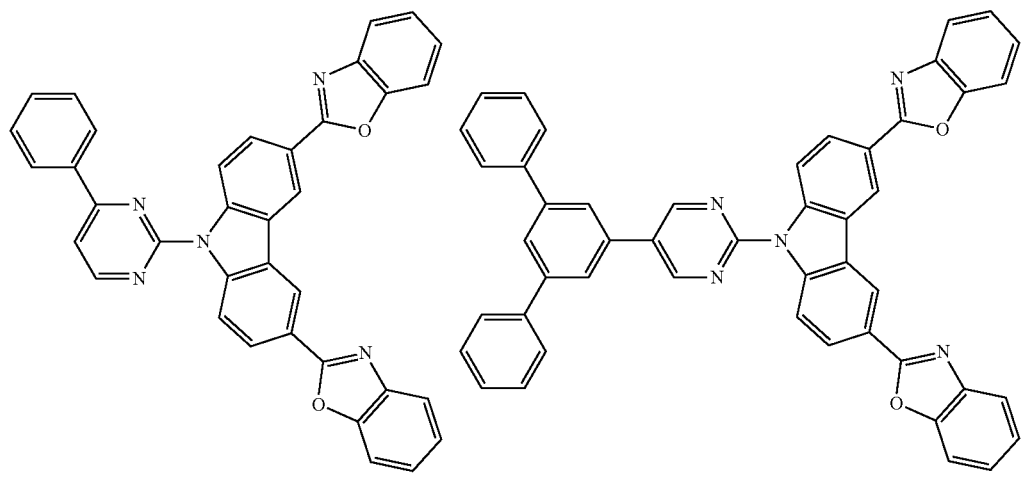
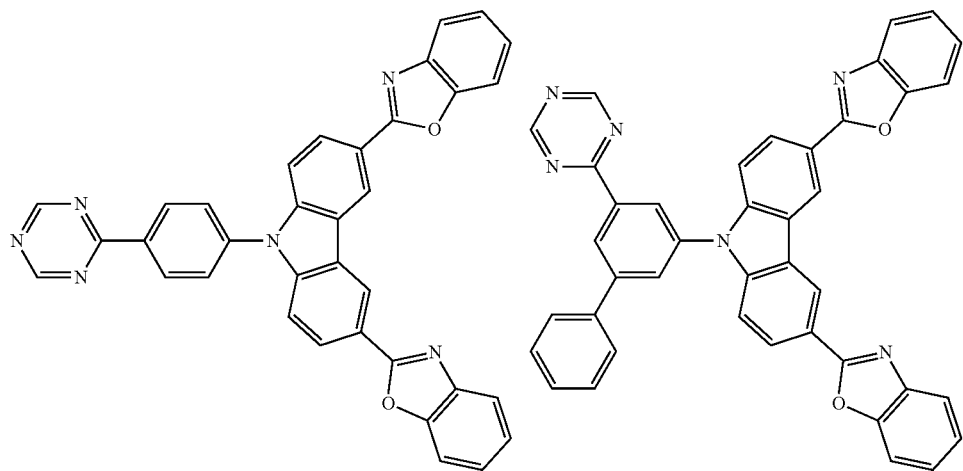

-continued
161 162
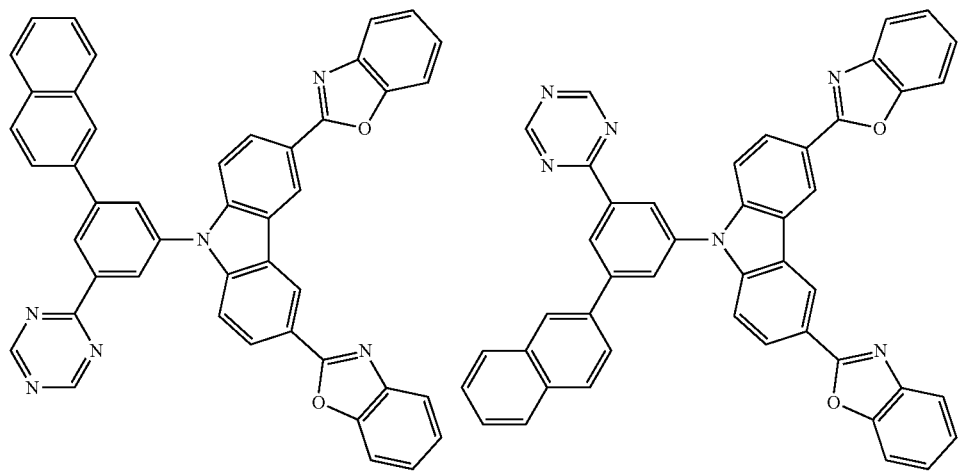
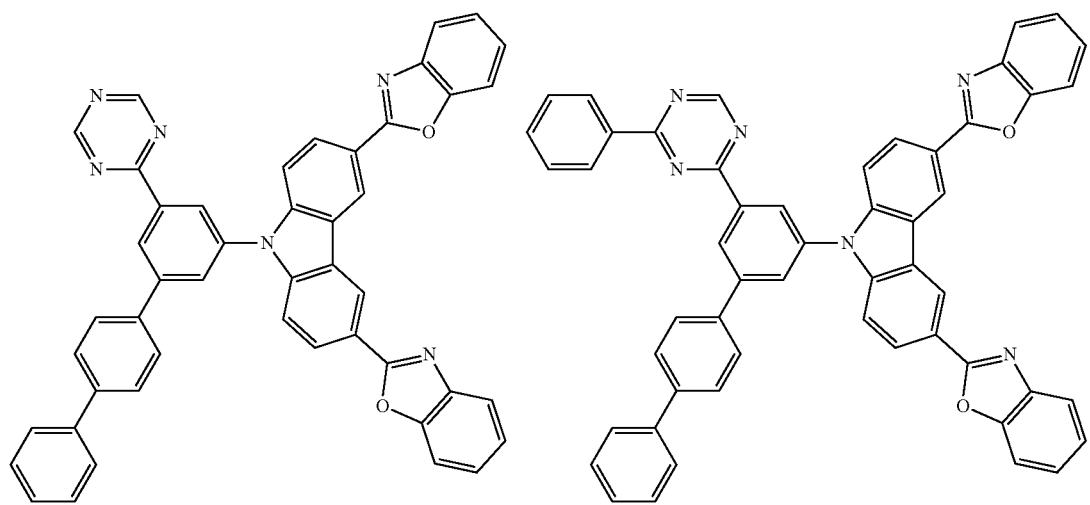
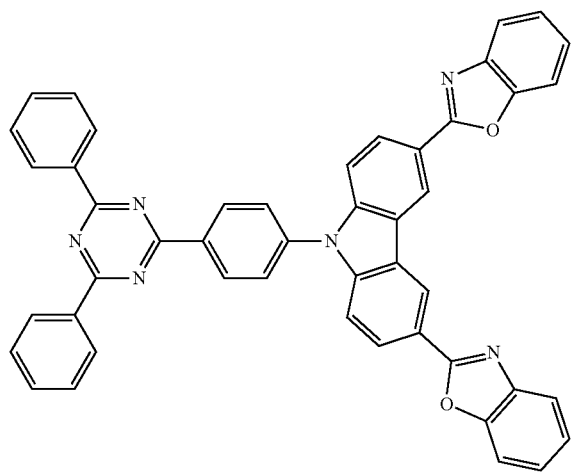

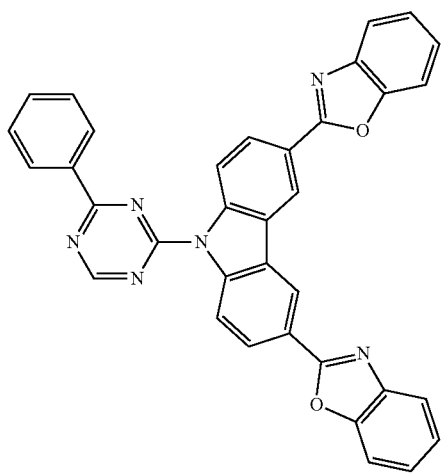
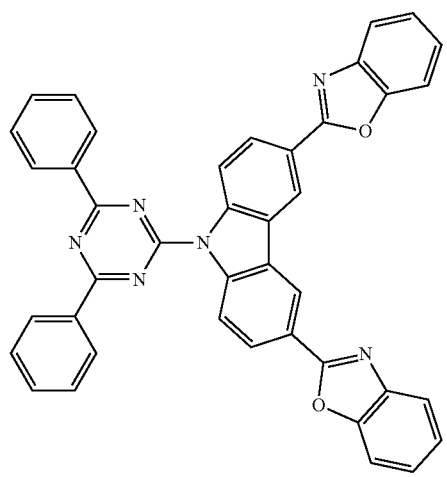
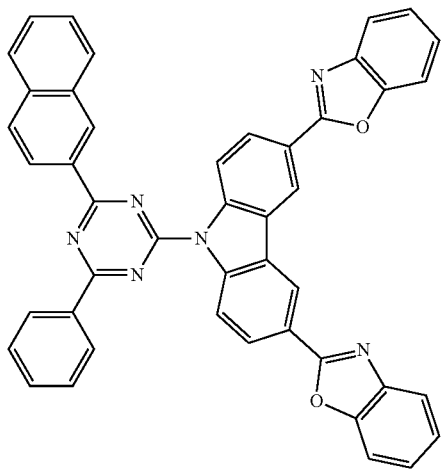
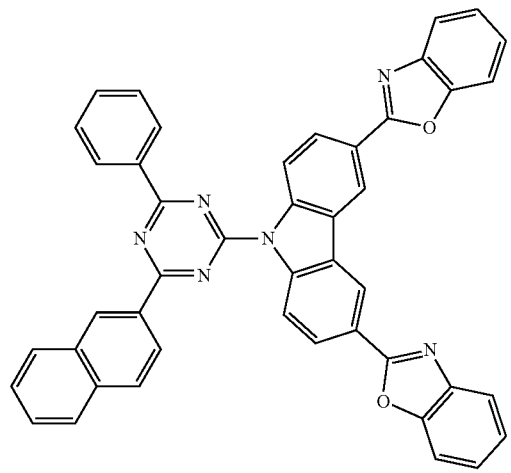
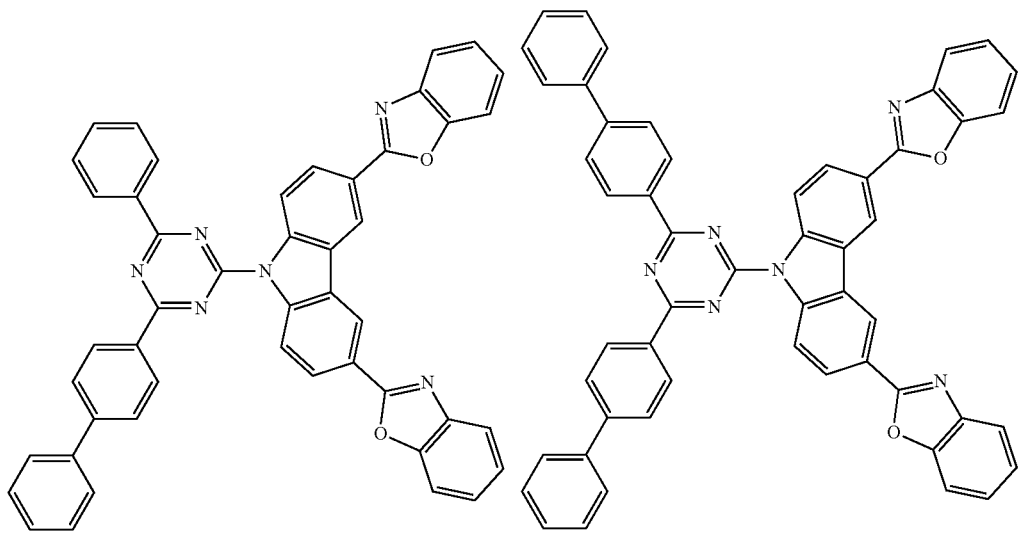

-continued
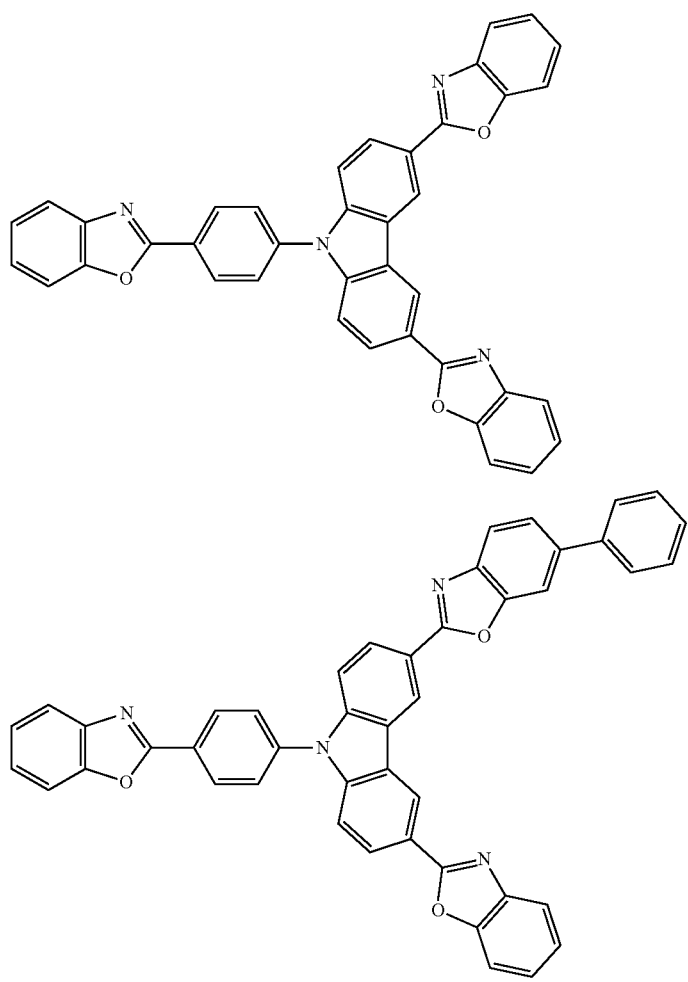
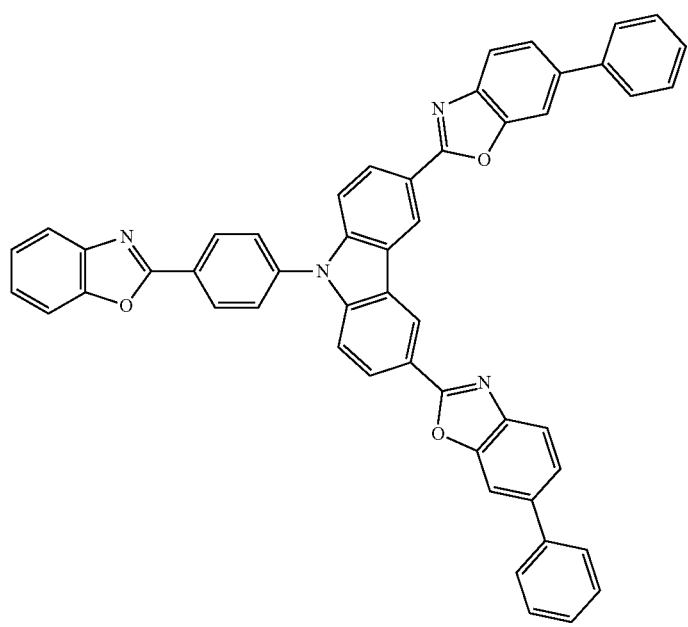

-continued
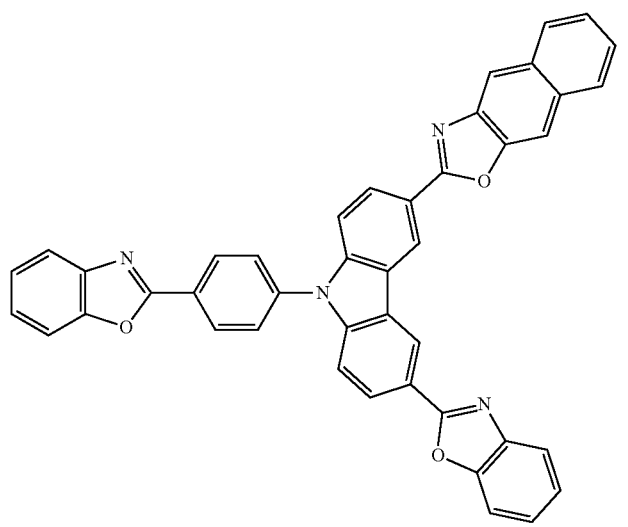
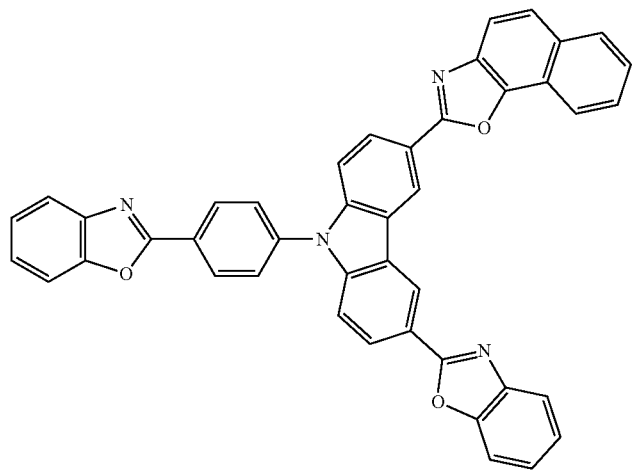
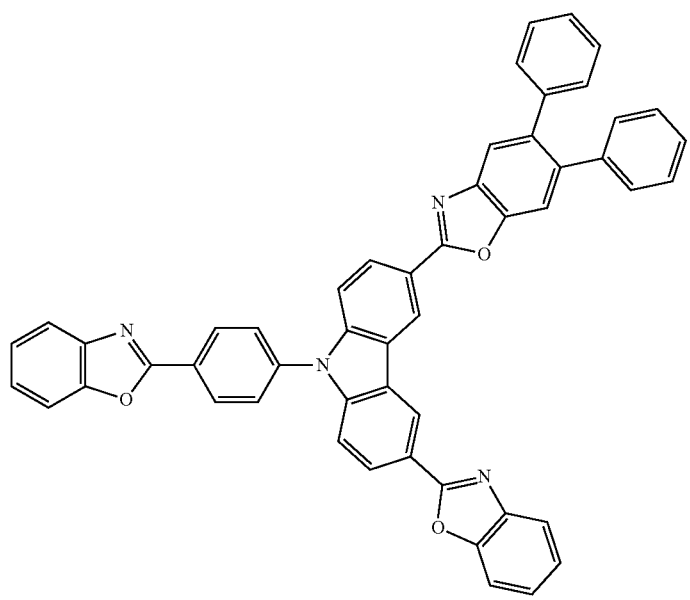

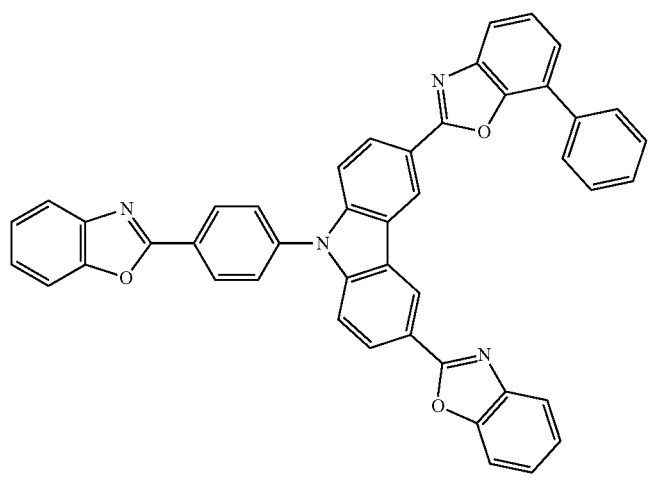
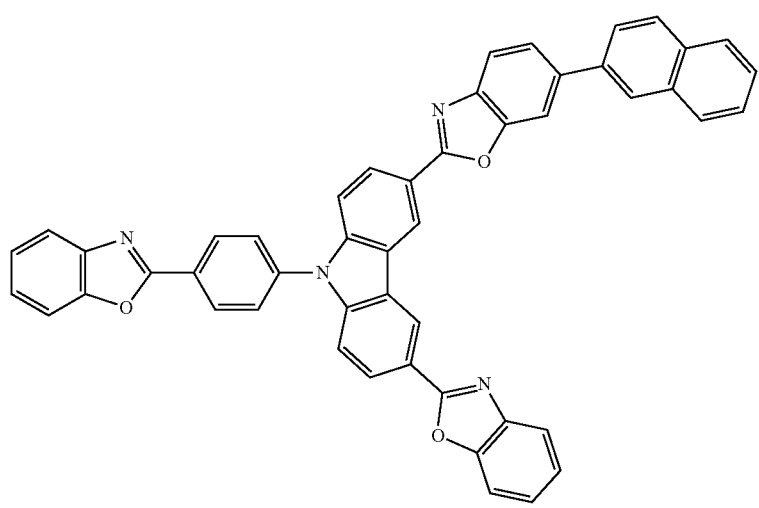
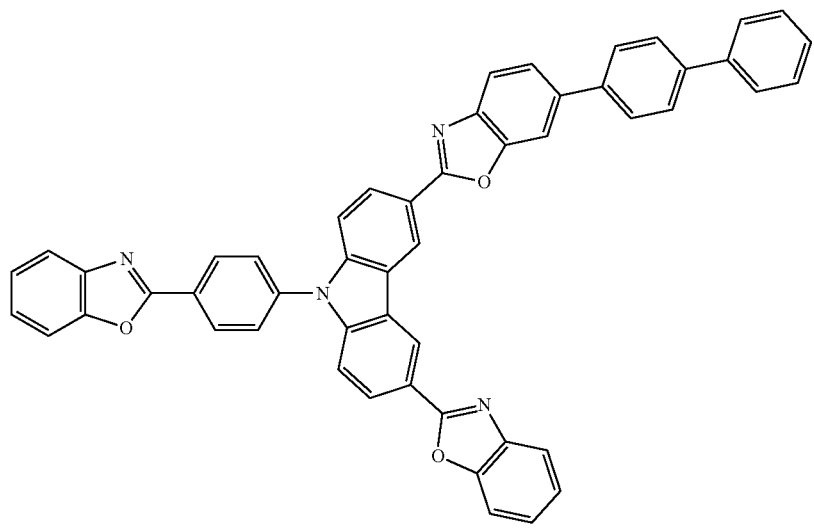

-continued
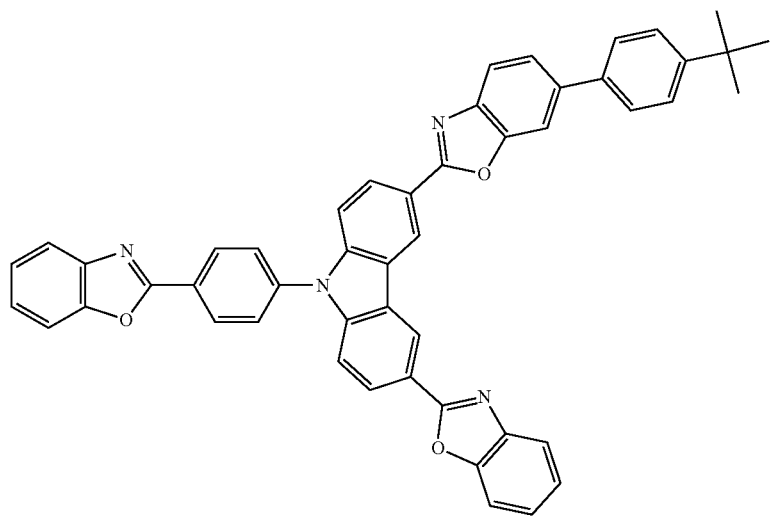
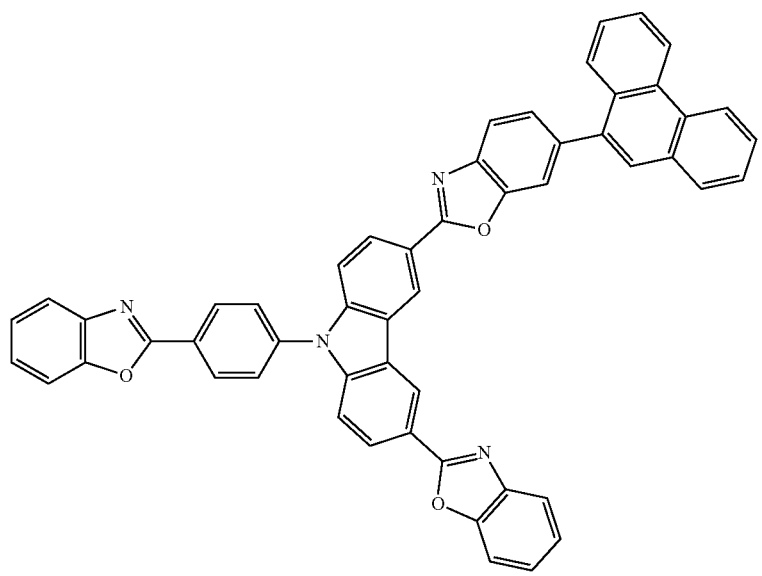
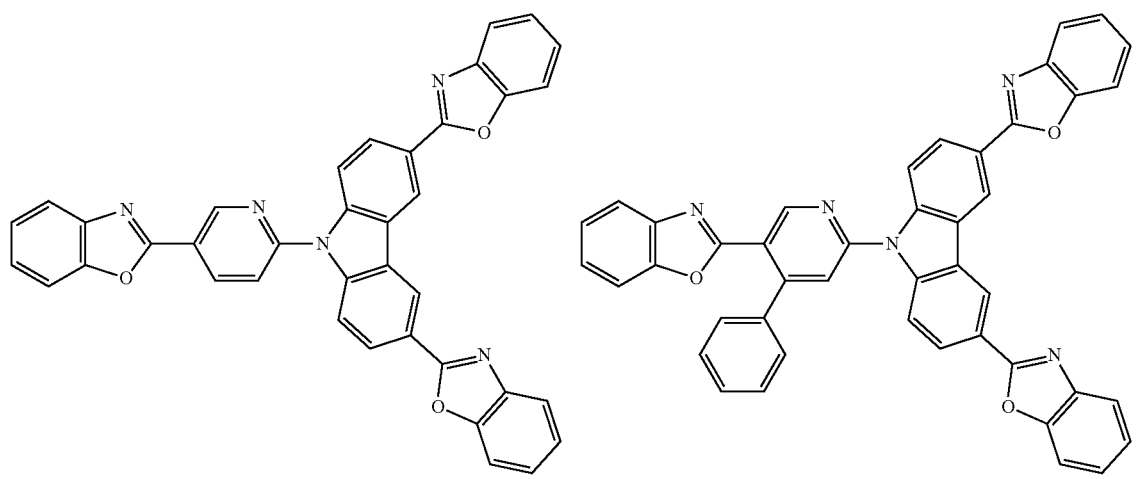

173
174
-continued
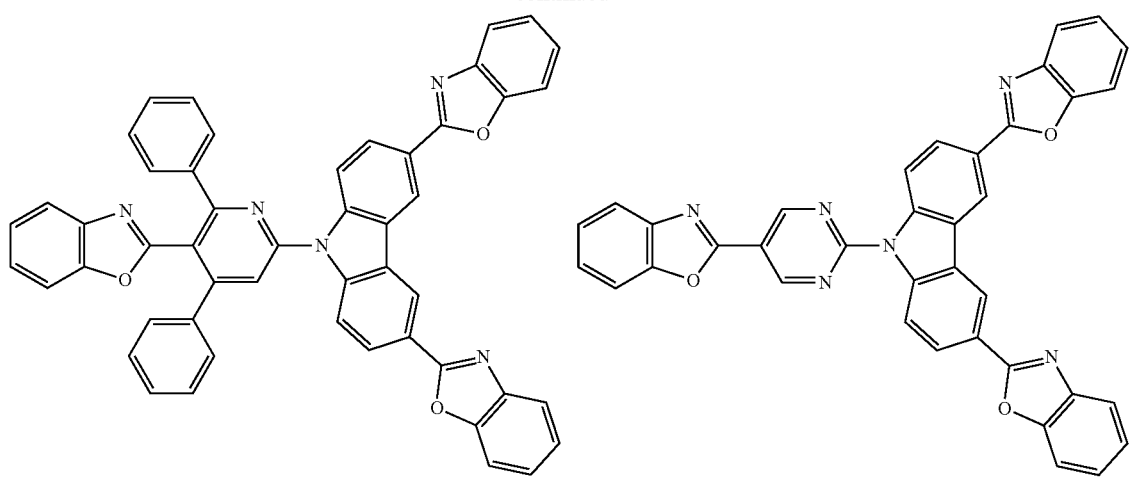
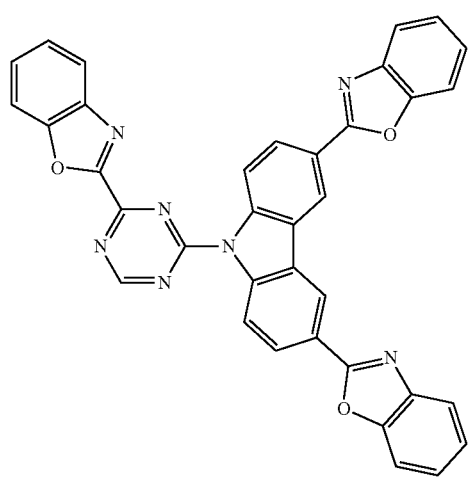
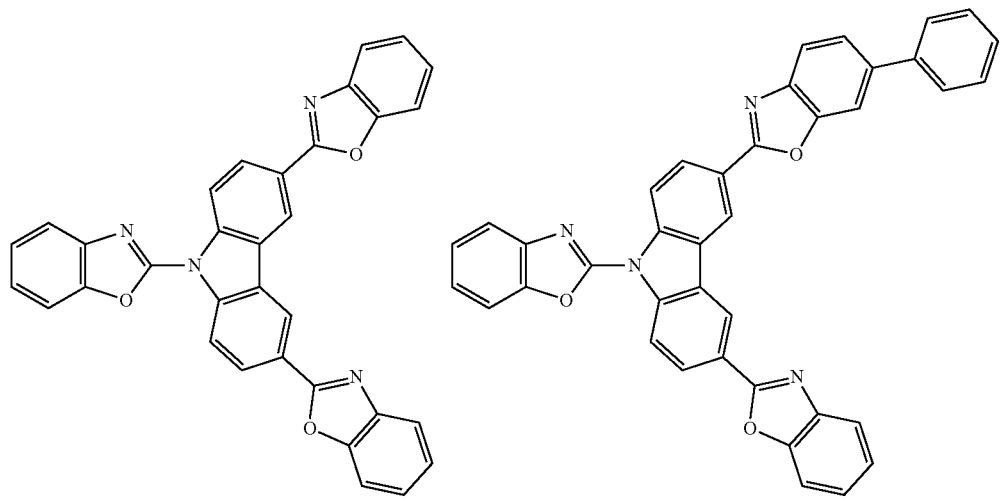

-continued
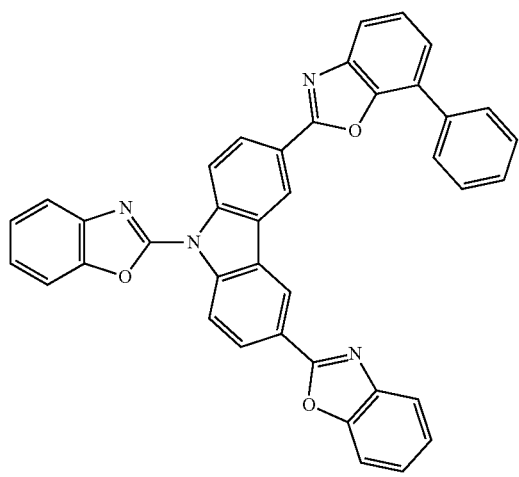
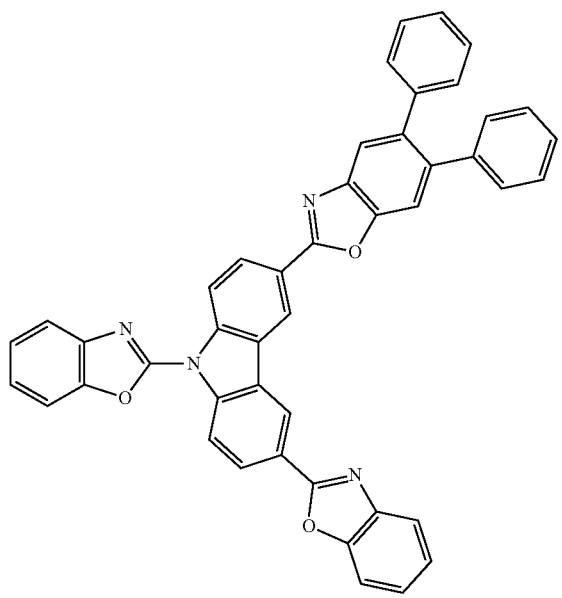
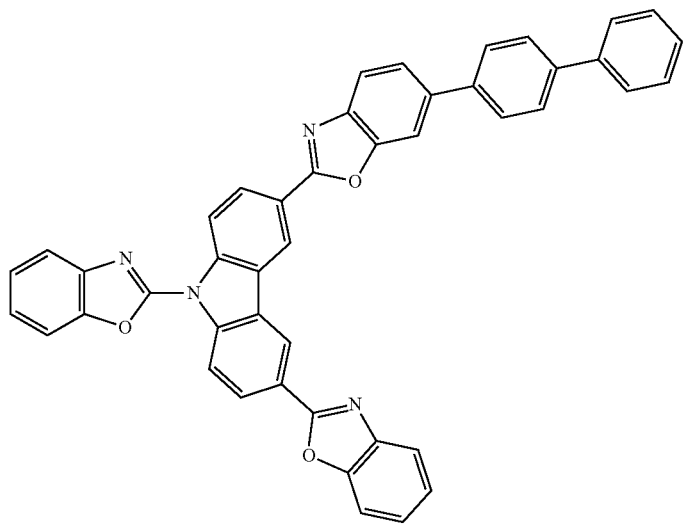

-continued
177
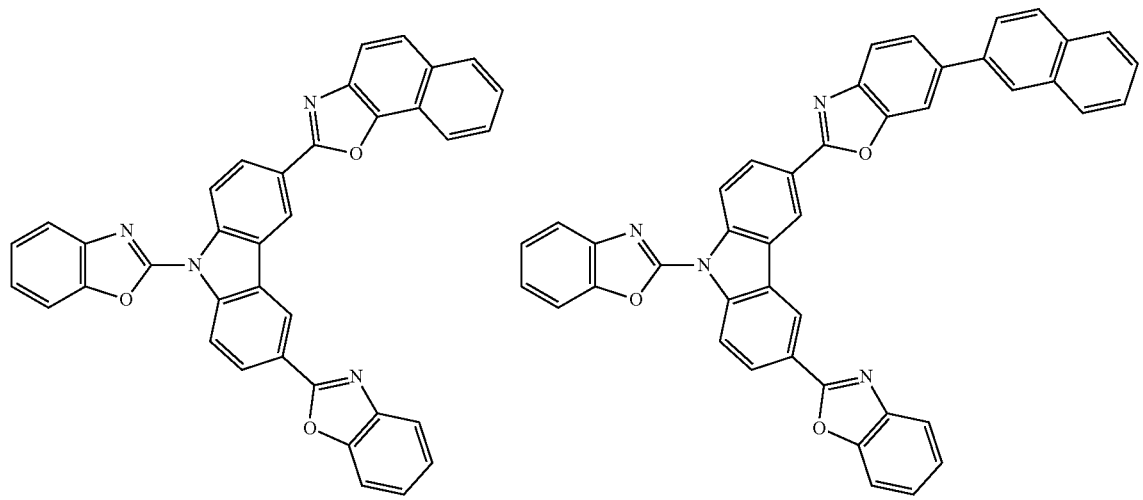
178
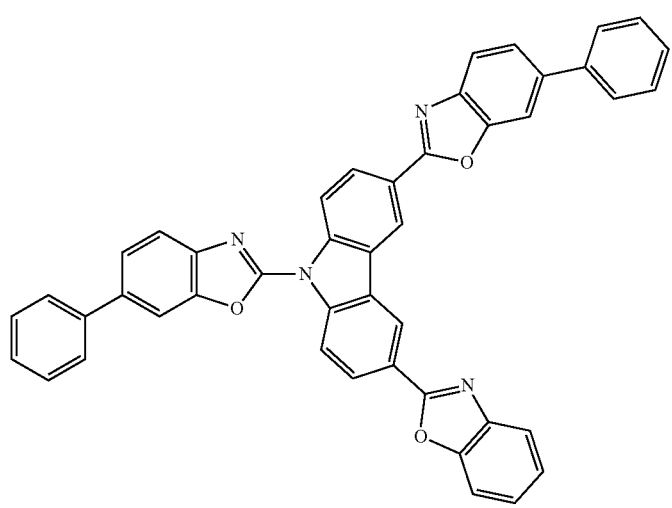
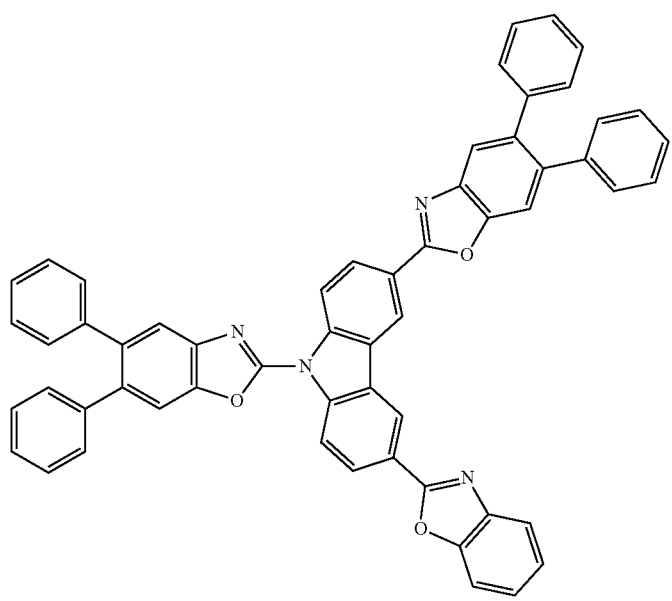

-continued
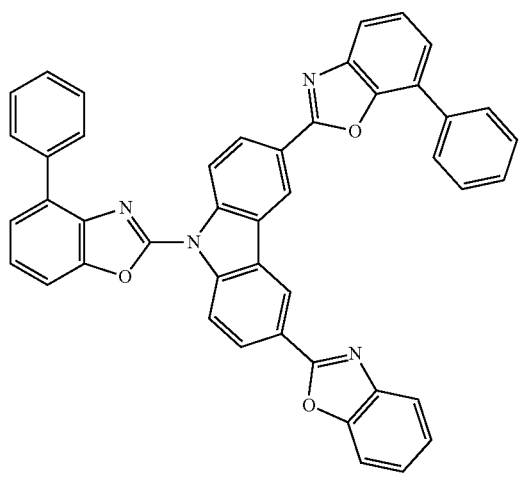
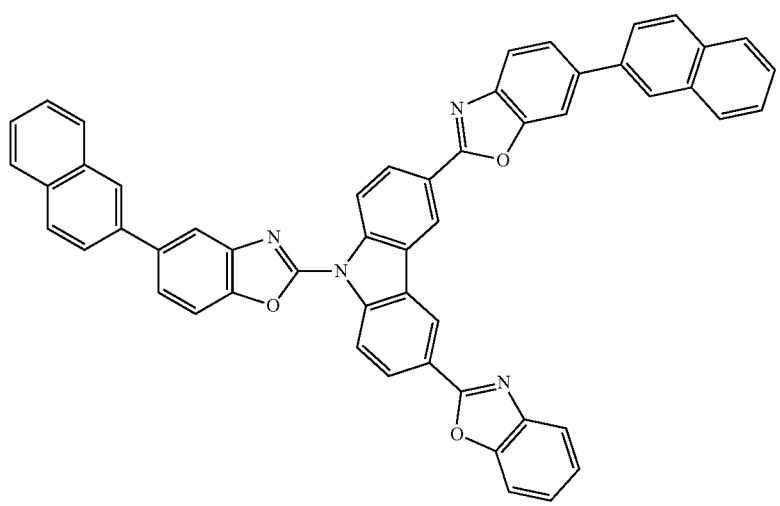
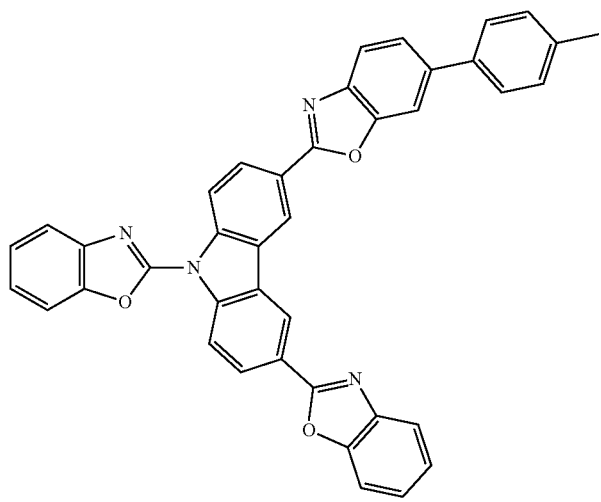

-continued
181
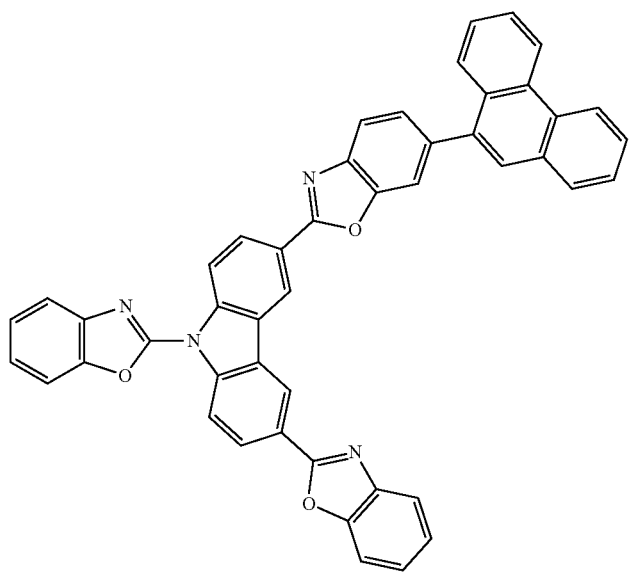
182
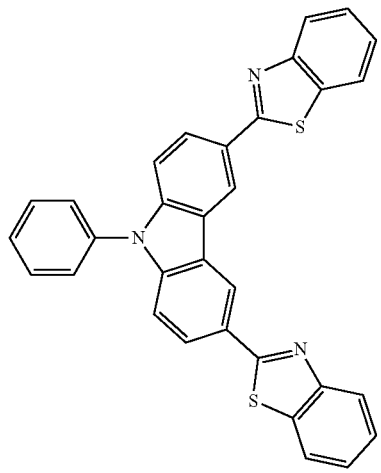
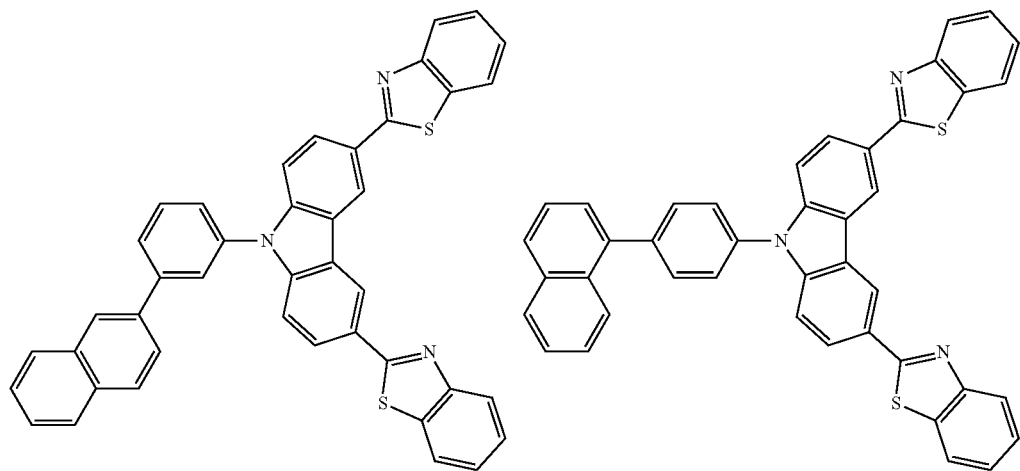
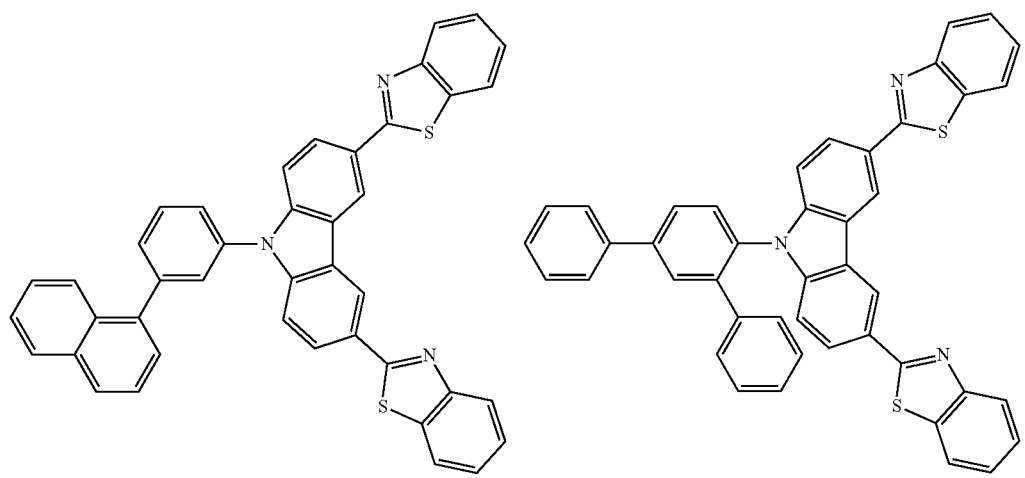

183
184
-continued
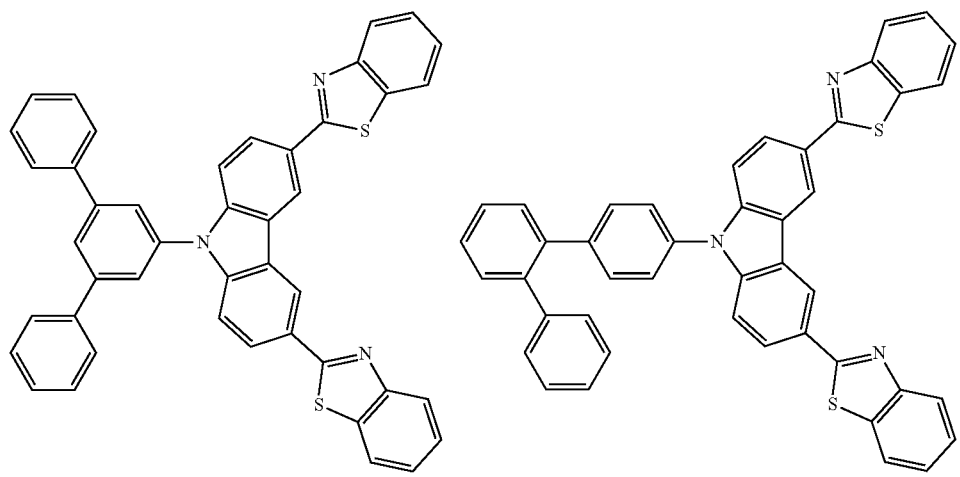
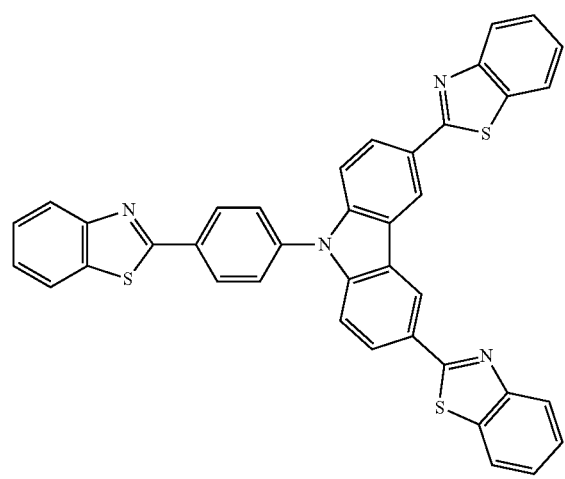
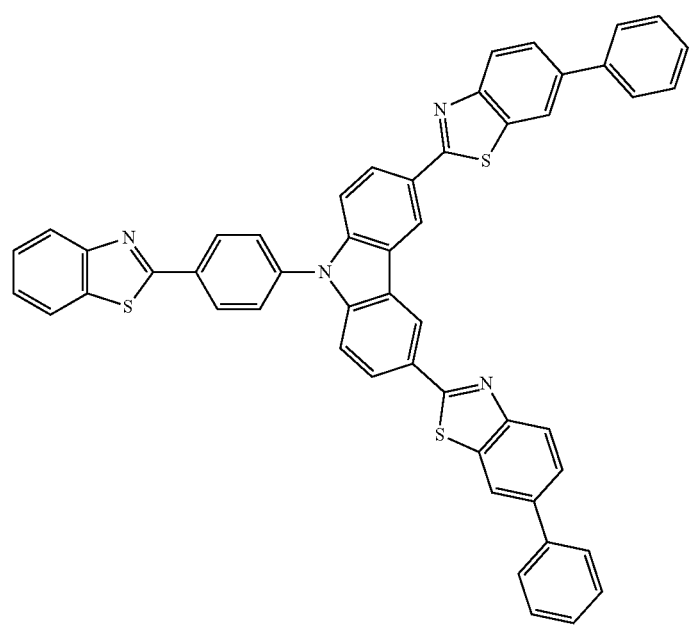

-continued
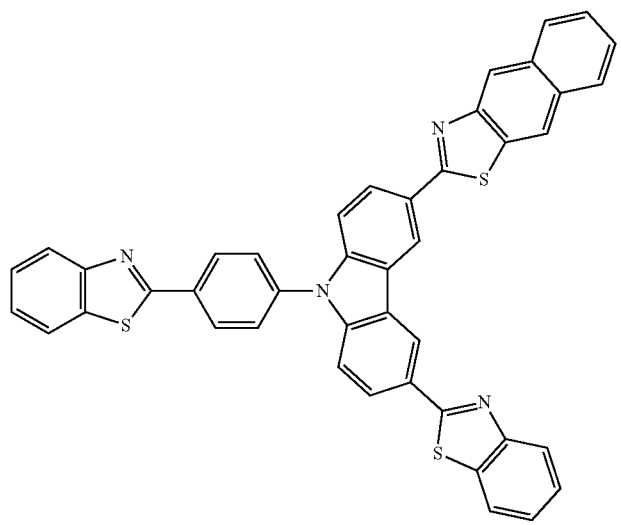
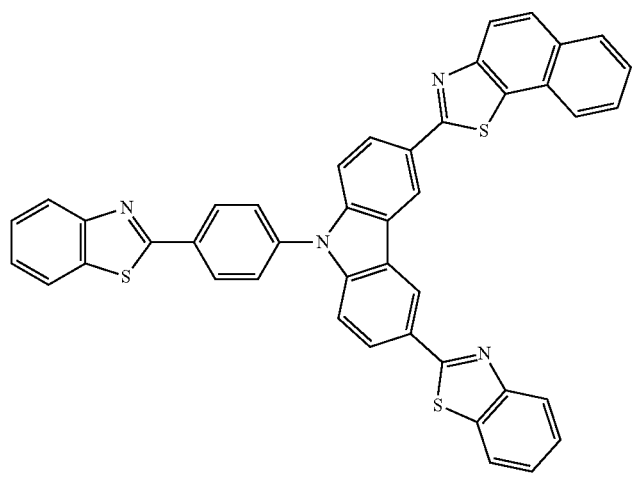
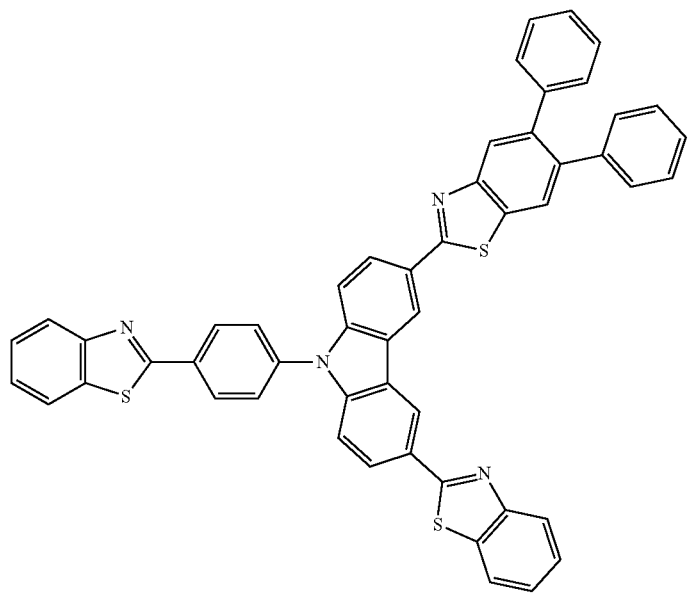

-continued
187
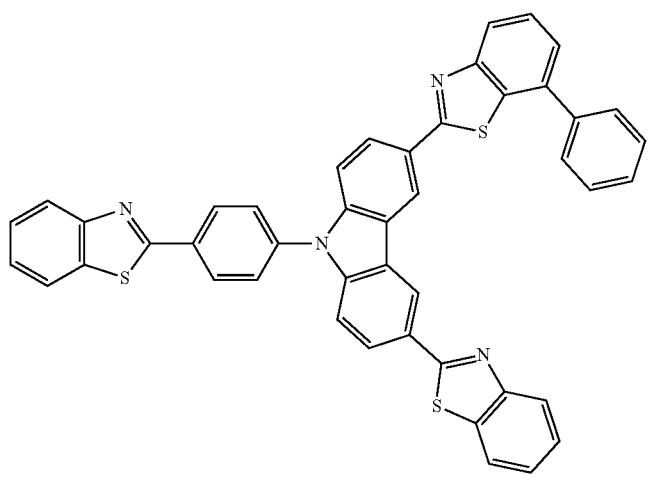
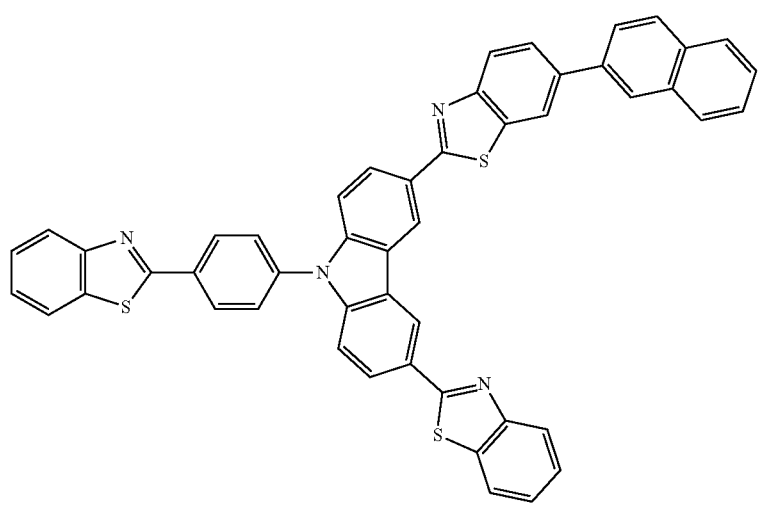
188
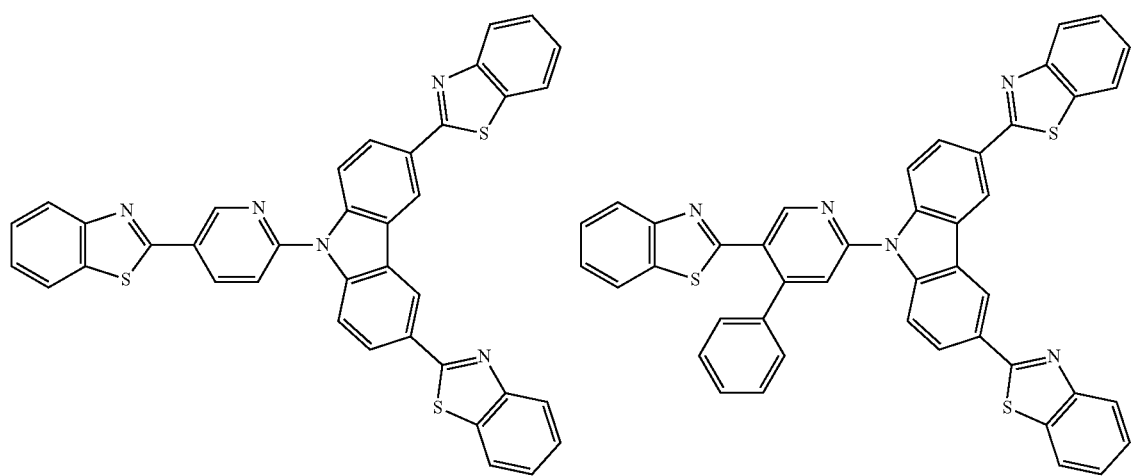

-continued
| 189 | 190 |
|---|---|
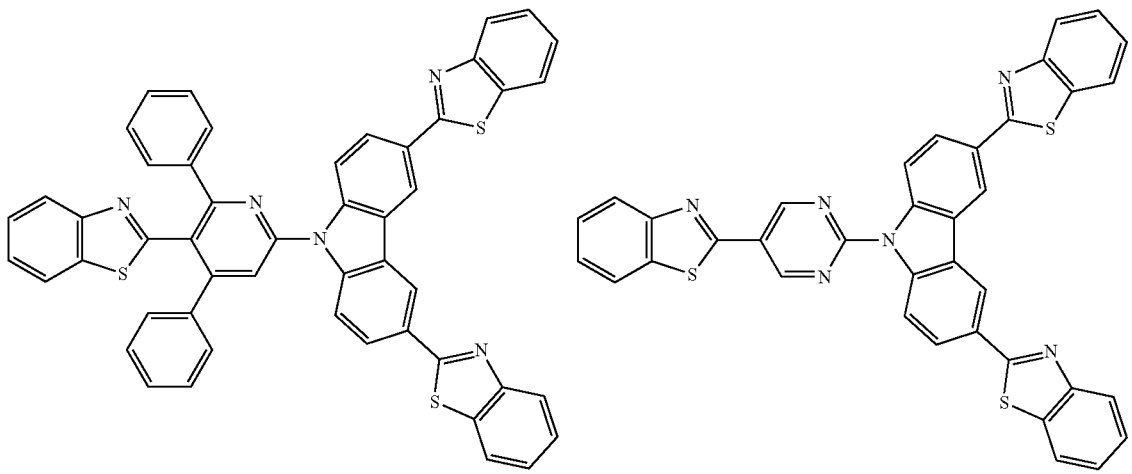
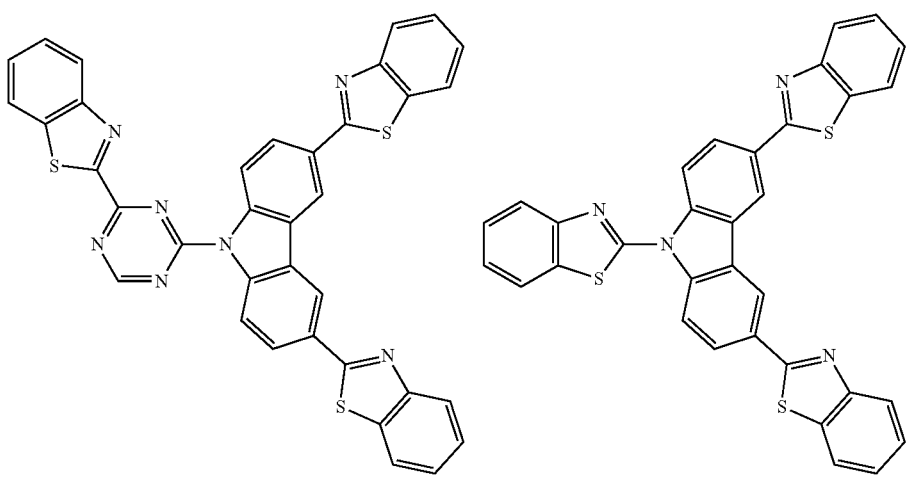
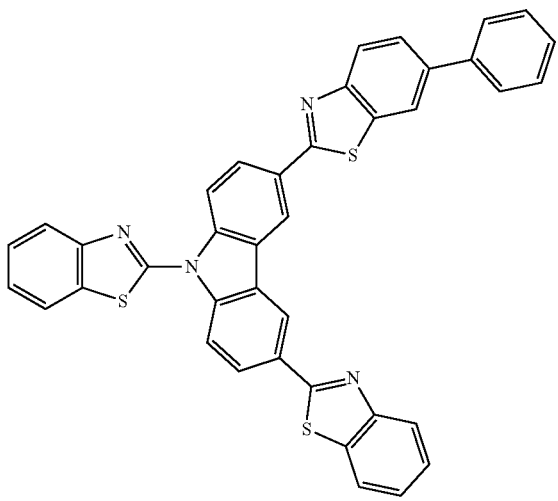

191 192
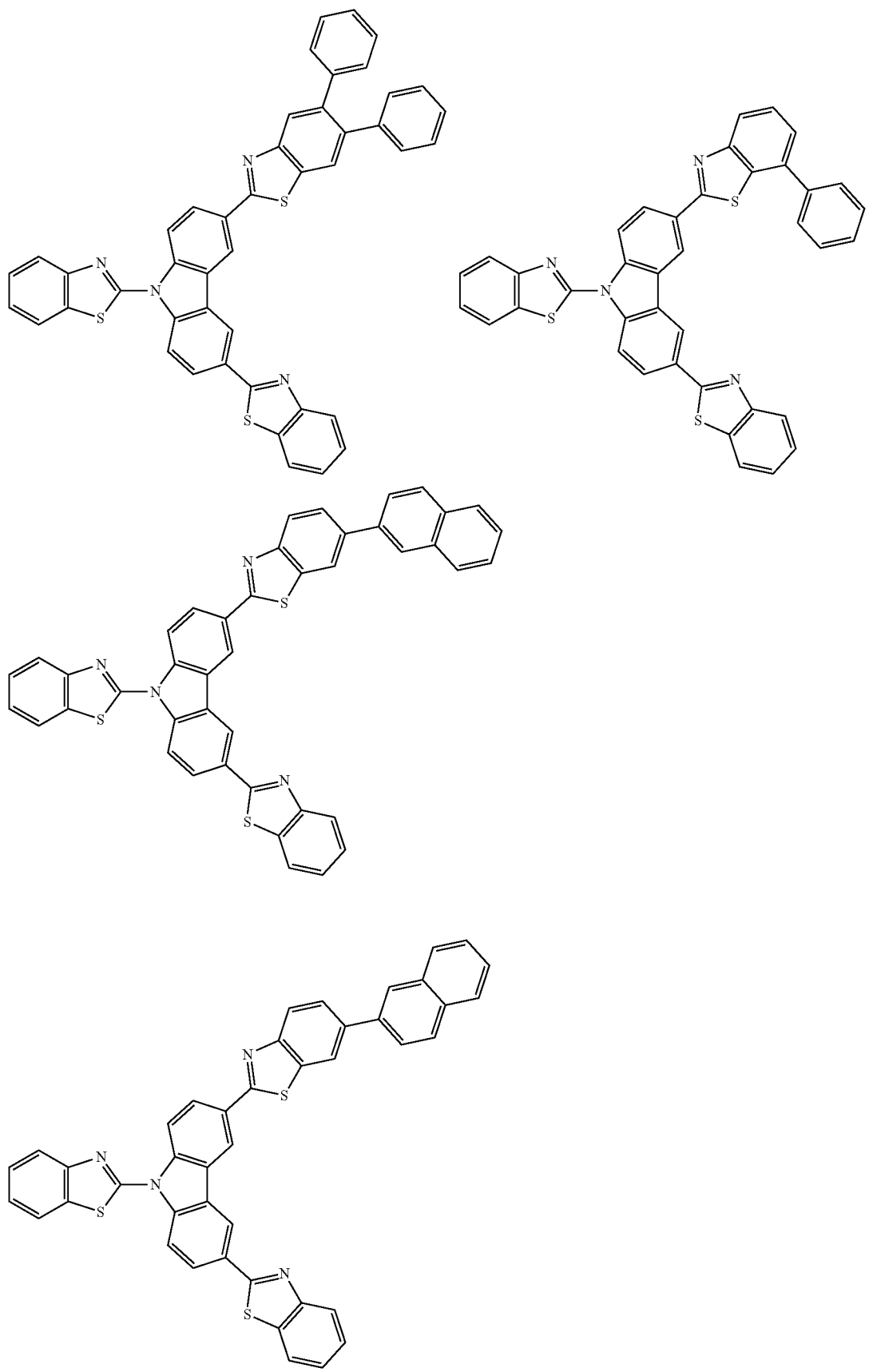

-continued
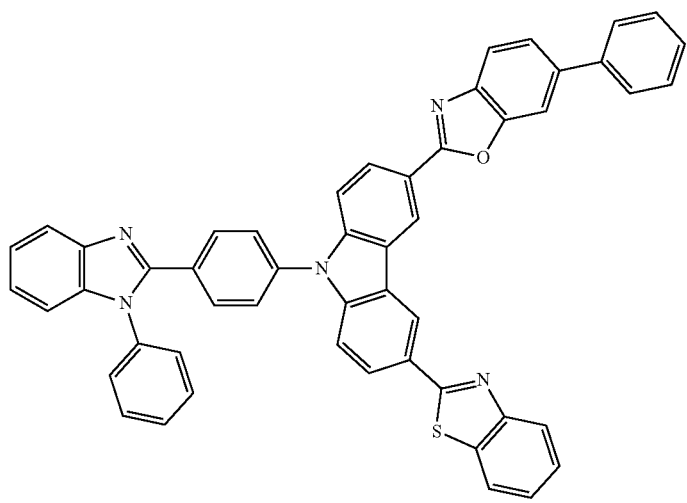
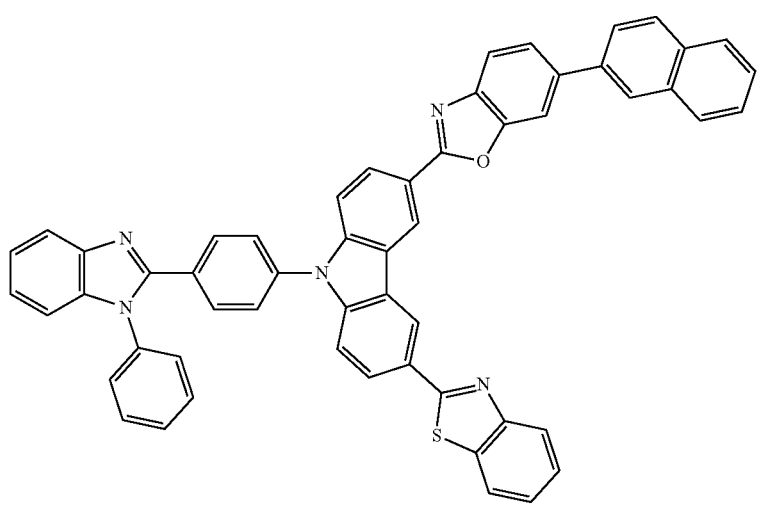
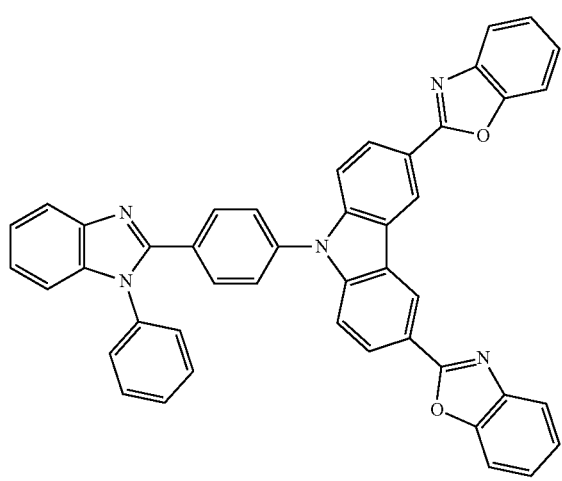

-continued
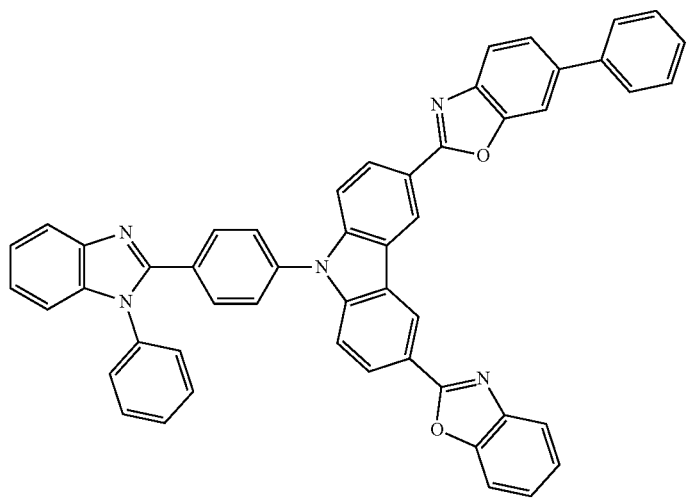
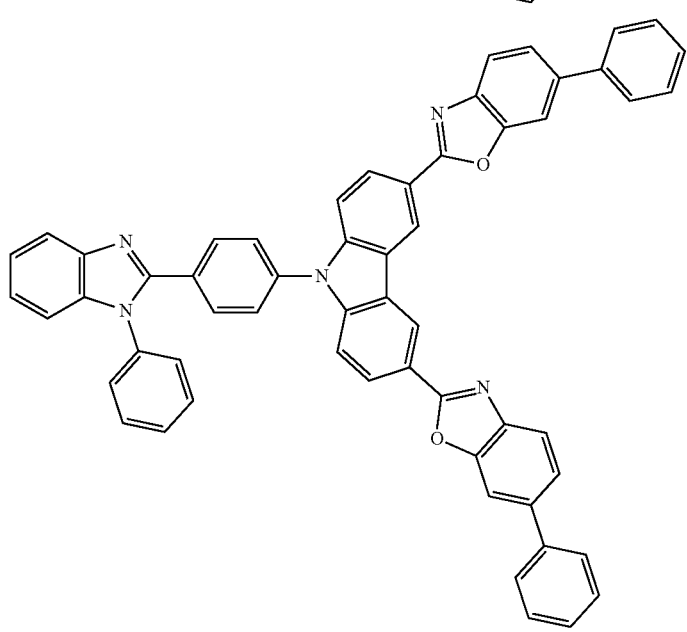
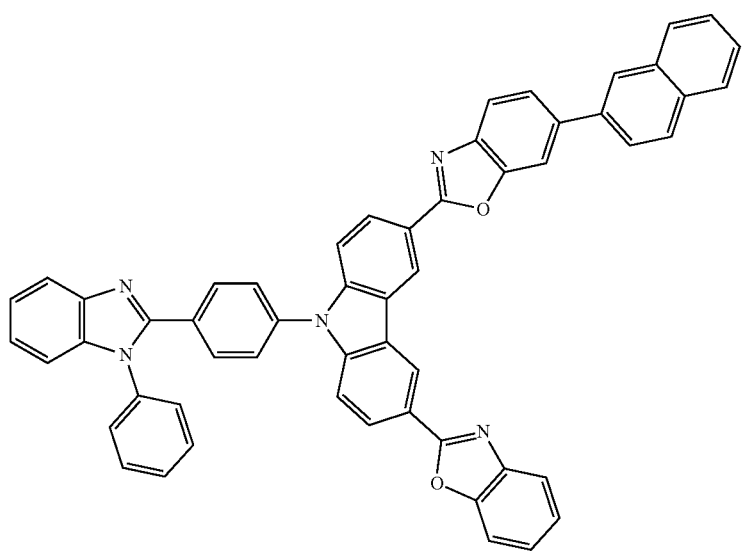

-continued
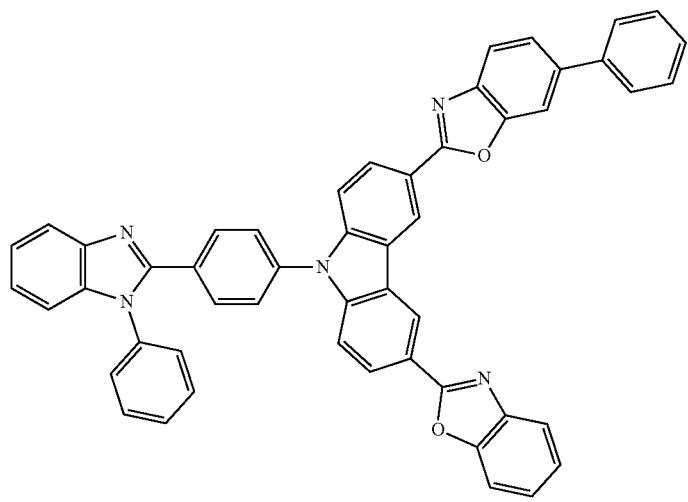
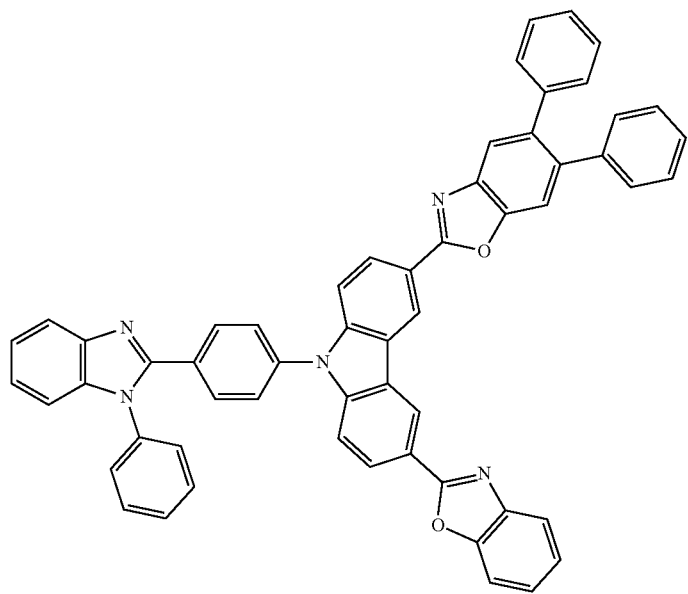
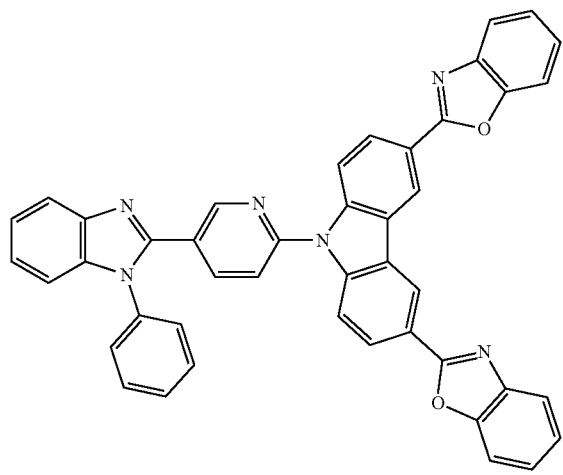

-continued
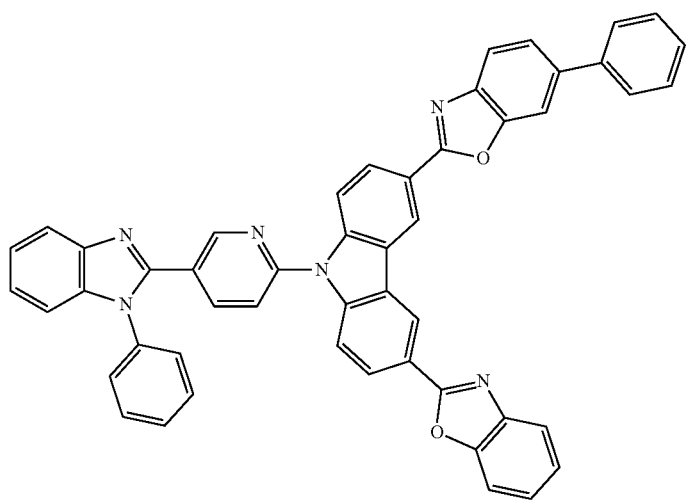
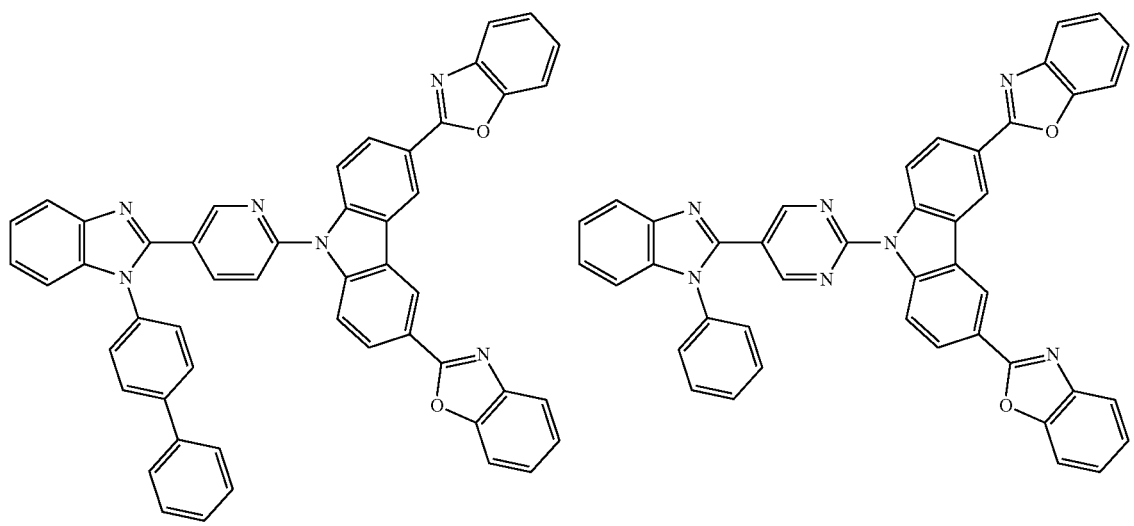
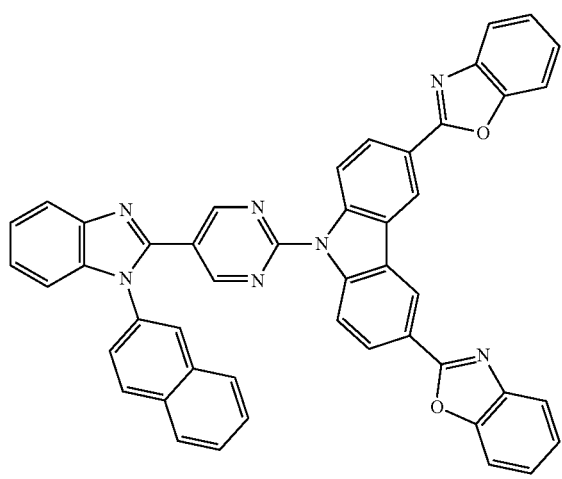

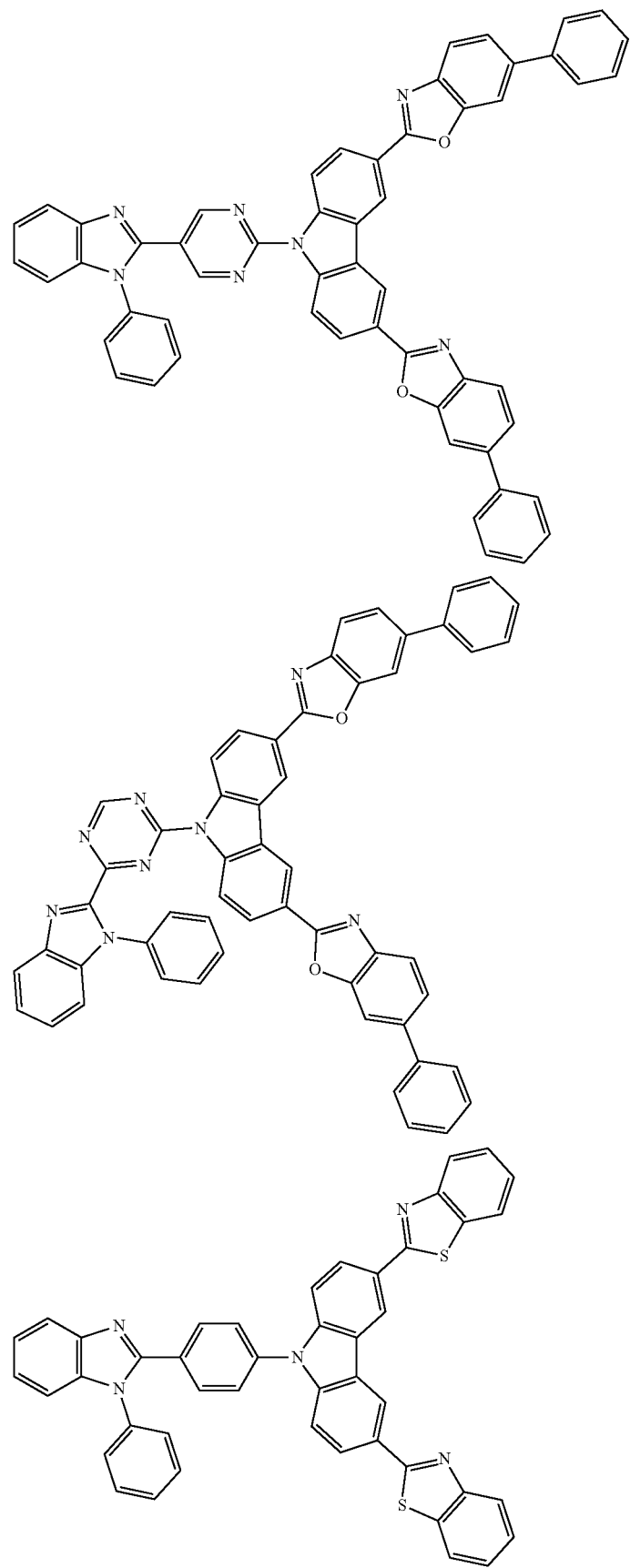

-continued
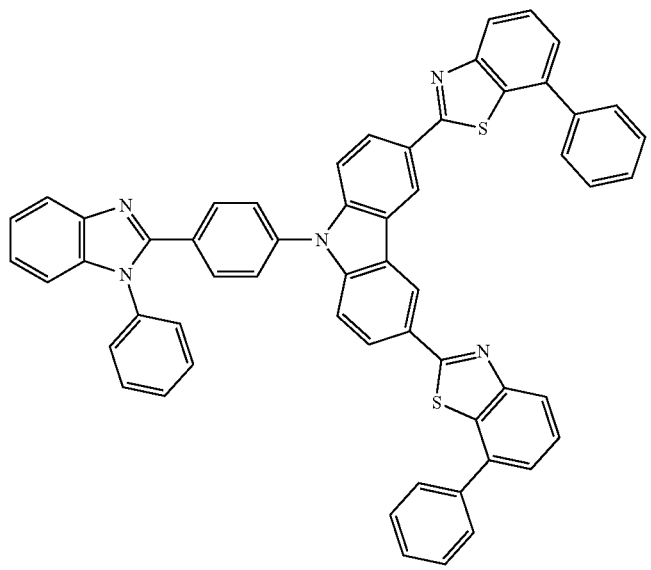
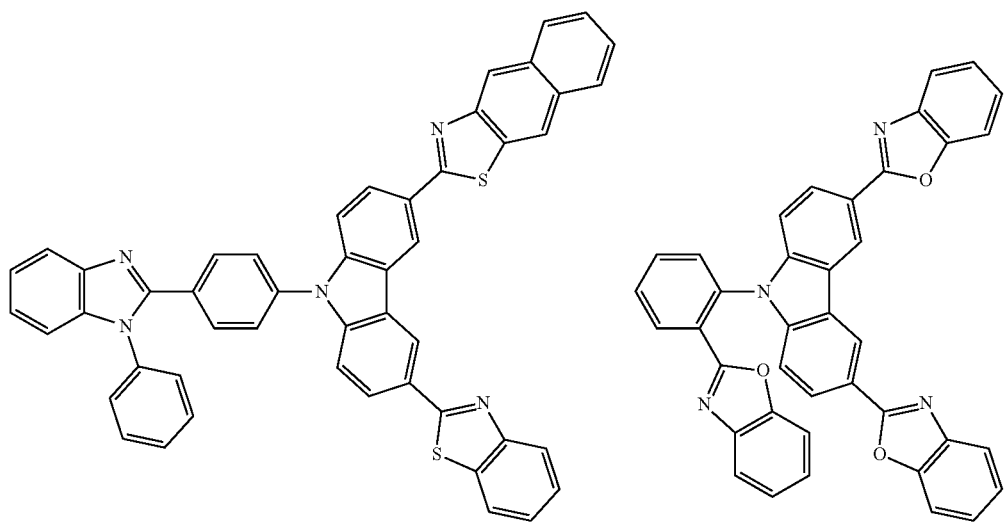
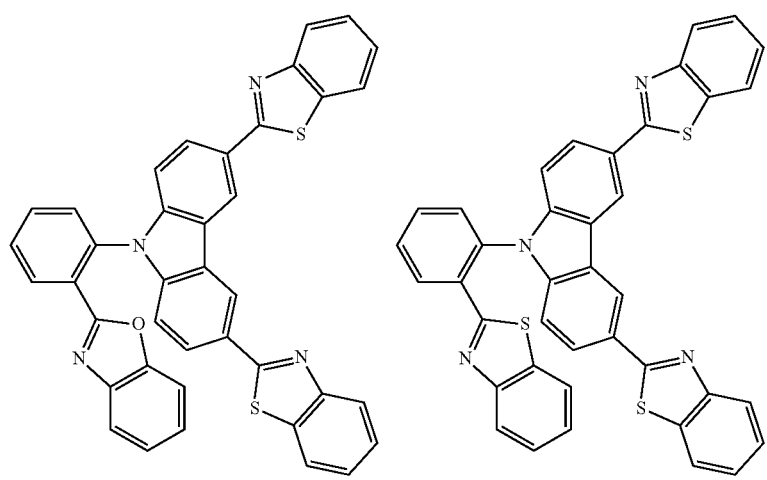

-continued
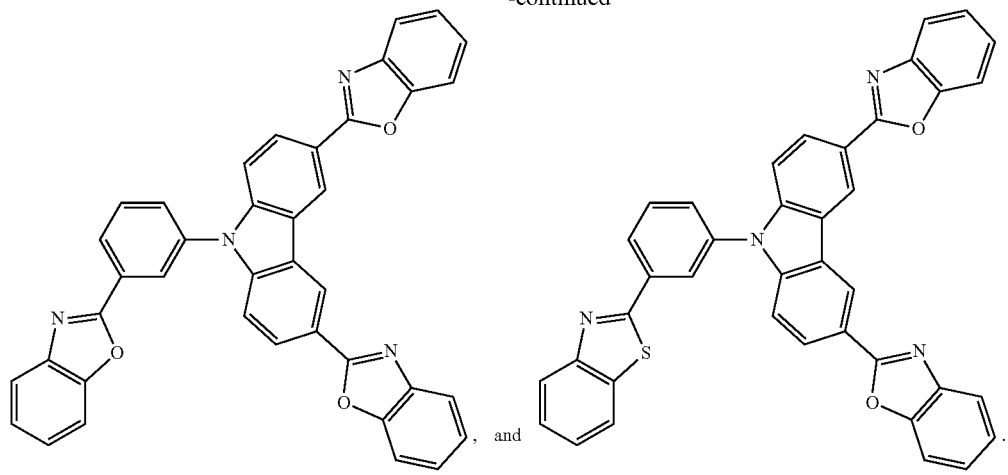
4. The compound according to claim 1, wherein the compound of Formula (I) is selected from the group consisting of the following compounds:
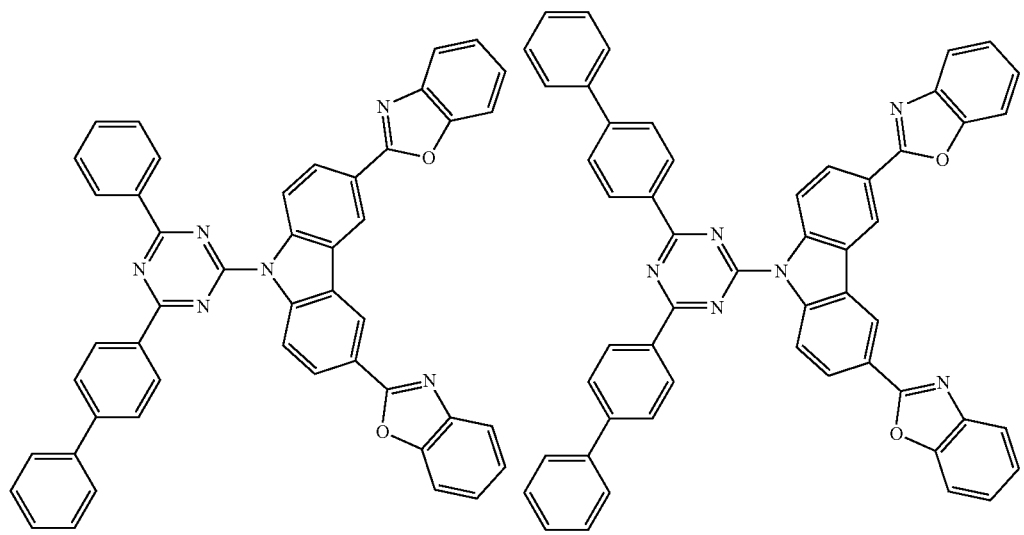
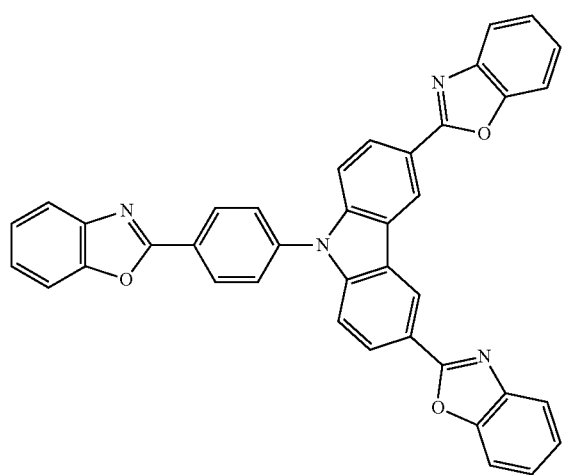

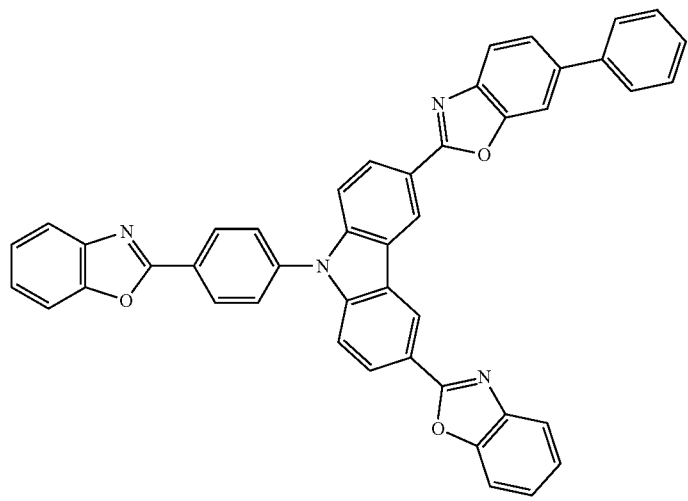
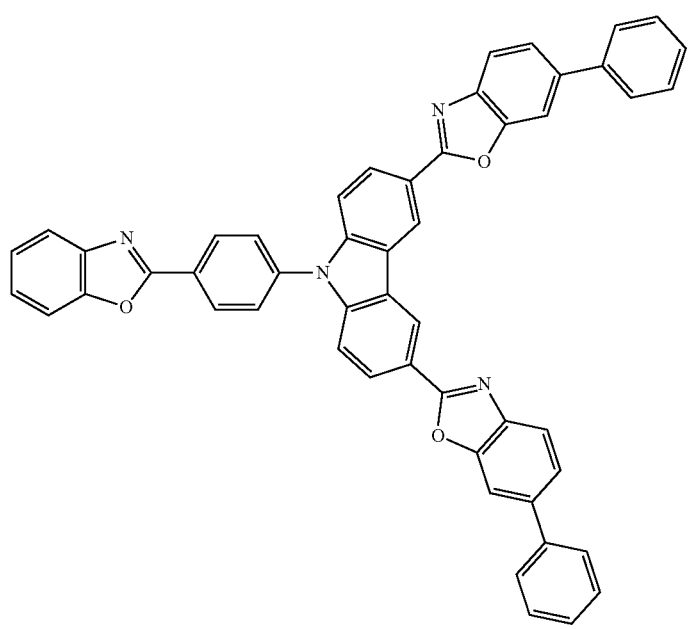
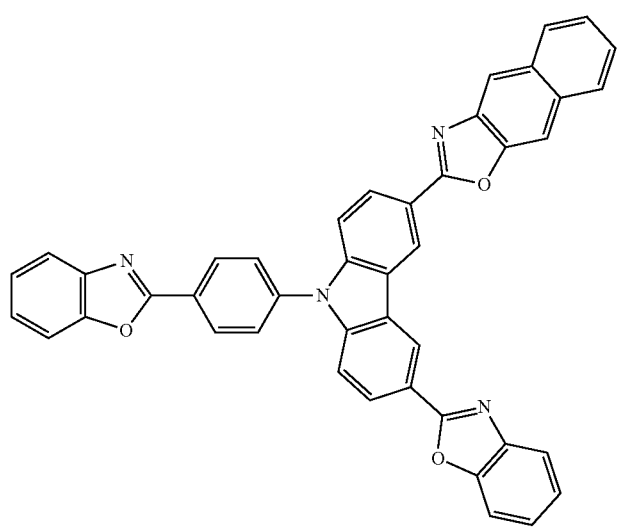

-continued
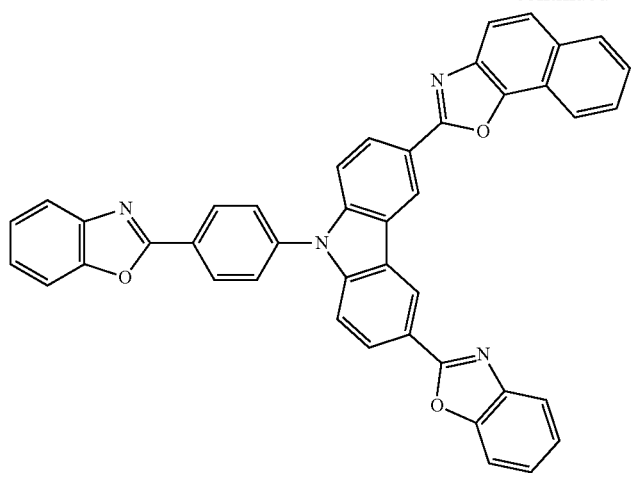
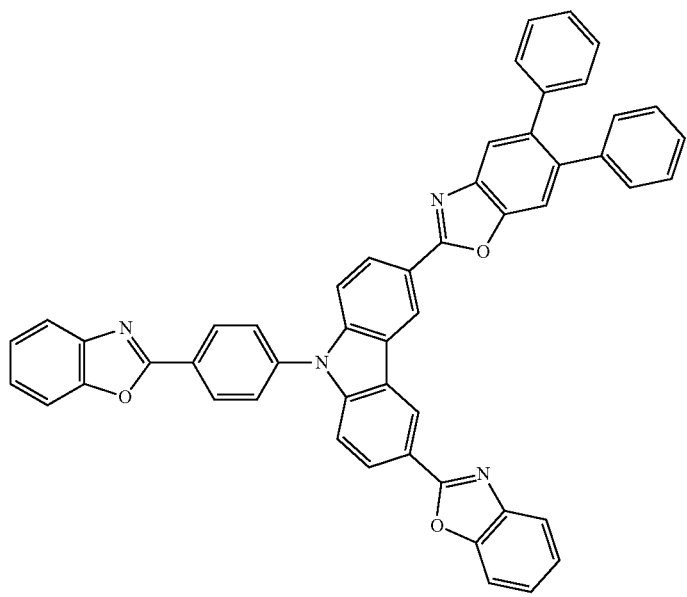
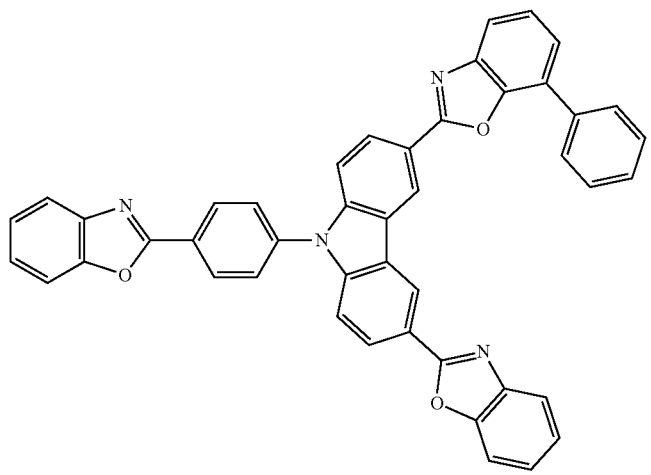

-continued
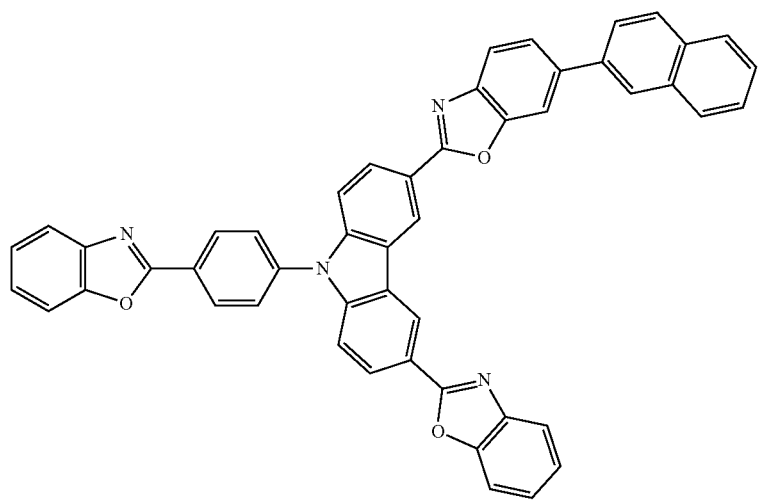
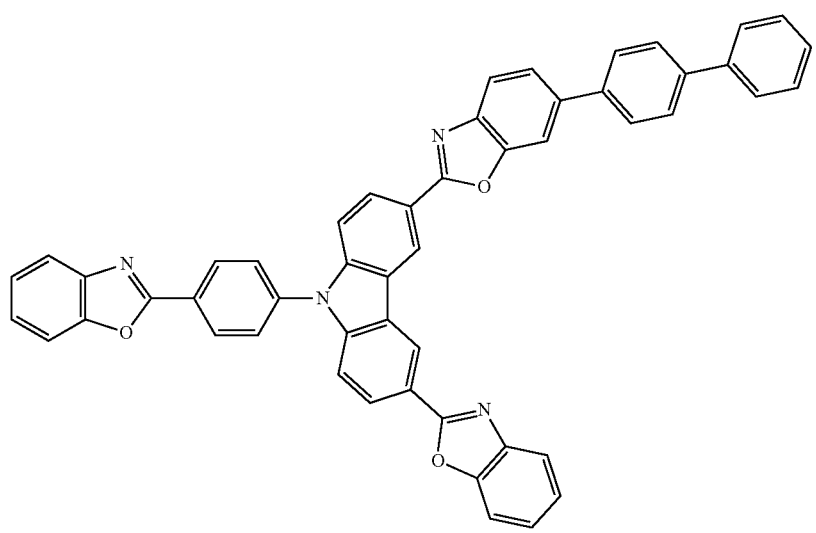
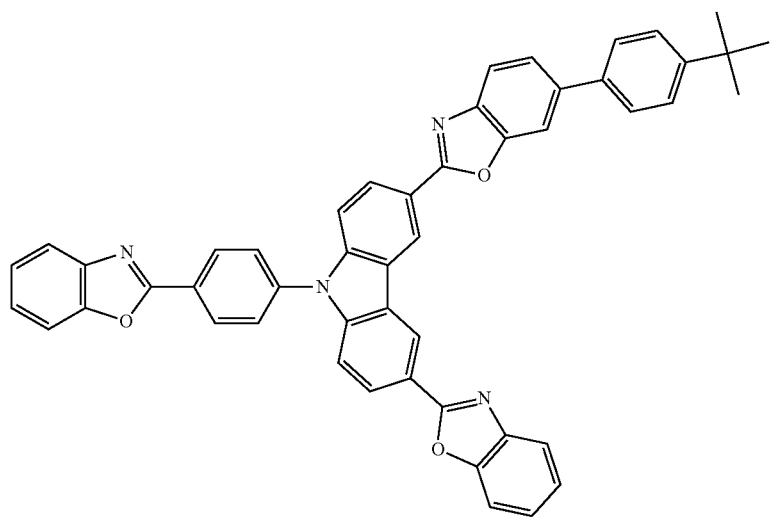

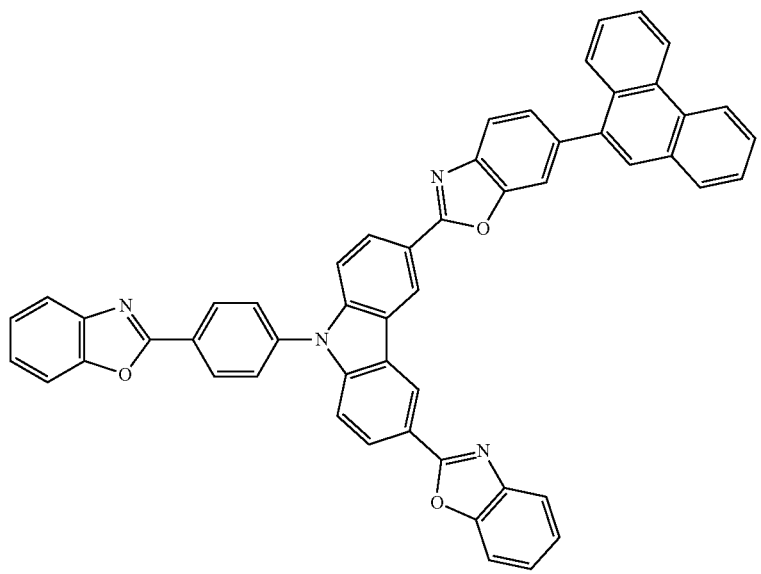
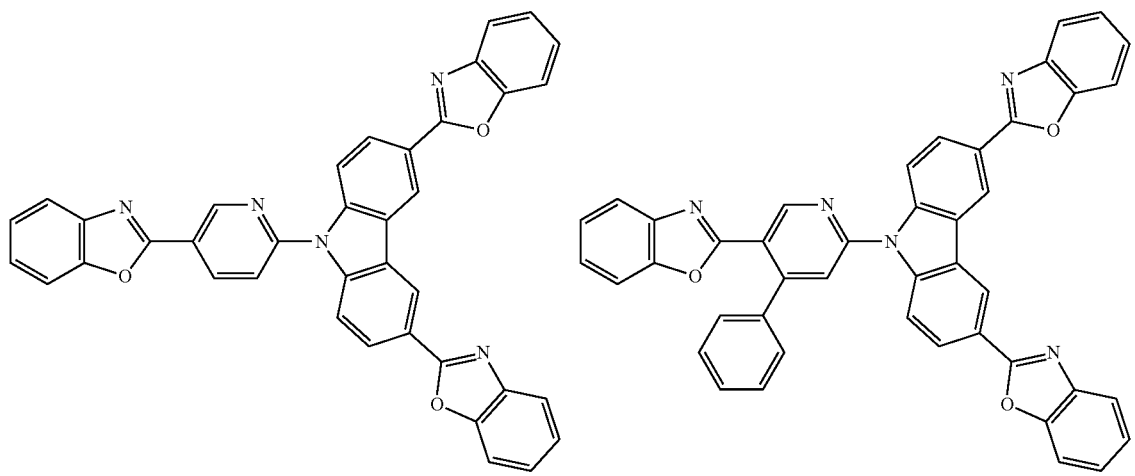
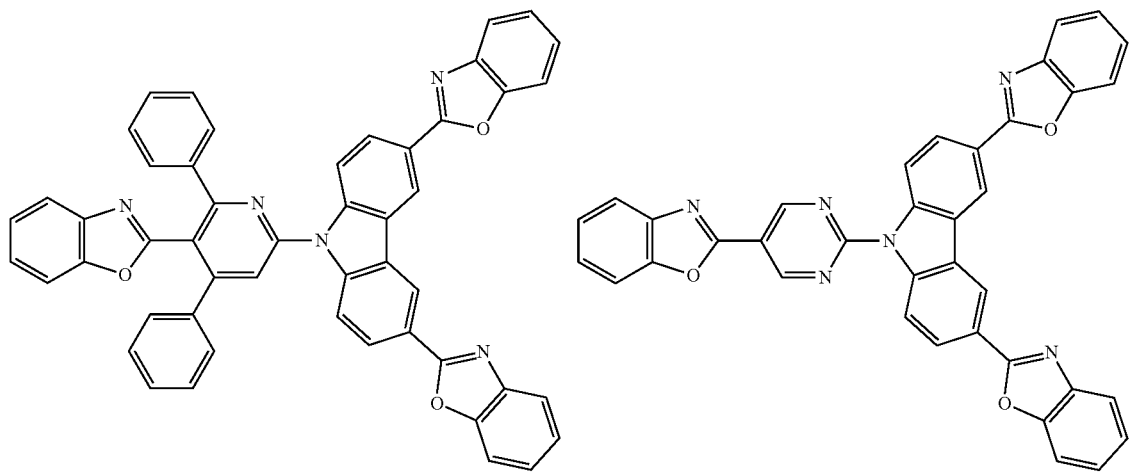

-continued
215
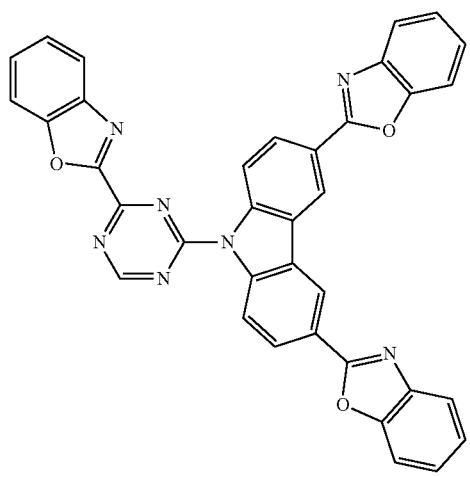
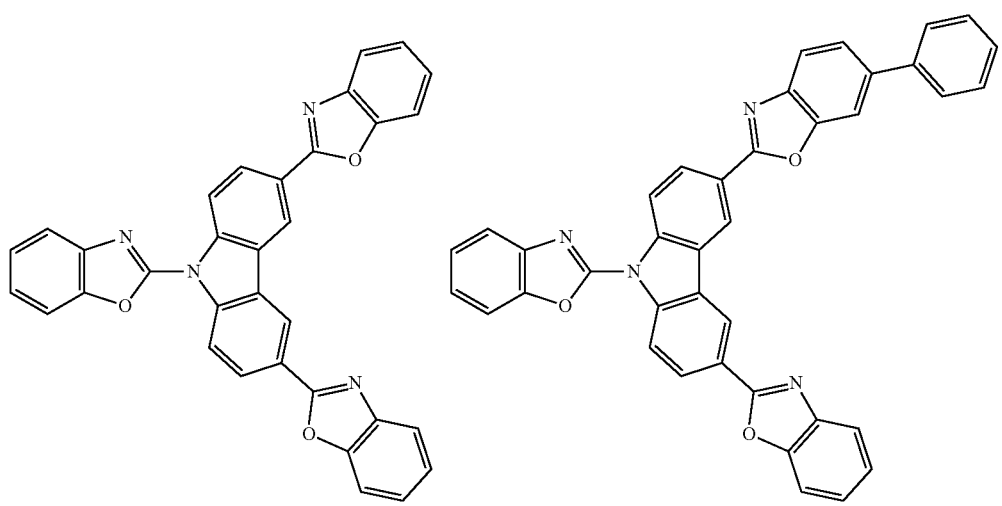
216
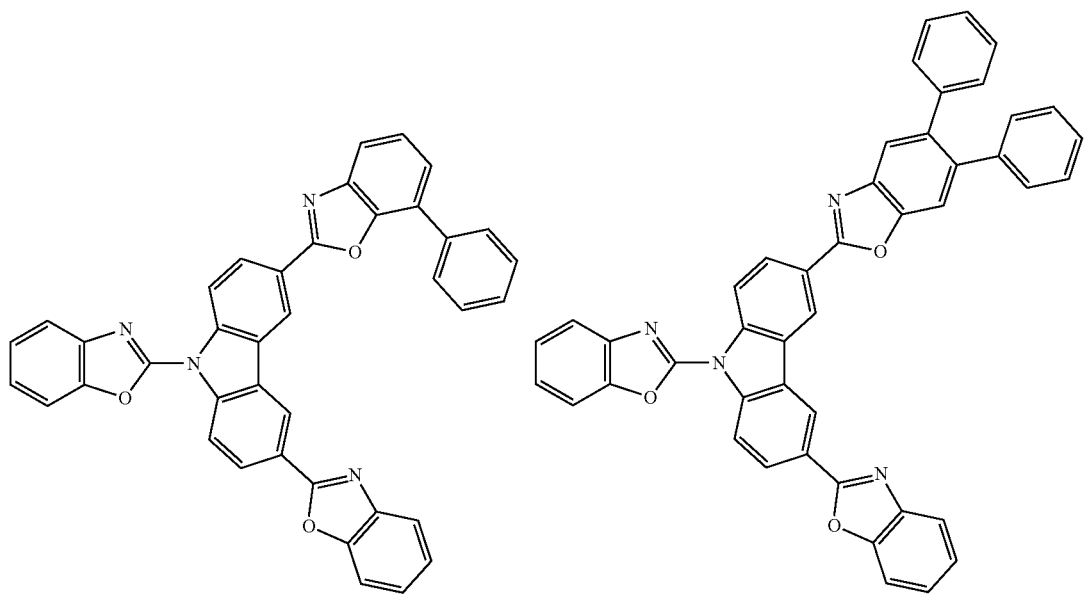

217
-continued
218
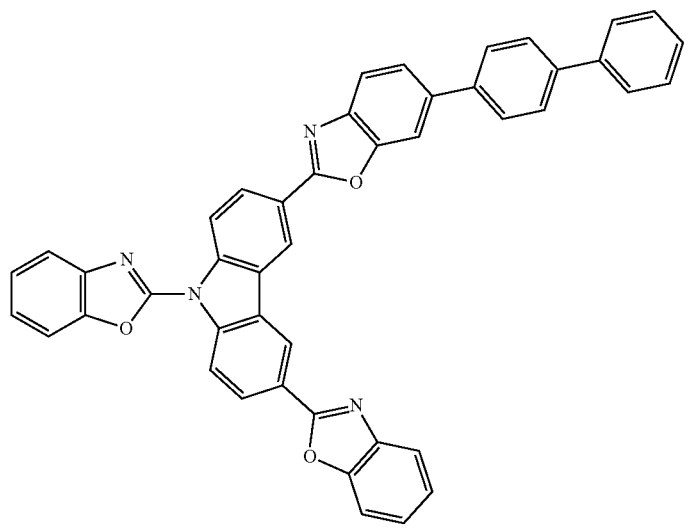
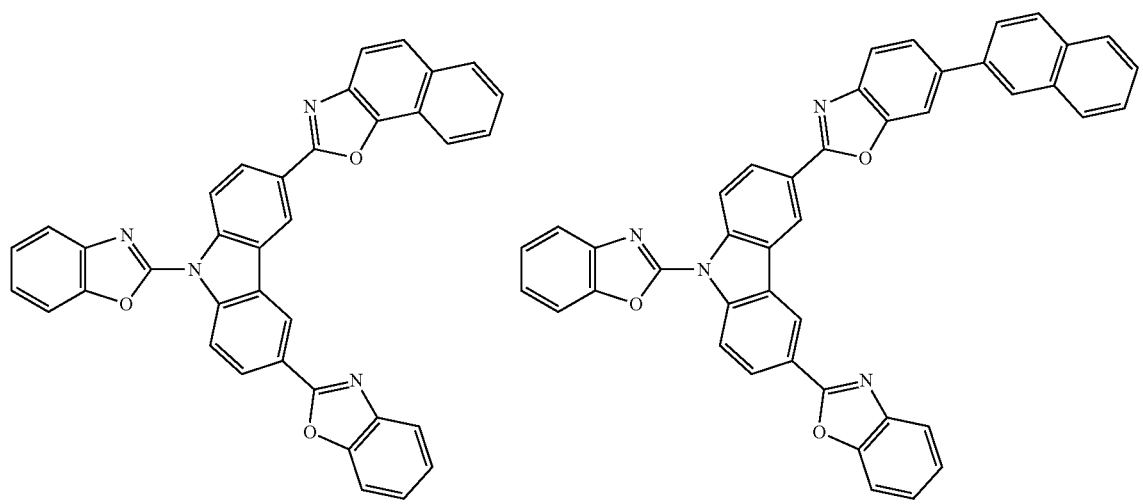
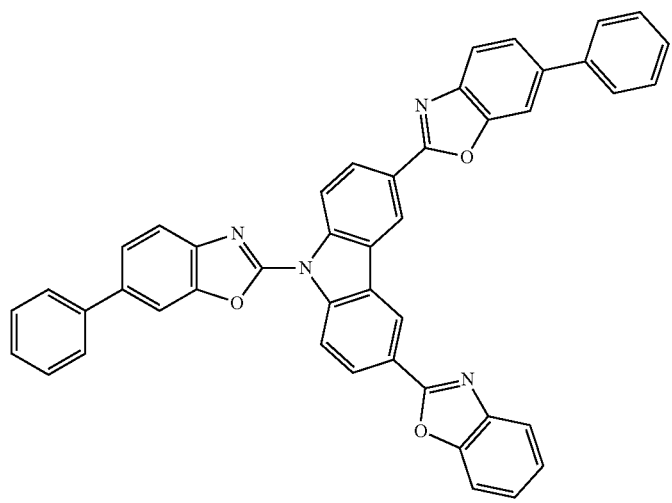

-continued
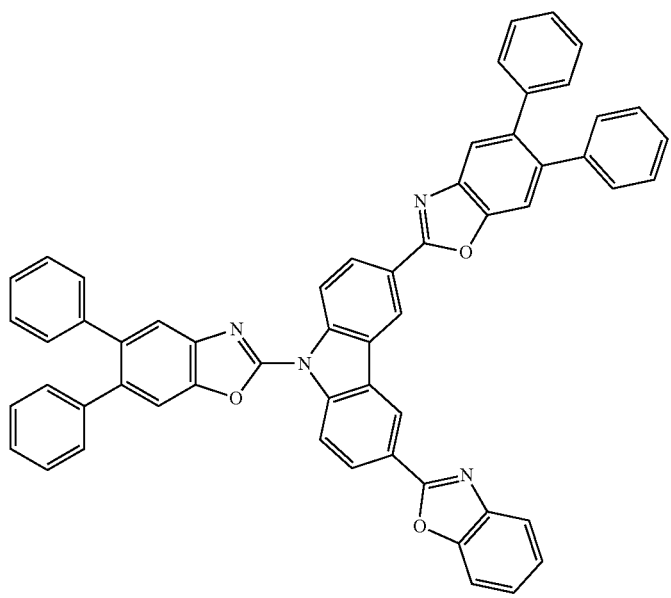
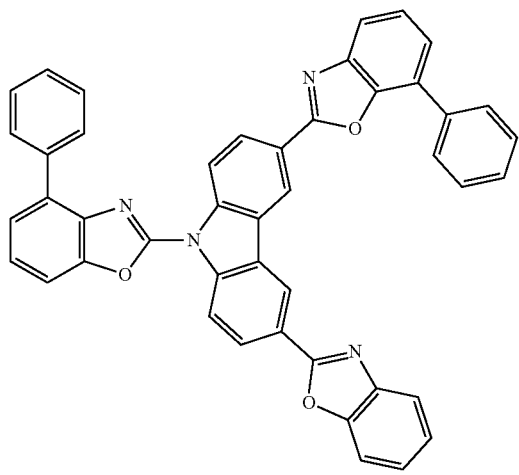
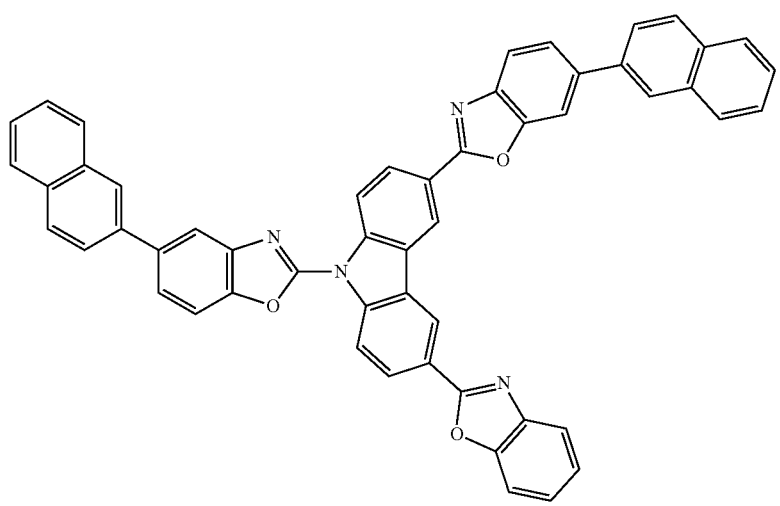

-continued
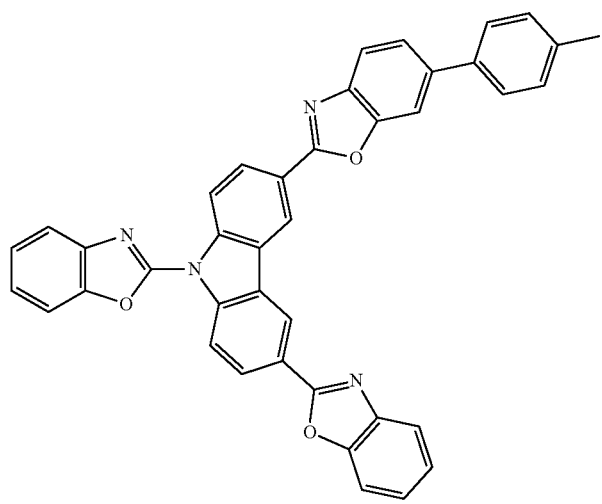
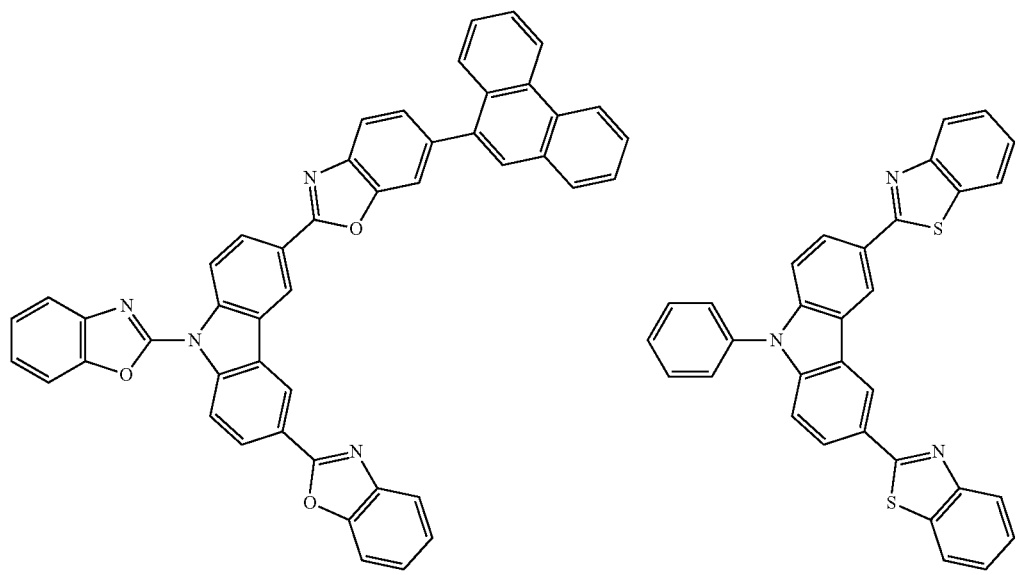
, and
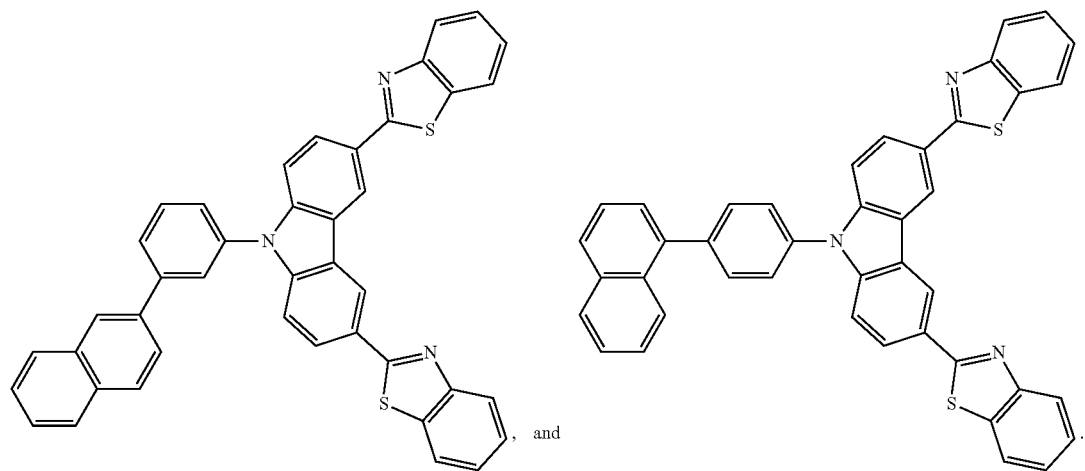

5. The compound according to claim 1, wherein the compound of Formula (I) is selected from the group consisting of the following compounds:
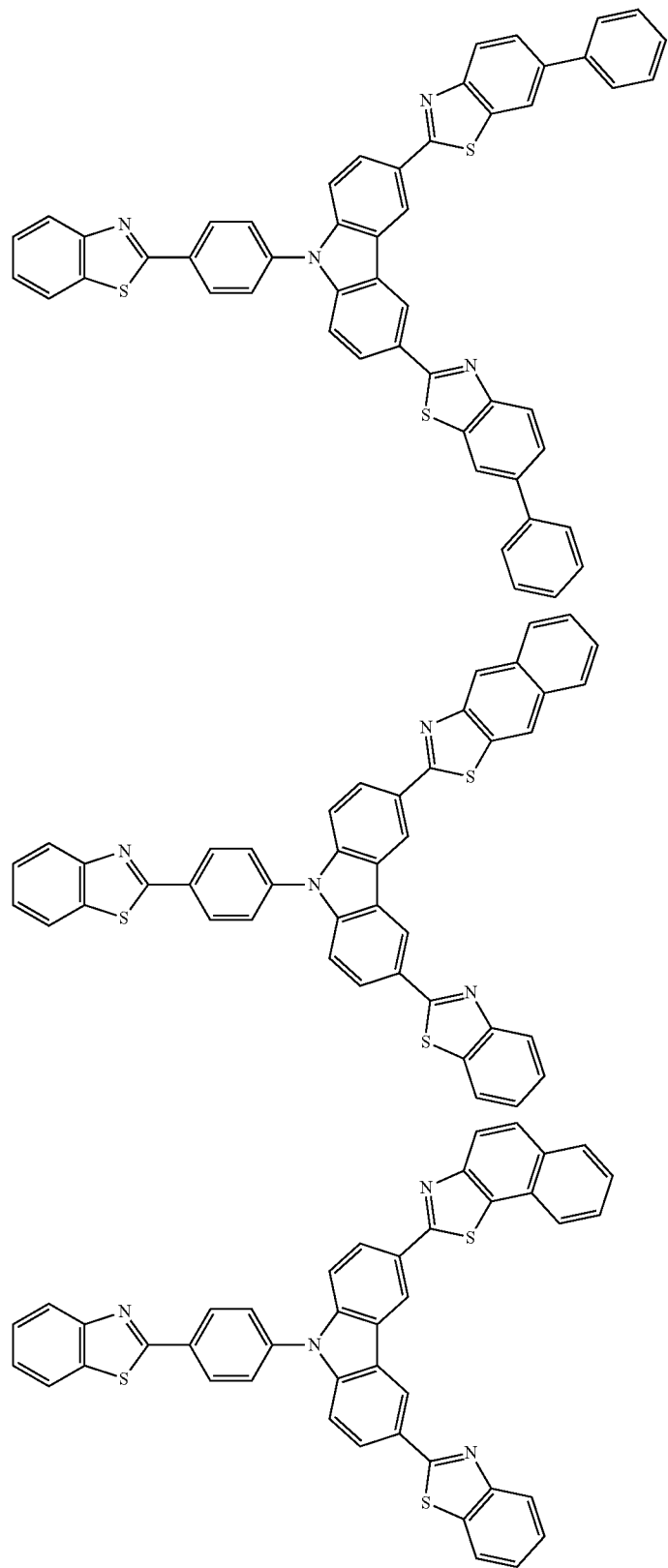

-continued
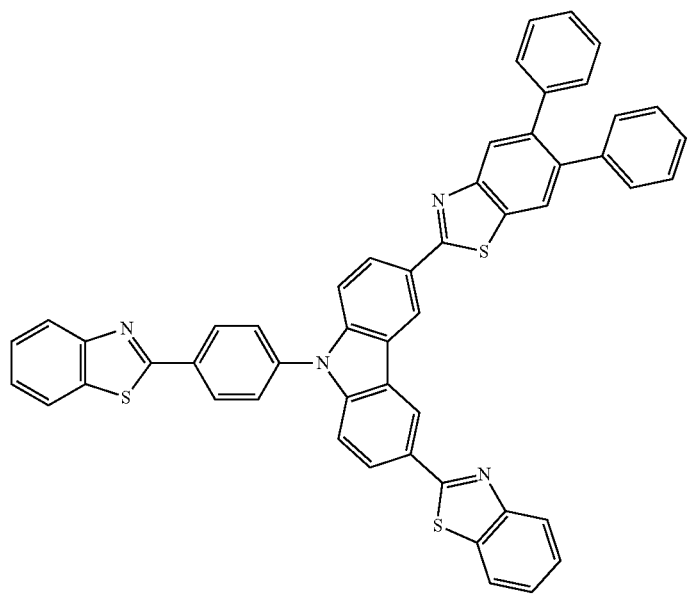
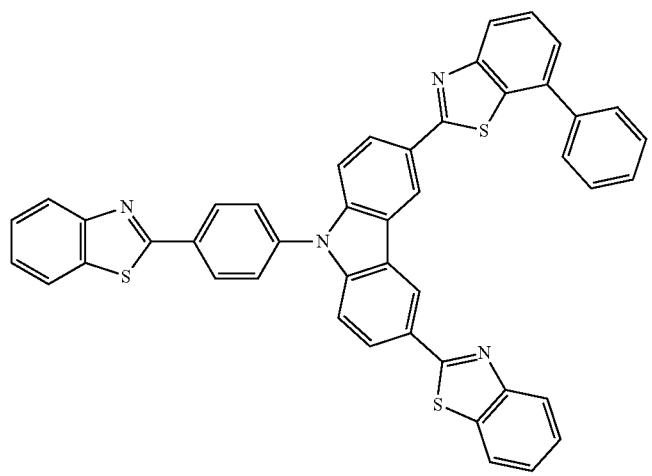
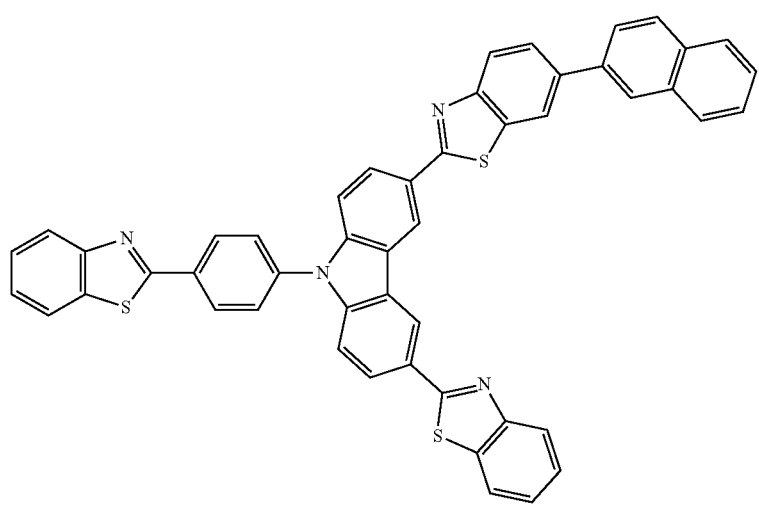

227 228
-continued
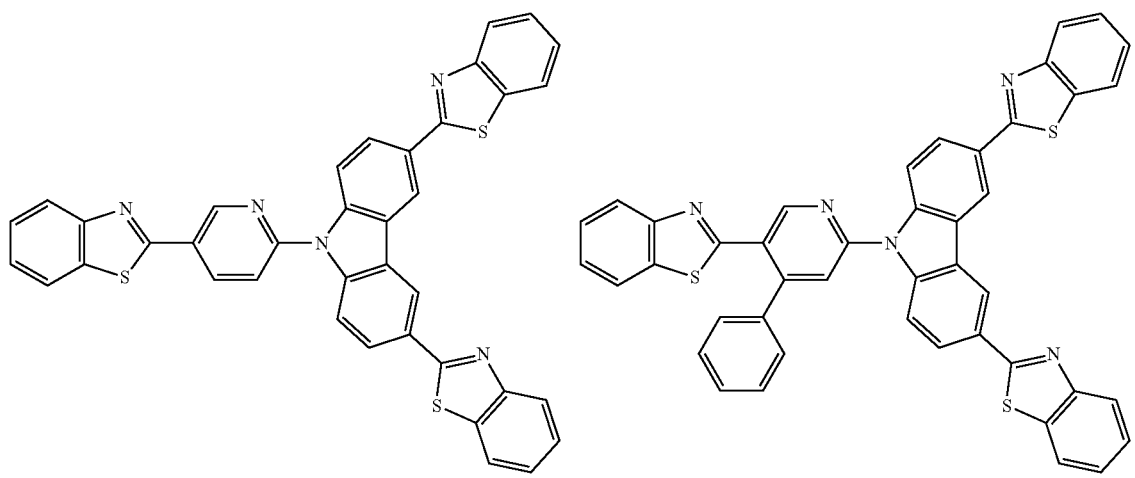
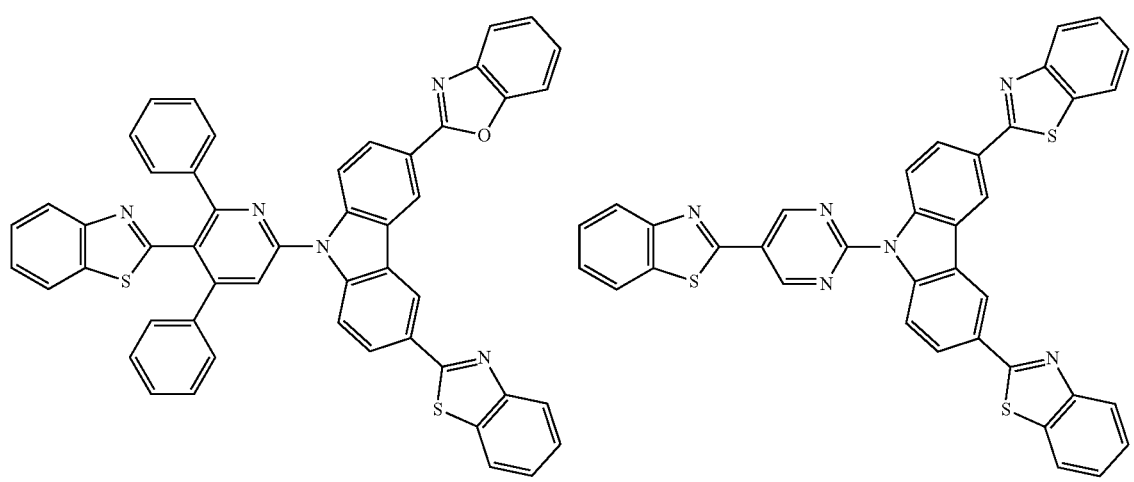
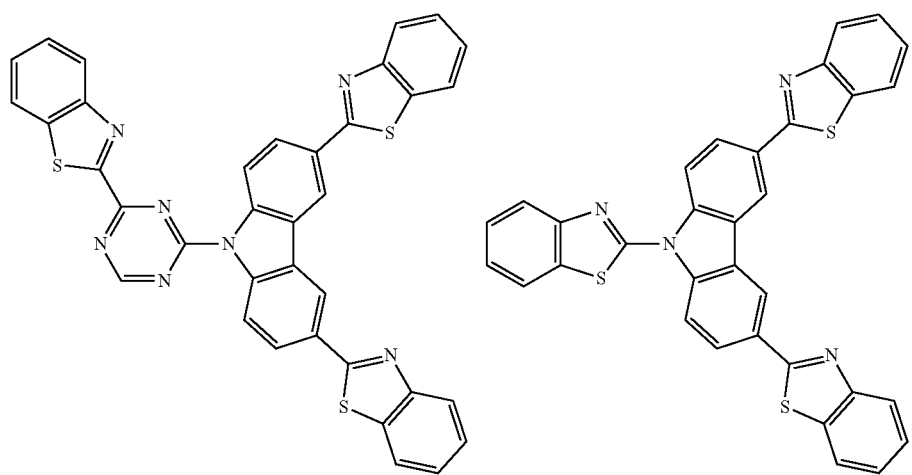

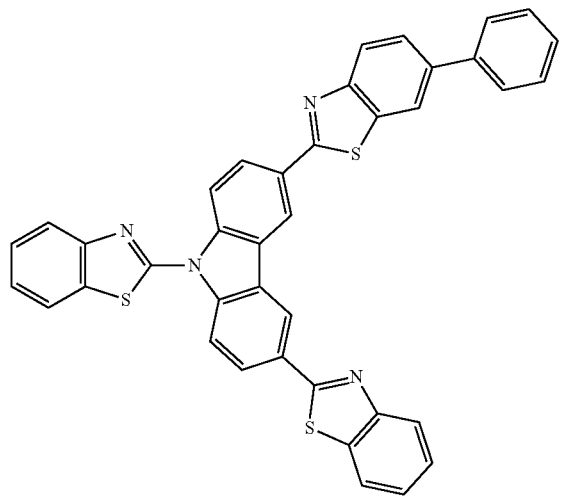
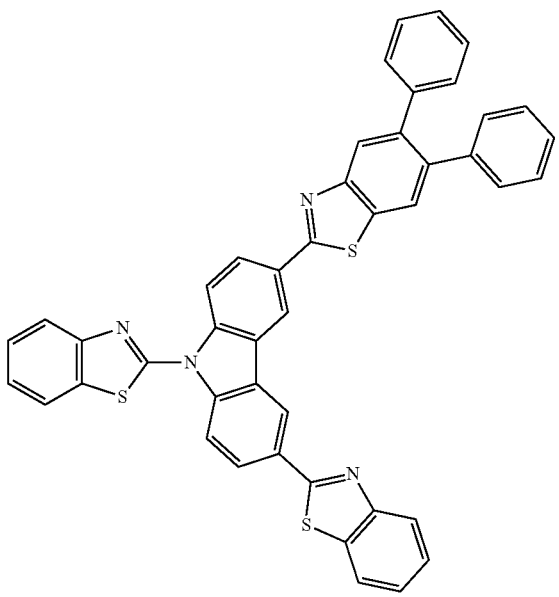
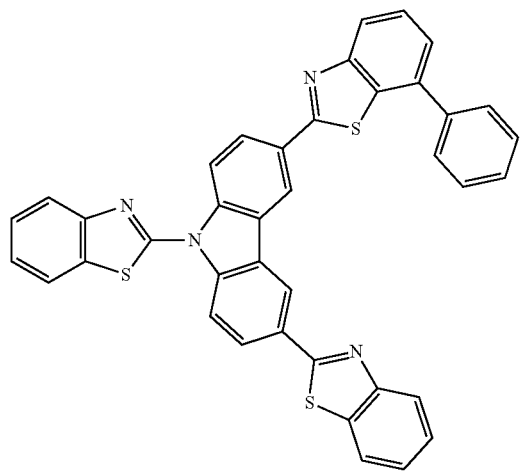
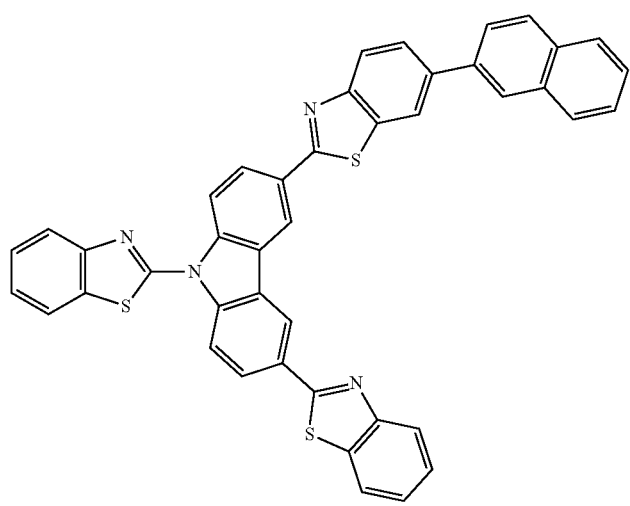

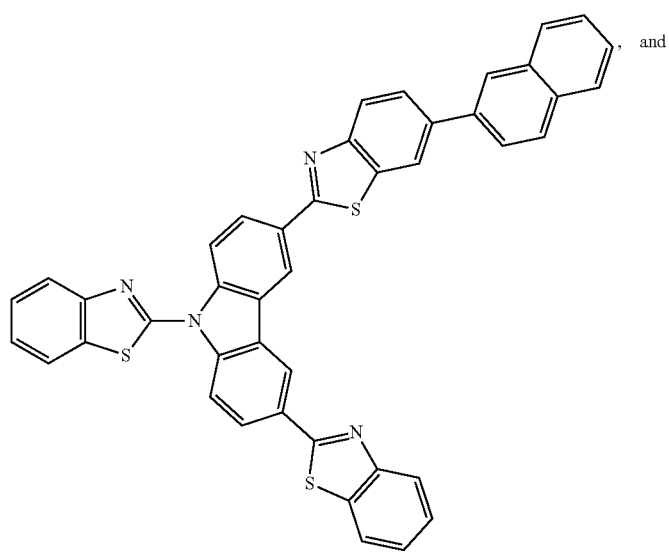
, and
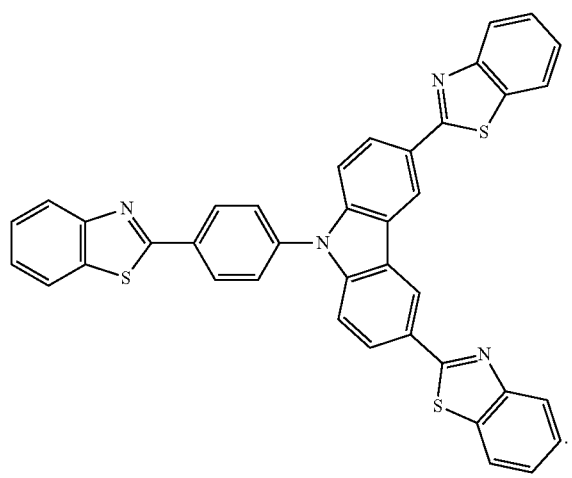
6. The compound according to claim 1, wherein the compound of Formula (I) is selected from the group consisting of the following compounds:
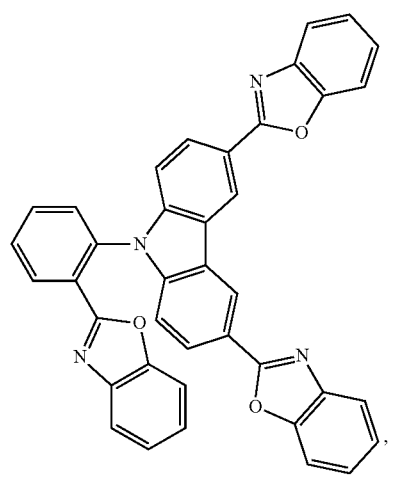
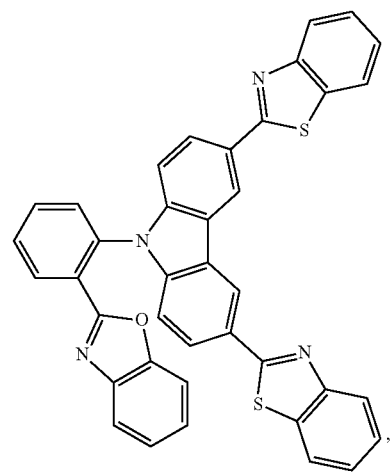

-continued

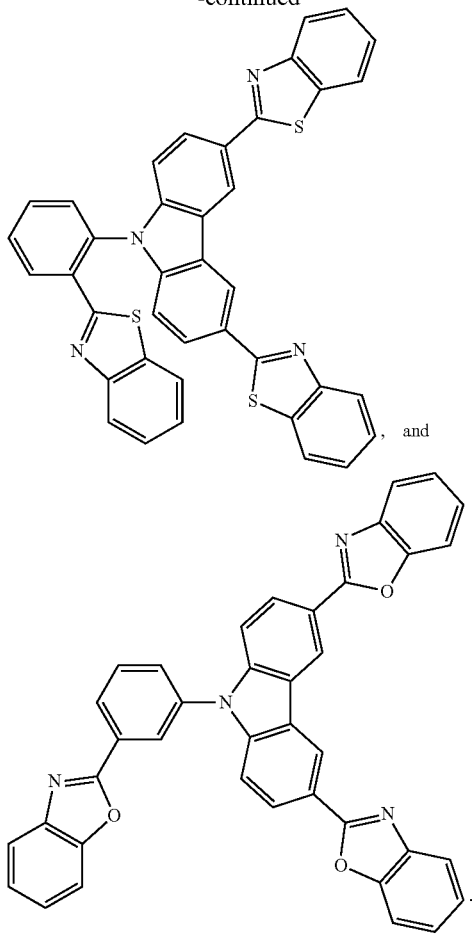, and

7. A device comprising:
a first electrode,
a second electrode, and
one or more organic layers placed between the first and second electrodes, wherein the one or more organic layers comprise the compound of claim 1.

8. The device according to claim 7, wherein the organic layers comprises one or more layers selected from a hole injecting layer, a hole transport layer, a layer having functions of both hole injection and hole transport, an electron transport layer, a layer having functions of both electron transport and electron injection, an electron blocking layer, a hole blocking layer, a capping layer, and a light emitting layer.

9. The device according to claim 8, wherein the light emitting layer comprises one or more host compounds, one of which is the compound of claim 1.

10. The device according to claim 7, wherein a capping layer is formed at an upper or a lower side, or both sides of the first electrode or the second electrode or both first and second electrodes, and wherein the capping layer comprises the compound of claim 1.

11. The device according to claim 10, wherein the capping layer is formed at the lower side of the first electrode or the upper side of the second electrode, or both of the lower side of the first electrode and the upper side of the second electrode.

* * * * *